(12) United States Patent
Luo et al.

(10) Patent No.: US 7,569,578 B2
(45) Date of Patent: *Aug. 4, 2009

(54) HETEROCYCLIC ANTI-MIGRAINE AGENTS

(75) Inventors: Guanglin Luo, Madison, CT (US); Ling Chen, Middletown, CT (US); Andrew P. Degnan, New Haven, CT (US); Gene M. Dubowchik, Middlefield, CT (US); John E. Macor, Guilford, CT (US); George O. Tora, Meriden, CT (US); Prasad V. Chaturvedula, Cheshire, CT (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 661 days.

This patent is subject to a terminal disclaimer.

(21) Appl. No.: 11/004,706

(22) Filed: Dec. 3, 2004

(65) Prior Publication Data

US 2005/0153959 A1  Jul. 14, 2005

Related U.S. Application Data

(60) Provisional application No. 60/527,438, filed on Dec. 5, 2003.

(51) Int. Cl.
A61K 31/517 (2006.01)
C07D 239/95 (2006.01)
A61K 31/497 (2006.01)
C07D 403/04 (2006.01)

(52) U.S. Cl. .............................. 514/266.22; 514/266.3; 544/286

(58) Field of Classification Search ............ 514/266.22, 514/266.3; 544/286
See application file for complete search history.

(56) References Cited

U.S. PATENT DOCUMENTS

| | | |
|---|---|---|
| 6,313,097 B1 | 11/2001 | Eberlein et al. |
| 6,344,449 B1 | 2/2002 | Rudolf et al. |
| 6,521,609 B1 | 2/2003 | Doods et al. |
| 6,552,043 B1 | 4/2003 | Patchett et al. |
| 2001/0036946 A1 | 11/2001 | Rudolf et al. |
| 2003/0139417 A1 | 7/2003 | Eberlein et al. |
| 2003/0181462 A1 | 9/2003 | Doods et al. |
| 2003/0191068 A1 | 10/2003 | Trunk et al. |
| 2003/0212057 A1 | 11/2003 | Rudolf et al. |
| 2003/0236282 A1 | 12/2003 | Hurnaus et al. |
| 2004/0014679 A1 | 1/2004 | Trunk et al. |
| 2004/0063735 A1 | 4/2004 | Chaturvedula et al. |
| 2004/0076587 A1 | 4/2004 | Kruss et al. |
| 2004/0132716 A1 | 7/2004 | Rudolf et al. |
| 2004/0192729 A1 | 9/2004 | Rudolf et al. |
| 2004/0204397 A1 | 10/2004 | Chaturvedula et al. |
| 2004/0214819 A1 | 10/2004 | Rudolf et al. |
| 2004/0229861 A1 | 11/2004 | Burgey et al. |
| 2004/0248816 A1 | 12/2004 | Doods et al. |
| 2005/0032783 A1 | 2/2005 | Doods et al. |
| 2005/0065094 A1 | 3/2005 | Davidai |
| 2005/0215546 A1 | 9/2005 | Hurnaus et al. |
| 2005/0215576 A1* | 9/2005 | Degnan et al. ......... 514/266.22 |
| 2005/0227968 A1 | 10/2005 | Lustenberger et al. |
| 2005/0233980 A1 | 10/2005 | Doods |
| 2005/0234054 A1 | 10/2005 | Mueller et al. |
| 2005/0234067 A1 | 10/2005 | Mueller et al. |
| 2005/0250763 A1 | 11/2005 | Mueller et al. |
| 2005/0256098 A1 | 11/2005 | Burgey et al. |
| 2005/0256099 A1 | 11/2005 | Mueller et al. |
| 2005/0272955 A1 | 12/2005 | Zimmer et al. |
| 2006/0094707 A1 | 5/2006 | Chaturvedula et al. |

FOREIGN PATENT DOCUMENTS

| | | |
|---|---|---|
| CA | 2 387 613 | 5/2001 |
| CA | 2503455 | 4/2005 |
| EP | 1 227 090 A1 | 7/2002 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 99/52875 | 10/1999 |
| WO | WO 00/18764 | 4/2000 |

(Continued)

OTHER PUBLICATIONS

Ashina, M. et al., "Evidence for increased plasma levels of calcitonin gene-related peptide in migraine outside of attacks", *Pain*, 2000, 86(1-2):133-138.
Brain, S.D. et al., "CGRP receptors: a headache to study, but will antagonists prove therapeutic in migraine?", *TiPS*, 2002, 23(2): 51-53.
Edvinsson, L., "Calcitonin Gene-Related Peptide (CGRP) and the Pathophysiology of Headache", *CNS Drugs*, 2001, 15(10):745-753.
Evans, B.N. et al., "CGRP-RCP, a Novel Protein Required for Signal Transduction at Calcitonin Gene-related Peptide and Adrenomedullin Receptors", *J. Biol. Chem.* 2000, 275(4): 31438-31443.

(Continued)

*Primary Examiner*—James O Wilson
*Assistant Examiner*—Tamthom N Truong
(74) *Attorney, Agent, or Firm*—Shah R. Makujina; James Epperson

(57) ABSTRACT

The present invention relates to compounds of Formula (I)

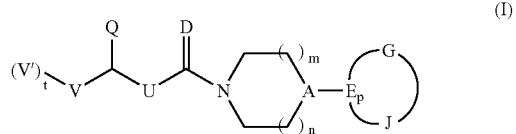

as antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

31 Claims, No Drawings

FOREIGN PATENT DOCUMENTS

| | | |
|---|---|---|
| WO | WO 00/55154 | 9/2000 |
| WO | WO 01/32648 | 3/2001 |
| WO | WO 01/32649 | 3/2001 |
| WO | WO 01/25228 | 4/2001 |
| WO | WO 01/49676 | 7/2001 |
| WO | WO 02/10140 | 2/2002 |
| WO | WO 03/027252 | 4/2003 |
| WO | WO 03/070753 | 8/2003 |
| WO | WO 03/076432 | 9/2003 |
| WO | WO 03/104236 | 12/2003 |
| WO | WO 2004/037810 | 5/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2005/000807 | 1/2005 |
| WO | WO 2005/009962 | 2/2005 |
| WO | WO 2005/013894 | 2/2005 |
| WO | WO 2005/056550 | 6/2005 |
| WO | WO2005/065779 | 7/2005 |
| WO | WO 2005/072308 | 8/2005 |
| WO | WO2005/084672 | 9/2005 |
| WO | WO 2005/092880 | 10/2005 |
| WO | WO 2005/095383 | 10/2005 |
| WO | WO 2005/100343 | 10/2005 |
| WO | WO 2005/100352 | 10/2005 |
| WO | WO/2005/100360 | 10/2005 |
| WO | WO 2005/102322 | 11/2005 |
| WO | WO 2005/103037 | 11/2005 |
| WO | WO 2005/121078 | 12/2005 |
| WO | WO 2006/052378 | 5/2006 |
| WO | WO 2006/060678 | 6/2006 |

OTHER PUBLICATIONS

Gallai, V. et al. "Vasoactive peptide levels in the plasma of young migraine patients with and without aura assessed byoth interictally and ictally", *Cephalalgia* 1995;15: 384-390.

Goadsby, P.J. et al., "Vasoactive peptide release in the extracerebral circulation of humans during migrain headache". *Annals of Neurology*, 1990, 28(2):183-187.

Grant, A.D., "Evidence of a role for NK, and CGRP receptors in mediating neurogenic vasodilatation in the mouse ear", *Brit. J. Pharmacol.* 2002, 135: 356-362.

Juaneda, C. et al. "The molecular pharmacology of CGRP and related peptide receptor subtypes", *TiPS*, 2000, 21: 432-438.

Lassen, L.H. et al. "CGRP may play a causative role in migraine", *Cephalalgia*, 2002 22(1): 54-61.

Mallee, J.J. et al. "Receptor Activity-modifying Protein 1 Determines the Species Selectivity of Non-peptide CGRP Receptor Antagonist", *J., Biol. Chem.*, 2002, 277(16): 14294-14298.

McLatchie, L.M. et al., "RAMPs regulate the transport and ligand specificity of the calcitonin-receptor-like receptor", *Nature*, 1998, 393: 333-339.

Olesen, J. et al., "Calcitonin Gene-Related Peptide Receptor Antagonist BIBN 4096 BS for the Acute Treatment of Migraine", *New England J. of Medicine*, 2004, 350 (11): 1104-1110.

Poyner, D.R. et al., "Pharmacological characterization of a receptor for calcitonin gene-related peptide on rat, L6 myocytes", *Brit. J. of Pharm.*, 1992, 105: 441-447.

Rosenfeld, et al., "Production of a novel neuropeptide encoded by the calcitonin gene via tissue-specific RNA processing", *Nature*, 1983, 304:129-135.

Shen, Y-T. et al., "Functional Role of α-Calcitonin Gene-Related Peptide in the Regulation of the Cardiovascular System", *J. Pharm. Exp. Ther.*, 2001, 298:551-558.

Van Valen, F. et al., "Calcitonin gene-related peptide (CGRP) receptors are linked to cyclic adenosine monophosphate production in SK-N-MC human neuroblastoma cells", *Neuroscience Letters*, 1990, 119: 195-198.

Williamson, D.J. and Hargreaves, R.J., "Neurogenic Inflammation in the Context of Migraine", *Microsc. Res. Tech.*, 2001, 53: 167-178.

U.S. Appl. No. 11/091,429, filed Mar. 28, 2005, Degnan, et al., (copending application).

U.S. Appl. No. 60/624,655, filed Nov. 3, 2004, Chaturvedula, et al.

U.S. Appl. No. 60/678,099, filed May 5, 2005, Chaturvedula, et al.

U.S. Appl. No. 60/633,159, filed Dec. 3, 2004, Chaturvedula, et al.

Chu, et al., "The calcitonin gene-related peptide (CGRP) antagonist CGRP8-37 block vasodilatation in inflammed rat skin: involvement of adrenomedullin in addition to CGRP," *Neuroscience Letters*, 310, 2001, 169-172.

De Vries, et al., "Pharmacological aspects of experimental headache models in relation to acute antimigraine therapy," *European Journal of Pharmacology*, 375, 1999, 61-74.

Doods, et al., "Pharmacological profile of BIBN4096BS, the first selective small molecule CGRP antagonist," *British Journal of Pharmacology*, 2000, 129, 420-423.

Escott, et al., "Effect of a calcitonin gene-related peptide antagonist (CGRP8-37) on skin vasodilatation and oedema induced by stimulation of the rat saphenous nerve", *British Journal of Pharmacology*, 1993, 100, 772-776.

Escott, et al., "Trigeminal ganglion stimulation increases facial skin blood flow in the rat: a major role for calcitonic gene-related peptide", *Brian Research*, 1995, 669: 93-99.

Hall, et al., "Interaction of amylin with calcitonin gene-related peptide receptors in microvasculature of the hamster cheek pouch in vivo," *British Journal of Pharmacology*, 1999, 126, 280-284.

Hall, et al., "Interaction of human adrenomedullin 13-52 with calcitonin gene-related peptide receptors in the microvasculature of the rat and hamster,"*British Journal of Pharmacology*, 1995, 114, 592-597.

Pasternak, et al., "Potent, orally bioavailable somatostatin agonists: good absorption achieved by urea backbone cyclization", *Bioorganic & Medicinal Chemistry* Letters, Oxford GB, vol. 9, No. 3, Feb. 8,1999, 491-496.

Williamson, et al., "Intravital microscope studies on the effects of neurokinin agonists and calcitonin gene-related peptide on dural vessel diameter in the anaesthetized rat," *Cephalalgia*, 1997, 17, 518-524.

Williamson, et al., "Sumatriptan inhibits neurogenic vasodilation of dural blood vessels in the anaesthetized rat-intravital microscope studies," *Cephalalgia*, 1997, 17, 525-531.

U.S. Appl. No. 11/417,325, filed May 3, 2005, Chaturvedula, et al., (copending application).

U.S. Appl. No. 11/247,697, filed Oct. 11, 2005, Chaturvedula, et al., (copending application).

U.S. Appl. No. 11/291,670, filed Dec. 1, 2005, Chaturvedula, et al., (copending application).

Carlström, A.-S. and Frejd, T., Palladium-Catalyzed Synthesis of Didehydroamino Acid Derivatives, *Synthesis*, 1989, 6, 414-418.

Carlström, A.-S. and Frejd, T., "Palladium-Catalyzed Bis-coupling of Dihaloaromatics with 2-Amidoacrylates", *J. Org. Chem.*, 1991, 56, 1289-1293.

Dygos, J.H., et al., "A Convenient Asymmetric Synthesis of the Unnatural Amino Acid 2,6-Dimethyl-L-tyrosine", *Synthesis*, 1992, 741-743.

Rudolf, K., et al., "Development of Human Calcitonin Gene-Related Peptide (CGRP) Receptor Antagonists. 1. Potent and Selective Small Molecule CGRP Antagonists. 1-[$N^2$-[3,5-Dibromo-$N$-[[4-(3,4-dihydro-2(1$H$)-oxoquinazolin-3-yl)-1-piperidinyl]carbonyl]-D-tyrosyl]L-lysyl]-4-(4-pyridinyl)piperazine: The First CGRP Antagonist for Clinical Trials in Acute Migraine", *J. Med. Chem*, 2005, 48, 5921-5931.

Xin, Z., et al., "Potent, Selective Inhibitors of Protein Tyrosine Phosphatase IB", *Bioorg. & Med. Chem. Lett.*, 2003, 13, 1887-1890.

* cited by examiner

HETEROCYCLIC ANTI-MIGRAINE AGENTS

CROSS-REFERENCE TO RELATED APPLICATIONS

This is a non-provisional application which claims the benefit of U.S. Provisional Application No. 60/527,438 filed Dec. 5, 2003.

FIELD OF THE INVENTION

The present invention relates to novel small molecule antagonists of calcitonin gene-related peptide receptors ("CGRP-receptor"), pharmaceutical compositions comprising them, methods for identifying them, methods of treatment using them and their use in therapy for treatment of neurogenic vasodilation, neurogenic inflammation, migraine, cluster headache and other headaches, thermal injury, circulatory shock, flushing associated with menopause, airway inflammatory diseases, such as asthma and chronic obstructive pulmonary disease (COPD), and other conditions the treatment of which can be effected by the antagonism of CGRP-receptors.

BACKGROUND OF THE INVENTION

Calcitonin gene-related peptide (CGRP) is a naturally occurring 37-amino-acid peptide first identified in 1982 (Amara, S. G. et al, *Science* 1982, 298, 240-244). Two forms of the peptide are expressed ($\alpha$CGRP and $\beta$CGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, *Br J Pharmacol* 1992, 105, 441-7; Van Valen, F. et al, *Neurosci Lett* 1990, 119, 195-8.). Two classes of CGRP receptors, $CGRP_1$ and $CGRP_2$, have been proposed based on the antagonist properties of the peptide fragment CGRP (8-37) and the ability of linear analogues of CGRP to activate $CGRP_2$ receptors (Juaneda, C. et al. *TiPS* 2000, 21, 432-438). However, there is lack of molecular evidence for the $CGRP_2$ receptor (Brain, S. D. et al, *TiPS* 2002, 23, 51-53). The $CGRP_1$ receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., *J. Biol. Chem.* 2000, 275, 31438-43). RAMP1 is required for transport of CRLR to the plasma membrane and for ligand binding to the CGRP-receptor (McLatchie, L. M. et al, *Nature* 1998, 393, 333-339). RCP is required for signal transduction (Evans B. N. et al., *J. Biol. Chem.* 2000, 275, 31438-43). There are known species-specific differences in binding of small molecule antagonists to the CGRP-receptor with typically greater affinity seen for antagonism of the human receptor than for other species (Brain, S. D. et al, *TiPS* 2002, 23, 51-53). The amino acid sequence of RAMP1 determines the species selectivity, in particular, the amino acid residue Trp74 is responsible for the phenotype of the human receptor (Mallee et al. *J Biol Chem* 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. *CNS Drugs* 2001;15(10): 745-53; Williamson, D. J. *Microsc. Res. Tech.* 2001, 53, 167-178; Grant, A. D. *Brit. J. Pharmacol.* 2002, 135, 356-362.). Serum levels of CGRP are elevated during migraine (Goadsby P J, et al. *Ann Neurol* 1990;28: 183-7) and treatment with anti-migraine drugs returns CGRP levels to normal coincident with alleviation of headache (Gallai V. et al. *Cephalalgia* 1995; 15: 384-90). Migraineurs exhibit elevated basal CGRP levels compared to controls (Ashina M, et al., Pain. 2000;86(1-2):133-8.2000). Intravenous CGRP infusion produces lasting headache in migraineurs (Lassen L H, et al. *Cephalalgia.* 2002 February; 22(1):54-61). Preclinical studies in dog and rat report that systemic CGRP blockade with the peptide antagonist CGRP (8-37) does not alter resting systemic hemodynamics nor regional blood flow (Shen, Y-T. et al, *J Pharmacol Exp Ther* 2001, 298, 551-8). Thus, CGRP-receptor antagonists may present a novel treatment for migraine that avoids the cardiovascular liabilities of active vasoconstriction associated with non-selective $5-HT_{1B/1D}$ agonists, 'triptans' (e.g., sumatriptan). See Olesen, et al., New England Journal of Medicine, 2004, 350 (11), 1104-1110.

A number of non-peptidic, small molecule CGRP-receptor antagonists have been recently reported. WO 97/09046 and equivalents disclose inter alia quinine and quinidine related compounds which are ligands, in particular antagonists, of CGRP-receptor. WO 98/09630 and WO 98/56779 and equivalents disclose inter alia variously substituted, nitrobenzamide compounds as CGRP-receptor antagonists. WO 01/32649, WO 01/49676, and WO 01/32648 and equivalents disclose inter alia a series of 4-oxobutanamides and related cyclopropane derivatives as CGRP-receptor antagonists. WO 00/18764, WO 98/11128 and WO 00/55154 and equivalents disclose inter alia benzimidazolinyl piperidines as antagonists to CGRP-receptor. Unrelated to CGRP, a series of somatostatin antagonists have been disclosed in WO 99/52875 and WO 01/25228 and equivalents. See also U.S. Pat. Nos. 6,344, 449, 6,313,097, 6,521,609, 6,552,043, US20030181462, US20030191068 and WO 03/076432 and related applications. Yet other CGRP-receptor antagonist and related applications include US20030139417A1, US20030181462, US20030191068A1, US20030212057A1, US20030236282A1, US20040014679A1, US20040076587A1, US20040132716A1, US20040192729A1, WO2004082602A2, WO2004082605A2, WO2004082678A1, WO2004083187A1, WO2004092168A1, WO2004092166A2 and WO2004091514A2. A great need for the development of novel CGRP-receptor antagonists effective for the treatment of neurogenic inflammation, migraine and other disorders exists.

SUMMARY OF THE INVENTION

Thus according to a first embodiment of the first aspect of the present invention are provided compounds of Formula (I)

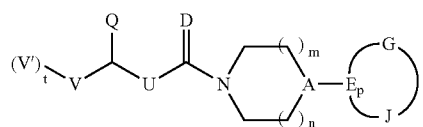

(I)

or pharmaceutically acceptable salts or solvates thereof wherein
V is
a 5-membered ring selected from the group consisting of imidazolyl, pyrazolyl, thiazolyl, isothiazolyl, oxazolyl, furanyl, isoxazolyl, oxadiazolyl, triazolyl, thiadiazolyl and tetrazolyl; or a 6-membered ring selected from the group consisting of pyridyl, pyrimidinyl, triazinyl, pyrazinyl, pyridazinyl and tetrazinyl; or a fused bicyclic ring system selected from the group consisting of indolyl, isoindolyl, indazolyl, benzimidazolyl, benzythiazolyl, triazolopyridinyl, imidazopyridinyl, quinolinyl, isoquinolinyl, cinnolinyl, phthalazinyl, quinazolinyl, quinoxalinyl and benzfuranyl;

wherein V is optionally substituted with one to three of the same or different substituents selected from the group consisting of $C_{1-4}$alkyl, $C_{1-4}$alkoxy, $C_{1-4}$hydroxyalkyl, $C(O)OC_{2-3}$alkyl, $C_{1-4}$alkylcarbonyl, carboxy, $C_{1-4}$alkylcarboxy, trifluoromethyl, halo, cyano, amino, amido, nitro, carbamoyl, ureido, $C_{1-4}$alkylamino, $C_{1-4}$dialkylamino, $C_{1-4}$dialkylamino$C_{1-2}$alkyl, sulphonamide and sulphonyl; and V optionally contains 1 or 2 carbonyls;

provided that if t is 1, then V is optionally substituted with one of the substitutents selected from the group consisting of halo, $C_{1-4}$alkyl, $C_{1-4}$alkylidine, $_4$alkylidine, $C_{1-4}$alkoxy, $C_{1-4}$hydroxyalkyl, $C_{1-4}$alkylcarbonyl, trifluoromethyl, halo and cyano; and V optionally contains 1 or 2 carbonyls;

$(V')_t$ wherein t is 0 or 1; and

V' is selected from the group consisting of $C_{3-7}$cycloalkyl, phenyl, adamantyl, quinuclidyl, azabicyclo[2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and wherein V' is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-4}$alkylamino, $C_{1-4}$dialkylamino, $(C_{1-3}$alkyl$)_{0-2}$ ureido, $C(O)OC_{2-3}$alkyl, carboxy, amido, nitro, phenyl and benzyl; and wherein V' optionally contains 1 or 2 carbonyls; and V and V' are optionally interrupted by $C_{1-3}$alkylene, O, —$(CH_2)_{0-2}$C(O)—$(CH_2)_{0-2}$—; or —N—$C_{1-4}$alkyl, said $C_{1-3}$alkylene being optionally interrupted by or having attached thereto O, N or S;

U is $CH_2$, O, or NH;

Q is $(S^y)_sR^3$;

$S^y$ is $C_{1-3}$alkylene or $C_{1-3}$alkylidene and s is 0 or 1;

$R^3$ is $R^{3a}$ or $R^{3b}$ wherein $R^{3a}$ is (i) a heterocycle having two fused rings with 5 to 7 members in each of said rings, said heterocycle containing one to five of the same or different heteroatoms selected from the group consisting of O, N and S and said heterocycle optionally containing 1 or 2 carbonyls wherein the carbon atom of said carbonyl is a member of said fused rings;

(ii) a 4 to 6 membered heterocycle containing one to three of the same or different heteroatoms selected from the group consisting of O, N and S, optionally containing 1 to 2 carbonyls, wherein the carbon atom of said carbonyl is a member of said 4 to 6 membered heterocycle;

(iii) $C_{3-7}$cycloalkyl;

(iv) carbazolyl, fluorenyl, phenyl, —O-phenyl, —O—$C_{1-4}$alkylene-phenyl, or napthyl; or (v) $C_{1-8}$alkyl, $C_{2-7}$alkenyl, —C(O)$R^{3'}$, CHC(O)O—$R^{3'}$, CH(CH$_3$)C(O)O—$R^{3'}$, —C(O)O—$R^{3'}$ or $C_{2-7}$alkynyl; and wherein $R^{3a}$ is optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, $(C_{1-3}$alkyl$)_{1-2}$amine, —O$R^{3'}$, —C(O)$R^{3'}$, —C(O)O—$R^{3'}$, —O—C(O)$R^{3'}$, —N$(R^{3'})_2$, —C(O)N$(R^{3'})_2$, —N$(R^{3'})$C(O)$(R^{3'})_2$, —N$(R^{3'})$C(O)N$(R^{3'})_2$, —N$(R^{3'})$C(O)O$R^{3'}$, —O—C(O)N$(R^{3'})_2$, —N$(R^{3'})$SO$_2R^{3'}$, —SO$_2$N$(R^{3'})_2$ and —SO$_2R^{3'}$; $R^{3'}$ is H or —$C_{1-6}$alkyl;

$R^{3b}$ is $R^{3a}$ but is not said phenyl or said substituted phenyl;

provided that if V and V' together form substituted or unsubstituted imidazol-2-yl or a substituted or unsubstituted fused bicyclic system containing imidazol-2-yl, then $R^3$ is $R^{3b}$;

D is O, NCN or NSO$_2C_{1-3}$alkyl;

A is C, N or CH;

m and n are independently 0, 1 or 2;

provided that if m and n are 0, then A is not N;

if m is 2, then n is not 2; or if n is 2, then m is not 2;

E is N, CH or C;

p is 0 or 1;

if p is 1, then G, J and E together form $A^x$ or $A^y$;

$A^x$ is a fused heterocycle having two fused rings with 5 to 7 members in each of said rings, said heterocycle containing one to four of the same or different heteroatoms selected from the group consisting of O, N and S; and optionally containing 1 or 2 carbonyls wherein the carbon atom of said carbonyl is a member of said fused heterocycle;

$A^y$ is a 4 to 6 membered heterocycle containing one to three heteroatoms selected from the group consisting of O, N and S; and optionally containing 1 to 2 carbonyls, wherein the carbon atom of said carbonyl is a member of said 4 to 6 membered heterocycle;

wherein $A^x$ and $A^y$ are optionally substituted with $C_{1-4}$alkyl, $C_{1-4}$alkoxy, $C_{1-4}$haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino; or if p is 0 such that G and J are each attached to A, then A is C, and G, J and A together form a spirocyclic ring system with said rings of said system containing A and wherein GJA is $A^x$ or $A^y$.

According to a another embodiment of the first aspect of the present invention are compounds of Formula (I) or pharmaceutically acceptable salts or solvates thereof wherein m is 1 and n is 1.

According to a another embodiment of the first aspect of the present invention are compounds of Formula (I) or pharmaceutically acceptable salts or solvates thereof wherein p is 1.

According to a another embodiment of the first aspect of the present invention are compounds of Formula (I) or pharmaceutically acceptable salts or solvates thereof wherein p is 1 and E is N.

According to a another embodiment of the first aspect of the present invention are compounds of Formula (I) or pharmaceutically acceptable salts or solvates thereof wherein p is 1 and E is C.

According to a another embodiment of the first aspect of the present invention are compounds of Formula (I) or pharmaceutically acceptable salts or solvates thereof wherein p is 1 and E is CH.

According to a another embodiment of the first aspect of the present invention are compounds of Formula (I) or pharmaceutically acceptable salts or solvates thereof wherein p is 1 and G, J and A form a $A^x$.

According to a another embodiment of the first aspect of the present invention are compounds of Formula (I) or pharmaceutically acceptable salts or solvates thereof wherein p is 1 and G, J and A form a $A^x$ and wherein $A^x$ is a fused heterocycle with two fused rings each having 6 members.

According to a another embodiment of the first aspect of the present invention are compounds of Formula (I) or pharmaceutically acceptable salts or solvates thereof wherein p is 1 and G, J and A form a $A^x$ and wherein $A^x$ is 3,4-dihydro-1H-quinazolin-2-one.

According to a another embodiment of the first aspect of the present invention are compounds of Formula (I) or pharmaceutically acceptable salts or solvates thereof wherein p is 1 and G, J and A form a $A^x$ and wherein $A^x$ is 3,4-dihydro-1H-quinazolin-2-one optionally halogenated.

According to a another embodiment of the first aspect of the present invention are compounds of Formula (I) or pharmaceutically acceptable salts or solvates thereof wherein p is 1 and G, J and A form a $A^x$ and wherein $A^x$ is 8-fluoro-2-oxo-1,2-dihydroquinazolin-3(4H)-yl.

According to a another embodiment of the first aspect of the present invention are compounds of Formula (I) or pharmaceutically acceptable salts or solvates thereof wherein p is 0.

According to a another embodiment of the first aspect of the present invention are compounds of Formula (I) or pharmaceutically acceptable salts or solvates thereof wherein p is 0 and G, J and A form a $A^x$.

According to a another embodiment of the first aspect of the present invention are compounds of Formula (I) or pharmaceutically acceptable salts or solvates thereof wherein p is 0 and G, J and A form a $A^x$ and wherein $A^x$ is a fused heterocycle with two fused rings each having 6 members and where said fused heterocycle forms a spirocyclic ring system containing A.

According to a another embodiment of the first aspect of the present invention are compounds of Formula (I) or pharmaceutically acceptable salts or solvates thereof wherein p is 0 and G, J and A form a $A^x$ and wherein $A^x$ is a fused heterocycle with two fused rings each having 6 members, wherein one of said 6-membered rings, which contains A, further contains a nitrogen and an oxygen which are interrupted by a carbonyl said oxygen attached to A and wherein said fused heterocycle forms a spirocyclic ring system containing A.

According to a another embodiment of the first aspect of the present invention are compounds of Formula (I) or pharmaceutically acceptable salts or solvates thereof wherein is s is 1 and $S^y$ is methylene.

According to a another embodiment of the first aspect of the present invention are compounds of Formula (I) or pharmaceutically acceptable salts or solvates thereof wherein is s is 1, $S^y$ is methylene and $R^3$ is $R^{3a}$.

According to a another embodiment of the first aspect of the present invention are compounds of Formula (I) or pharmaceutically acceptable salts or solvates thereof wherein is s is 1, $S^y$ is methylene and R is $R^{3a}$ wherein $R^{3a}$ is a heterocycle having two fused rings, one of said fused rings having six members and being attached to $S^y$ and the other of said rings having 5 members and containing two nitrogens.

According to a another embodiment of the first aspect of the present invention are compounds of Formula (I) or pharmaceutically acceptable salts or solvates thereof wherein is s is 1, $S^y$ is methylene and $R^3$ is $R^{3a}$ wherein $R^{3a}$ is 7-methyl-1H-indazol-5-yl.

According to a another embodiment of the first aspect of the present invention are compounds of Formula (I) or pharmaceutically acceptable salts or solvates thereof wherein is s is 1, $S^y$ is methylene and $R^3$ is $R^{3a}$ wherein $R^{3a}$ is 7-ethyl-3-methyl-1H-indazol-5-yl.

According to a another embodiment of the first aspect of the present invention are compounds of Formula (I) or pharmaceutically acceptable salts or solvates thereof wherein D is O and U is O.

According to a another embodiment of the first aspect of the present invention are compounds of Formula (I) or pharmaceutically acceptable salts or solvates thereof wherein D is O and U is $CH_2$.

According to a another embodiment of the first aspect of the present invention are compounds of Formula (I) or pharmaceutically acceptable salts or solvates thereof wherein D is O and U is NH.

According to a another embodiment of the first aspect of the present invention are compounds of Formula (I) or pharmaceutically acceptable salts or solvates thereof wherein t is 0.

According to a another embodiment of the first aspect of the present invention are compounds of Formula (I) or pharmaceutically acceptable salts or solvates thereof wherein t is 1.

According to a another embodiment of the first aspect of the present invention are compounds of Formula (I) or pharmaceutically acceptable salts or solvates thereof wherein t is 1 and V' is selected from the group consisting of $C_{3-7}$cycloalkyl, phenyl, tetrahydrofuranyl, furanyl, thienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, triazinyl, piperidinyl, piperazinyl, morpholino and thiomorpholino and dioxolanyl.

According to a another embodiment of the first aspect of the present invention are compounds of Formula (I) or pharmaceutically acceptable salts or solvates thereof wherein t is 1 and V' is selected from the group consisting of phenyl, pyridyl and piperidinyl.

According to a another embodiment of the first aspect of the present invention are compounds of Formula (I) or pharmaceutically acceptable salts or solvates thereof wherein t is 1 and V' is selected from the group consisting of phenyl, pyridyl and piperidinyl and V' is substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-4}$alkylamino, $C_{1-4}$dialkylamino, $(C_{1-3}alkyl)_{0-2}$ureido, $C(O)OC_{2-3}$alkyl, carboxy, amido, nitro, phenyl and benzyl.

According to a another embodiment of the first aspect of the present invention are compounds of Formula (I) or pharmaceutically acceptable salts or solvates thereof wherein t is 1 and V' is selected from the group consisting of phenyl, pyridyl and piperidinyl and V' is substituted with 1 or 2 of the same or different substituents selected from the group consisting of $C_{1-4}$dialkylamino, $C(O)OC_{2-3}$alkyl, carboxy, amido, nitro and phenyl.

According to a another embodiment of the first aspect of the present invention are compounds of Formula (I) or pharmaceutically acceptable salts or solvates thereof wherein V is said 5-membered ring.

According to a another embodiment of the first aspect of the present invention are compounds of Formula (I) or pharmaceutically acceptable salts or solvates thereof wherein V is said 6-membered ring.

According to a another embodiment of the first aspect of the present invention are compounds of Formula (I) or pharmaceutically acceptable salts or solvates thereof wherein V is said fused bicyclic ring system.

According to a another embodiment of the first aspect of the present invention are compounds of Formula (I) or pharmaceutically acceptable salts or solvates thereof wherein V is furanyl, imidazolyl, oxadiazolyl, tetrazolyl, pyridyl, pyrimidine, quinolinyl, $C_{1-4}$alkylcarbonyl, carboxy, indazolyl, triazolopyridinyl or imidazopyridinyl.

According to a another embodiment of the first aspect of the present invention are compounds of Formula (I) or pharmaceutically acceptable salts or solvates thereof wherein V contains a carbonyl.

According to a another embodiment of the first aspect of the present invention are compounds of Formula (I) or pharmaceutically acceptable salts or solvates thereof wherein V is furanyl, imidazolyl, oxadiazolyl, tetrazolyl, pyridyl, pyrimidine, quinolinyl, $C_{1-4}$alkylcarbonyl, carboxy, indazolyl or [1,2,4]Triazolo[4,3-a]pyridin-3-yl or H-Imidazo[1,5-a]pyridin-3-yl).

According to a another embodiment of the first aspect of the present invention are compounds of Formula (I) or pharmaceutically acceptable salts or solvates thereof wherein V and V' are interrupted by methylene, ethylene and—$(CH_2)_{0-2}$C(O)—$(CH_2)_{0-2}$—.

According to a another embodiment of the first aspect of the present invention are compounds of Formula (I) or pharmaceutically acceptable salts or solvates thereof wherein V and V' are interrupted by methylene, ethylene and —$(CH_2)_{0-2}$C(O)—$(CH_2)_{0-2}$— wherein said interrupting substituents are unsubstituted.

According to a another embodiment of the first aspect of the present invention are compounds of Formula (I) or pharmaceutically acceptable salts or solvates thereof wherein s is 1, $S^y$ is methylene and $R^3$ is $R^{3a}$ wherein $R^{3a}$ is an optionally $C_{1-3}$alkyl-substituted indazolyl;

U is $CH_2$, O, or NH;

D is O;

A is CH;

m and n are each 1;

E is N;

p is 1; and

G, J and E together form $A^x$, wherein $A^x$ is an optionally halogenated dihydroquinazolinone.

According to a another embodiment of the first aspect of the present invention are compounds of Formula (I) or pharmaceutically acceptable salts or solvates thereof wherein V is furanyl, imidazolyl, oxadiazolyl, tetrazolyl, pyridyl, pyrimidine, quinolinyl, $C_{1-4}$alkylcarbonyl, carboxy, indazolyl, triazolopyridinyl or imidazopyridinyl;

t is 0 or 1;

V' is selected from the group consisting of phenyl, pyridyl and piperidinyl and V' is substituted with 1 or 2 of the same or different substituents selected from the group consisting of $C_{1-4}$dialkylamino, $C(O)OC_{2-3}$alkyl, carboxy, amido, nitro and phenyl;

wherein V and V' are interrupted by methylene, ethylene and —$(CH_2)_{0-2}$C(O)—$(CH_2)_{0-2}$— wherein said interrupting substituents are unsubstituted;

s is 1, $S^y$ is methylene and $R^3$ is $R^{3a}$ wherein $R^{3a}$ is an optionally $C_{1-3}$alkyl-substituted indazolyl;

U is $CH_2$, O, or NH;

D is O;

A is CH;

m and n are each 1;

E is N;

p is 1; and

G, J and E together form $A^x$, wherein $A^x$ is an optionally halogenated dihydroquinazolinone.

According to various embodiments of a second aspect of the present invention are provided pharmaceutical compositions comprising compounds of Formula (I) as defined herein.

According to various embodiments of a third aspect of the present invention are provided methods of treating inflammation (particularly neurogenic inflammation), headache (tension see US20040097562A1 and particularly migraine), pain, thermal injury, psoriasis (see WO2004014351A2), circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising compounds of Formula (I) as defined herein.

According to various embodiments of a fourth aspect of the present invention are uses of the compounds of the present invention selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, et al. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, et al. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; et al. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin1 receptors by rat spinal neurons. Seybold V S, et al. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, et al. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; et al. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, et al. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218 all incorporated by reference herein.

According to various embodiments of a fifth aspect of the present invention are provided combinations of the compounds of the present invention with one or more agents selected from the group consisting of COX-2 inhibitors, NSAIDS, aspirin, acetaminophen, triptans, ergotamine and caffeine for the treatment of migraine.

Other embodiments of the present invention may comprise a suitable combination of two or more of the embodiments and/or aspects disclosed herein.

Yet other embodiments of the present invention may comprise a suitable subset of an embodiment and/or aspect disclosed herein.

Still yet other embodiments and aspects of the invention will be apparent according to the description provided below.

DETAILED DESCRIPTION OF THE INVENTION

The description of the invention herein should be construed in congruity with the laws and principals of chemical bonding. For example, it may be necessary to remove a hydrogen atom in order accommodate a substitutent at any given location.

As used herein, "heterocyclic" or "heterocycle" includes cyclic moieties containing one or more heteroatoms, (e.g., O, N or S) said heterocycles include those that are aromatic and those that are not, i.e., "alicyclic", unless otherwise specified.

As used herein, the term "fused bicyclic system" when describing for example a 5.6-fused bicyclic system containing 1 to 4 nitrogen atoms includes aromatic and alicyclic systems, e.g. indolizine, indole, isoindole, 3H-indole, indoline, indazole or benzimidazole.

If a substitutent is named generically, then any and all species of that genus comprise that aspect of the invention. For example, a substituent generically named as "pyrrolonyl" (the radical of "pyrrolone", a pyrrole having a carbonyl) includes pyrrol-2-onyls wherein the carbonyl is adjacent to the nitrogen and pyrrol-3-onyls wherein the carbonyl and nitrogen have an intervening methylene.

Similarly, the present invention comprises that a substituent may be attached at any and all suitable points of attachement on said substituent unless otherwise specified.

However, it is also understood that the compounds encompassed by the present invention are those that are chemically stable, i.e., heteroalicyclic substituents of the present invention should not be attached in such a way that a heteroatom in said heteroalicyclic substituent is alpha to a point of attachment wherein said point of attachment is also a heteroatom.

An embodiment or aspect which depends from another embodiment or aspect, will describe only the variables having values or provisos that differ from the embodiment or aspect from which it depends. If for example a dependent embodiment only addresses $R^2$, then the variables and provisos not related to $R^2$ should reflect that of the embodiment from which it depends.

If a variable is quantified with a value of zero, then a bond attaching said variable should no longer be represented.

As used herein, "alkylene" means a divalent alkane, i.e., an alkane having two hydrogen atoms removed from said alkane (said hydrogen removed from two different carbon atoms when said alkane contains more than one carbon atom), e.g., —$CH_2CH_2CH_2$—.

As used herein, "alkylidene" means an alkane having two hydrogen atoms removed from one carbon atom in said alkane, e.g.,

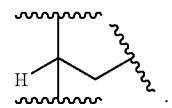

It should be understood that the alternating double bond designations in the six-membered ring of the 5,6-membered fused structure represented in Formula (I) are relative and represent the delocalized π orbital electrons of said ring.

As used herein, "aryl" or "ar-" includes phenyl or napthyl.

As used herein, "heterocyclic" or "heterocyclo" includes both heteroaryl and heteroalicyclic.

As used herein, "halo" or "halogen" includes fluoro, chloro, bromo and iodo and further means one or more of the same or different halogens may be substituted on a respective moiety.

Unless specificied otherwise, acyclic hydrocarbons such as alkyl, alkoxy, alkenyl and alkynyl may be branched or straight chained.

It is to be understood that the present invention may include any and all possible stereoisomers, geometric isomers, diastereoisomers, enantiomers, anomers and optical isomers, unless a particular description specifies otherwise.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

While dosing from 0.01 mg/kg to 30 mg/kg is envisaged for compounds of the present invention, the dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Synthesis

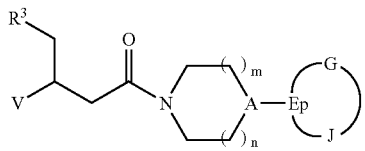
I

Compounds of the present invention may be synthesized according to the general schemes provided below. Variables provided in the schemes are defined in accordance with the description of compounds of Formula (I) in the first asepct of the invention unless otherwise specified. It may also be possible to use variations of said schemes to prepare the compounds of the present inventions, said variations discernible to those skilled in the art.

The compounds of the present invention may be prepared according to Scheme 1.

Representative V-Metal:

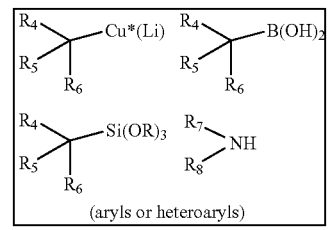

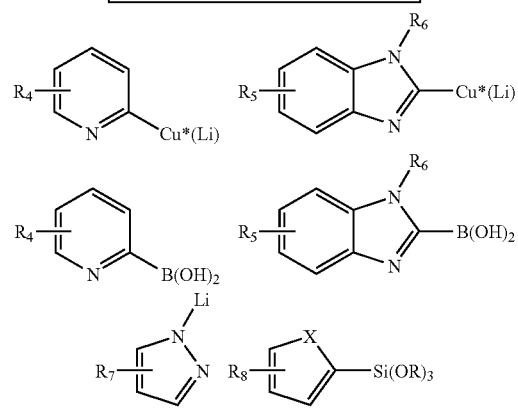

The synthesis described in Scheme I begins with commercially available or synthesized aldehydes. The three-carbon homologation and the conjugated double-bond formation with two consecutive Wittig reactions are well-known in the literature leading to compounds of Formula V. Some Formula

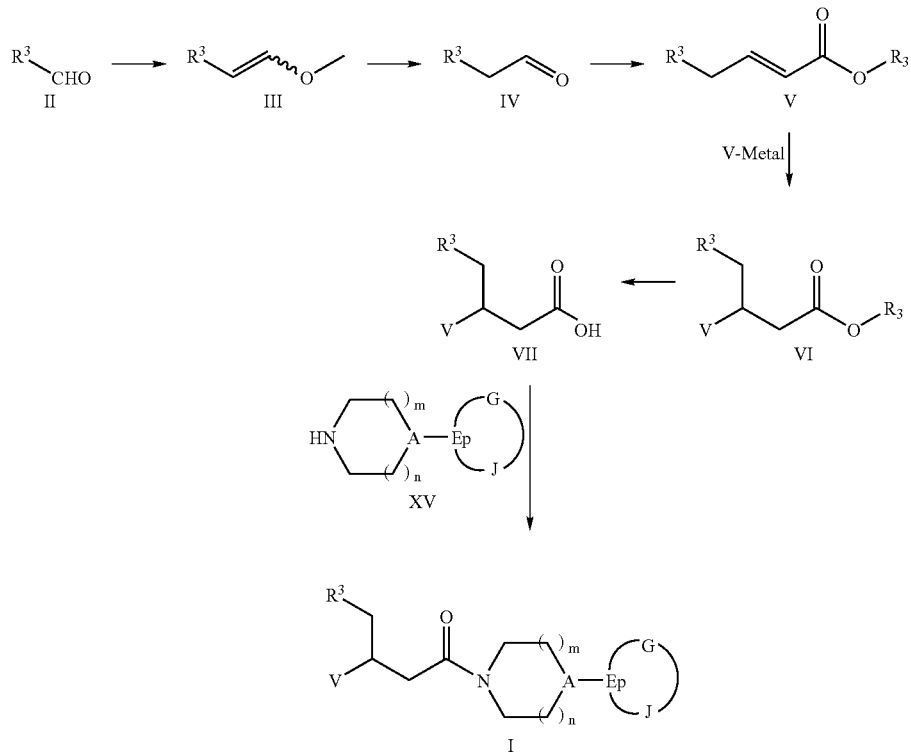

Scheme 1. Synthesis of Formula I Compounds

V compounds are also commercially available and can be prepared by other literature methods. The group V can be any carbon (C) or nitrogen (N) based nucleophile that can add to the double bond in a process known as 1,4-Michael addition leading to compounds of Formula VI. Nitrogen based nucleophiles usually undergo the desired 1,4-addition. For carbon based nucleophiles, known modifications using copper salts usually favor the desired 1,4-addition. Aryl boronic acid or organosiloxane can be added to the desired beta-position through rhodium catalysis and asymmetric synthesis through chiral ligands is also known (*JOC*, 2000, 65, 5951-5955; *Tetrahedron Asymmetry* 1999, 10, 4047-4056; *JACS* 1998, 120, 5579-5580; *Org. Lett.* 2002, 4, 667-669). Hydrolysis of compounds of Formula VI leads to Formula VII, free carboxylic acids, which react with amines to afford Formula I compounds.

Oxadiazole-containing compounds of Formula I may be prepared according to Scheme 2.

Scheme 2. Synthesis of Formula I Compounds

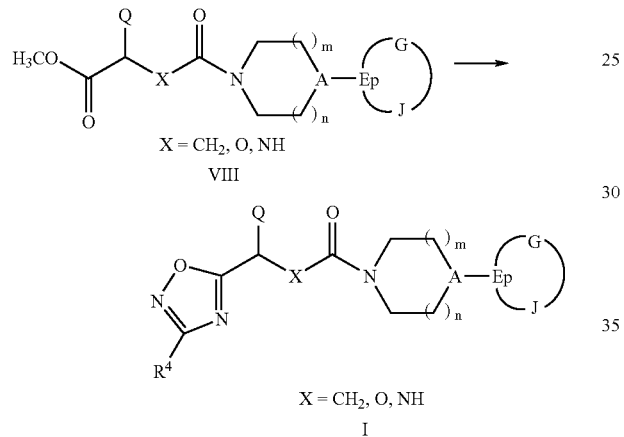

Treatment of N-hydroxyamidines with bases such as sodium hydride followed by addition of esters of Formula VIII and heating give [1,2,4]oxadiazoles of Formula I, after heating.

Tetrazole-containing compounds of Formula I may be prepared according to Scheme 3.

Scheme 3. Synthesis of Formula I Compounds

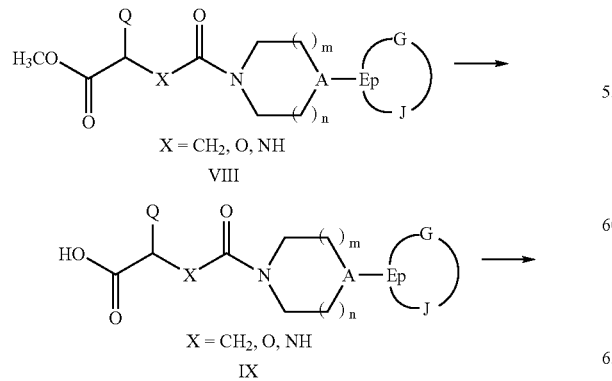

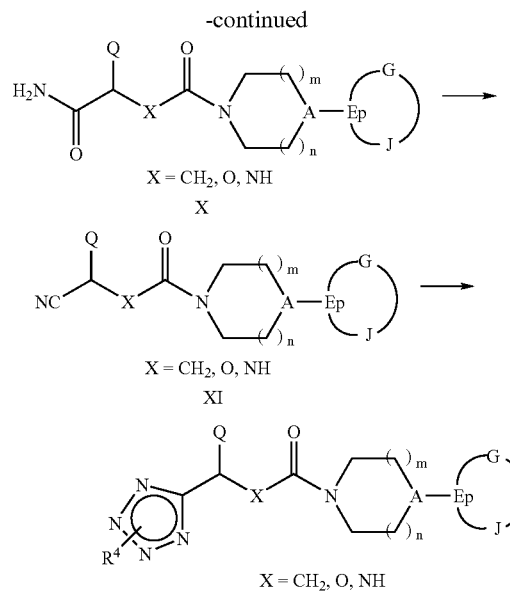

Esters of Formula VIII can be hydrolyzed to the corresponding carboxylic acids using either acids or bases, controlling conditions to spare other functionality. Acids of Formula IX can be converted to the primary amides of Formula X by simple coupling with ammonia using various amide coupling agents well known in the art. Nitriles of Formula XI are available from the amides by dehydration using agents such as trifluoroacetic anhydride. These are converted to the corresponding tetrazoles of Formula I (where $R^4$=H) by treatment with azidotrimethyltin. Deprotonation of these compounds with bases such as sodium hydride, followed by alkylation with various agents such as alkyl halides and alkyl sulfonates gives further compounds of Formula I that are substituted on the tetrazole ring.

Compounds of Formula VIII in which X=CH$_2$ can be prepared according to Scheme 4.

Scheme 4. Synthesis of Formula VIII Compounds

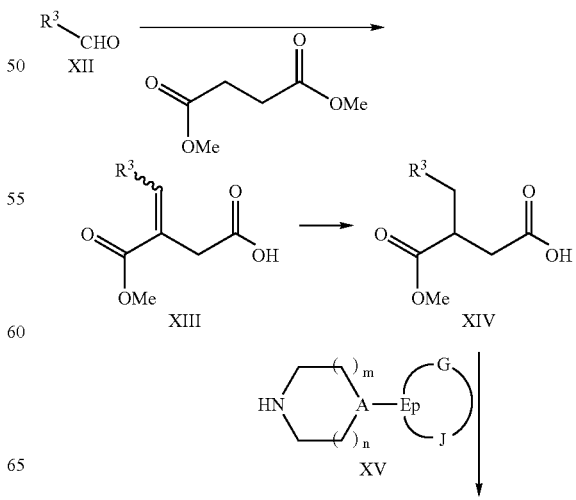

-continued

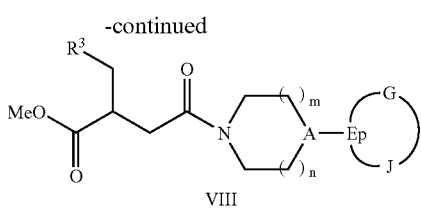

VIII

Scheme 4 starts with commercially available or synthesized aldehydes. These are reacted with dimethyl succinate in the presence of bases to give compounds of Formula XIII. The double bond of the Formula XIII compound is reduced to give compounds of Formula XIV. Reduction can be carried out to give either a racemate or by use of a stereoselective catalyst to give either enantiomer of Formula XIV. Such reductions can result from transfer hydrogenation from hydrogen donors such as formic acid or cyclohexadiene, or hydrogenation using gaseous hydrogen, both in the presence of a suitable catalyst. Amide coupling with amines of Formula XV leads to compounds of Formula VIII using well known amide synthesis protocols.

Compounds of Formula XX and XXI in which X=O or NH can be prepared according to Scheme 5.

carbonyl, tert-butoxycarbonyl, a trisubstituted silyl, or another appropriate protecting group. Compound XVI need not be the trimethyl phosphonoacetate. The methyl groups of XVI may be exchanged with other alkyl groups such as ethyl, t-butyl, benzyl groups, or combinations thereof. Such modifications are familiar to those with ordinary skill in the art. In some cases, there exists functionality on $R^3$ that requires protection with an appropriate protecting group such that subsequent chemistry can proceed as described. The use of such protecting groups is also well known to those of ordinary skill in the art. The double bond of the Formula XVII compound is reduced to give compounds of Formula XVIII. Reduction can be carried out to give either a racemate or by use of a stereoselective catalyst to give either enantiomer of Formula XVIII. Such reductions can result from transfer hydrogenation from hydrogen donors such as formic acid or cyclohexadiene, or hydrogenation using gaseous hydrogen, both in the presence of a suitable catalyst. Deprotection of the protecting group (PG) under standard deprotection protocols affords Formula XXI compounds. In some cases, removal of the protecting group gives rise to concomitant hydrolysis of the methyl ester to give compounds of Formula XX. The carboxylic acids can be protected to give Formula XXI compounds by treatment with diazomethane or another suitable

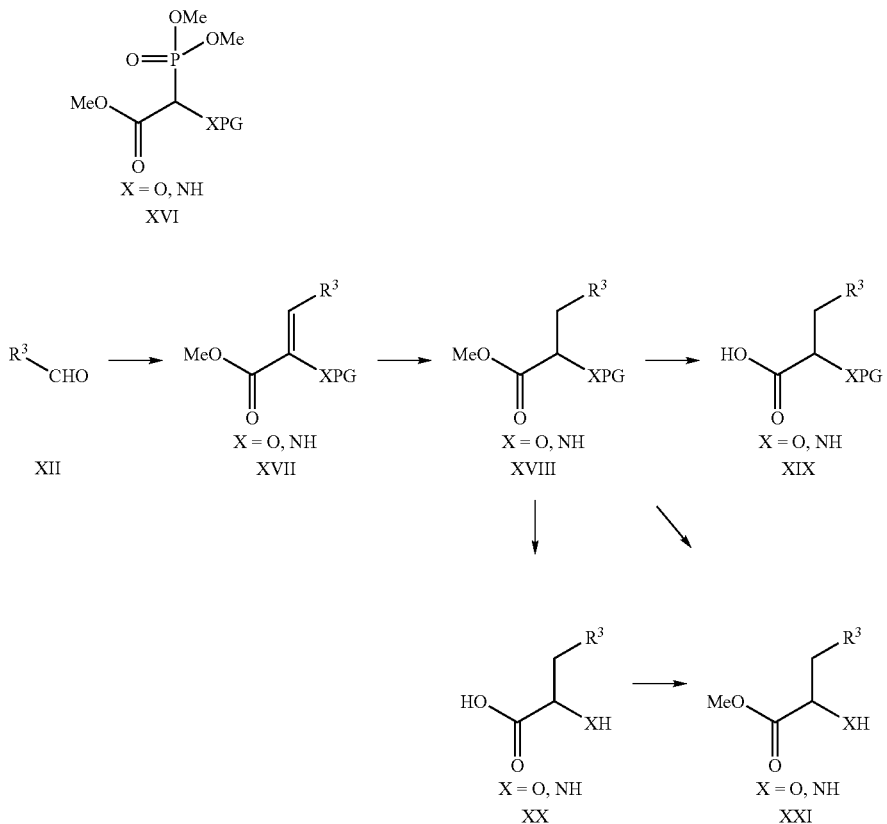

Scheme 5. Synthesis of Formula XX and XXI Compounds

Scheme 5 starts with commercially available or synthesized aldehydes of Formula XII. These are reacted in the presence of a base with phosphonates of Formula XVI where PG is a protecting group such as acetyl, benzoyl, benzyloxyalkylating agent. Alternately, esters of Formula XVIII can be hydrolyzed to the corresponding carboxylic acids of Formula XIX, using either acids or bases, controlling reaction conditions to spare other functional groups.

Compounds of Formula VIII can be prepared according to Scheme 6.

Scheme 6. Synthesis of Formula VIII Compounds

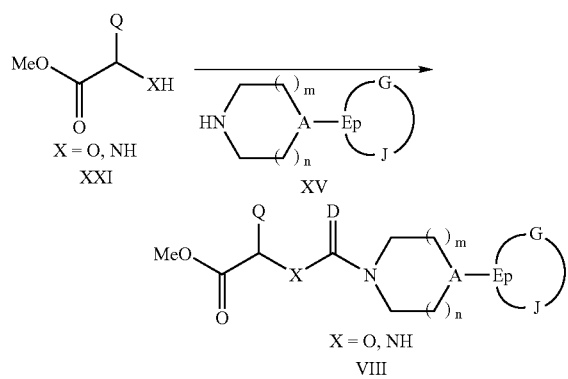

The synthesis described by Scheme 6 begins with a compound of Formula XXI, which is an amino acid (where X=NH) or a hydroxy acid (where X=O) with a protected carboxylate terminus. The protecting group is generally a methyl ester, but other protecting groups such as ethyl, t-butyl, and benzyl esters may also be used. The Formula XXI compound is coupled with an amine of Formula XV in a mixed urea or urea isostere reaction, as above, to generate a Formula VIII compound. This can involve activation of either Compound XXI or XV with a reagent such as carbonyl diimidazole or p-nitrophenylchloroformate, giving an intermediate that is activated toward nucleophilic addition, and treating that intermediate with Compound XXI or XV in the presence of a base, if necessary.

Imidazole-containing compounds of Formula I can be prepared according to Scheme 7.

The synthesis described by Scheme 7 begins with an ester of Formula VIII. The ester may be reduced directly to an aldehyde of Formula XXIII using diisobutylaluminum hydride or other appropriate reducing agent. Alternately, compounds of Formula VIII can be reduced to an alcohol of Formula XXII by using lithium borohydride or another appropriate reducing agent. Alcohols of Formula XXII are oxidized to aldehydes of Formula XXIII by treatment with an appropriate oxidant. Such oxidations and reductions are well known to those skilled in the art. Aldehydes of Formula XXIII are condensed with dicarbonyl compounds of Formula XXIV in the presence of ammonia to afford N-unsubstituted imidazoles ($R^7$=H) of Formula I. These Formula I compounds can be further derivatized by alkylation with appropriate electrophiles such as alkyl halides or alkyl sulfonates in the presence of a base or aryl halides in the presence of a base and an appropriate catalyst to give Formula I compounds where $R^7$ is not H. In cases where a protecting group is employed on the group $R^3$, deprotection conditions appropriate to the protecting group and compatible with the rest of the molecule can be employed to remove it. Such protecting group manipulations are well known to those skilled in the art.

Imidazole-containing compounds of Formula I can also be prepared according to Scheme 8.

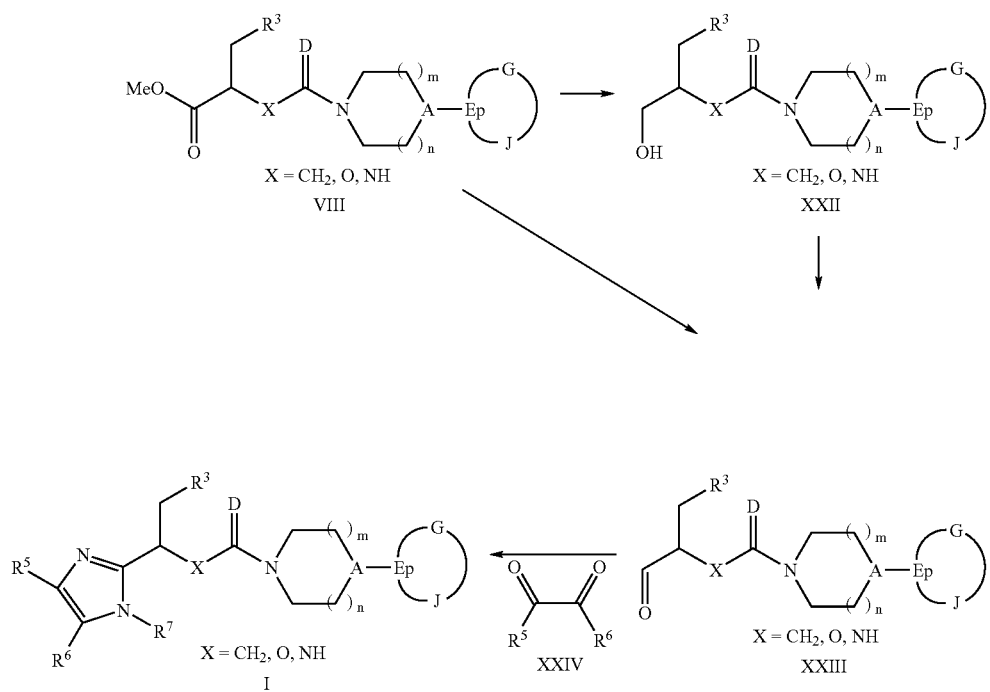

Scheme 8. Synthesis of Formula I Compounds

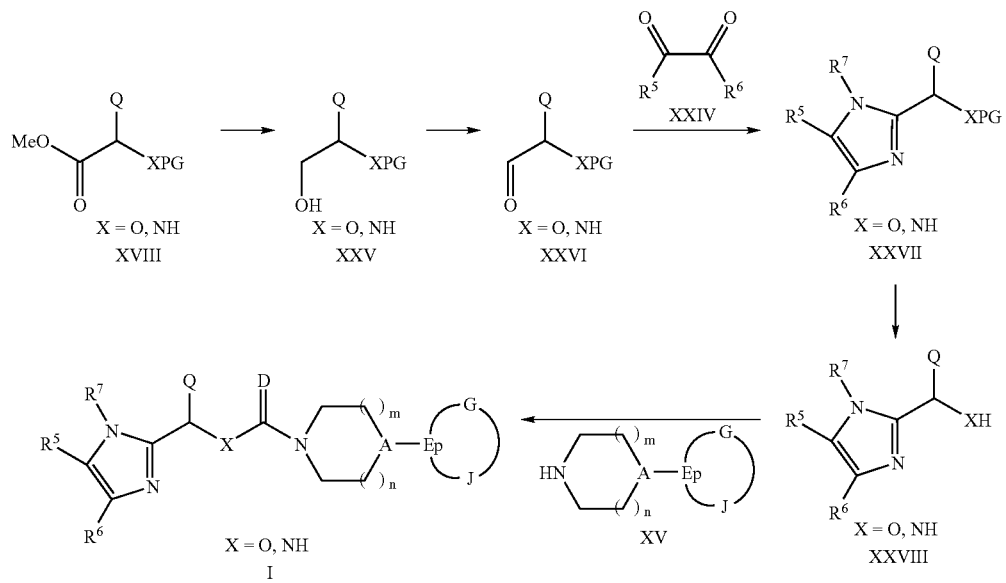

Scheme 8 begins with reduction of a methyl ester of Formula XVIII to an alcohol of Formula XXV using an appropriate reducing reagent such as lithium borohydride. The resulting alcohol can then be oxidized to an aldehyde of Formula XXVI by treatment with an appropriate oxidant. In some cases it is possible to reduce compounds of Formula XVIII directly to compounds of Formula XXVI by use of diisobutylaluminum hydride or another appropriate reducing agent. Such oxidations and reductions are well known to those skilled in the art. The Formula XXVI aldehyde can be condensed with a Formula XXIV dicarbonyl compound to afford an N-unsubstituted ($R^7$=H) imidazole of Formula XXVII. In some cases, it is desirable to alkylate the imidazole with an appropriate electrophilic reagent such as alkyl halides or alkyl sulfonates in the presence of a base, or aryl halides in the presence of a base and an appropriate catalyst to afford substituted imidazoles of Formula XXVII where $R^7$ is not H. The protecting group (PG) can then be removed to liberate the hydroxyl group (when X=O) or the primary amine (when X=NH) by application of deprotection conditions appropriate to the protecting group. Such deprotections are well known in the art. Compounds of Formula XXVIII are coupled with an amine of Formula XV in the presence of phosgene or a phosgene equivalent to generate a urethane (when X=O) or mixed urea (when X=NH) of Formula I. Compounds of Formula XXVIII can also be used in a urea isostere reaction, as above, to generate a Formula I compound. Where protecting groups have been utilized on the group Q, they are removed by conditions appropriate to the protecting group and compatible with the rest of the molecule.

Tetrazole-containing compounds of Formula I may also be prepared according to Scheme 9.

Scheme 9. Synthesis of Formula I Compounds

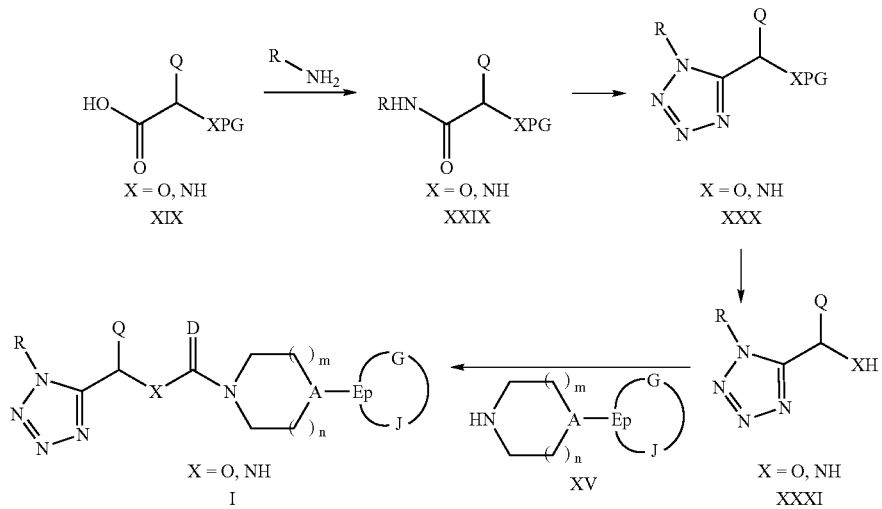

Scheme 9 begins with the coupling of a carboxylic acid of Formula XIX to a primary amine to give secondary amides of Formula XXIX using various amide coupling agents well known in the art. Conversion of Formula XXIX amides to tetrazoles of Formula XXX can be accomplished by treatment with a dehydrating agent such as phosphorous pentachloride or phosphorous oxychloride followed by treatment with an azide source such as tributyltin azide. The protecting group (PG) can then be removed to liberate the hydroxyl group (when X=O) or the primary amine (when X=NH) by application of deprotection conditions appropriate to the protecting group. Such deprotections are well known in the art. Resulting compounds of Formula XXXI can be coupled with an amine of Formula XV in the presence of phosgene or a phosgene equivalent to generate a urethane (when X=O) or mixed urea (when X=NH) of Formula I. Compounds of Formula XXXI can also be used in a urea isostere reaction, as above, to generate Formula I compounds. Where protecting groups have been utilized on Q, they are removed by conditions which are appropriate to the protecting group.

Compounds of Formula I may also be prepared according to Scheme 10.

Scheme 10 begins with the coupling of a carboxylic acid of Formula XIX to a compound of Formula XXXII to give secondary amides of Formula XXXIII using various amide coupling agents well known in the art. The pyridinyl-amide of Formula XXXIII can be made to undergo cyclization to give heterocycles of Formula XXXIV by use of a dehydrating agent such as phosphorous pentachloride or phosphorous oxychloride either alone or in the presence of an amine base such as pyridine or quinoline. The protecting group (PG) can then be removed to liberate the hydroxyl group (when X=O) or the primary amine (when X=NH) by application of deprotection conditions appropriate to the protecting group. Such deprotections are well known in the art. Compounds of Formula XXXV are coupled with an amine of Formula XV in the presence of phosgene or a phosgene equivalent to generate a urethane (when X=O) or mixed urea (when X=NH) of Formula I. Compounds of Formula XXXV can also be used in a urea isostere reaction, as above, to generate Formula I compounds. Where protecting groups have been utilized on Q, they are removed by conditions which are appropriate to the protecting group and compatible with the rest of the molecule.

Compounds of Formula I may also be prepared according to Scheme 11.

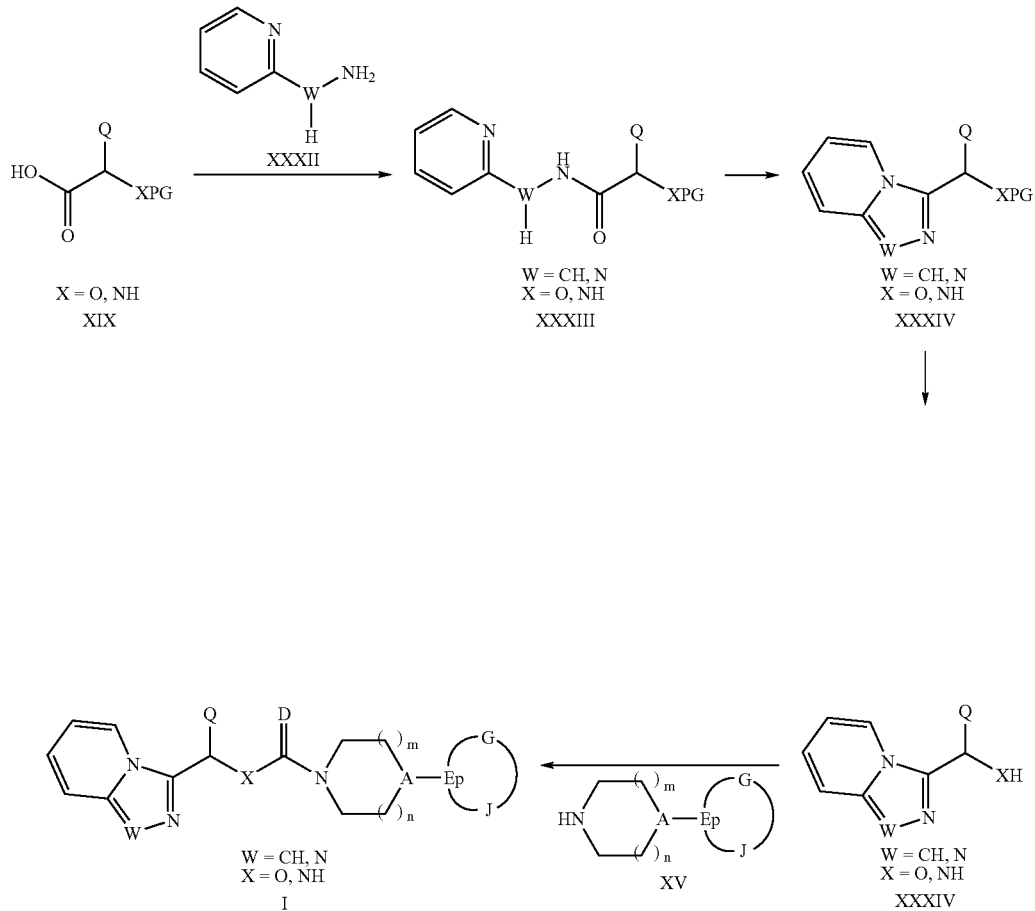

Scheme 11. Synthesis of Formula I Compounds

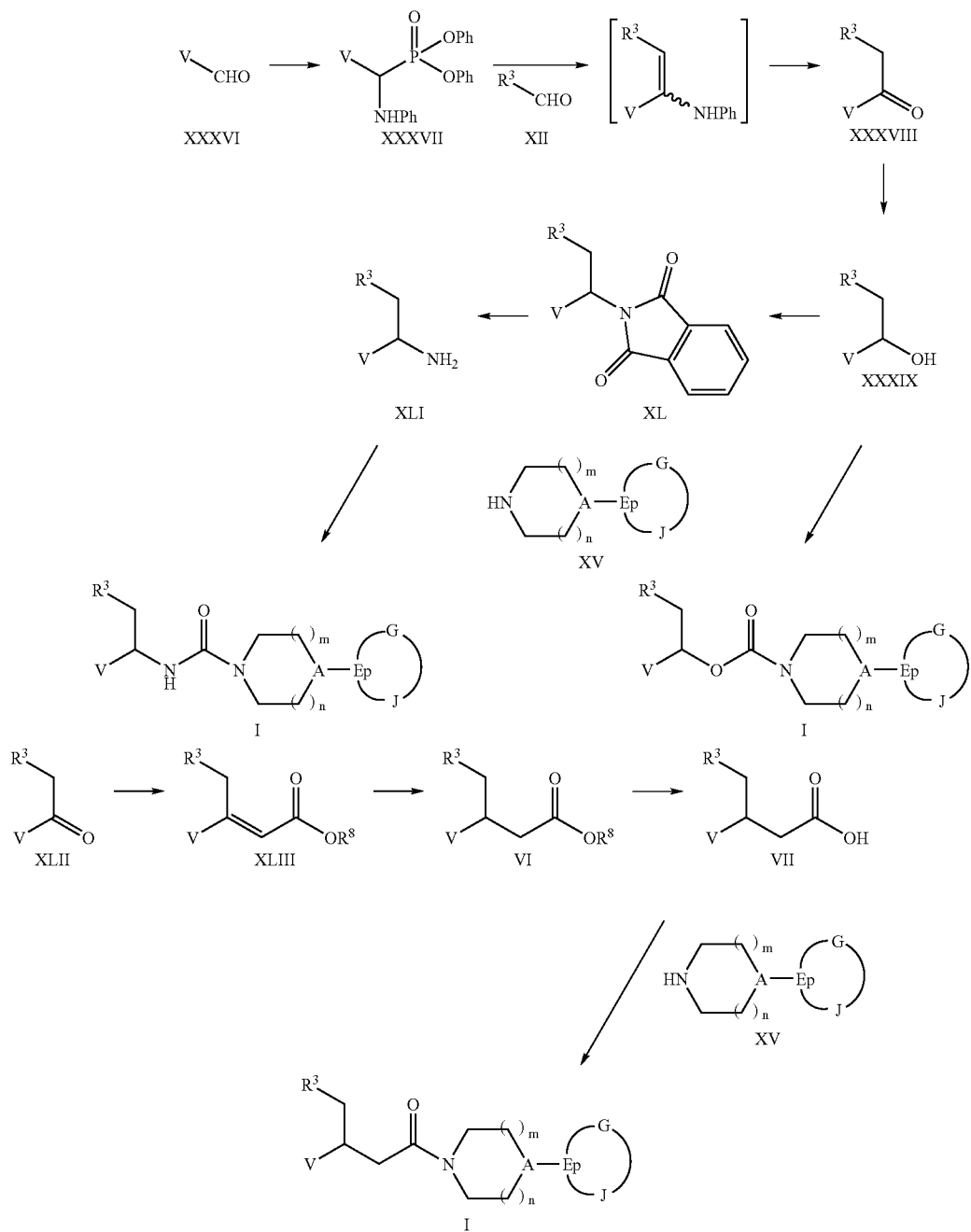

The general synthesis described in Scheme 11 begins with commercially available or synthesized aldehydes of Formula XXXVI. Conversion of Formula XXXVI aldehydes to α-aminophosphonates XXXVII and the following Wittig reactions with other commercially available or synthesized aldehydes of Formula XII followed by acidic hydrolysis afford ketones of Formula XXXVIII (*Tetrahedron Lett.* 1998, 39, 1717-1720). The ketones of Formula XXXVIII can be conveniently reduced to the corresponding alcohols XXXIX. Completion of the synthesis of Formula I compounds with X=O can be achieved through formation of activated intermediates such as p-nitrophenyl or N-succinimidyl carbonates followed by coupling with amines of Formula XV. On the other hand, alcohols of Formula XXXIX can also be converted to phthalimides XL using Mitsunobu conditions that are well known in the art. Treatment of Formula XL compounds with hydrazine affords amines XLI which can be further converted to compounds of Formula I with X=NH through activation with carbonyl diimidazole or similar activating agents. Furthermore, the ketones of Formula XXXVIII can be converted to esters of Formula XLII using Wittig conditions. Reduction of the double bond affords compounds of Formula VI. Hydrolysis of Formula VI esters leads to carboxylic acids of Formula VII which can be coupled with amines of formula XV to afford Formula I compounds with $X=CH_2$ using amide coupling agents well known in the art. Furthermore, Formula I compounds can be further expanded to other Formula I compounds if the aldehydes of Formula XXXVI contain suitable functional groups that can be modified using general synthetic methods known in the art.

Imidazole-containing compounds of Formula I may also be prepared as shown in Scheme 12.

ing with glyoxal or other suitable dicarbonyl compounds of Formula XXIV such as pyruvic aldehyde in the presence of ammonia in a polar, non-nucleophilic solvent such as dioxane. The imidazole ring can be further functionalized by alkylation of one of the nitrogen atoms with a suitable electrophile, such as an alkyl halide, in the presence of a base in a non-nucleophilic solvent to give N-substituted derivatives XLVII. Removal of the ester protecting group (PG) and amide coupling gives imidazole-containing compounds of Formula I.

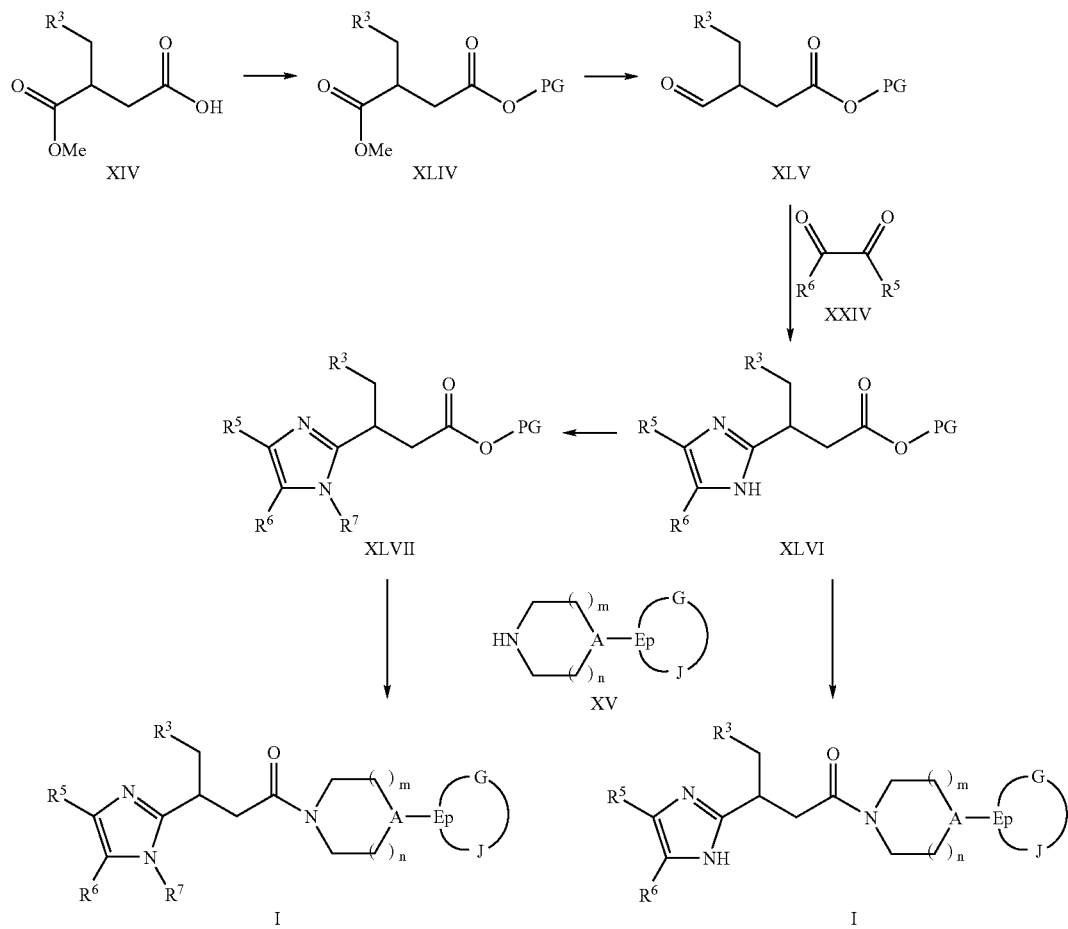

The synthesis begins with succinyl monoesters XIV from Scheme 4. The free carboxyl group can be protected with various blocking groups (PG) such as tert-butyl, using methods well known in the art, to give diesters XLIV. The methyl ester can be selectively hydrolyzed using mild basic conditions and the resulting carboxyl group reduced to the corresponding aldehydes XLV. This can be accomplished either by direct reduction of the ester using a selective hydride source such as diisobutylaluminum hydride or by reduction of the carboxyl group first to the corresponding alcohol, through an activated ester, and then oxidation to the aldehyde using, for example, Dess-Martin protocols. There are numerous alternative methods for these transformations well known to those skilled in the art. Aldehydes XLV can be converted to substituted or unsubstituted imidazoles of Formula XLVI by heat- Compounds of Formula XVII where $X=NH$, and where $R^3$ is an aromatic ring, can also be prepared as shown in Scheme 13.

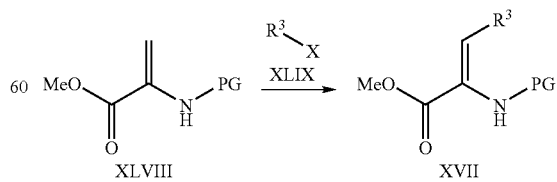

Scheme 13 starts with an N-protected aminoacrylate of Formula XLVIII that can be coupled to a compound of Formula XLIX comprising an aromatic ring to which is attached a leaving group such as iodine or bromine in the presence of a transition metal catalyst such as palladium (II) acetate in a non-reactive solvent with or without heating.

Preparation of Intermediates and Examples

General $^{1}$H- and $^{13}$C-NMR spectra were run on a Bruker 500 or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a YMC C18 column (3×50 mm) employing a 2 min linear gradient of 0% to 100% solvent B in A in a 3 min run. For LC/MS and for Shimadzu Preparative HPLC system, Solvent A-was: 10% methanol/90% water/0.1% trifluoroacetic acid, and solvent B was 90% methanol/10% water/0.1% trifluoroacetic acid with a UV detector set at 220 nm.

tert-Butyl 2-fluorophenylcarbamate

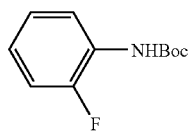

To a solution of di-tert-butyldicarbonate (45.2 g, 207 mmol, 1.0 equiv) in tetrahydrofuran (210 mL) at room temperature was added 2-fluoroaniline (20.0 mL, 207 mmol). The reaction was heated to reflux and held there for 6 h. It was cooled, concentrated, dissolved in pentane, washed with 5% citric acid, then 1 M potassium bisulfate (2×), then water, then 20% potassium hydroxide, then brine, dried over magnesium sulfate, and concentrated to give 48.0 g (quant) as an amber oil which was used without purification. $^{1}$H-NMR (CDCl$_3$, 500 MHz) δ 1.52 (s, 9H), 6.68 (bs, 1H), 6.85-7.20 (m, 3H), 8.07 (dd, J=8.1, 8.1, 1H). Mass spec.: 234.18 (MNa)$^+$.

2-(tert-Butoxycarbonylamino)-3-fluoro-benzoic acid

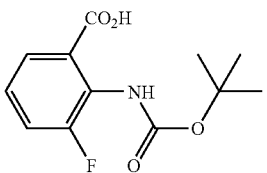

To a solution of tert-butyl 2-fluorophenylcarbamate (44.0 g, 208 mmol) in tetrahydrofuran (660 mL) at −78° C. was added tert-butyllithium in pentane (1.7 M, 306 mL, 2.5 equiv) drop wise. After addition was complete, the reaction was stirred at −78° C. for 30 min. The solution was allowed to gradually reach −20° C. before being recooled to −78° C. and transferred via canula to a slurry of carbon dioxide (excess) and tetrahydrofuran (500 mL). The solution was allowed to slowly warm to room temperature. The reaction mixture was concentrated to remove most of the tetrahydrofuran, and poured into a sep funnel containing water and diethyl ether. The layers were separated, and the aqueous extracted with diethyl ether twice more. The ethereals were discarded. The aqueous was acidified with 5% citric acid, extracted with diethyl ether (3×). The ethereal was dried over magnesium sulfate, and concentrated to give a light yellow solid which was recrystallized from hot toluene to give 37.1 g (70%) as a faint yellow solid. $^{1}$H-NMR (CDCl$_3$, 500 MHz) δ 1.50 (s, 9H), 6.25 (bs, 1H), 7.18 (ddd, J=7.9, 7.9, 4.9, 1H), 7.33 (dd, J=9.5, 9.2, 1H), 7.79 (d, J=7.9, 1H), 7.94 (s, 1H). Mass spec.: 278.21 (MNa)$^+$.

tert-Butyl 2-(1-benzylpiperidin-4-ylcarbamoyl)-6-fluorophenylcarbamate

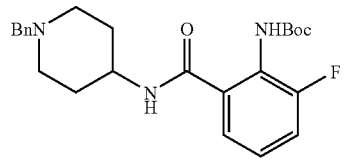

To a solution of 2-(tert-butoxycarbonylamino)-3-fluorobenzoic acid (37.1 g, 145 mmol), 4-amino-1-benzylpiperidine (35.6 mL, 1.20 equiv.), 1-hydroxybenzotriazole (21.6 g, 1.1 equiv), and triethylamine (44.1 g, 3.0 equiv.) in ethyl acetate (450 mL) was added 1-(3-dimethylaminopropyl)-3-ethylcarbodiimide hydrochloride (30.7 g, 1.1 equiv) in one portion. Initially, everything went into solution, but a precipitate formed very rapidly. The reaction was fitted with a reflux condenser and heated at reflux for 5 h. The reaction was diluted with ethyl acetate, washed with water (2×), then 1N sodium hydroxide (2×), then brine, dried over magnesium sulfate, and concentrated to give 67.0 g (quant) as a white solid which was used without purification. $^{1}$H-NMR (CDCl$_3$, 500 MHz) δ 1.48 (s, 9H), 1.55 (m, 2H), 1.99 (bd, J=11.0, 2H), 2.17 (dd, J=1.0, 11.0, 2H), 2.84 (bd, J=11.3, 2H), 3.51 (s, 2H), 3.94 (m, 1H), 6.13 (bd, J=7.6, 1H), 7.10-7.28 (m, 4H), 7.31 (m, 4H), 7.59 (s, 1H). Mass spec.: 428.41 (MH)$^+$.

2-Amino-N-(1-benzylpiperidin-4-yl)-3-fluorobenzamide

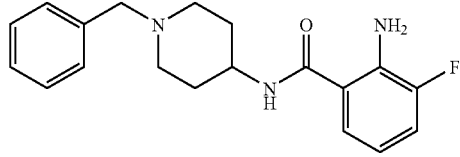

To a solution of tert-butyl 2-(1-benzylpiperidin-4-ylcarbamoyl)-6-fluorophenylcarbamate (67.0 g, 157 mmol) in dichloromethane (700 mL) at 0° C. was added trifluoroacetic acid (100 mL). The ice bath was removed and the reaction stirred at room temperature overnight. The reaction was concentrated and partitioned between ethyl acetate and saturated sodium bicarbonate. The aqueous portion was extracted with ethyl acetate (2×), which were washed with water (3×), then brine, dried over magnesium sulfate, and concentrated to give 47.6 g (93%) as a white solid which was used without purification. Mass spec.: 328.33 (MH)$^+$.

N-(2-Amino-3-fluorobenzyl)-1-benzylpiperidin-4-amine

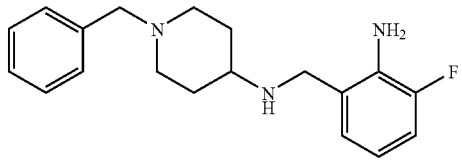

To a refluxing suspension of lithium aluminum hydride (16.1 g, 424 mmol, 3.50 equiv) in dioxane (800 mL) was added a solution of 2-amino-N-(1-benzylpiperidin-4-yl)-3-fluorobenzamide (39.7 g, 121 mmol) in dioxane (250 mL) at such a rate that gas evolution was limited to a safe flow. Upon completion of the addition, the resulting suspension was heated at reflux for 4 h. The reaction was cooled to 0° C., and quenched by the cautious addition of 20% potassium hydroxide. Upon formation of a white, filterable precipitate, the solid was filtered through a course glass sintered funnel, and the eluent concentrated to give 36.3 g (96%) as a light yellow oil which was used without purification. Mass spec.: 314.29 (MH)$^+$.

3-(1-Benzylpiperidin-4-yl)-8-fluoro-3,4-dihydro-quinazolin-2(1H)-one

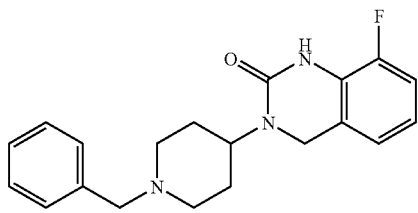

To a solution of N-(2-amino-3-fluorobenzyl)-1-benzylpiperidin-4-amine (36.3 g, 116 mmol) in tetrahydrofuran (600 mL) at room temperature was added carbonyl diimidazole (20.7 g, 1.10 equiv) in one portion. The reaction was stirred at room temperature for 3 h, heated at reflux for 30 min, and concentrated. The resulting solid was dissolved in 1:1 diethyl ether/ethyl acetate, washed with water (3×), then brine, dried over magnesium sulfate, and concentrated to give the crude product as a wet, yellow solid. The solid was triturated with diethyl ether and filtered to give 30.0 g (76%) as a white powder. $^1$H-NMR (CDCl$_3$, 500 MHz) δ 1.68 (m, 2H), 1.86 (dddd, J=11.9, 11.9, 11.9, 3.4, 2H), 2.14 (dd, J=11.6, 10.1, 2H), 2.98 (d, J=11.6, 2H), 3.51 (s, 2H), 4.34-4.44 (m, 3H), 6.71 (bs, 1H), 6.79-6.89 (m, 2H), 6.94 (dd, J=9.2, 9.2, 1H), 7.21-7.34 (m, 5H). Mass spec.: 340.30 (MH)$^+$.

8-Fluoro-3,4-dihydro-3-(piperidin-4-yl)quinazolin-2(1H)-one

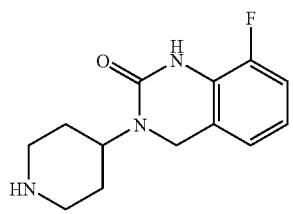

A 250 mL flask was charged with 3-(1-benzylpiperidin-4-yl)-8-fluoro-3,4-dihydroquinazolin-2(1H)-one (1.40 g, 4.12 mmol) and methanol (25.0 mL). The suspension was heated with a heat gun to aid in dissolution. The flask was flushed with nitrogen, treated with palladium on charcoal (141 mg, 0.032 equiv), flushed with nitrogen, then hydrogen, and vigorously stirred under an atmosphere of hydrogen overnight. The reaction was flushed with nitrogen, filtered through celite, and concentrated to give 0.99 g (97%) as a white solid which was used without purification. $^1$H-NMR (CDCl$_3$, 500 MHz) δ 1.71 (m, 4H), 2.75 (m, 2H), 3.16 (m, 2H), 4.38 (s, 2H), 4.46 (m, 1H), 6.77 (bs, 1H), 6.81-6.89 (m, 2H), 6.95 (m, 1H). Mass spec.: 250.22 (MH)$^+$.

4-Bromo-2,6-dimethylphenyldiazo-t-butyl sulfide

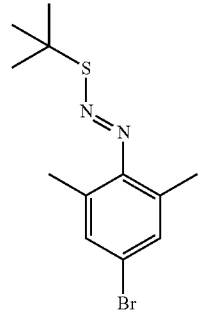

4-Bromo-2,6-dimethylaniline (20.00 g, 100 mmol) was ground to a powder with a mortar and pestle and then suspended in 24% hydrochloric acid (41 mL). The stirred mixture was cooled to −20° C. and treated with sodium nitrite (7.24 g, 1.05 equiv) in water (16 mL), dropwise over 40 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (11.3 mL, 1 equiv) in ethanol (100 mL) at 0° C. over ca. 10 min. Following addition, the mixture was stirred at 0° C. for 30 min and then crushed ice (ca. 150 mL) was added. The mixture was stored in the refrigerator overnight. The resulting light-brown solid was collected by filtration, washed with water, and dried under high vacuum for several hours. (26.90 g, 89%). The compound appeared to be stable as a solid but underwent significant decomposition when recrystallization from ethanol was attempted. $^1$H-NMR (CDCl$_3$, 500 MHz) δ 1.58 (9H, s), 1.99 (6H, s), 7.21 (2H, s). Mass spec.: 303.05 (MH)$^+$.

5-Bromo-7-methylindazole

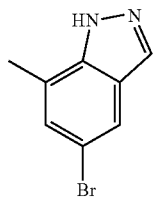

Into a flame-dried round bottom flask, 4-bromo-2,6-dimethylphenyldiazo-t-butyl sulfide (12.50 g, 41.5 mmol) and potassium t-butoxide (46.56 g, 10 equiv) were combined. A stir bar was added and the mixture placed under nitrogen. To this was added dry dimethylsulfoxide (120 mL). The mixture was stirred vigorously overnight at to room temperature. The reaction mixture was then carefully poured into a mixture of crushed ice (400 mL) and 10% hydrochloric acid (200 mL). The resulting suspension was left to stand at 4° C. overnight and the solid was collected by filtration and washed with water. The crude solid was dissolved in 5:1 methylene chloride/methanol and the solution dried over magnesium sulfate and evaporated to give the product as an off-white solid (7.60 g, 87%). $^1$H-NMR (CDCl$_3$/CD$_3$OD, 500 MHz) δ 2.51 (3H, s), 7.22 (1H, s), 7.69 (1H, s), 7.94 (1H, s). Mass spec.: 211.03 (MH)$^+$.

7-methylindazole-5-carboxaldehyde

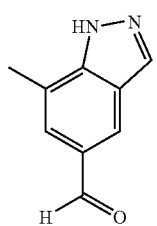

5-Bromo-7-methylindazole (6.10 g, 28.9 mmol) and sodium hydride (60% in mineral oil, 1.27 g, 1.1 equiv) were weighed into a flame-dried round-bottom flask containing a magnetic stir bar. Under a nitrogen atmosphere at room temperature, dry tetrahydrofuran (30 mL) was added. The mixture was stirred at room temperature for 15 min, during which time it became homogeneous. The stirred mixture was cooled to −70° C. and a solution of sec-butyllithium in cyclohexane (1.4M, 45 mL, 2.2 equiv) was added over several minutes. After 1 h at −70° C., dimethylformamide (10 mL) was added over several minutes. The mixture was allowed to warm to room temperature and was stirred overnight. It was then cooled to 0° C. and carefully treated with 1N hydrochloric acid (60 mL). After a few minutes, solid sodium bicarbonate was added to basify the mixture to pH 9-10. The layers were separated and the aqueous phase washed twice with ethyl acetate. The combined organic phases were extracted with 0.8M sodium hydrogen sulfate (3×125 mL). The combined aqueous phases were washed with ethyl acetate (100 mL) and then the pH was adjusted to ca. 10 with solid sodium hydroxide. The resulting suspension was extracted with ethyl acetate (3×150 mL). The combined organic phases were washed with brine, dried (magnesium sulfate) and evaporated to give the product as a light-tan solid (3.01 g, 65%). $^1$H-NMR (CDCl$_3$, 500 MHz) δ 2.63 (3H, s), 7.73 (1H, s), 8.12 (1H, s), 8.25 (1H, s), 10.03 (1H, s). Mass spec.: 161.06 (MH)$^+$.

5-(2-methoxy-vinyl)-7-methyl-1H-indazole

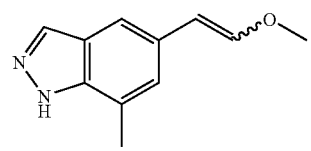

Methoxymethyl triphenylphosphonium chloride (2.74 g, 8 mmol, 2.0 equiv.) and potassium tert-butoxide (1.35 g, 12 mmol, 3.0 equiv.) were weighed into a 250-mL oven-dried flask. Tetrahydrofuran (15 mL) was slowly introduced via syringe under nitrogen. After the resulting red solution was stirred at room temperature for 10 min, 7-methylindazole aldehyde (641 mg, 1.0 equiv.) was added in one portion. LCMS indicated that the reaction was complete within 1 h. The reaction was quenched with water and the mixture was then diluted with ethyl acetate. The layers were separated and the organic layer was washed with brine, dried over sodium sulfate and concentrated in vacuo to give a tan oil. The crude product was purified by flash column chromatography on silica gel (1:1 hexane/ethyl acetate) to afford the desired product as an off-white solid (710 mg, 94%). MS (ESI) [M+H]$^+$=189; $^1$H NMR indicated a mixture of isomers (trans/cis ~3:1). Trans isomer: $^1$H-NMR (400 MHz, CDCl$_3$) δ 12.3 (br., 1H), 8.13 (s, 1H), 7.88 (s, 1H), 7.42 (s, 1H), 6.12 (d, J=7.0 Hz, 1H), 5.31 (d, J=7.0 Hz, 1H), 3.80 (s, 3H), 2.60 (s, 3H).

(7-methyl-1H-indazol-5-yl)-acetaldehyde

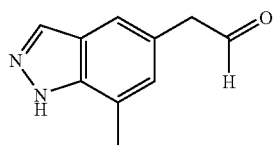

To a solution of 5-(2-methoxy-vinyl)-7-methyl-1H-indazole (365 mg, 1.94 mmol, 1.0 equiv.) in tetrahydrofuran (8 mL) was added 60% perchloric acid (0.63 mL, 3 equiv) in one portion under nitrogen. After 2 h, more perchloric acid (0.63 mL) was added. After 4 h, LCMS indicated that no starting material was present. The reaction mixture was diluted with water and ethyl acetate. The layers were separated and the organic layer was washed with water (3×). The organic layer was separated, dried over sodium sulfate and concentrated in vacuo to give an off-white solid. The crude material was carried on without further purification. MS (ESI) [M+H]$^+$= 175.

4-(7-methyl-1H-indazol-5-yl)-but-2-enoic acid tert-butyl ester

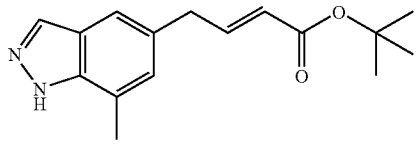

Tetrahydrofuran (8 mL) was added to a flask containing (7-methyl-1H-indazol-5-yl)-acetaldehyde (1.94 mmol, 1.0 equiv) and (tert-butoxycarbonyl-methylene)triphenylphosphorane (1.46 g, 3.88 mmol, 2.0 equiv) at room temperature under nitrogen. The resulting yellow solution was stirred overnight (15 h). LCMS indicated completion. The mixture was partitioned between water and ethyl acetate. The organic layer was separated and washed with brine, dried over sodium sulfate and concentrated in vacuo. The residue was purified by flash column chromatography to afford the desired product as a yellow oil (272 mg, 51.5% for two steps). MS (ESI) [M+H]$^+$=273; $^1$H NMR (400 MHz, CDCl$_3$) δ 12.3 (br., 1H), 8.06 (s, 1H), 7.36 (s, 1H), 7.04 (m, 1H), 6.96 (s, 1H), 5.74 (dd, J=15.6 and 1.6 Hz, 1H), 3.54 (d, J=6.8 Hz; 2H), 2.57 (s, 3H), 1.47 (s, 9H).

(±)-4-(7-methyl-1H-indazol-5-yl)-3-pyridin-2-yl-butyric acid tert-butyl ester

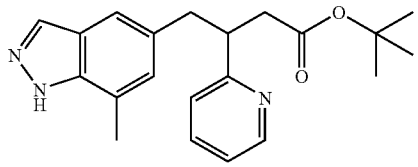

To a solution of 2-bromopyridine (281.4 mg, 1.781 mmol, 6.4 equiv.) in anhydrous ether (1 mL) at −70° C. in an oven-dried flask was added n-butyllithium (2.5 M, 0.713 mL, 1.781 mmol, 6.4 equiv), dropwise under nitrogen. The resulting deep-red solution was stirred for 5 min before being used in the next step.

To a 50-mL oven-dried flask was added di-n-butylsulfide (261 mg, 1.781 mmol, 6.4 equiv) and cuprous iodide (170 mg, 0.891 mmol, 3.2 equiv) under nitrogen. Anhydrous ether (1 mL) was added and the suspension was cooled to 0° C. before the solution of 2-pyridinyl lithium was added via canuula. A yellowish brown precipitate was formed. After stirring at 0° C. for 15 min, the cooling bath was removed and 4-(7-methyl-1H-indazol-5-yl)-but-2-enoic acid tert-butyl ester (75.8 mg, 0.278 mmol, 1.0 equiv) in anhydrous ether (1 mL) was added via syringe. The dark solution was stirred at room temperature for 40 min. LCMS indicated the formation of the desired product. The reaction mixture was then partitioned between an aqueous ammonium hydroxide/ammonium chloride solution and ethyl acetate (upon shaking, the solids gradually dissolved to a blue aqueous solution). The layers were separated and the organic layer was washed with water, brine, dried over sodium sulfate and concentrated in vacuo to an oil. Careful flash column chromatography (5% methanol in methylene chloride) afforded the desired product (10.4 mg, 11%) which was carried on without farther purification. MS (ESI) 352 (M H)$^+$, 296 (M-$^t$Bu)$^+$.

(±)-4-(7-methyl-1H-indazol-5-yl)-3-pyridin-2-yl-butyric acid

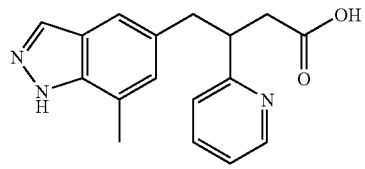

To a flask containing 4-(7-Methyl-1H-indazol-5-yl)-3-pyridin-2-yl-butyric acid tert-butyl ester (10 mg, 0.028 mmol) was added hydrogen chloride in dioxane (4 M, 0.8 mL). The suspension was stirred at room temperature overnight (LCMS indicated 2/3 conversion after 2 h). The reaction mixture was concentrated in vacuo to dryness. Dioxane (1 mL) was added and the mixture again concentrated to dryness. The residue was carried on without further characterization. MS (ESI) 296 (MH)$^+$.

EXAMPLE 1

(±)-3-{1-[4-(7-Methyl-1H-indazol-5-yl)-3-pyridin-2-yl-butyryl]-piperidin-4-yl}-3,4-dihydro-1H-quinazolin-2-one

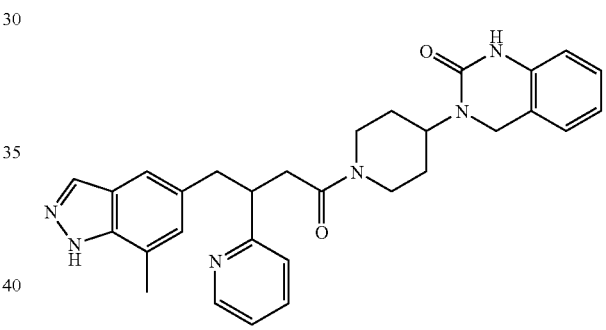

To a solution of 4-(7-methyl-1H-indazol-5-yl)-3-pyridin-2-yl-butyric acid (white solid, 0.028 mmol) in methylene chloride (2 mL) was added 3,4-dihydro-3-(4-piperidinyl-2 (1H)-quinazolinone (7.2 mg, 0.031 mmol, 1.1 equiv). Triethylamine (30 µL) was added followed by 3-(diethoxyphosphoryloxy)-1,2,3-benzotriain-4(3H)-one (DEPBT, 9.4 mg, 0.031 mmol 1.1 equiv). The resulting yellow solution was stirred at room temperature for 1 h and LCMS. A further 1 equivalent of the amine and DEPBT were added. After stirring for another 4 h, LCMS indicated complete conversion. The reaction mixture was diluted with ethyl acetate and quenched with 0.5 N sodium hydroxide. The layers were separated and the organic layer was washed with brine, dried over sodium sulfate and concentrated in vacuo. The residue was purified by flash column chromatography (10% methanol in methylene chloride) to afford the desired product (9.0 mg, 62% for two steps) as a glassy solid. MS (ESI) [M+H]$^+$ =509, $^1$H-NMR (400 MHz, CDCl$_3$) δ 11.5 (br., 1H), 8.61-8.52 (m, 1H), 7.93 (d, J=4.8 Hz, 1H), 7.50-7.38 (m, 1H), 6.90 (m, 8H), 6.66 (d, J=7.6 Hz, 1H), 4.72-4.62 (m, 1H), 4.59-4.48 (m, 1H), 4.24 (s, 1H), 4.09 (s, 1H), 4.07-3.94 (m, 1H), 3.80-3.66 (m, 1H), 3.20-2.80 (m, 4H), 2.72-2.46 (m, 2H), 2.45 (d, J=4.8 Hz, 3H), 1.85-1.48 (m, 4H).

2-(7-Methyl-1H-indazol-5-ylmethylene)-succinic acid 1-methyl ester

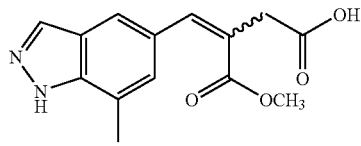

To a mixture of 7-methyl indazole aldehyde (0.2619 g, 1.64 mmol) and DBE-4 dibasic ester (dimethyl succinate) (0.32 mL, 2.45 mmol) in t-butanol (20 mL) was added potassium t-butoxide (0.4036 g, 3.60 mmol). The reaction mixture was heated at 50° C. for 2 h under nitrogen. After a further 16 h at room temperature, the solvent was removed in vacuo and the residue was taken up in water (100 mL) and extracted with ethyl acetate (3×50 mL). The aqueous layer was acidified with 1N hydrochloric acid to pH 3~4 and extracted with ethyl acetate (3×50 mL). The combined ethyl acetate solution was dried and concentrated in vacuo to give the crude product as a yellow solid (99%, cis/trans isomer approximately 40:60). The crude mixture was carried to next step without further purification. Mass spec.: 275 (MH)$^+$.

(±)-2-(7-Methyl-1H-indazol-5-ylmethyl)-succinic acid 1-methyl ester

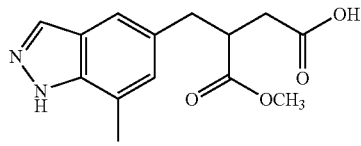

A suspension of 2-(7-methyl-1H-indazol-5-ylmethylene)-succinic acid 1-methyl ester (0.4440 g, 1.62 mmol) and 10% palladized charcoal (0.04 g) in ethyl acetate (15 mL) and methanol (5 mL) was hydrogenated in a Parr apparatus overnight at 50 psi. The reaction mixture was filtered through a pad of celite and the filtrate evaporated to give the desired product as a yellow solid (100%). Mass spec.: 277 (MH)$^+$.

(±)-2-(7-Methyl-1H-indazol-5-ylmethyl)-4-oxo-4-[1',2'-dihydro-2'-oxospiro-[4H-3',1-benzoxazine-4,4'-piperidinyl]-butyric acid methyl ester

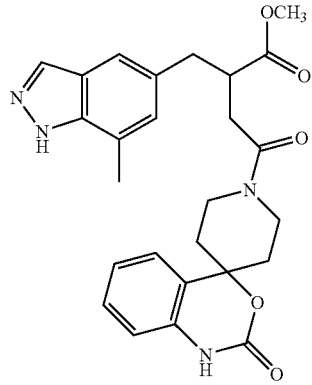

A solution of 2-(7-methyl-1H-indazol-5-ylmethyl)-succinic acid 1-methyl ester (0.2253 g, 0.82 mmol), 1,2-dihydro-2-oxospiro-4H-3,1-dihydro-benzoxazine-4'4-piperidine (0.1938 g, 0.89 mmol) and triethylamine (0.099 g, 0.98 mmol) in methylene chloride (15 mL) was treated with 3-(diethoxyphosphoryloxy)-1,2,3-benzotriain-4(3H)-one (DEPBT, 0.2685 g, 0.90 mmol). The mixture was stirred overnight and then washed with water (3×5 mL). The organic layer was dried, and concentrated in vacuo. The residue was purified by flash chromatography on silica gel, eluting with 0-10% 2M ammonia in methanol/methylene chloride, to afford the desired product (53%). LC/MS: t$_R$=1.40 min, 477.28 (MH)$^+$.

Similarly prepared:

(±)-2-(7-Methyl-1H-indazol-5-ylmethyl)-4-oxo-4-[4-(2-oxo-1,4-dihydro-2H quinazolin-3-yl)-piperidin-1-yl]-butyric acid methyl ester

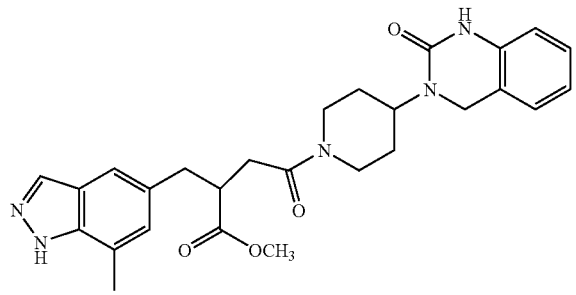

$^1$H-NMR (400 MHz, CDCl$_3$) δ 8.02 (1H, s), 7.98 (1H, m), 7.90 (1H, m), 7.35-6.89 (4H, m), 6.72 (1H, m), 4.71 (1H, m), 4.57 (1H, m), 4.27 (1H, s), 4.22 (1H, m), 3.85 (1H, m), 3.65 (3H, m), 3.30 (1H, m), 3.11 (2H, m), 2.83 (2H, m), 2.81-2.54 (4H, m), 2.35 (1H, m), 1.73-1.67 (4H, m). Mass spec.: 490.32 (MH)$^+$.

EXAMPLE 2

(±)-3-{1-[3-(3-Benzyl-[1,2,4]oxadiazol-5-yl)-4-(7-methyl-1H-indazol-5-yl)-butyryl]-piperidin-4-yl}-3,4-dihydro-1H-quinazolin-2-one

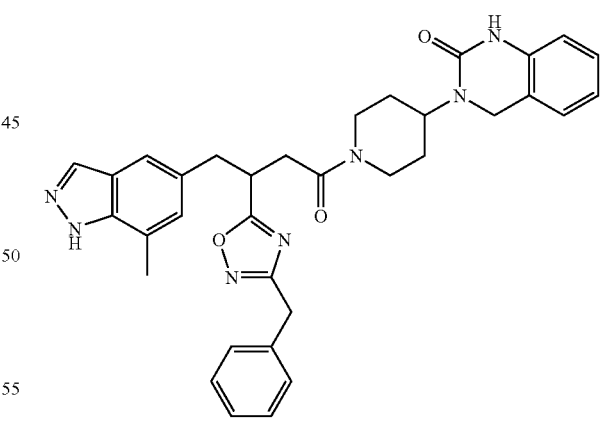

To a solution of N-hydroxy-2-phenyl-acetamidine (0.27 mmol, 3 equiv, this and the other amidine intermediates of the present invention were prepared as described in J. Med. Chem. 1993, 1529-1538) in anhydrous tetrahydrofuran (4 mL) was added sodium hydride (0.27 mmol, 3 equiv) under nitrogen. The mixture was heated at 65° C. for 30 min before addition of a solution of (±)-2-(7-methyl-1H-indazol-5-ylmethyl)-4-oxo-4-[4-(2-oxo-1,4-dihydro-2H-quinazolin-3-yl)-piperidin-1-yl]-butyric acid methyl ester (0.09 mmol, 1 equiv) in tetrahydrofuran (3 mL). The reaction mixture was heated at 65° C. overnight. Tetrahydrofuran was removed in vacuo and the reaction mixture was taken up in methylene chloride, washed with water (3×4 mL), dried over sodium sulfate and concentrated. Flash chromatography on silica gel using methanol/methylene chloride from 0 to 10% gave an impure product. The final product was obtained by preparative HPLC in 27% yield. LC/MS: $t_R$=1.60 min, 590 (MH)$^+$. $^1$H-NMR (400 MHz, CD$_3$OD) δ 7.92 (1H, s), 6.90-7.25 (10H, m), 6.74 (1H, d, J=8.00 Hz), 4.32-4.57 (2H, m), 4.24-4.29 (2H, m), 3.79-4.06 (5H, m), 2.79-3.31 (5H, m), 2.57 (1H, m), 2.44 (3H, s), 1.50-1.82 (4H, m).

EXAMPLE 3

(±)-3-{1-[4-(7-Methyl-1H-indazol-5-yl)-3-(3-piperidin-1-ylmethyl [1,2,4]oxadiazol-5-yl)-butyryl]-piperidin-4-yl}-3,4-dihydro-1H-quinazolin-2-one

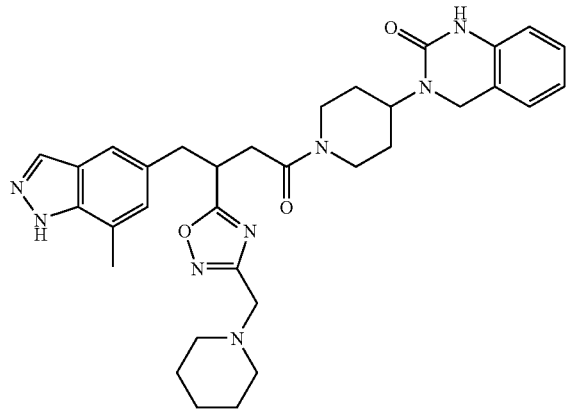

Prepared as described above for Example 2. LC/MS: $t_R$=1.23 min, 597.48 (MH)$^+$.

EXAMPLE 4

(±)-3-{1-[4-(7-Methyl-1H-indazol-5-yl)-3-(3-phenyl-[1,2,4]oxadiazol-5-yl)-butyryl]-piperidin-4-yl}-3,4-dihydro-1H-quinazolin-2-one

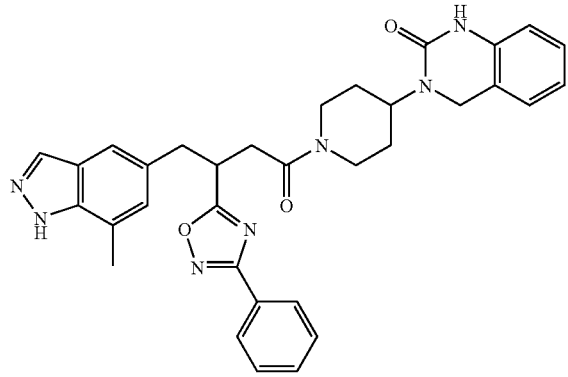

Prepared as described above for Example 2. LC/MS: $t_R$=1.69 min, 576.37 (MH)$^+$. $^1$H-NMR (400 MHz, CDCl$_3$) δ 9.07 (3H, m), 670-7.47 (10H, m), 4.55-4.73 (2H, m), 3.94-4.26 (4H, m), 3.11-3.30 (4H, m), 2.54-2.82 (2H, m), 2.53 (3H, s), 1.65-1.77 (4H, m).

EXAMPLE 5

(±)-3-{1-[4-(7-Methyl-1H-indazol-5-yl)-3-(3-methyl-[1,2,4]oxadiazol-5-yl)-butyryl]-piperidin-4-yl}-3,4-dihydro-1H-quinazolin-2-one

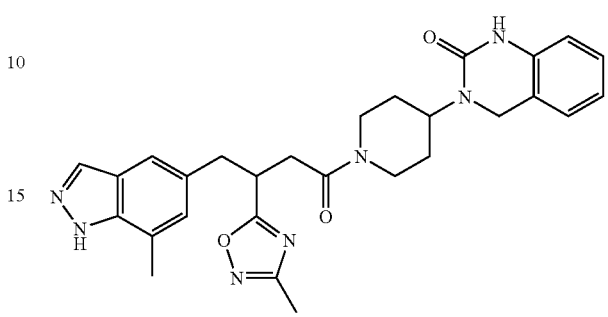

Prepared as described above for Example 2. LC/MS: $t_R$=1.40 min, 514.41 (MH)$^+$. $^1$H-NMR (400 MHz, CDCl$_3$) δ 8.05 (1H, d, J=5.20 Hz), 7.45 (1H, d, J=7.6 Hz), 7.32 (1H, d, J=6.0 Hz), 7.14 (1H, m), 6.90-7.05 (3H, m), 6.72 (1H, m) 4.45-4.72 (2H, m), 3.85-4.28 (3H, m), 2.60-3.21 (7H, m), 2.55 (3H, s), 2.36 (3H, m), 1.61-1.82 (5H, m).

EXAMPLE 6

(±)-3-{1-[4-(7-Methyl-1H-indazol-5-yl)-3-(3-pyridin-4-ylmethyl-[1,2,4]oxadiazol-5-yl)-butyryl]-piperidin-4-yl}-3,4-dihydro-1H-quinazolin-2-one

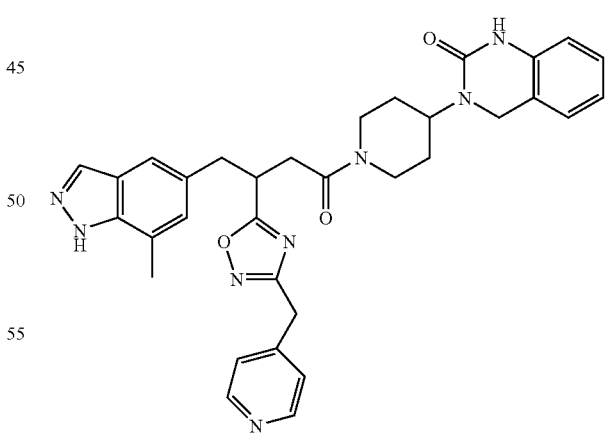

Prepared as described above for Example 2. LC/MS: $t_R$=1.24 min, 577.33 (MH)$^+$. $^1$H-NMR (400 MHz, CDCl$_3$) δ 8.47 (2H, m), 7.95 (1H, d, J=4.0 Hz), 6.86-7.25 (6H, m), 6.85 (1H, s), 6.66-6.68 (2H, d, J=8.0 Hz), 4.44-4.78 (2H, m), 3.82-4.28 (6H, m), 2.58-3.14 (6H, m), 2.43 (3H, s), 1.55-1.79 (4H, m).

EXAMPLE 7

(±)-3-{1-[3-(3-Dimethylaminomethyl-[1,2,4]oxadiazol-5-yl)-4-(7-methyl-1H-indazol-5-yl)-butyryl]-piperidin-4-yl}-3,4-dihydro-1H-quinazolin-2-one

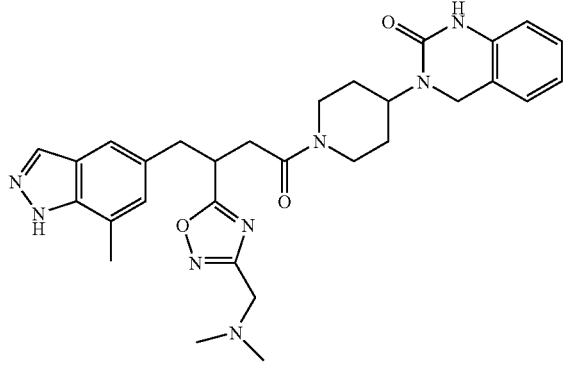

Prepared as described above for Example 2. LC/MS: $t_R$=1.19 min, 557.55 (MH)$^+$.

EXAMPLE 8

(±)-3-{1-[3-(3-Benzyl-[1,2,4]oxadiazol-5-yl)-4-(7-methyl-1H-indazol-5-yl)-butyryl]-4,4'-piperidinyl}-1',2'-dihydro-2'-oxospiro-[4H-3',1-benzoxazine

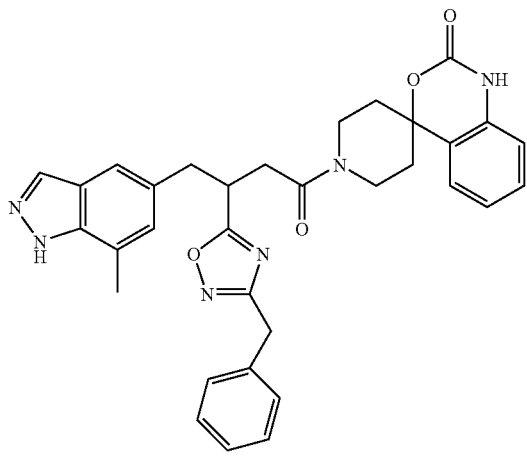

Prepared as described above for Example 2. LC/MS: $t_R$=1.57 min, 577.29 (MH)$^+$.

EXAMPLE 9

(±)-3-{1-[3-(3-Methyl-[1,2,4]oxadiazol-5-yl)-4-(7-methyl-1H-indazol-5-yl)-butyryl]-4,4'-piperidinyl}-1',2'-dihydro-2'-oxospiro-[4H-3',1-benzoxazine

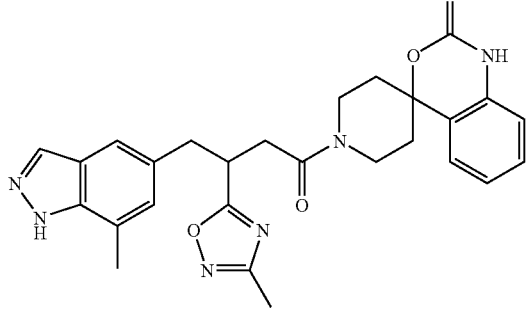

Prepared as described above for Example 2. LC/MS: $t_R$=1.35 min, 501.31 (MH)$^+$. $^1$H-NMR (400 MHz, CD$_3$OD) δ 8.01 (1H, m), 6.84-7.38 (7H, m), 4.45 (1H, m), 3.89 (2H, m), 3.40-3.64 (2H, m), 2.71-3.18 (4H, m), 2.51 (3H, m), 2.26 (3H, s), 1.85-2.14 (4H, m).

2-Benzyloxycarbonylamino-3-(7-methyl-1H-indazol-5-yl)-acrylic acid methyl ester

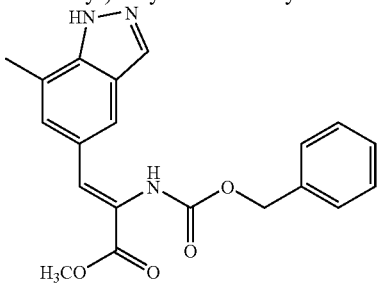

A stirred solution of N-benzyloxycarbonyl-α-phosphonoglycine trimethyl ester (5.51 g, 1.2 equiv) in tetrahydrofuran (30 mL) at room temperature was treated with tetramethylguanidine (1.91 mL, 1.1 equiv). After 10 min, 7-methylindazole-5-carboxaldehyde (2.22 g, 13.86 mmol) in tetrahydrofuran (20 mL) was added. Disappearance of starting material was monitored by TLC and LC/MS. After 5 days at room temperature, the solvent was evaporated and the residue dissolved in ethyl acetate. The solution was washed with 2% phosphoric acid and brine, dried over magnesium sulfate and evaporated. The residue was purified by flash chromatography on silica gel, eluting with 1) 1:1 and 2) 2:1 ethyl acetate/hexane, to give the product as a colorless foam (4.93 g, 97%). $^1$H-NMR (CDCl$_3$, 500 MHz) δ 2.43 (3H, s), 3.80 (3H, s), 5.12 (2H, s), 6.66 (1H, s), 7.28 (5H, brs), 7.33 (1H, s), 7.47 (1H, s), 7.74 (1H, s), 7.96 (1H, s). Mass spec.: 366.16 (MH)$^+$.

(±)-2-Amino-3-(7-methyl-1H-indazol-5-yl)-propionic acid methyl ester

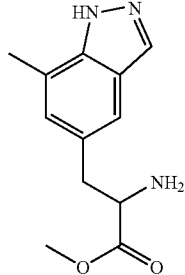

A solution of 2-benzyloxycarbonylamino-3-(7-methyl-1H-indazol-5-yl)-acrylic acid methyl ester (4.93 g, 13.49 mmol) in methanol (125 mL) was degassed by bubbling nitrogen through it for 30 min and then 10% palladium on charcoal (0.6 g) was carefully added. The mixture was hydrogenated at 40 psi in a Parr shaker apparatus overnight. The catalyst was removed by filtration through a pad of celite and the filtrate was concentrated in vacuo to give the product as a colorless foam (3.62 g, quant.). $^1$H-NMR (CD$_3$OD, 500 MHz) δ 2.45 (3H, s), 2.99 (1H, Abq), 3.22 (1H, Abq), 3.74 (3H, s), 3.89 (1H, m), 6.91 (1H, s), 7.31 (1H, s), 7.73 (1H, s). Mass spec.: 234.11 (MH)$^+$.

(±)-3-(7-Methyl-1H-indazol-5-yl)-2-{[4-(2-oxo-1,4-dihydro-2H-quinazolin-3-yl)-piperidine-1-carbonyl]-amino}-propionic acid methyl ester

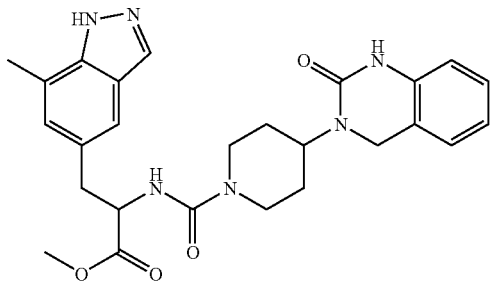

A stirred solution of (±)-2-amino-3-(7-methyl-1H-indazol-5-yl)-propionic acid methyl ester (162.9 mg, 0.698 mmol) in methylene chloride (3 mL) at room temperature was treated with carbonyl diimidazole (113.2 mg, 1 equiv). After 1.5 h at room temperature, 3-piperidin-4-yl-3,4-dihydro-1H-quinazolin-2-one (161.5 mg, 1 equiv.) was added. The mixture was stirred at room temperature overnight. A white precipitate had formed that was shown to be the desired product. The solvent was evaporated and the residue triturated with methylene chloride. The product was collected by filtration, washed with methylene chloride and dried in vacuo to give a white solid (241.5 mg, 71%). Some product remained in the mother liquors. $^1$H-NMR (dimethylformamide-$d_7$, 500 MHz) δ 1.75 (4H, m), 2.78 (3H, s), 2.7-3.1 (4H, m), 3.35 (2H, m), 3.86 (3H, s), 4.44 (2H, s), 4.57 (1H, m), 4.72 (1H, m), 7.11 (3H, m), 7.31 (1H, s), 7.34 (2H, m), 7.72 (1H, s), 9.34 (1H, s). Mass spec.: 491.13 (MH)$^+$.

EXAMPLE 10

(±)-4-(2-Oxo-1,4-dihydro-2H-quinazolin-3-yl)-piperidine-1-carboxylic acid [1-(3-benzyl-[1,2,4]oxadiazol-5-yl)-2-(7-methyl-1H-indazol-5-yl)-ethyl]-amide

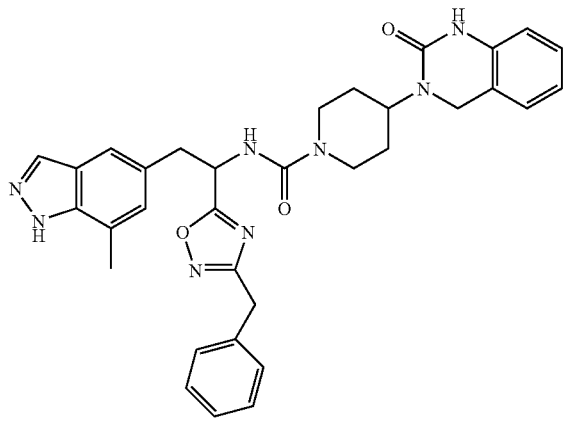

Sodium hydride (8 mg, 0.366 mmol) was added to a solution of N-hydroxy-2-phenyl-acetamidine (50 mg, 0.366 mmol) in tetrahydrofuran (15 mL). The solution was stirred at 60° C. for 15 min. A solution of (±)-3-(7-methyl-1H-indazol-5-yl)-2-{[4-(2-oxo-1,4-dihydro-2H-quinazolin-3-yl)-piperidine-1-carbonyl]-amino}-propionic acid methyl ester (60 mg, 0.122 mmol) in tetrahydrofuran (5 mL) was added. The reaction mixture was stirred at 60° C. for 18 h. The reaction was then cooled to room temperature and the solvent removed under reduced pressure. The residue was dissolved with methylene chloride and partitioned with water and extracted with methylene chloride (3×50 mL). The organic layer was dried over magnesium sulfate, filtered and concentrated under reduce pressure. Purification was carried out by preparative HPLC. LC/MS: $t_R$=1.79 min, 591 (MH)$^+$.

EXAMPLE 11

(±)-4-(2-Oxo-1,4-dihydro-2H-quinazolin-3-yl)-piperidine-1-carboxylic acid [2-(7-methyl-1H-indazol-5-yl)-1-(3-methyl-[1,2,4]oxadiazol-5-yl)-ethyl]-amide

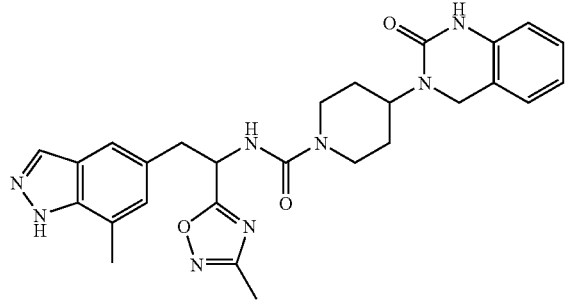

Prepared as described above for Example 10. $^1$H-NMR (DMSO-$d_6$); 9.21 (s, 1H), 7.99 (s, 1H), 7.41 (s, 1H), 7.11-7.03, (m, 3H), 6.91-6.86 (m, 2H), 6.76-6.74 (m, 2H), 4.29-4.25 (m, 2H), 4.11 (s, 1H), 4.06-4.03 (m,3H), 3.59 (s, 3H), 3.05-3.00 (m, 2H), 2.67 (m, 2H), 1.46-1.43 (m, 4H). LC/MS: $t_R$=1.83 min, 515 (MH)$^+$.

EXAMPLE 12

(±)-4-(2-Oxo-1,4-dihydro-2H-quinazolin-3-yl)-piperidine-1-carboxylic acid [2-(7-methyl-1H-indazol-5-yl)-1-(3-pyridin-4-ylmethyl-[1,2,4]oxadiazol-5-yl)-ethyl]-amide

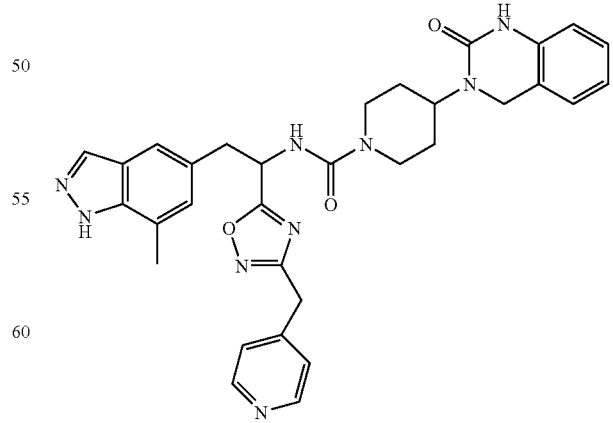

Prepared as described above for Example 10. LC/MS: $t_R$=1.30 min, 592 (MH)$^+$.

EXAMPLE 13

(±)-4-(2-Oxo-1,4-dihydro-2H-quinazolin-3-yl)-piperidine-1-carboxylic acid [1-(3-dimethylaminomethyl-[1,2,4]oxadiazol-5-yl)-2-(7-methyl-1H-indazol-5-yl)-ethyl]-amide

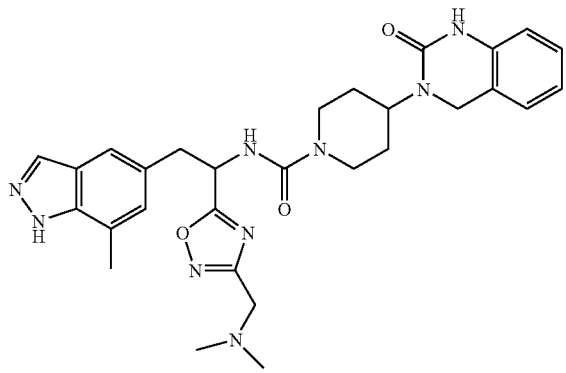

Prepared as described above for Example 10. LC/MS: $t_R$=1.16 min, 557 (MH)$^+$.

4-Bromo-2,6-diethylphenyldiazo-t-butyl sulfide

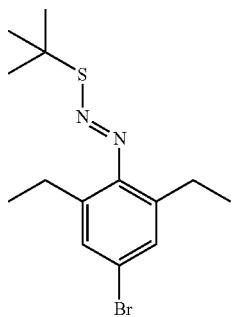

4-Bromo-2,6-diethylaniline (6.3 g, 27.6 mmol) was suspended in 24% hydrochloric acid (15 mL). The stirred mixture was cooled to −20° C. and treated with sodium nitrite (2.0 g, 1.05 equiv) in water (5 mL), dropwise over 30 min while the temperature was maintained below −5° C. After a further 30 min at −5° C. to −20° C., the mixture was buffered to ca. pH 5 with solid sodium acetate. This mixture (kept at ca. −10° C.) was added in portions to a stirred solution of t-butyl thiol (3.15 mL, 1.0 equiv) in ethanol (25 mL) at 0° C. over ca. 30 min. Following addition, the mixture was stirred at 0° C. for 30 min and then crushed ice (ca. 50 mL) was added. The resulting light-brown solid was collected by filtration, washed with water, and dried under high vacuum for several hours to afford 6.0 g (66%) of the desired product. $^1$H-NMR (CDCl$_3$) δ 1.15 (t, J=7.6, 6H), 1.50 (s, 9H), 2.27 (m, 4H), 7.21 (s, 2H). Mass spec.: 331.08 (MH)$^+$.

5-Bromo-7-ethyl-3-methylindazole

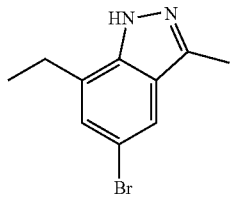

A flame-dried round bottom flask was charged with 4-bromo-2,6-diethylphenyldiazo-t-butyl sulfide (4.0 g, 12.1 mmol) and potassium t-butoxide (13.2 g, 121 mmol). A stir bar was added and the mixture placed under nitrogen. To this was added dry dimethylsulfoxide (35 mL). The mixture was stirred vigorously overnight at room temperature. The reaction mixture was then carefully poured into a mixture of crushed ice (130 mL) and 10% hydrochloric acid (60 mL). The resulting suspension was collected by filtration and washed severally with water. The solid was collected and dried in vacuo to give 2.85 g (98%) as a beige solid. $^1$H-NMR (CD$_3$OD) δ 1.32 (t, J=7.6, 3H), 2.50 (s, 3H), 2.88 (m, 2H), 7.25 (s, 1H), 7.68 (s, 1H). Mass spec.: 239.26 (MH)$^+$.

7-Ethyl-3-methylindazole-5-carboxaldehyde

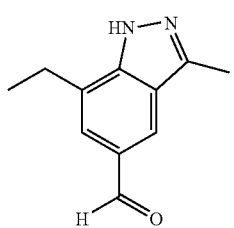

5-Bromo-7-ethyl-3-methylindazole (2.85 g, 11.9 mmol) and sodium hydride (0.31 g, 1.1 equiv) were weighed into a flame-dried round-bottom flask containing a magnetic stir bar. Under a nitrogen atmosphere at room temperature, dry tetrahydrofuran (15 mL) was added. The mixture was stirred at room temperature for 15 min, during which time it became homogeneous. The stirred mixture was cooled to −78° C. and a solution of tert-butyllithium in pentane (1.4 M, 18.7 mL, 2.0 equiv) was added over several minutes. After 1 h at −78° C., dimethylformamide (2.8 mL) was slowly added and the mixture allowed to warm to room temperature overnight. The solution was cooled to 0° C. and carefully treated with 1N hydrochloric acid (30 mL). After a few minutes, solid sodium bicarbonate was added until a pH of 9-10 was attained. The two layers were separated and the aqueous phase washed twice with ethyl acetate. The combined organic layers were washed with water (2×), brine (2×), dried over sodium sulfate, and concentrated. Column chromatography gave 1.5 g (67%) of pure material. LC/MS: $t_R$=1.15 min, 189.12 (MH)$^+$.

2-Benzyloxycarbonylamino-3-(7-ethyl-3-methyl-1H-indazol-5-yl)-acrylic acid methyl ester

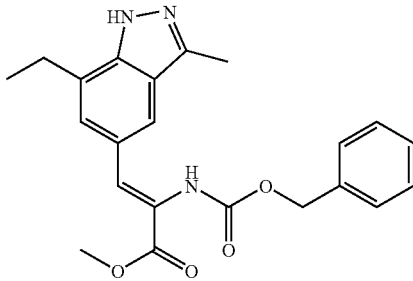

A stirred solution of N-benzyloxycarbonyl-α-phosphonoglycine trimethyl ester (3.17 g, 9.57 mmol, 1.2 equiv) in tetrahydrofuran (15 mL) at room temperature was treated with tetramethylguanidine (1.1 mL, 1.1 equiv). After 10 minutes, 7-ethyl-3-methylindazole-5-carboxaldehyde (1.5 g, 7.98 mmol) was added. After stirring at room temperature for 3 days, the solvent was evaporated and the residue purified by flash chromatography on silica gel to give 2.5 g (80%) of product. LC/MS: $t_R$=1.61 min, 394.16 (MH)$^+$.

(±)-2-Amino-3-(7-ethyl-3 methyl-1H-indazol-5-yl)-propionic acid methyl ester

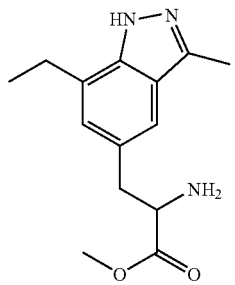

2-Benzyloxycarbonylamino-3-(7-ethyl-3-methyl-1H-indazol-5-yl)-acrylic acid methyl ester (1.0 g, 2.54 mmol) in methanol (15 mL) was flushed with nitrogen, and treated with palladium on charcoal (10%, 100 mg). The flask was flushed with hydrogen and allowed to stir under an atmosphere of hydrogen overnight. The reaction was flushed with nitrogen, filtered through celite, and concentrated. Column chromatography gave 0.6 g (91%) of the desired material. $^1$H-NMR (CD$_3$OD) δ 1.32 (m, 3H), 2.5 (s, 3H), 2.88 (dd, J=7.3, 7.6, 1H), 2.89 (dd, J=7.6, 7.6, 1H), 3.02 (dd, J=6.4, 7.0, 1H), 3.11 (dd, J=7.6, 5.8, 1H), 3.35 (s, 1H), 3.65 (m, 3H), 7.0 (s, 1H), 7.33 (s, 1H). Mass spec.: 262.24 (MH)$^+$.

(±)-3-(7-Ethyl-3-methyl-1H-indazol-5-yl)-2-{[4-(2-oxo-1,4-dihydro-2H-quinazolin-3-yl)-piperidine-1-carbonyl]-amino}-propionic acid methyl ester

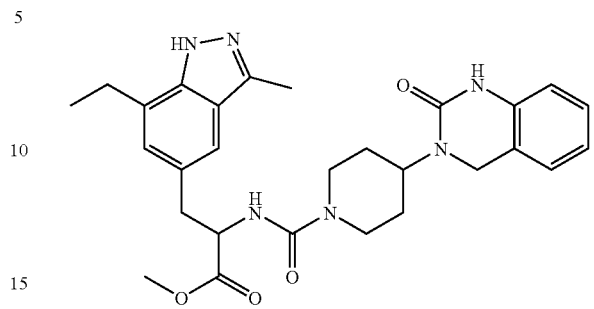

A stirred solution of (±)-2-amino-3-(7-ethyl-3 methyl-1H-indazol-5-yl)-propionic acid methyl ester (0.55 g, 2.1 mmol) in tetrahydrofuran (6 mL) at 0° C. was treated with carbonyl diimidazole (0.37 g, 1.1 equiv). The reaction was stirred for 5 min at 0° C., warmed to room temperature, stirred 10 min, and treated with 3-piperidin-4-yl-3,4-dihydro-1H-quinazolin-2-one (0.53 g, 1.1 equiv). The mixture was stirred at room temperature overnight. The solvent was evaporated and the residue purified by column chromatography to give 0.94 g (86%) as a white powder. $^1$H-NMR (DMSO-d$_6$) δ 1.26 (t, J=7.5, 3H), 1.49 (m, 1H), 2.44 (s, 3H), 2.83 (dd, J=7.3, 7.6, 1H), 2.84 (dd, J=115.0, 7.6, 1H), 2.88-3.10 (m, 1.5H), 3.18 (d, J=5.5, 0.5H), 3.61 (s, 3H), 4.04-4.16 (m, 3H), 4.28 (m, 2H), 6.76 (d, J=7.9, 1H), 6.86 (m, 2H), 7.04-7.25 (m, 3H), 7.36 (s, 1H), 7.40 (s, 1H), 9.18 (s, 1H), 12.59 (s, 1H). Mass spec.: 519.37 (MH)$^+$.

(±)-3-(7-Ethyl-3-methyl-1H-indazol-5-yl)-2-{[4-(2-oxo-1,4-dihydro-2H-quinazolin-3-yl)-piperidine-1-carbonyl]-amino}-propionic acid A suspension of (±)-3-(7-ethyl-3-methyl-1H-indazol-5-yl)-2-{[4-(2-oxo-1,4-dihydro-2H-quinazolin-3-yl)-piperidine-1-carbonyl]-amino}-propionic acid methyl ester (0.94 g, 1.81 mmol) in 1:1 tetrahydrofuran/methanol (30 mL) at room temperature was treated with a solution of lithium hydroxide monohydrate in water (10 mL). The solution was stirred at room temperature for 1 h and the solvents evaporated. The resultant residue was diluted with water (10 mL) and the pH adjusted to ca. 1 with 1N hydrochloric acid. The resultant white suspension was stored at 4° C. overnight and the product was collected by filtration, washed by a small amount of water and dried in vacuo for several hours to give 0.82 g (90%) of the desired product. LC/MS: $t_R$=1.57 min, 505.29 (MH)$^+$.

(±)-4-(2-Oxo-1,4-dihydro-2H-quinazolin-3-yl)-piperidine-1-carboxylic acid [1-carbomoyl-2-(7-ethyl-3-methyl-1H-indazol-5-yl)-ethyl]-amide

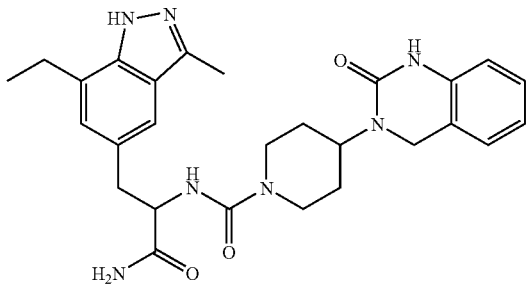

A stirred solution of (±)-3-(7-ethyl-3-methyl-1H-indazol-5-yl)-2-{[4-(2-oxo-1,4-dihydro-2H-quinazolin-3-yl)-piperidine-1-carbonyl]-amino}-propionic acid (0.35 g, 0.7 mmol) in dimethylformamide (10 mL) was cooled to 0° C. and sequentially treated with methylene chloride (5 mL), 7N ammonia in methanol (0.2 mL, 2 equiv), N,N-diisopropylethylamine (0.3 mL, 2.5 equiv), and PyBop (0.38 mg, 0.73 mmol). The solution was stirred for 1.5 h and concentrated. The product was purified by column chromatography to give 0.28 g (80%) of the desired product. $^1$H-NMR (CD$_3$OD) δ 1.35 (m, 4H), 1.46-1.65 (m, 3H), 2.53 (s, 3H), 2.70-3.05 (m, 5H), 3.95-4.15 (m, 4H), 4.33 (bs, 1H), 4.55 (bs, 1H), 6.75 (m, 2H), 6.94 (bs, 1H), 7.00-7.10 (m, 3H). Mass spec.: 504.35 (MH)$^+$.

(±)-4-(2-Oxo-1,4-dihydro-2H-quinazolin-3-yl)-piperidine-1-carboxylic acid [1-cyano-2-(7-ethyl-3-methyl-1H-indazol-5-yl)-ethyl]-amide

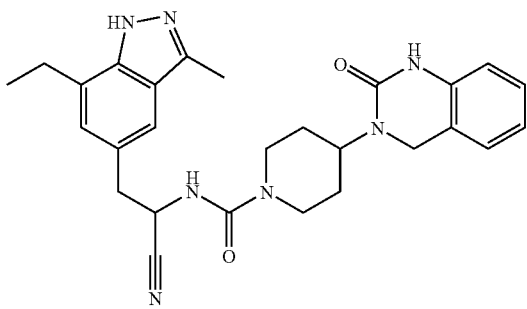

A stirred solution of 4-(2-oxo-1,4-dihydro-2H-quinazolin-3-yl)-piperidine-1-carboxylic acid [1-carbomoyl-2-(7-ethyl-3-methyl-1H-indazol-5-yl)-ethyl]-amide (0.25 g, 0.5 mmol) in pyridine (8 mL) at 0° C. was treated with trifluoroacetic anhydride (0.35 mL, 5.0 equiv). The mixture was stirred for 30 min, and quenched by the addition of excess methanol. The solvents were evaporated and the crude mixture dissolved in ethyl acetate and washed with 5% citric acid (2×), water (2×) and brine (2×), dried over sodium sulfate, and concentrated. The residue was purified by column chromatography to afford 0.24 g (99%) of the desired nitrile. $^1$H-NMR (CD$_3$OD) δ 1.35 (t, J=7.6, 3H), 1.53-1.69 (m, 4H), 2.54 (s, 3H), 2.84 (m, 2H), 2.92 (dd, J=7.6, 7.6, 1H), 3.19-3.28 (m, 2H), 4.10 (m, 2H), 4.18 (s, 1H), 4.19 (s, 1H), 4.38 (m, 1H), 4.93 (dd, J=7.9, 7.9, 1H) 6.77 (d, J=7.9, 1H), 6.93 (dd, J=7.3, 7.6, 1H), 7.0 (d, J=7.3, 1H), 7.15 (m, 2H), 7.46 (s, 1H). Mass spec.: 486.22 (MH)$^+$.

EXAMPLE 14

(±)-4-(2-Oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide

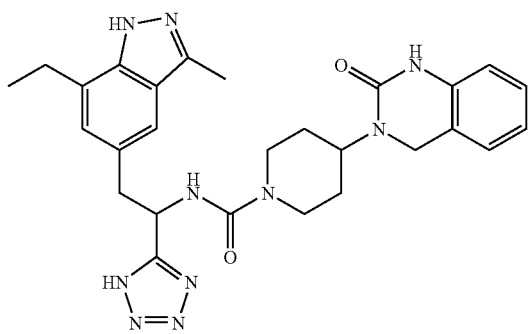

A stirred solution of 4-(2-oxo-1,4-dihydro-2H-quinazolin-3-yl)-piperidine-1-carboxylic acid [1-cyano-2-(7-ethyl-3-methyl-1H-indazol-5-yl)-ethyl]-amide (0.25 g, 0.5 mmol) in tetrahydrofuran (6 mL) was treated with azidotrimethyltin (0.16 g, 0.77 mmol). The resulting suspension was heated at reflux overnight. The solvents were evaporated, dissolved in ethyl acetate and washed with water (2×), brine (2×), dried over sodium sulfate, and concentrated. Column chromatography afforded the desired tetrazole. $^1$H-NMR (CD$_3$OD) δ 1.3 (t, J=7.6, 3H), 1.45-1.70 (m, 4H), 1.87 (m, 1H), 2.0 (s, 3H), 2.75-2.90 (m, 4H), 3.42 (m, 1H), 3.72 (d, J=6.6, 1H), 4.12 (m, 4H), 4.88 (m, 1H), 5.48 (dd, J=7.0, 7.9, 1H), 6.77 (d, J=7.9, 1H), 6.94 (m, 1H) 6.98 (s, 1H), 7.09 (d, J=7.3, 1H), 7.14 (dd, J=7.9, 7.6, 1H), 7.30 (s, 1H). Mass spec.: 529.26 (MH)$^+$.

EXAMPLE 15

(±)-4-(2-Oxo-1,4-dihydro-2H-quinazolin-3-yl)-piperidine-1-carboxylic acid [2-(7-ethyl-3-methyl-1H-indazol-5-yl)-1-(phenethyl-1H-tetrazol-5-yl)-ethyl]-amide and

EXAMPLE 16

(±)-4-(2-Oxo-1,4-dihydro-2H-quinazolin-3-yl)-piperidine-1-carboxylic acid [2-(7-ethyl-3-methyl-1H-indazol-5-yl)-1-(2-phenethyl-2H-tetrazol-5-yl)-ethyl]-amide

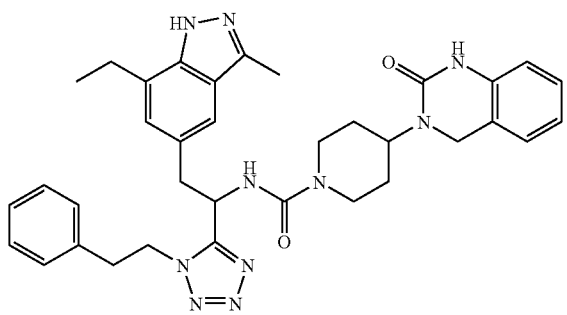

-continued

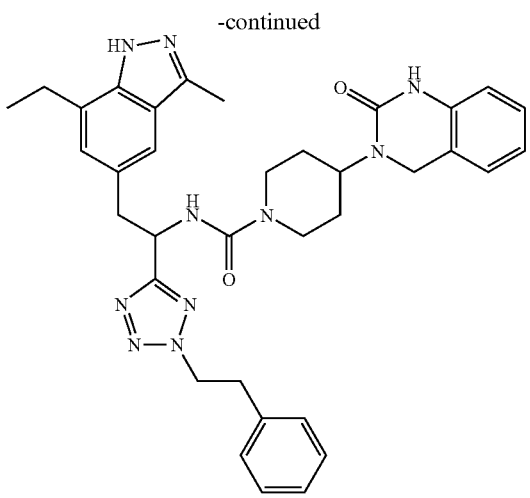

A mixture of 4-(2-oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide (30 mg, 0.05 mmol, 1.0 equiv), sodium carbonate (18.0 mg, 3.0 equiv), and 2-bromoethyl-benzene (11 mg, 1.1 equiv) were combined in dimethylsulfoxide and the mixture stirred at room temperature overnight. The mixture was then diluted with water and extracted with ethyl acetate (3×). The combined organic extracts were washed with water (3×), brine (3×), dried over sodium sulfate, and concentrated. Purification by preparative HPLC afforded the title regioisomers. $^1$H-NMR (CD$_3$OD) δ 1.24-1.35 (m, 6H), 1.43-1.72 (m, 5H), 2.5 (s, 3H), 3.40 (m, 1H), 4.14 (m, 3H), 4.38 (m, 1H), 4.84 (m, 1H), 4.85 (dd, J=7.0, 7.0, 1H), 5.45 (m, 1H), 6.75 (d, J=7.6, 1H), 6.93 (dd, J=7.3, 8.5, 1H), 7.04 (m, 3H), 7.10 (s, 1H), 7.15 (m, 4H). Mass spec.: 633.89 (MH)$^+$ and 4-(2-Oxo-1,4-dihydro-2H-quinazolin-3-yl)-piperidine-1-carboxylic acid [2-(7-ethyl-3-methyl-1H-indazol-5-yl)-1-(2-Phenethyl-2H-tetrazol-5-yl)-ethyl]-amide. $^1$H-NMR (CD$_3$OD) δ 1.15 (m, 7H), 1.29 (m, 3H), 2.5 (m, 3H), 2.82 (m, 1H), 2.85 (dd, J=7.3, 8.2, 1H), 3.4-3.6 (m, 2H) 14.3, 3H), 3.75-4.0 (m, 3H), 4.85 (m, 1H), 6.90-7.12 (m, 3H), 7.40 (s, 1H), 7.57 (dd, J=7.9, 6.4, 1H), 8.02 (s, 1H), 8.03 (s, 1H). Mass spec.: 633.89 (MH)$^+$.

EXAMPLE 17

(±)-4-(2-Oxo-1,4-dihydro-2H-quinazolin-3-yl)-piperidine-1-carboxylic acid [2-(7-ethyl-3-methyl-1H-indazol-5-yl)-1-(1-methyl-1H-tetrazol-5-yl)-ethyl]-amide

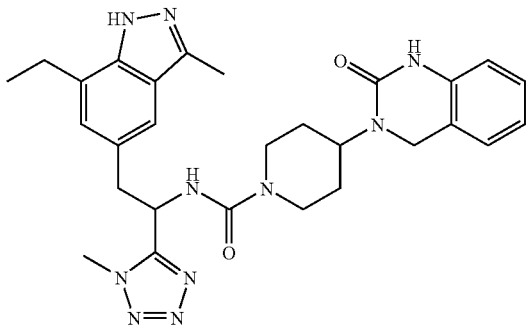

A mixture of 4-(2-oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide (50 mg, 0.1 mmol, 1.0 equiv), sodium carbonate (40.0 mg, 3.0 equiv), and iodomethane (24 μL, 3.0 equiv) were combined in dimethylsulfoxide and the mixture stirred at room temperature overnight. The mixture was then diluted with water and extracted with ethyl acetate (3×). The combined organic extracts were washed with water (3×), brine (3×), dried over sodium sulfate, and concentrated. Purification by preparative HPLC afforded the title compound. $^1$H-NMR (CD$_3$OD) δ 1.30 (m, 4H), 1.57 (m, 3H), 2.50 (s, 3H), 2.75-2.95 (m, 5H), 3.40 (m, 2H), 3.68 (m, 3H), 4.05-4.40 (m, 6H), 5.35 (m, 1H), 6.75 (m, 1H), 6.95 (dd, J=7.3, 7.6, 1H), 6.98 (s, 1H), 7.12 (m, 2H), 7.35 (s, 1H). Mass spec.: 543.42 (MH)$^+$.

EXAMPLE 18

(±)-4-(2-Oxo-1,4-dihydro-2H-quinazolin-3-yl)-piperidine-1-carboxylic acid [1-(1-benzyl-1H-tetrazol-5-yl)-2-(7-ethyl-3-methyl-1H-indazol-5-yl)-ethyl]-amide

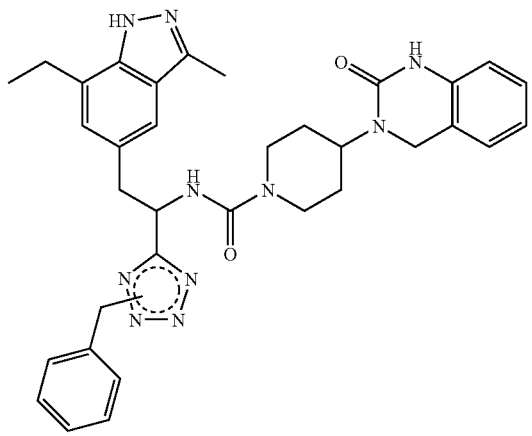

A mixture of 4-(2-oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide (30 mg, 0.05 mmol, 1.0 equiv), sodium carbonate (18.0 mg, 3.0 equiv), and benzyl bromide (8 μL, 1.1 equiv) were combined in dimethylsulfoxide and the mixture stirred at room temperature overnight. The mixture was then diluted with water and extracted with ethyl acetate (3×). The combined organic extracts were washed with water (3×), brine (3×), dried over sodium sulfate, and concentrated. Purification by preparative HPLC afforded a mixture of the two alkylated regioisomers which were not separated. LC/MS: $t_R$=1.68 min, 619.44 (MH)$^+$.

EXAMPLE 19

(±)-4-(2-Oxo-1,4-dihydro-2H-quinazolin-3-yl)-piperidine-1-carboxylic acid [2-(7-ethyl-3-methyl-1H-indazol-5-yl)-1-pyridin-4-yl methyl-1H-tetrazol-5-yl)-ethyl]-amide

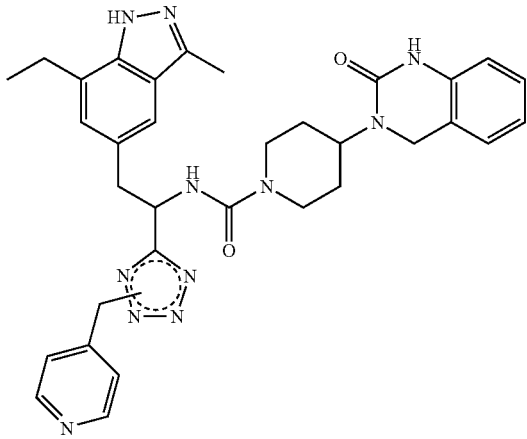

A mixture of 4-(2-oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide (30 mg, 0.05 mmol, 1.0 equiv), sodium carbonate (18.0 mg, 3.0 equiv), and benzyl bromide (17 mg, 1.1 equiv) were combined in dimethylsulfoxide and the mixture stirred at room temperature overnight. The mixture was then diluted with water and extracted with ethyl acetate (3×). The combined organic extracts were washed with water (3×), brine (3×), dried over sodium sulfate, and concentrated. Purification by preparative HPLC afforded a mixture of the two alkylated regioisomers which were not separated. LC/MS: $t_R$=1.68 min, 619.44 (MH)⁺.

EXAMPLE 20

(±)-4-(2-Oxo-1,4-dihydro-2H-quinazolin-3-yl)-piperidine-1-carboxylic acid [2-(7-ethyl-3-methyl-1H-indazol-5-yl)-1-(2-oxo-2Phenethyl-2H-tetrazol-5-yl)-ethyl]-amide and

EXAMPLE 21

(±)-4-(2-Oxo-1,4-dihydro-2H-quinazolin-3-yl)-piperidine-1-carboxylicacid [2-(7-ethyl-3-methyl-1H-indazol-5-yl)-1-[1-(2-oxo-2-phenyl-ethyl)-1H-tetrazol-5-yl)-ethyl]-amide

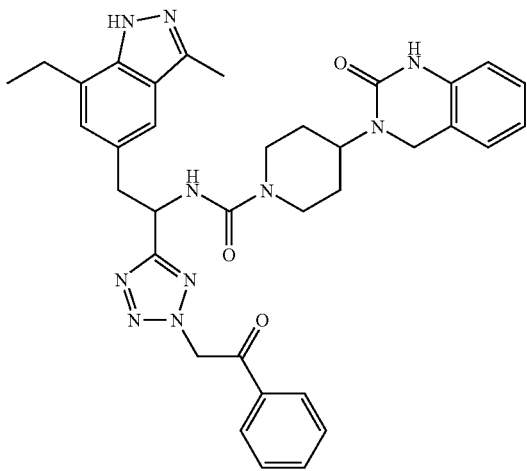

-continued

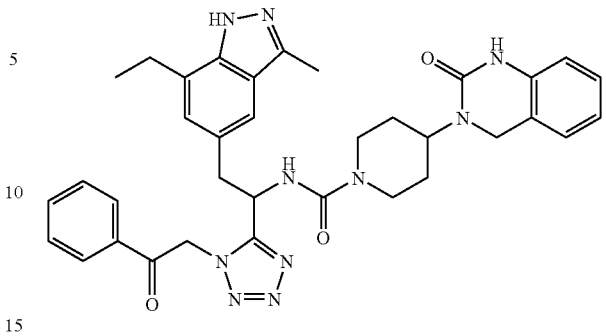

A mixture of 4-(2-oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide (30 mg, 0.05 mmol, 1.0 equiv), sodium carbonate (18.0 mg, 3.0 equiv), and 2-bromoethyl-benzene (8 µL, 1.1 equiv) were combined in dimethylsulfoxide and the mixture stirred at room temperature overnight. The mixture was then diluted with water and extracted with ethyl acetate (3×). The combined organic extracts were washed with water (3×), brine (3×), dried over sodium sulfate, and concentrated. Purification by preparative HPLC afforded the title regioisomers. ¹H-NMR (CD₃OD) δ 0.88 (m, 3H), 1.10-1.40 (m, 8H), 1.46-1.78 (m, 6H), 1.94 (s, 1H), 2.5 (m, 2H), 2.78-2.93 (m, 2H), 3.33-3.68 (m, 3H), 4.06-4.43 (m, 3H), 5.50 (m, 1H), 6.87 (m, 1H), 6.91 (m, 1H), 7.10 (m, 2H), 7.65-7.80 (m, 3H), 8.07 (d, J=8.6, 1H). Mass spec.: 647.83 (MH)+ and 4-(2-Oxo-1,4-dihydro-2H-quinazolin-3-yl)-piperidine-1-carboxylicacid [2-(7-ethyl-3-methyl-1H-indazol-5-yl)-1-[1-(2-oxo-2-phenyl-ethyl)-1H-tetrazol-5-yl)-ethyl]-amide. ¹H-NMR (CD₃OD) δ 1.25-1.40 (m, 6H), 1.58 (d, J=15.87, 1H), 2.48 (m, 2H), 2.50-2.60 (m, 2H), 2.77-2.93 (m, 2H), 3.30-3.60 (m, 6H), 3.80 (dd, J=11.9, 13.1, 1H), 3.92 (d, J=14.0, 14.0, 1H), 3.96 (d, J=14.0, 1H), 4.07-4.22 (m, 2.5H), 5.40-5.55 (m, 1H), 6.10-6.30 (m, 2H), 6.75 (dd, J=7.3, 7.3, 1H), 6.92 (m, 1H), 7.03-7.16 (m, 3H) 7.41 (s, 1H), 7.57 (m, 2H), 7.70 (m,1H). Mass spec.: 647.85 (MH)⁺.

Ethyl 4-(7-methyl-2-((2-(trimethylsilyl)ethoxy)methyl)-2H-indazol-5-yl)but-2-enoate

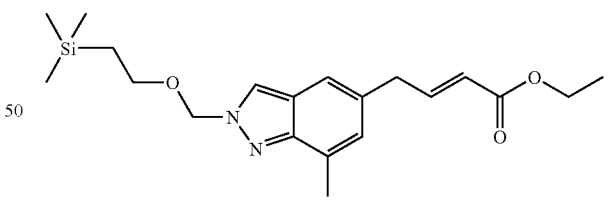

To the clear solution of ethyl 4-(7-methyl-1H-indazol-5-yl)but-2-enoate (760 mg, 3.11 mmol, 1.0 equiv.) in tetrahydrofuran (10 mL) was added dicyclohexylmethyl amine (2.6 mL, 6.2 mL, 2.0 equiv) followed by 2-(trimethylsilyl) ethoxymethyl chloride (0.66 mL, 3.73 mmol, 1.2 equiv). The reaction mixture was stirred at room temperature for 2 h. The mixture was partitioned between 0.5 N sodium hydroxide and ethyl acetate. The organic layer was separated and washed with brine, dried over sodium sulfate and concentrated in vacuo. The residual colorless oil was purified by flash column chromatography (20% ethyl acetate in hexanes) to afford the desired product as a colorless oil (1.08 g, 93%). MS (ESI) [M+H]⁺=375.

(±)-Ethyl 3-(4-ethylpyridin-2-yl)-4-(7-methyl-2-((2-(trimethylsilyl)ethoxy)methyl)-2H-indazol-5-yl)butanoate

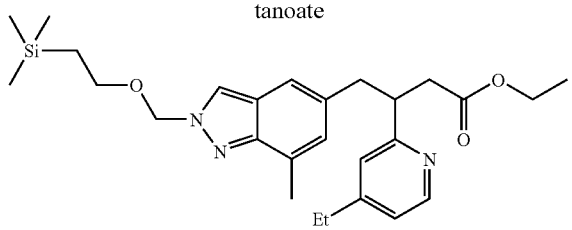

To a solution of 2-bromo-4-ethylpyridine (310 mg, 1.665 mmol, 4.4 equiv) in anhydrous ether (1.2 mL) at −70° C. in an oven-dried flask was added n-butyllithium (2.5 M, 0.67 mL, 1.66 mmol, 4.4 equiv) dropwise under nitrogen via syringe. The resulting deep-red solution was stirred for 5 min before use in the next step.

To a 50-mL oven-dried flask was added di-n-butylsulfide (244 mg, 1.665 mmol, 4.4 equiv) and cuprous iodide (159 mg, 0.832 mmol, 2.2 equiv) under nitrogen. Anhydrous ether (1.2 mL) was added and the suspension was cooled to 0° C. before the solution of 2-pyridinyl lithium was added via canuula. A yellowish brown precipitate was formed. After stirring at 0° C. for 20 min, the cooling bath was removed and ethyl 4-(7-methyl-2-((2-(trimethylsilyl)ethoxy)methyl)-2H-indazol-5-yl)but-2-enoate (141.7 mg, 0.378 mmol, 1.0 equiv.) in anhydrous ether (1.2 mL) was added via syringe. The solution was stirred at room temperature for 1 h. The reaction mixture was then partitioned between an aqueous ammonium hydroxide/ammonium chloride solution and ethyl acetate (upon shaking, the solids gradually dissolved to a give blue aqueous solution). The layers were separated and the organic layer was washed with water, brine, dried over sodium sulfate and concentrated in vacuo. Flash column chromatography (5% methanol in methylene chloride) afforded the desired product (80 mg, 44%) which was carried on without farther purification. MS (ESI) 482 (MH)⁺.

(±)-3-(4-Ethylpyridin-2-yl)-4-(7-methyl-2-((2-(trimethylsilyl)ethoxy)methyl)-2H-indazol-5-yl)butanoic acid

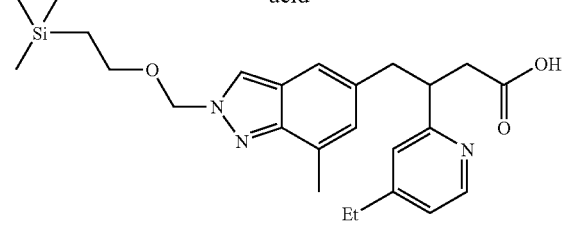

To a flask containing (±)-ethyl 3-(4-ethylpyridin-2-yl)-4-(7-methyl-2-((2-(trimethylsilyl)ethoxy)methyl)-2H-indazol-5-yl)butanoate (80 mg, 0.166 mmol, 1.0 equiv) in tetrahydrofuran (4 mL) was added lithium hydroxide (2.0 M, 0.34 mL, 4.0 equiv). The suspension was heated at 60° C. under nitrogen overnight. The reaction mixture was concentrated in vacuo. Hydrochloric acid (1 N, 0.6 mL) was added and the solution was extracted with ethyl acetate. The aqueous solution was adjusted to pH 7 with sodium hydroxide (1 N) and re-extracted with ethyl acetate. The combined ethyl acetate layers were washed with brine, dried over sodium sulfate and concentrated in vacuo to give a light yellow oil. MS (ESI) 454 (MH)⁺.

(±)-3-(1-(3-(4-Ethylpyridin-2-yl)-4-(7-methyl-2-((2-(trimethylsilyl)ethoxy)methyl)-2H-indazol-5-yl)butanoyl)piperidin-4-yl)-3,4-dihydroquinazolin-2(1H)-one

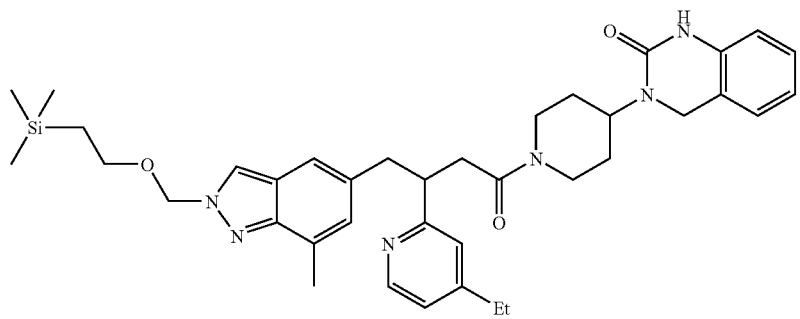

To a solution of (±)-3-(4-ethylpyridin-2-yl)-4-(7-methyl-2-((2-(trimethylsilyl)ethoxy)methyl)-2H-indazol-5-yl)butanoic acid (0.166 mmol, 1.0 equiv) in methylene chloride (3 mL) was added 3,4-dihydro-3-(4-piperidinyl-2(1H)-quinazolinone (46 mg, 0.199 mmol, 1.2 equiv). Triethylamine (70 μL) was then added followed by 3-(diethoxyphosphoryloxy)-1,2,3-benzotriain-4(3H)-one (DEPBT, 60 mg, 0.199 mmol 1.2 equiv) under nitrogen. The resulted cloudy yellow solution was stirred at room temperature overnight. The reaction mixture was diluted with ethyl acetate and quenched with 0.5 N sodium hydroxide solution. The layers were separated and the organic layer was washed with brine, dried over sodium sulfate and concentrated in vacuo. The residue was purified by flash column chromatography (10% methanol in methylene chloride) to afford the desired product (72 mg, 65% for two steps): (ESI) 667 (MH)⁺.

EXAMPLE 22

(±)-3-(1-(3-(4-Ethylpyridin-2-yl)-4-(7-methyl-1H-indazol-5-yl)butanoyl)piperidin-4-yl)-3,4-dihydroquinazolin-2(1H)-one

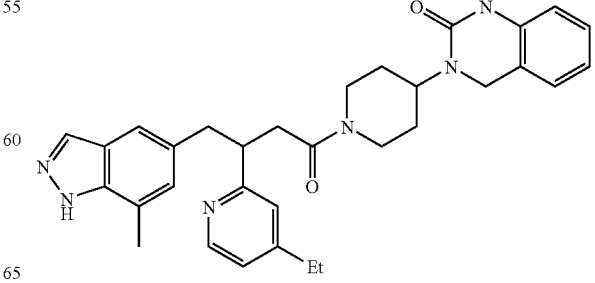

To the solution of (±)-3-(1-(3-(4-ethylpyridin-2-yl)-4-(7-methyl-2-((2-(trimethylsilyl)ethoxy)methyl)-2H-indazol-5- yl)butanoyl)piperidin-4-yl)-3,4-dihydroquinazolin-2(1H)-one (69 mg, 0.103 mmol) in tetrahydrofuran (2 mL) was added 1M tetrabutylammonium fluoride in tetrahydrofuran (0.21 mL, 0.207 mmol, 2 equiv). The mixture was stirred at 60° C. under nitrogen for 4 h. Tetrahydrofuran was removed in vacuo and the residue was partitioned between water and ethyl acetate. The layers were separated and the organic layer was washed with brine, dried over sodium sulfate and concentrated in vacuo. The residue was purified by flash column chromatography (10% methanol in methylene chloride) to afford the desired product (50.3 mg, 91%) as a white powder: MS (ESI) [M+H]$^+$=537. $^1$H-NMR (400 MHz, CDCl$_3$) δ 8.48-8.42 (m, 1H), 7.95-7.91 (m, 2H), 7.22-7.10 (m, 2H), 7.06-6.60 (m, 6H), 4.70-4.64 (m, 1H), 4.60-4.42 (m, 1H), 4.24-3.90 (m, 3H), 3.78-3.60 (m, 1H), 3.26-2.92 (m, 3H), 2.92-2.38 (m, 8H), 1.78-1.50 (m, 3H), 1.50-1.12 (m, 2H), 1.12-0.94 (m, 3H).

The following examples were prepared using methodologies analogous to those used to prepare Example 22:

EXAMPLE 23

(±)-8-Fluoro-3-(1-(4-(7-methyl-1H-indazol-5-yl)-3-(pyridin-2-yl)butanoyl)piperidin-4-yl)-3,4-dihydroquinazolin-2(1H)-one

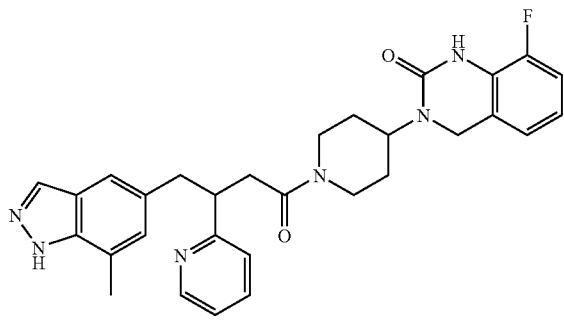

MS (ESI) [M+H]$^+$=527, $^1$H-NMR (400 MHz, CDCl$_3$) δ 8.68-8.50 (m, 1H), 7.92 (d, J=4.8 Hz, 1H), 7.56-7.36 (m, 2H), 7.24-6.70 (m, 7H), 4.76-4.60 (m, 1H), 4.60-4.42 (m, 1H), 4.26 (s, 1H), 4.13 (s, 1H), 4.01 (t, 1H), 3.80-3.62 (m, 1H), 3.20-2.76 (m, 4H), 2.72-2.32 (m, 5H), 1.78-1.46 (m, 3H), 1.46-1.12 (m, 2H).

EXAMPLE 24

(±)-3-(1-(4-(7-Methyl-1H-indazol-5-yl)-3-(pyridin-2-yl)butanoyl)piperidin-4-yl)quinolin-2(1H)-one

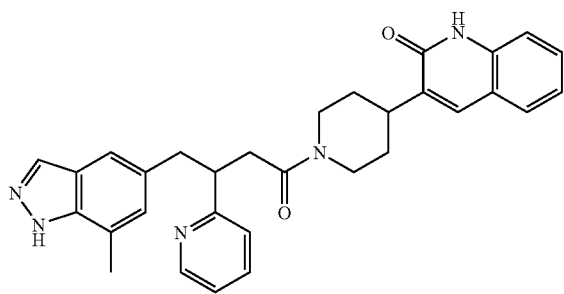

MS (ESI) [M+H]$^+$=506, $^1$H-NMR (400 MHz, CDCl$_3$) δ 8.60-8.54 (m, 1H), 7.92 (s, 1H), 7.50-6.86 (m, 10H), 4.72 (d, J=12.8 Hz, 1H), 4.03 (d, J=13.0 Hz, 1H), 3.78-3.70 (m, 1H), 3.20-2.90 (m, 5H), 2.80-2.50 (m, 2H), 2.42 (s, 3H), 2.42-2.10 (br, 1H), 2.06-1.80 (m, 2H), 1.58-0.96 (m, 3H). HPLC t$_R$=1.23 min.

EXAMPLE 25

(±)-3-(1-(4-(7-Methyl-1H-indazol-5-yl)-3-(3-methylpyridin-2-yl)butanoyl)piperidin-4-yl)-3,4-dihydroquinazolin-2(1H)-one

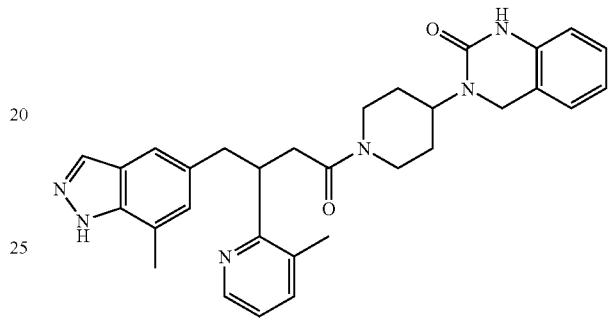

MS (ESI) [M+H]$^+$=523, $^1$H-NMR (400 MHz, CDCl$_3$) δ 8.52-8.40 (m, 1H), 7.93 (s, 1H), 7.26-6.60 (m, 9H), 4.72-4.36 (m, 2H), 4.24 (s, 1H), 4.20-3.90 (m, 2H), 3.20-2.78 (m, 2H), 2.46 (s, 3H), 2.30-1.96 (m, 2H), 1.90-1.24 (m, 8H), 1.24 (s, 3H).

EXAMPLE 26

(±)-3-(1-(4-(7-Methyl-1H-indazol-5-yl)-3-(5-methylpyridin-2-yl)butanoyl)piperidin-4-yl)-3,4-dihydroquinazolin-2(1H)-one

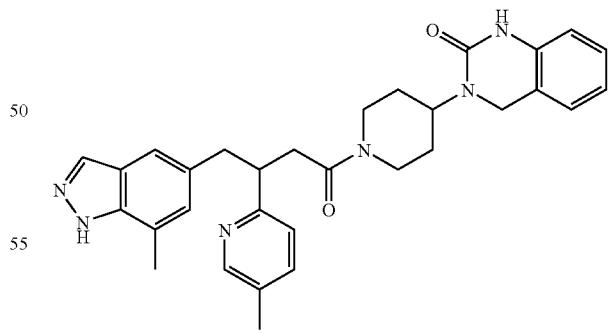

MS (ESI) [M+H]$^+$=523, $^1$H-NMR (400 MHz, CDCl$_3$) δ 8.39 (d, J=11.2 Hz, 1H), 8.02 (d, J=16.8 Hz, 1H), 7.93 (d, J=4.8 Hz, 1H), 7.32-7.05 (m, 3H), 7.05-6.78 (m, 4H), 6.78-6.65 (m, 1H), 4.72-4.60 (m, 1H), 4.60-4.42 (m, 1H), 4.22 (s, 1H), 4.10 (s, 1H), 4.08-3.90 (m, 1H), 3.78-3.60 (m, 1H), 3.20-2.78 (m, 4H), 2.70-2.56 (m, 1H), 2.44 (d, J=6.8 Hz, 3H), 2.25 (s, 3H), 1.80-1.52 (m, 4H), 1.52-1.10 (m, 2H).

EXAMPLE 27

(±)-3-(1-(3-(5-(Hydroxymethyl)pyridin-2-yl)-4-(7-methyl-1H-indazol-5-yl)butanoyl)piperidin-4-yl)-3,4-dihydroquinazolin-2(1H)-one

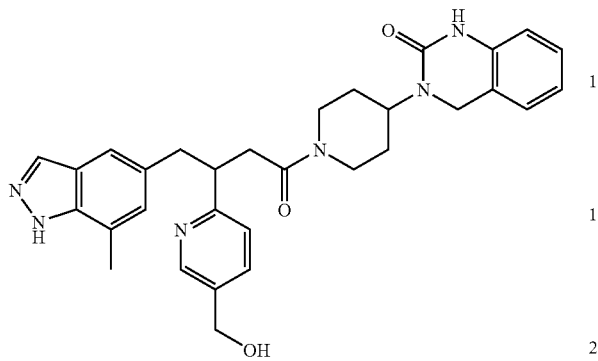

MS (ESI) [M+H]⁺=539, ¹H-NMR (500 MHz, CD₃OD) δ 8.53 (d, J=26.0 Hz, 1H), 7.89 (d, J=7.5 Hz, 1H), 7.66-7.58 (m, 1H), 7.23 (d, J=8.5 Hz, 1H), 7.20-7.07 (m, 4H), 6.98 (d, J=8.5 Hz, 1H), 6.96-6.90 (m, 1H), 6.78 (dd, J=8.0 and 2.0 Hz, 1H), 4.61 (s, 2H), 4.60-4.48 (m, 2H), 4.45-4.32 (m, 1H), 4.32 (s, 1H), 4.20 (s, 1H), 4.06 (t, J=15.0 Hz, 1H), 3.72-3.64 (m, 1H), 3.34-3.31 (m, 1H), 3.28-2.94 (m, 5H), 2.82-2.50 (m, 2H), 1.90-1.20 (m, 6H).

EXAMPLE 28

(±)-6-(1-(7-Methyl-1H-indazol-5-yl)-4-oxo-4-(4-(2-oxo-1,2-dihydroquinazolin-3(4H)-yl)piperidin-1-yl)butan-2-yl)nicotinaldehyde

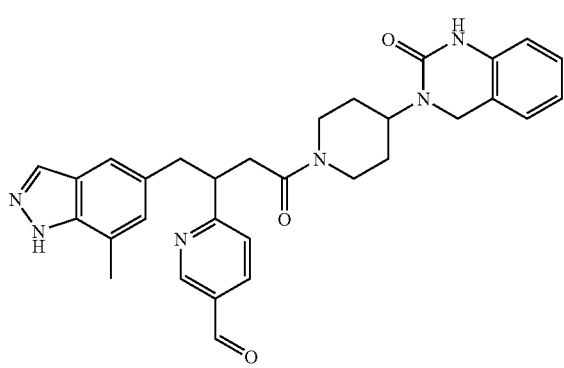

Solid (±)-3-(1-(3-(5-(hydroxymethyl)pyridin-2-yl)-4-(7-methyl-1H-indazol-5-yl)butanoyl)piperidin-4-yl)-3,4-dihydroquinazolin-2(1H)-one (20.9 mg, 0.025 mmol, 1.0 equiv) and Dess-Martin reagent (21.8 mg, 2.0 equiv) were dissolved in anhydrous methylene chloride (2 mL). The cloudy solution was stirred at room temperature for 1 h. The reaction was quenched with 0.5 N sodium hydroxide. The layers were separated and the organic layer was washed with brine, dried over sodium sulfate and concentrated to give an off-white solid. Purification by flash column chromatography (10% MeOH in methylene chloride) afforded the desired product (9.5 mg, 69%) as a colorless oily solid. ¹H-NMR (400 MHz, CDCl₃) δ 10.02 (d, J=8.0 Hz, 1H), 9.06 (d, J=16.4 Hz, 1H), 7.94-7.82 (m, 2H), 7.18-7.08 (m, 4H), 7.08-6.84 (m, 3H), 6.65 (d, J=7.6 Hz, 1H), 4.68-4.44 (m, 2H), 4.24, 4.16 (2s, 1H), 4.05-3.95 (m, 1H), 3.88-3.76 (br. 1H), 3.30-2.92 (m, 4H), 2.72-2.47 (m, 2H), 2.47 (s, 3H), 1.84-1.35 (m, 6H).

EXAMPLE 29

(±)-3-(1-(4-(7-Methyl-1H-indazol-5-yl)-3-(5-(piperidin-1-ylmethyl)pyridin-2-yl)butanoyl)piperidin-4-yl)-3,4-dihydroquinazolin-2(1H)-one

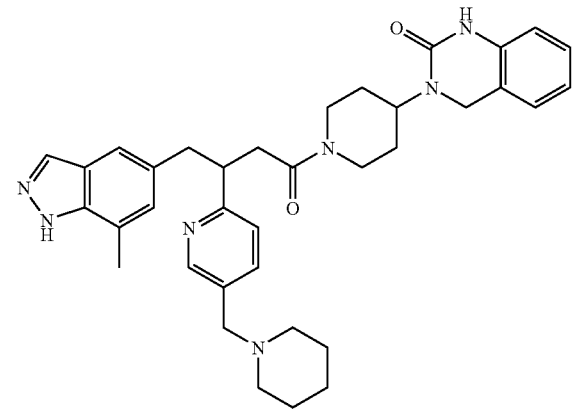

A solution of (±)-6-(1-(7-methyl-1H-indazol-5-yl)-4-oxo-4-(4-(2-oxo-1,2-dihydroquinazolin-3(4H)-yl)piperidin-1-yl)butan-2-yl)nicotinaldehyde (previous example, 8 mg, 0.015 mmol, 1.0 equiv.) in dichloroethane (1 mL) was treated with by 2 drops of piperidine. Excess Na(OAc)₃BH was added and the reaction mixture was stirred at room temperature overnight. The mixture was directly purified by flash column chromatography (10% of 2M ammonia in methanol in methylene chloride) afforded the desired product (10.1 mg, 72% for two steps).

MS (ESI) [M+H]⁺=606, ¹H-NMR (400 MHz, CDCl₃) δ 8.47 (d, J=16.0 Hz, 1H), 7.89 (d, J=8.0 Hz, 1H), 7.42-7.33 (m, 1H), 7.16-7.10 (m, 2H), 7.04-6.97 (m, 2H), 6.94-6.85 (m, 3H), 6.64 (d, J=8.0 Hz, 1H), 4.67 (d, J=14.0 Hz, 1H), 4.60-4.45 (m, 1H), 4.24, 4.14 (2s, 1H), 4.10-3.90 (m, 1H), 3.70-3.64 (m, 1H), 3.41-3.37 (m, 2H), 3.18-2.80 (m, 5H), 2.72-2.10 (m, 12H), 1.75-1.28 (m, 8H). HPLC t_R=1.22 min.

4-Nitrophenyl 4-(2-oxo-1,2-dihydroquinazolin-3(4H)-yl)piperidine-1-carboxylate

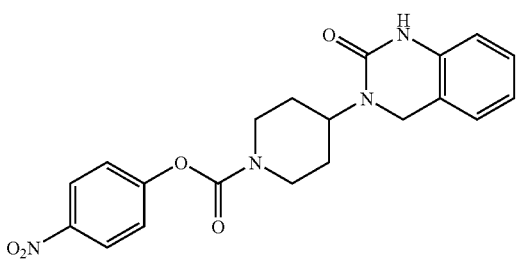

To a solution of 3-(piperidin-4-yl)-3,4-dihydroquinazolin-2(1H)-one hydrochloride salt (1.5347 g, 5.73 mmol) in methylene chloride (100 mL) and triethylamine (2.39 mL, 3.0 equiv) was added nitrophenylchloroformate (1.3863 g, 1.2 equiv) at room temperature under nitrogen. The reaction was stirred at room temperature overnight. The solvent was removed in vacuo to give a yellow solid. This solid was taken up in methylene chloride (60 mL) and washed with 1 N sodium hydroxide (30 mL). The methylene chloride layer was dried over sodium sulfate, filtered and concentrated to give a solid. The solid was further tritrated with methylene chloride (20 mL) to give the desired product (1.41 g, 62%). HPLC $t_R$=1.85 min, MS(ESI)[M+H$^+$=397.07.

Similarly prepared:

4-Nitrophenyl 4-(8-fluoro-2-oxo-1,2-dihydro-quinazolin-3(4H)-yl)piperidine-1-carboxylate

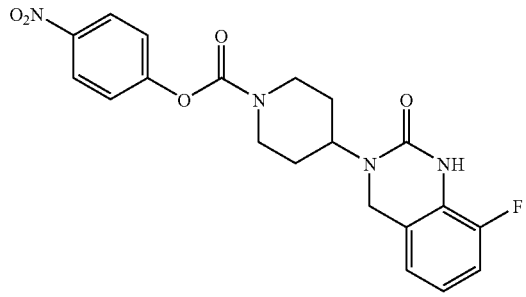

Yield: 60%. $^1$H-NMR (500 MHz, DMSO-d$_6$) δ 9.28 (s, 1H), 8.30 (d, J=9.2 Hz, 2H), 7.47 (d, J=9.2 Hz, 2H), 7.08-7.04 (m, 1H), 6.98 (d, J=7.3 Hz, 1H), 6.91-6.88 (m, 1H), 4.46-4.40 (m, 1H), 4.41 (s, 2H), 4.32-4.26 (m, 1H), 4.18-4.13 (m, 1H), 3.19-3.14 (m, 1H), 3.05-2.99 (m, 1H), 1.95-1.80 (m, 2H), 1.68-1.66 (m, 2H).

Mass spec.: 415 (MH)$^+$.

Isoquinoline-3-carbaldehyde

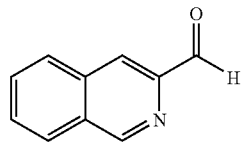

A solution of methyl 3-isoquinolinecarboxylate (2.0 g, 10.7 mmol) in toluene was cooled to −78° C. To the solution was added diisobutylaluminum hydride (1M in toluene, 21.4 mL, 21.4 mmol) slowly over 15 minutes via syringe. While still at −78° C., the reaction was quenched with a solution of ether (80 mL), acetic acid (20 mL) and water (8 mL) and then the mixture was allowed to slowly warm to room temperature overnight. The organics were decanted and the solvent was evaporated. Flash column chromatography (gradient 1:4 ethyl acetate/hexanes to 1:3 ethyl acetate/hexanes) provided 1.1 grams of the title compound (65% yield). $^1$H-NMR (CDCl$_3$, 300 MHz) δ 10.24 (s, 1H), 9.35 (s, 1H), 8.36 (s, 1H), 8.07-7.98 (m, 2H), 7.82-7.32 (m, 2H). Mass spec.: 158 (MH)$^+$.

Diphenyl (6-bromopyridin-2-yl)(phenylamino)methylphosphonate

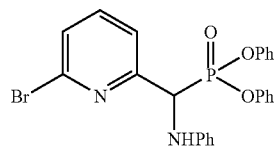

To 2-bromopyridyl-6-carboxaldehyde (1.92 g, 10 mmol) dissolved in isopropanol (22 mL) at room temperature, was added aniline (1.1 mL, 12 mmol) followed by (PhO)$_2$P(O)H (3.4 mL, 16 mmol). The mixture was stirred at room temperature for 1 h. The mixture was left to stand at room temperature for 2 h and was cooled in a refrigerator for 20 min before the solids were filtered and washed three times with isopropanol. Drying under high vacuum afforded the desired product as a white solid (4.38 g, 88%). MS (ESI) [M+H]$^+$=495.

The following intermediates were similarly prepared:

Diphenyl (4-nitropyridin-2-yl)(phenylamino)methylphosphonate

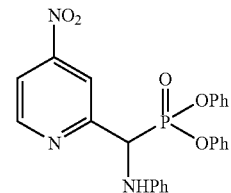

MS (ESI) [M+H]$^+$=484. HPLC $t_R$=1.83 min.

Diphenyl (phenylamino)(quinolin-2-yl)methylphosphonate

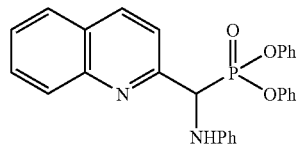

Yield: 83.2%. MS (ESI) [M+H]$^+$=467. HPLC $t_R$=1.93 min.

Diphenyl (6-tert-butoxypyridin-2-yl)(phenylamino)methylphosphonate

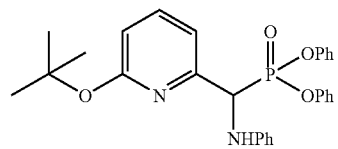

Yield: 82.3%. MS (ESI) [M+Na]$^+$=511. HPLC $t_R$=2.03 min.

Diphenyl (4-((tert-butyldimethylsilyloxy)methyl)pyridin-2-yl) (phenylamino) methyl-phosphonate

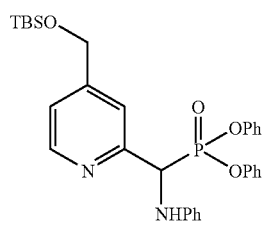

Yield: 78.2%. MS (ESI) [M+H]$^+$=561. HPLC $t_R$=2.36 min.

Methyl 2-((diphenoxyphosphoryl)(phenylamino)methyl)isonicotinate

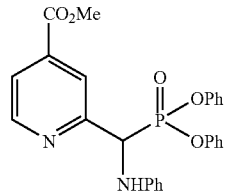

Yield: 74.6%. MS (ESI) [M+Na]⁺=496. HPLC $t_R$=2.03 min.

Diphenyl isoquinolin-3-yl(phenylamino)methylphosphonate

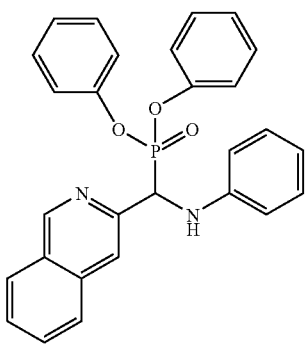

Yield: 84%. ¹H-NMR (DMSO-$d_6$, 300 MHz) δ 9.33 (s, 1H), 8.17-8.12 (m, 2H), 7.94 (d, J=8.1 Hz, 1H), 7.70 (t, J=7.0 Hz, 1H), 7.68 (t, J=7.4 Hz, 1H), 7.37-7.25 (m, 4H), 7.21-7.04 (m, 6H), 6.99-6.02 (m, 4H), 6.71 (dd, J=10.2, 4.8 Hz, 1H), 6.59 (t, J=7.0 Hz, 1H), 5.80 (d, J=10.2 Hz, 0.5H), 5.72 (d, J=10.2 Hz, 0.5H). Mass spec.: 467 (MH)⁺.

Diphenyl (4,6-dimethylpyrimidin-2-yl)(phenylamino)methylphosphonate

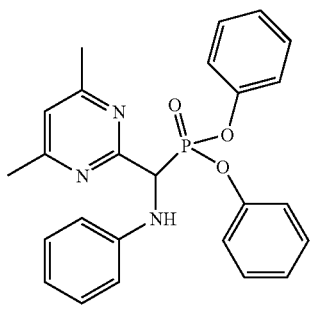

Yield: 92%. ¹H-NMR (400 MHz, CDCl₃) δ 7.24-6.74 (14H, m), 5.53 (1H, d, J=24.), 2.37 (6H, s). HPLC $t_R$=2.05 min, MS(ESI)[M+H⁺]=446.11.

Diphenyl furan-2-yl(phenylamino)methylphosphonate

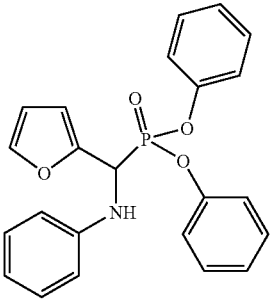

Yield: 98%. ¹H-NMR (400 MHz, CDCl₃) δ 7.37-6.31 (18H, m), 5.30 (1H, d, J=24.4 Hz). HPLC $t_R$=2.10 min, MS(ESI)[M+Na⁺]=428.04.

Diphenyl benzofuran-2-yl(phenylamino)methylphosphonate

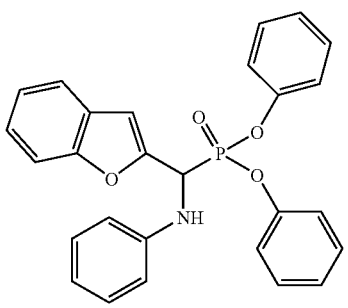

Yield: 98%. ¹H-NMR (400 MHz, CDCl₃) δ 7.37-6.31 (20H, m), 5.41 (1H, d, J=24.8 Hz). HPLC $t_R$=2.23 min, MS(ESI) [M+H⁺]=456.01.

7-Methyl-2-((2-(trimethylsilyl)ethoxy)methyl)-2H-indazole-5-carbaldehyde

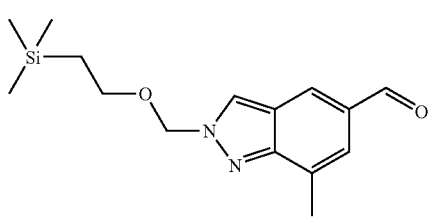

To a solution of 7-methyl-1H-indazole-5-carbaldehyde (5.0 g, 31.25 mmol) and N-methyl-dicyclohexylamine (13.5 mL, 62.35 mmol) in dry tetrahydrofuran (120 mL) at 0° C., was added 2-(trimethylsilyl)ethoxymethyl chloride (6.65 mL, 39.5 mmol). The ice-bath was removed and stirring continued for 5 h. The reaction mixture was diluted with ethyl acetate, washed with water (2×), brine (2×), dried over sodium sulfate, and concentrated in vacuo. Column chromatography afforded 8.5 g (93%). ¹H-NMR (400 MHz, CDCl₃) δ 12.3 (br., 1H), 8.13 (s, 1H), 7.88 (s, 1H), 7.42 (s, 1H), 6.12 (d, J=7.0 Hz, 1H), 5.31 (d, J=7.0 Hz, 1H), 3.80 (s, 3H), 2.60 (s, 3H).

1-(6-Bromopyridin-2-yl)-2-(7-methyl-2-((2-(trimethylsilyl)ethoxy)methyl)-2H-indazol-5-yl)ethanone

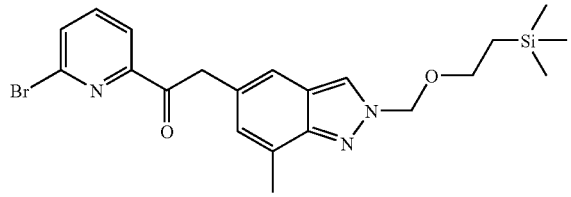

To an oven-dried flask under nitrogen was charged with cesium carbonate (1.98 g, 6.09 mmol, 1.3 equiv, dried at 150° C. under high vacuum for 16 h) followed by diphenyl (6-bromopyridin-2-yl)(phenylamino)methylphosphonate (2.32 g, 4.68 mmol) and 7-methyl-2-((2-(trimethylsilyl)ethoxy)methyl)-2H-indazole-5-carbaldehyde (1.36 g, 4.68 mmol). Anhydrous tetrahydrofuran (9.6 mL) was introduced followed by anhydrous isopropanol (2.4 mL) via syringe under nitrogen. The yellow suspension was stirred at room temperature under nitrogen overnight (16.5 h). To the resulting suspension was added 1N hydrochloric acid (16 mL) and the resulting red solution was stirred at room temperature for 2 h until LCMS showed complete hydrolysis to the desired product. The reaction mixture was neutralized with 1N sodium hydroxide (12 mL) and then extracted with ethyl acetate (3×). The combined organic layers was washed with brine, dried over sodium sulfate and concentrated in vacuo. The residue was purified by flash column chromatography to afford the desired product as a yellow oil (2.013 g, 93.6%). MS (ESI) [M+H]$^+$=461. HPLC $t_R$=2.09 min.

The following intermediates were similarly prepared:

2-(7-Methyl-2-((2-(trimethylsilyl)ethoxy)methyl)-2H-indazol-5-yl)-1-(quinolin-2-yl)ethanone

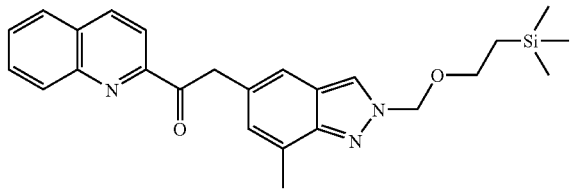

Yield: 75.4% (2 steps). MS (ESI) [M+H]$^+$=432. HPLC $t_R$=2.11 min.

1-(6-tert-Butoxypyridin-2-yl)-2-(7-methyl-2-((2-(trimethylsilyl)ethoxy)methyl)-2H-indazol-5-yl)ethanone

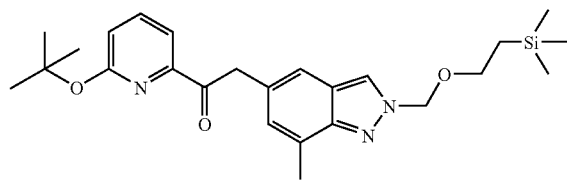

Yield: 100%. MS (ESI) [M+H]$^+$=454. HPLC $t_R$=2.16 min.

Methyl 2-(2-(7-methyl-2-((2-(trimethylsilyl)ethoxy)methyl)-2H-indazol-5-yl)acetyl)isonicotinate

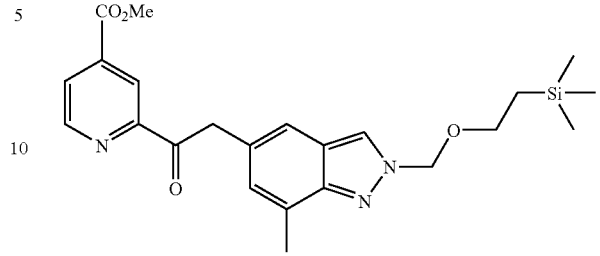

MS (ESI) [M+H]$^+$=440. HPLC $t_R$=2.20 min. Mixed with the isopropyl ester (from solvent exchange): MS (ESI) [M+H]$^+$=468. HPLC $t_R$=2.31 min.

2-(7-Methyl-2-((2-(trimethylsilyl)ethoxy)methyl)-2H-indazol-5-yl)-1-(pyridin-2-yl)ethanone

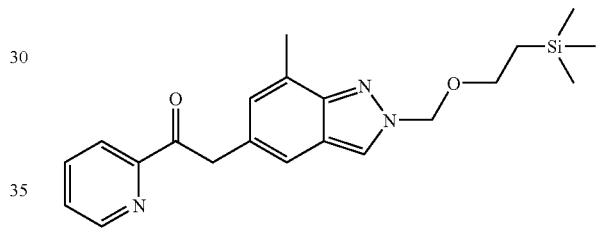

Yield: 80%. $^1$H-NMR (CDCl$_3$, 300 MHz) δ 8.71 (d, J=4.8 Hz, 1H), 8.04 (d, J=8.8 Hz, 1H), 7.98 (s, 1H), 7.83-7.77 (m, 1H), 7.47-7.43 (m, 1H), 7.42 (s, 1H), 7.00 (s, 1H), 5.68 (s, 2H), 4.55 (s, 2H), 3.60-3.55 (m, 2H), 2.57 (s, 3H), 0.93-0.87 (m, 2H), −0.06 (s, 9H). Mass spec.: 382 (MH)$^+$.

1-(Isoquinolin-3-yl)-2-(7-methyl-2-((2-(trimethylsilyl)ethoxy)methyl)-2H-indazol-5-yl)ethanone

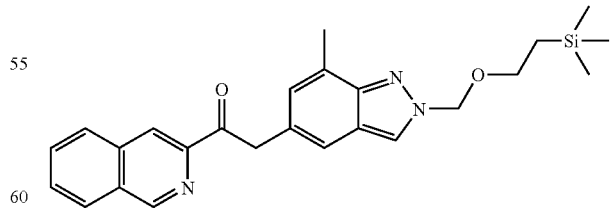

Yield: 53%. $^1$H-NMR (CDCl$_3$, 300 MHz) δ 9.31 (s, 1H), 8.48 (s, 1H), 8.05-8.02 (m, 1H), 7.98 (s, 1H), 7.97-7.94 (m, 1H), 7.77-7.68 (m, 2H), 7.46 (s, 1H), 7.06 (s, 1H), 5.68 (s, 2H), 4.66 (s, 2H), 3.60-3.54 (m, 2H), 2.58 (s, 3H), 0.92-0.85 (m, 2H), −0.07 (s, 9H). Mass spec.: 432 (MH)$^+$.

(±)-1-(6-Bromopyridin-2-yl)-2-(7-methyl-2-((2-(trimethylsilyl)ethoxy)methyl)-2H-indazol-5-yl)ethanol

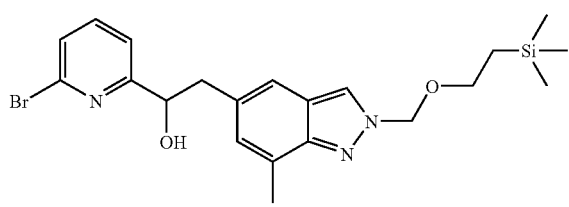

To a solution of (±)-1-(6-bromopyridin-2-yl)-2-(7-methyl-2-((2-(trimethylsilyl)ethoxy)methyl)-2H-indazol-5-yl)ethanone (977 mg, 2.12 mmol) in methanol (10 mL) at room temperature under nitrogen was added sodium borohydride (97 mg, 2.55 mmol, 1.2 equiv) in one portion. The solution was stirred at room temperature for 1 h. Methanol was then removed under vacuum and the residue was partitioned between water and ethyl acetate. The organic layer was separated, washed with brine, dried and concentrated to give a light yellow oil (1 g, 100%). MS (ESI) [M+H]$^+$=463. HPLC $t_R$=1.93 min.

The following intermediates were similarly prepared:

(±)-2-(7-Methyl-2-((2-(trimethylsilyl)ethoxy)methyl)-2H-indazol-5-yl)-1-(4-nitropyridin-2-yl)ethanol

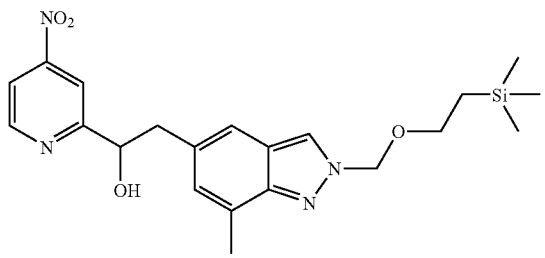

Yield: 11.3% (2 steps). MS (ESI) [M+H]$^+$=429. HPLC $t_R$=1.81 min.

(±)-1-(6-tert-Butoxypyridin-2-yl)-2-(7-methyl-2-((2-(trimethylsilyl)ethoxy)methyl)-2H-indazol-5-yl)ethanol

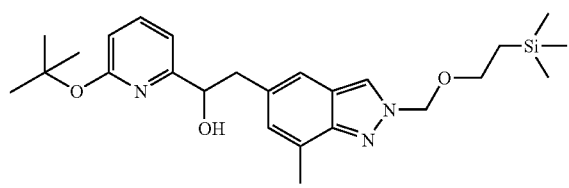

Yield: 51.8%. MS (ESI) [M+Na]$^+$=478. HPLC $t_R$=1.97 min.

(±)-Methyl 2-(1-hydroxy-2-(7-methyl-2-((2-(trimethylsilyl)ethoxy)methyl)-2H-indazol-5-yl)ethyl)isonicotinate

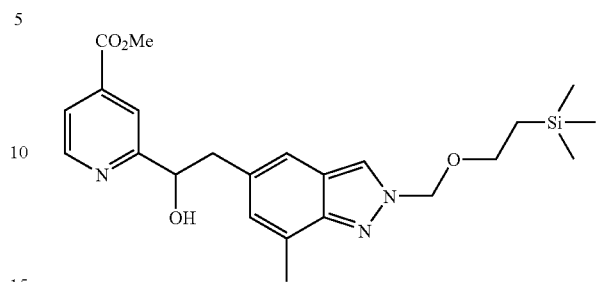

Yield: 30% (along with 28% of the isopropyl ester). MS (ESI) [M+Na]$^+$=464. $^1$H-NMR (400 MHz, CDCl$_3$) δ 8.47 (d, J=5.2 Hz, 1H), 7.84 (s, 1H), 7.81 (s, 1H), 7.58-7.52 (m, 1H), 7.16 (s, 1H), 6.81 (s, 1H), 5.53 (s, 2H), 5.02-4.95 (m, 1H), 4.30 (br., 1H), 3.77 (s, 3H), 3.50 (t, J=8.2 Hz, 2H), 3.12 (dd, J=13.8 and 3.8 Hz, 1H), 2.83 (dd, J=13.6 and 8.8 Hz, 1H), 2.42 (s, 3H), 0.81 (t, J=8.2 Hz, 2H), −0.14 (s, 9H). HPLC $t_R$=1.98 min.

2-(7-Methyl-2-((2-(trimethylsilyl)ethoxy)methyl)-2H-indazol-5-yl)-1-(pyridin-2-yl)ethanol

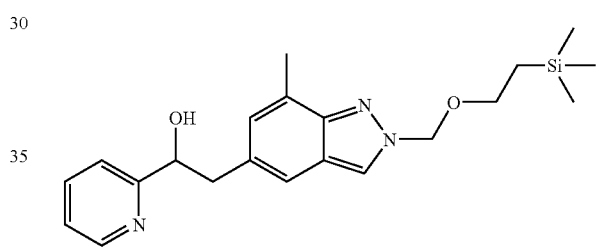

Yield: 68%. $^1$H-NMR (CDCl$_3$, 300 MHz) δ 8.53 (d, J=4.8 Hz, 1H), 7.96 (s, 1H), 7.60 (td, J=7.7, 1.8 Hz, 1H), 7.25 (bs, 1H), 7.17 (t, J=7.7 Hz, 2H), 5.68 (s, 2H), 5.01-4.97 (m, 1H), 3.62-3.56 (m, 2H), 3.16-3.09 (m, 1H), 3.02-2.95 (m, 1H), 2.56 (s, 3H), 0.93-0.88 (m, 2H), −0.06 (s, 9H). Mass spec.: 384 (MH)$^+$.

1-(Isoquinolin-3-yl)-2-(7-methyl-2-((2-(trimethylsilyl)ethoxy)methyl)-2H-indazol-5-yl)ethanol

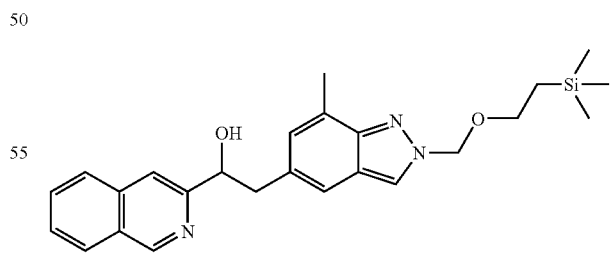

Yield: 68%. $^1$H-NMR (CDCl$_3$, 300 MHz) δ 9.22 (s, 1H), 7.96 (s, 1H), 7.95 (d, J=7.0 Hz, 1H), 7.73 (d, J=8.0 Hz, 1H), 7.65 (t, J=7.0 Hz, 1H), 7.58-7.53 (m, 2H), 7.30 (s, 1H), 6.95 (s, 1H), 5.68 (s, 2H), 5.16-5.11 (m, 1H), 3.62-3.56 (m, 2H), 3.30 (dd, J=13.5, 4.8 Hz, 1H), 3.04 (dd, J=13.9, 8.4 Hz, 1H), 2.55 (s, 3H), 0.94-0.88 (m, 2H), −0.06 (s, 9H). Mass spec.: 434 (MH)$^+$.

2-(7-Methyl-2-((2-(trimethylsilyl)ethoxy)methyl)-2H-indazol-5-yl)-1-(pyridin-3-yl)ethanol

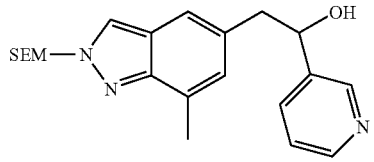

Yield: 14% (3 steps). HPLC $t_R$=1.72 min, MS(ESI)[M+H$^+$]=384.19.

1-(4,6-Dimethylpyrimidin-2-yl)-2-(7-methyl-2-((2-(trimethylsilyl)ethoxy)methyl)-2H-indazol-5-yl)ethanol

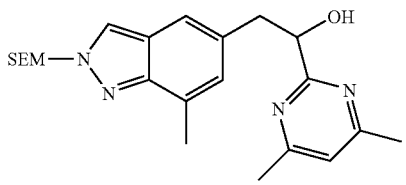

Yield: 36% (3 steps). $^1$H NMR (400 MHz, CDCl$_3$) δ 7.98 (1H, s), 7.36 (1H, s), 6.93 (1H, s), 6.92 (1H, s), 5.69 (2H, s), 5.05 (1H, m), 3.59 (2H, t, J=8.0 Hz), 3.36 (1H, m), 2.94 (1H, m), 2.56 (3H, s), 2.48 (6H, s), 0.92 (2H, t, J=8.0 Hz), −0.04 (9H, s). HPLC $t_R$=1.94 min, MS(ESI)[M+H$^+$]=413.21.

1-(Furan-2-yl)-2-(7-methyl-2-((2-(trimethylsilyl)ethoxy)methyl)-2H-indazol-5-yl)ethanol

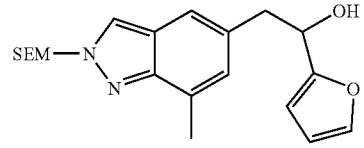

Yield: 27% (3 steps). $^1$H-NMR (400 MHz, CDCl$_3$) δ 8.21 (1H, s), 7.40 (1H, s), 7.32 (1H, s), 6.89 (1H, s), 6.23 (1H, m), 5.68 (2H, s), 4.96 (1H, m), 3.64 (2H, t, J=8.4 Hz), 3.23 (1H, m), 3.18 (1H, m), 2.56 (3H, s), 0.92 (2H, t, J=8.4 Hz), −0.06 (9H, s). HPLC $t_R$=2.06 min, MS(ESI)[M+H$^+$]=373.12.

1-(Benzofuran-2-yl)-2-(7-methyl-2-((2-(trimethylsilyl)ethoxy)methyl)-2H-indazol-5-yl)ethanol

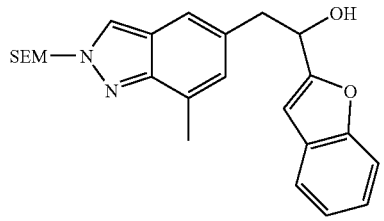

Yield: 35% (3 steps). HPLC $t_R$=2.15 min, MS(ESI)[M+H$^+$]= 423.06.

(±)-2-(1-(6-Bromopyridin-2-yl)-2-(7-methyl-2-((2-(trimethylsilyl)ethoxy)methyl)-2H-indazol-5-yl)ethyl)isoindoline-1,3-dione

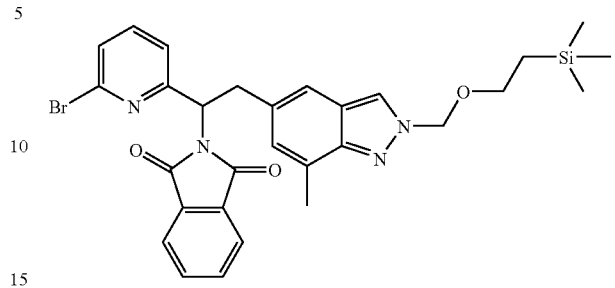

A solution of phthalimide (294 mg, 2 mmol) and triphenylphosphine (525 mg, 2 mmol) in anhydrous methylene chloride (10 mL) was added via syringe to (±)-1-(6-bromopyridin-2-yl)-2-(7-methyl-2-((2-(trimethylsilyl)ethoxy)methyl)-2H-indazol-5-yl)ethanol (460 mg, 1 mmol). To the resulting suspension was then added diisopropylazidodicarboxylate (0.3 mL, 1.5 mmol) under nitrogen at room temperature via syringe. The resulting mixture was stirred at room temperature overnight (17 h). The mixture was diluted with hexane and purified by flash column chromatography to give a light yellow oil (700 mg, 100%). MS (ESI) [M+H]$^+$=592. HPLC $t_R$=2.05 min.

The following intermediates were similarly prepared:

(±)-2-(2-(7-Methyl-2-((2-(trimethylsilyl)ethoxy)methyl)-2H-indazol-5-yl)-1-(pyridin-2-yl)ethyl)isoindoline-1,3-dione

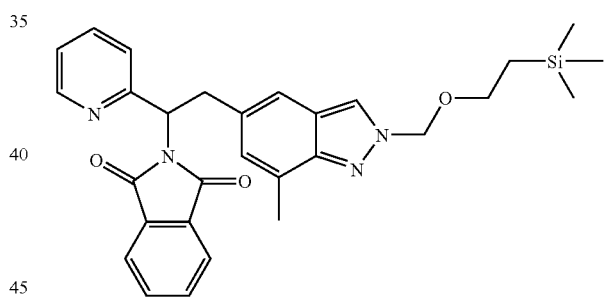

Yield: 79%. MS (ESI) [M+H]+=513. HPLC $t_R$=1.87 min.

(±)-2-(2-(7-Methyl-2-((2-(trimethylsilyl)ethoxy)methyl)-2H-indazol-5-yl)-1-(4-nitropyridin-2-yl)ethyl)isoindoline-1,3-dione

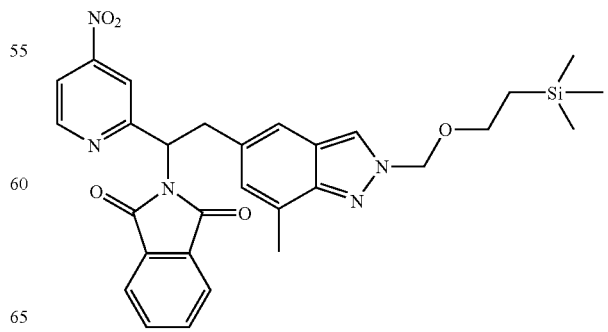

Yield: 83%. MS (ESI) [M+H]$^+$=558. HPLC $t_R$=1.99 min.

(±)-2-(2-(7-Methyl-2-((2-(trimethylsilyl)ethoxy) methyl)-2H-indazol-5-yl)-1-(quinolin-2-yl)ethyl) isoindoline-1,3-dione

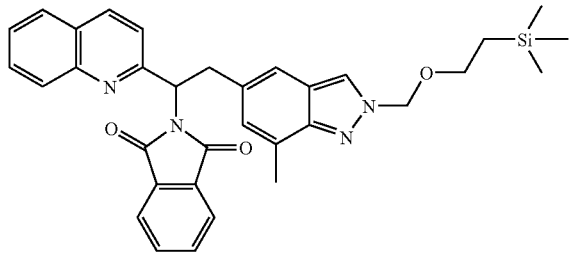

Yield: 89.4%. MS (ESI) [M+H]$^+$=563. HPLC $t_R$=2.03 min.

2-(1-(isoquinolin-3-yl)-2-(7-methyl-2-((2-(trimethylsilyl)ethoxy)methyl)-2H-indazol-5-yl)ethyl)isoindoline-1,3-dione

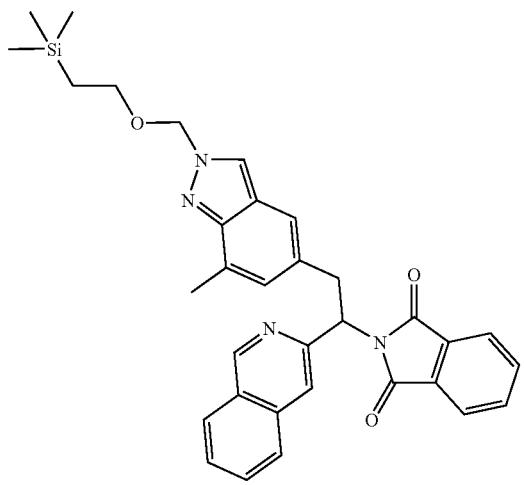

Yield: 44%. $^1$H-NMR (CDCl$_3$, 500 MHz) δ 9.24 (s, 1H), 7.95 (d, J=8.2 Hz, 1H), 7.91 (s, 1H), 7.84-7.81 (m, 2H), 7.76-7.73 (m, 2H), 7.68 (t, J=7.6 Hz, 1H), 7.64-7.62 (m, 2H), 7.58 (t, J=7.6 Hz, 1H), 7.39 (s, 1H), 7.08 (s, 1H), 6.09-6.06 (m, 1H), 5.64 (s, 2H), 4.04-3.99 (m, 1H), 3.90-3.86 (m, 1H), 3.61-3.57 (m, 2H), 2.53 (s, 3H), 0.92-0.88 (m, 2H), -0.07 (s, 9H). Mass spec.: 563 (MH)$^+$.

(±)-1-(6-Bromopyridin-2-yl)-2-(7-methyl-2-((2-(trimethylsilyl)ethoxy)methyl)-2H-indazol-5-yl)ethanamine

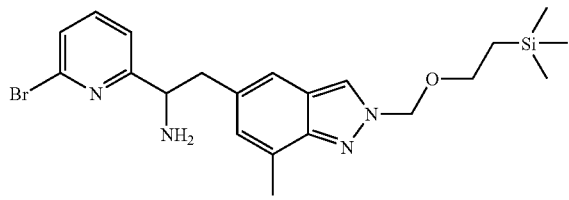

A solution of (±)-2-(1-(6-bromopyridin-2-yl)-2-(7-methyl-2-((2-(trimethylsilyl)ethoxy)methyl)-2H-indazol-5-yl) ethyl)isoindoline-1,3-dione (1 mmol) in methanol (10 mL) was treated with hydrazine (0.16 mL, 5 mmol) at room temperature for 30 min and at 70° C. for 5 h. The mixture was concentrated in vacuo and the residue was partitioned between 1N sodium hydroxide and ethyl acetate. The organic layer was washed with water, brine, dried and concentrated. The pale yellow oil (100%) was pure enough to carry on. MS (ESI) [M+H]$^+$=461. HPLC $t_R$=1.62 min.

The following intermediates were similarly prepared:

(±)-2-(7-Methyl-2-((2-(trimethylsilyl)ethoxy)methyl)-2H-indazol-5-yl)-1-(pyridin-2-yl)ethanamine

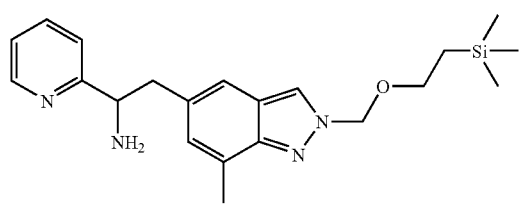

Yield: 100%. MS (ESI) [M+H]$^+$=383. $^1$H-NMR (400 MHz, CDCl$_3$) δ 8.58 (d, J=4.4 Hz, 1H), 7.97 (s, 1H), 7.62-7.54 (m, 1H), 7.24 (s, 2H), 7.16-7.10 (m, 1H), 6.89 (s, 1H), 5.69 (s, 2H), 4.30-4.24 (m, 1H), 3.64-3.56 (m, 2H), 3.15 (dd, J=13.4 and 5.0 Hz, 1H), 2.85 (dd, J=13.2 and 8.8 Hz, 1H), 2.57 (s, 3H), 2.15-1.85 (br., 2H), 0.95-0.86 (m, 2H), -0.051 (s, 9H). HPLC $t_R$=1.54 min.

(±)-2-(7-Methyl-2-((2-(trimethylsilyl)ethoxy)methyl)-2H-indazol-5-yl)-1-(4-nitropyridin-2-yl)ethanamine

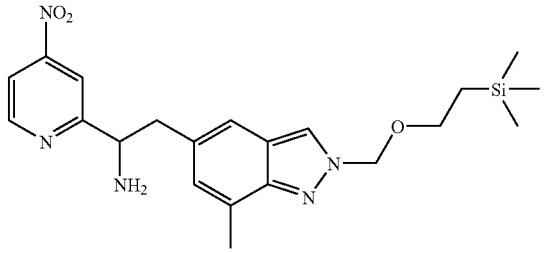

Yield: 100%. MS (ESI) [M+H]$^+$=428. HPLC $t_R$=1.51 min.

(±)-2-(7-Methyl-2-((2-(trimethylsilyl)ethoxy)methyl)-2H-indazol-5-yl)-1-(quinolin-2-yl)ethanamine

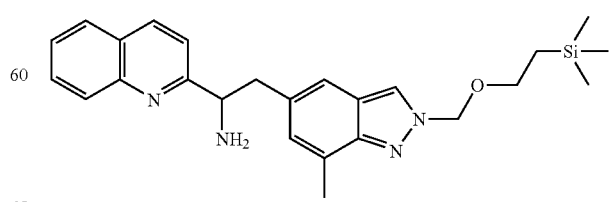

Yield: 96.4%. MS (ESI) [M+H]$^+$=433. HPLC $t_R$=1.67 min.

1-(Isoquinolin-3-yl)-2-(7-methyl-2-((2-(trimethylsi-lyl)ethoxy)methyl)-2H-indazol-5-yl)ethanamine

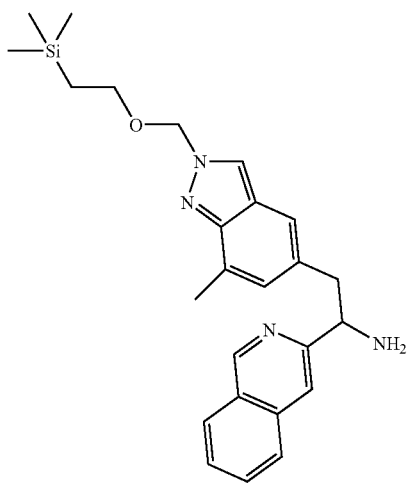

Yield: 88%. $^1$H-NMR (CDCl$_3$, 500 MHz) δ 9.26 (s, 1H), 7.98 (s, 1H), 7.97 (d, J=7.3 Hz, 1H), 7.75 (d, J=8.2 Hz, 1H), 7.66 (t, J=8.2 Hz, 1H), 7.62 (s, 1H), 7.57 (t, J=7.0 Hz, 1H), 7.31 (s, 1H), 6.95 (s, 1H), 5.70 (s, 2H), 4.52-4.49 (m, 1H), 3.64-3.60 (m, 2H), 3.35-3.32 (m, 1H), 3.02-2.98 (m, 1H), 2.57 (s, 3H), 0.95-0.92 (m, 2H), −0.03 (s, 9H). Mass spec.: 433 (MH)$^+$.

(±)-N-(1-(6-Bromopyridin-2-yl)-2-(7-methyl-2-((2-(trimethylsilyl)ethoxy)methyl)-2H-indazol-5-yl)ethyl)-4-(2-oxo-1,2-dihydroquinazolin-3(4H)-yl)piperidine-1-carboxamide

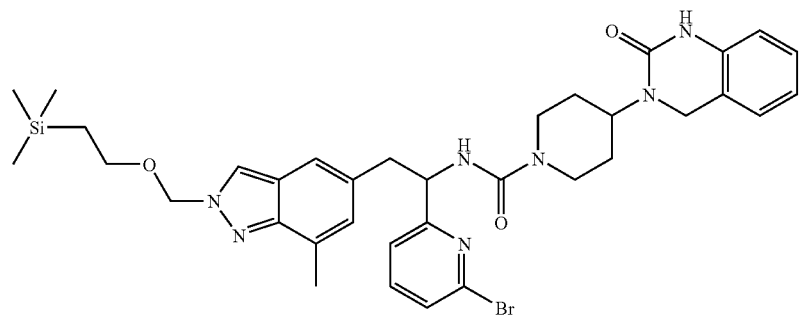

A solution of (±)-1-(6-bromopyridin-2-yl)-2-(7-methyl-2-((2-(trimethylsilyl)ethoxy)methyl)-2H-indazol-5-yl)ethanamine (389 mg, 0.843 mmol) and carbonyl diimidazole (144 mg, 0.885 mmol, 1.05 equiv) in anhydrous methylene chloride (6 mL) was stirred at room temperature for 1 h. Solid 3,4-dihydro-3-(4-piperidinyl-2(1H)-quinazolinone (HCl salt, 248 mg, 0.927 mmol, 1.1 equiv) was then added in one portion followed by diisopropylethylamine (0.22 mL, 1.26 mmol, 1.5 equiv). The resulting reaction mixture was stirred at room temperature overnight. The mixture was purified by flash column chromatography (10% methanol in methylene chloride) to afford the desired product (548 mg, 90.4%) as a light yellow oil: (ESI) 718 (MH)$^+$. $^1$H-NMR (400 MHz, CDCl$_3$) δ 8.10 (br. 1H), 7.91 (s, 1H), 7.28-7.26 (m, 1H), 7.17-6.75 (m, 7H), 6.71 (d, J=7.6 Hz, 1H), 5.73 (d, J=8.0 Hz, 1H), 5.62 (s, 2H), 5.20-5.10 (m, 1H), 5.00-4.84 (m, 2H), 4.58-4.45 (m, 1H), 4.06 (d, J=14.0 Hz, 2H), 3.57 (t, J=8.2 Hz, 2H), 3.25-3.18 (dd, 1H), 3.02-2.92 (dd, 1H), 2.90-2.78 (m, 2H), 2.52 (s, 3H), 1.78-1.46 (m, 4H), 0.88 (t, J=8.2 Hz, 2H), −0.083 (s, 9H). HPLC $t_R$=1.96 min.

The following intermediates were similarly prepared:

(±)-N-(2-(7-Methyl-2-((2-(trimethylsilyl)ethoxy)
methyl)-2H-indazol-5-yl)-1-(pyridin-2-yl)ethyl)-4-
(2-oxo-1,2-dihydroquinazolin-3(4H)-yl)piperidine-1-
carboxamide

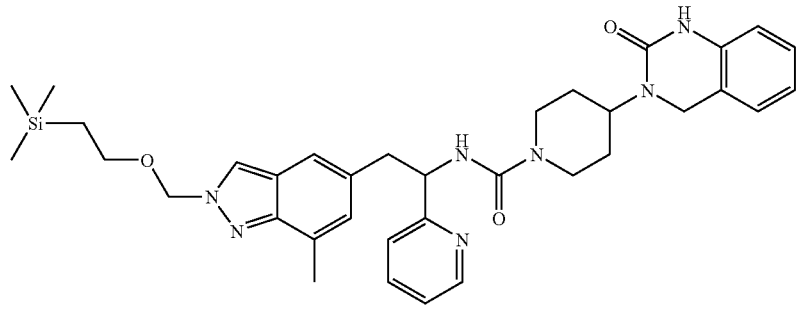

Yield: 62%. (ESI) 640 (MH)$^+$. HPLC $t_R$=1.61 min.

(±)-N-(2-(7-methyl-2-((2-(trimethylsilyl)ethoxy)
methyl)-2H-indazol-5-yl)-1-(4-nitropyridin-2-yl)
ethyl)-4-(2-oxo-1,2-dihydroquinazolin-3(4H)-yl)
piperidine-1-carboxamide

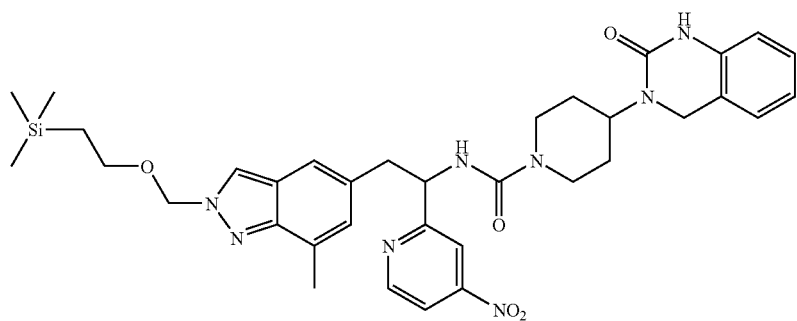

Yield: 79.5%. (ESI) 684 (MH)$^+$. HPLC $t_R$=1.89 min.

(±)-N-(2-(7-methyl-2-((2-(trimethylsilyl)ethoxy)
methyl)-2H-indazol-5-yl)-1-(quinolin-2-yl)ethyl)-4-
(2-oxo-1,2-dihydroquinazolin-3(4H)-yl)piperidine-1-
carboxamide

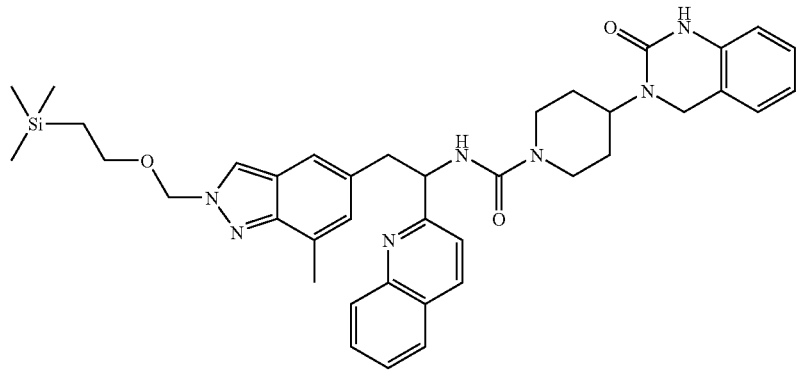

Yield: 16%. (ESI) 690 (MH)$^+$. HPLC $t_R$=1.71 min.

(±)-4-(8-Fluoro-2-oxo-1,2-dihydroquinazolin-3(4H)-yl)-N-(2-(7-methyl-2-((2-(trimethylsilyl)ethoxy)methyl)-2H-indazol-5-yl)-1-(quinolin-2-yl)ethyl)piperidine-1-carboxamide

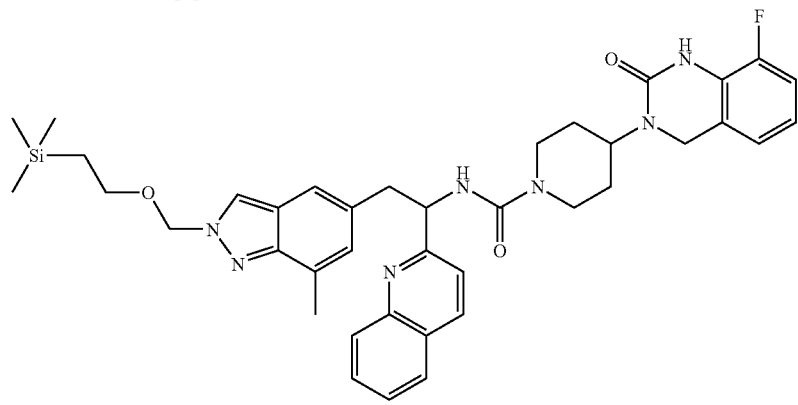

Yield: 28.4%. (ESI) 708 (MH)$^+$. HPLC t$_R$=1.74 min.

N-(1-(Isoquinolin-3-yl)-2-(7-methyl-2-((2-(trimethylsilyl)ethoxy)methyl)-2H-indazol-5-yl)ethyl)-4-(2-oxo-1,2-dihydroquinazolin-3(4H)-yl)piperidine-1-carboxamide

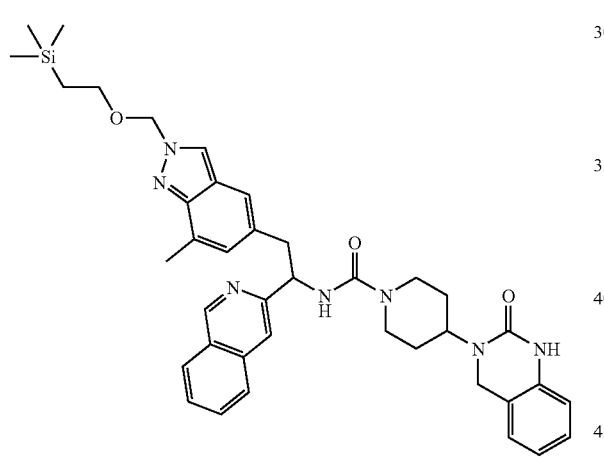

Yield: 61%. Mass spec.: 690 (MH)$^+$.

4-(8-Fluoro-2-oxo-1,2-dihydroquinazolin-3(4H)-yl)-N-(1-(isoquinolin-3-yl)-2-(7-methyl-2-((2-(trimethylsilyl)ethoxy)methyl)-2H-indazol-5-yl)ethyl)piperidine-1-carboxamide

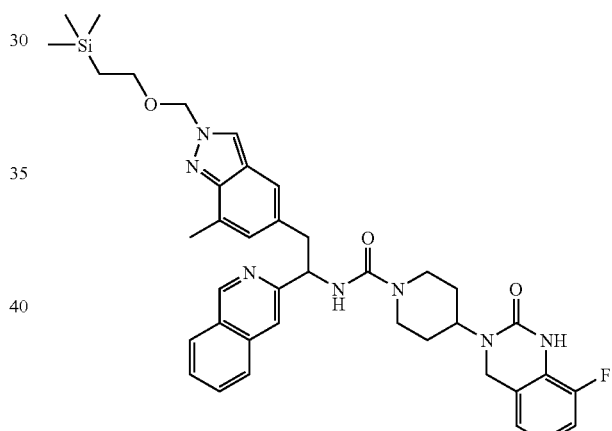

Yield: 85%. Mass spec.: 708 (MH)$^+$.

(±)-1-(6-Bromopyridin-2-yl)-2-(7-methyl-2-((2-(trimethylsilyl)ethoxy)methyl)-2H-indazol-5-yl)ethyl 4-(8-fluoro-2-oxo-1,2-dihydroquinazolin-3(4H)-yl)piperidine-1-carboxylate

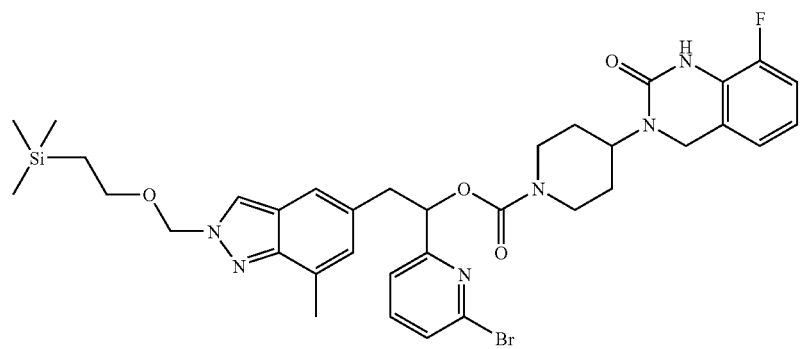

To an oven-dried flask was added (±)-1-(6-bromopyridin-2-yl)-2-(7-methyl-2-((2-(trimethylsilyl)ethoxy)methyl)-2H-indazol-5-yl)ethanol (102.6 mg, 0.222 mmol) and p-nitrophenyl chloroformate (89.4 mg, 0.444 mmol, 2.0 equiv) followed by methylene chloride (2 mL) under nitrogen and diisopropylethylamine (0.1 mL, 0.555 mmol, 2.5 equiv). The mixture was stirred at room temperature for 2 days. Solid 8-fluro-3,4-dihydro-3-(4-piperidinyl-2(1H)-quinazolinone (105 mg, 0.44 mmol, 2.0 equiv) was added followed by diisopropylethylamine (0.2 mL). The resulting mixture was stirred at room temperature overnight. It was then diluted with ethyl acetate and washed with 0.5 N sodium hydroxide, water, brine, dried and concentrated. The residue was purified by flash column chromatography (70% ethyl acetate in hexane) to afford the desired product (91 mg, 55.6%). (ESI) 737 (MH)$^+$. $^1$H-NMR (400 MHz, CDCl$_3$) δ 7.92 (s, 1H), 7.50-6.70 (m, 9H), 6.02-5.80 (m, 1H), 5.80-5.45 (m, 2H), 4.60-3.78 (m, 4H), 3.70-3.48 (m, 2H), 3.48-3.02 (m, 2H), 3.00-2.62 (m, 2H), 2.57 (s, 3H), 1.90-0.70 (m, 7H), −0.08 (s, 9H). HPLC t$_R$=2.04 min.

The following intermediates were similarly prepared:

(±)-1-(6-Bromopyridin-2-yl)-2-(7-methyl-2-((2-(trimethylsilyl)ethoxy)methyl)-2H-indazol-5-yl)ethyl 4-(2-oxo-1,2-dihydroquinazolin-3(4H)-yl)piperidine-1-carboxylate

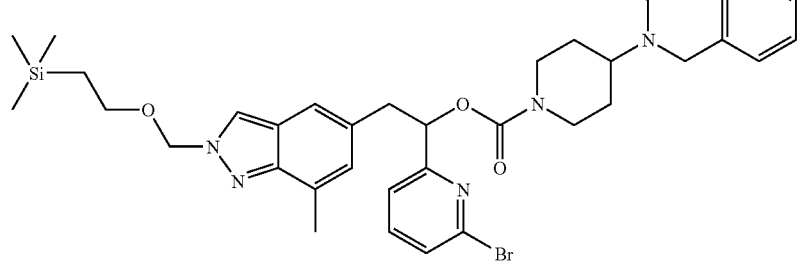

Yield: 45.9%. (ESI) 719 (MH)$^+$. HPLC t$_R$=2.07 min.

(±)-1-(6-tert-Butoxypyridin-2-yl)-2-(7-methyl-2-((2-(trimethylsilyl)ethoxy)methyl)-2H-indazol-5-yl)ethyl 4-(2-oxo-1,2-dihydroquinazolin-3(4H)-yl)piperidine-1-carboxylate

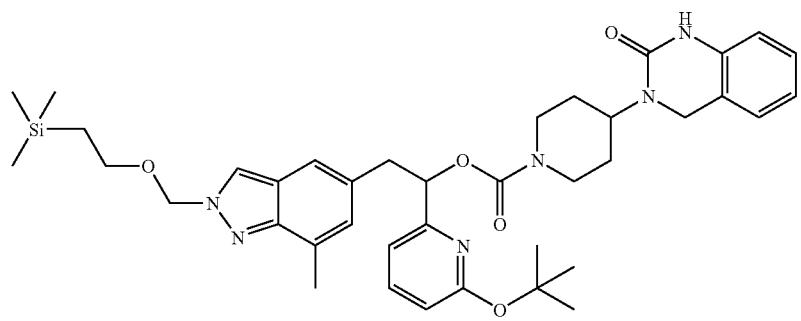

Yield: 67%. (ESI) 735 (M+Na)$^+$. HPLC t$_R$=2.69 min.

N-(1-(isoquinolin-3-yl)-2-(7-methyl-2-((2-(trimethylsilyl)ethoxy)methyl)-2H-indazol-5-yl)ethyl)-4-(2-oxo-1,2-dihydroquinolin-3-yl)piperidine-1-carboxamide

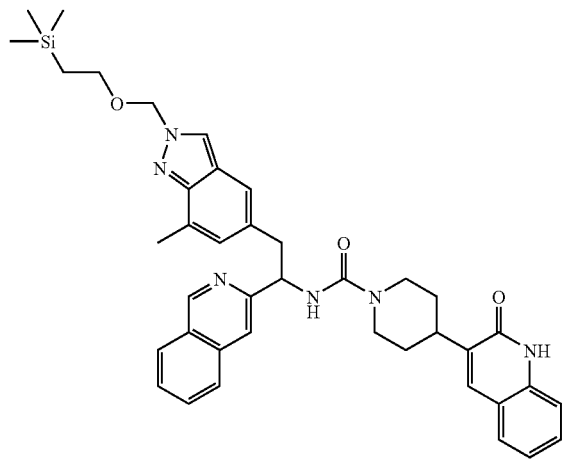

Yield: quantitative. $^1$H-NMR (CDCl$_3$, 500 MHz) δ 9.52 (s, 1H), 9.26 (s, 1H), 7.97 (d, J=7.0 Hz, 1H), 7.87 (s, 1H), 7.67-7.63 (m, 2H), 7.60-7.56 (m, 1H), 7.53 (d, J=7.0 Hz, 1H), 7.46-7.42 (m, 2H), 7.86-7.81 (m, 1H), 7.19 (t, J=7.0 Hz, 1H), 7.15 (d, J=8.2 Hz, 1H), 7.10-7.07 (m, 1H), 6.85 (bs, 1H), 5.63 (s, 2H), 5.41-5.37 (m, 1H), 4.22-4.13 (m, 2H), 3.60-3.56 (m, 2H), 3.45-3.37 (m, 1H), 3.25-3.17 (m, 1H), 3.13-3.08 (m, 1H), 2.50 (s, 3H), 3.00-2.91 (m, 2H), 1.98-1.92 (m, 2H), 1.58-1.43 (m, 3H), 0.99-0.93 (m, 1H), 0.91-0.88 (m, 2H), −0.06 (s, 9H).

Mass spec.: 687 (MH)$^+$.

(±)-2-(2-(7-Methyl-2-((2-(trimethylsilyl)ethoxy)
methyl)-2H-indazol-5-yl)-1-(4-(2-oxo-1,2-dihydro-
quinazolin-3(4H)-yl)piperidine-1-carbonyloxy)ethyl)
isonicotinic acid

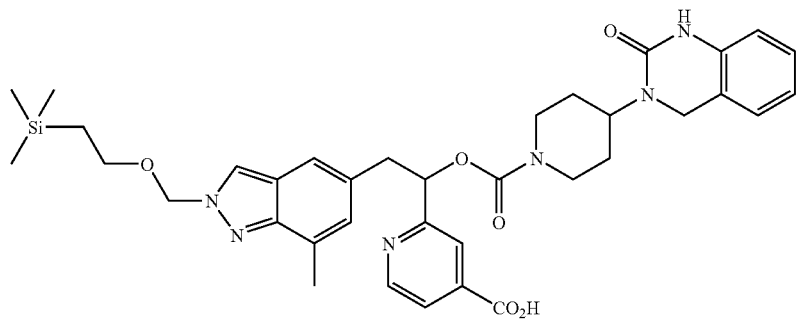

To a suspension of (±)-methyl 2-(1-hydroxy-2-(7-methyl-2-((2-(trimethylsilyl)ethoxy)methyl)-2H-indazol-5-yl)ethyl) isonicotinate (233 mg, 0.527 mmol 1.0 equiv) and 4-nitrophenyl 4-(2-oxo-1,2-dihydroquinazolin-3(4H)-yl)piperidine-1-carboxylate (251 mg, 0.632 mmol, 1.2 equiv) in tetrahydrofuran (6 mL) was added sodium hydride (91 mg, 7 equiv) in one portion. The resulting mixture was stirred at room temperature under nitrogen overnight. The mixture was partitioned between water and ethyl acetate. The layers were separated and the aqueous layer was acidified to pH 5 with acetic acid. The aqueous portion was extracted twice with ethyl acetate. The combined organic layers were washed with brine, dried and concentrated. The residue was purified by flash column chromatography (20% methanol in methylene chloride) to afford the desired acid (227 mg, 62.8%) as a tan solid. (ESI) 685 (MH)$^+$. HPLC $t_R$=2.19 min.

EXAMPLE 30

(±)-N-(1-(6-Bromopyridin-2-yl)-2-(7-methyl-1H-indazol-5-yl)ethyl)-4-(2-oxo-1,2-dihydroquinazolin-3(4H)-yl)piperidine-1-carboxamide

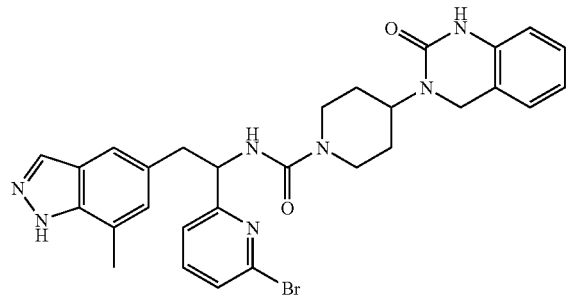

To the solution of (±)-N-(1-(6-bromopyridin-2-yl)-2-(7-methyl-2-((2-(trimethylsilyl)ethoxy)methyl)-2H-indazol-5-yl)ethyl)-4-(2-oxo-1,2-dihydroquinazolin-3(4H)-yl)piperidine-1-carboxamide (197.4 mg, 0.274 mmol) in tetrahydrofuran (8 mL) was added 1M tetrabutylammonium fluoride in tetrahydrofuran (0.55 mL, 0.549 mmol, 2 equiv). The mixture was stirred under nitrogen at 60° C. for 4 h. Another 0.5 mL of TBAF was added and the mixture was stirred overnight. Tetrahydrofuran was removed in vacuo and the residue was partitioned between water and ethyl acetate. The layers were separated and the organic layer was washed with brine, dried over sodium sulfate and concentrated in vacuo. The solid residue was purified by flash column chromatography (10% methanol in methylene chloride) to afford the desired product (98 mg, 61%) as a white solid. MS (ESI) [M+H]$^+$=588, $^1$H-NMR (400 MHz, CDCl$_3$) δ 7.93 (s, 1H), 7.32-6.78 (m, 9H), 6.69 (d, J=7.6 Hz, 1H), 5.79 (d, J=7.2 Hz, 1H), 5.17 (q, J=6.8 Hz, 1H), 4.60-4.48 (m, 1H), 4.25-4.00 (m, 4H), 3.27 (dd, J=13.2 and 6.4 Hz, 1H), 3.06 (dd, J=13.6 and 8.0 Hz, 1H), 2.85 (t, J=11.4 Hz, 2H), 2.45 (s, 3H), 1.80-1.50 (m, 5H). HPLC $t_R$=1.62 min.

The following examples were similarly prepared:

EXAMPLE 31

(±)-N-(2-(7-Methyl-1H-indazol-5-yl)-1-(pyridin-2-yl)ethyl)-4-(2-oxo-1,2-dihydroquinazolin-3(4H)-yl)piperidine-1-carboxamide

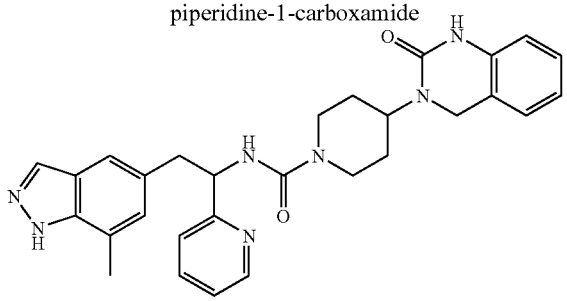

Yield: 95%. MS (ESI) [M+H]$^+$=510. $^1$H-NMR (400 MHz, CDCl$_3$) δ 8.52 (m, 1H), 7.90 (s, 1H), 7.58-7.40 (m, 2H), 7.20-6.77 (m, 7H), 6.67 (d, J=8.0 Hz, 1H), 6.18 (d, J=7.2 Hz, 1H), 5.20 (q, J=7.6 Hz, 1H), 4.58-4.48 (m, 1H), 4.21 (s, 2H), 4.21-4.05 (m, 1H), 3.33 (dd, J=13.2 and 5.6 Hz, 1H), 3.08 (dd, J=13.4 and 8.2 Hz, 1H), 3.00-2.77 (m, 2H), 2.45 (s, 3H), 1.80-1.50 (m, 6H). HPLC $t_R$=1.07 min.

EXAMPLE 32

(±)-N-(2-(7-Methyl-1H-indazol-5-yl)-1-(4-nitropyridin-2-yl)ethyl)-4-(2-oxo-1,2-dihydroquinazolin-3(4H)-yl)piperidine-1-carboxamide

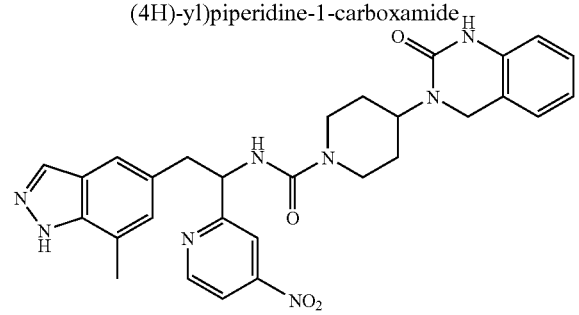

Yield: 6.2%. MS (ESI) [M+H]$^+$=555. HPLC $t_R$=1.46 min.

EXAMPLE 33

(±)-N-(1-(4-Fluoropyridin-2-yl)-2-(7-methyl-1H-indazol-5-yl)ethyl)-4-(2-oxo-1,2-dihydroquinazolin-3(4H)-yl)piperidine-1-carboxamide

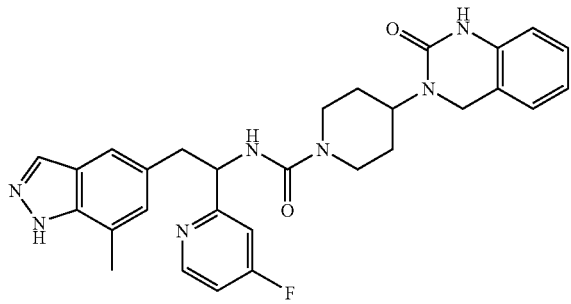

Yield: 8.7% (This was formed as a co-product along with (±)-N-(2-(7-methyl-1H-indazol-5-yl)-1-(4-nitropyridin-2-yl)ethyl)-4-(2-oxo-1,2-dihydroquinazolin-3(4H)-yl)piperidine-1-carboxamide). MS (ESI) [M+H]$^+$=528. HPLC $t_R$=1.23 min.

EXAMPLE 34

(±)-N-(2-(7-Methyl-1H-indazol-5-yl)-1-(quinolin-2-yl)ethyl)-4-(2-oxo-1,2-dihydroquinazolin-3(4H)-yl)piperidine-1-carboxamide

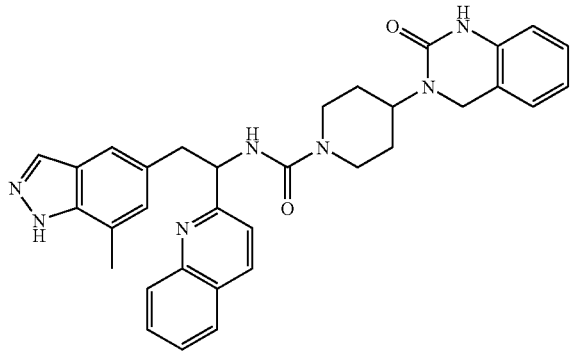

Yield: 80%. MS (ESI) [M+H]+=560. $^1$H-NMR (400 MHz, CDCl$_3$) δ 8.20-7.42 (m, 5H), 7.20-6.78 (m, 8H), 6.65 (d, J=8.0 Hz, 1H), 5.48-5.30 (m, 1H), 4.65-4.48 (m, 1H), 4.23-4.12 (m, 4H), 3.58-3.40 (m, 1H), 3.28-3.08 (m, 1H), 3.02-2.82 (m, 2H), 2.42 (s, 3H), 1.90-1.48 (m, 6H). HPLC $t_R$=1.22 min.

EXAMPLE 35

(±)-4-(8-Fluoro-2-oxo-1,2-dihydroquinazolin-3(4H)-yl)-N-(2-(7-methyl-1H-indazol-5-yl)-1-(quinolin-2-yl)ethyl)piperidine-1-carboxamide

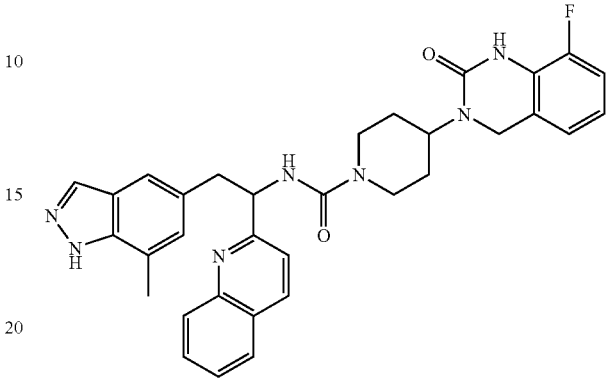

Yield: 56%. MS(ESI)[M+H]$^+$=578. $^1$H-NMR(400 MHz, CDCl$_3$) δ 8.20-7.42 (m, 5H), 7.20-6.40 (m, 8H), 5.50-5.35 (m, 1H), 4.67-4.50 (m, 1H), 4.31-4.12 (m, 4H), 3.54-3.40 (m, 1H), 3.24-3.08 (m, 1H), 3.02-2.84 (m, 2H), 2.41 (s, 3H), 1.90-1.45 (m, 6H). HPLC $t_R$=1.23 min.

EXAMPLE 36

N-(1-(Isoquinolin-3-yl)-2-(7-methyl-1H-indazol-5-yl)ethyl)-4-(2-oxo-1,2-dihydroquinolin-3-yl)piperidine-1-carboxamide

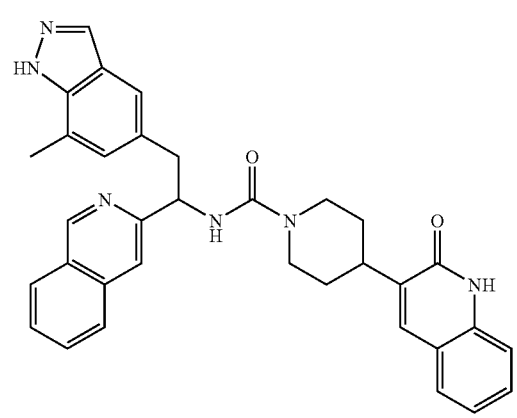

Yield: 75%. $^1$H-NMR (CDCl$_3$, 500 MHz) δ 10.80 (bs, 1H), 9.23 (s, 1H), 7.93 (d, J=7.9 Hz, 1H), 7.86 (s, 0.7H), 7.78 (s, 0.3H), 7.65-7.59 (m, 2H), 7.56-7.53 (m, 1H), 7.51 (d, J=7.3 Hz, 1H), 7.46-7.40 (m, 2H), 7.33 (s, 0.3H), 7.30 (s, 0.7H), 7.25-7.23 (m, 1H), 7.18-7.12 (m, 2H), 6.93-6.92 (m, 1H), 5.96-5.90 (m, 1H), 5.40-5.35 (m, 1H), 4.16-4.12 (m, 2H), 3.43-3.37 (m, 1H), 3.25-3.20 (m, 1H), 3.14-3.09 (m, 1H), 2.99-2.91 (m, 2H), 2.62 (s, 1H), 2.41 (s, 2H), 1.52-1.43 (m, 3H). Mass spec.: 557 (MH)$^+$.

EXAMPLE 37

(±)-N-(2-(7-Methyl-1H-indazol-5-yl)-1-(6-phenylpyridin-2-yl)ethyl)-4-(2-oxo-1,2-dihydroquinazolin-3(4H)-yl)piperidine-1-carboxamide

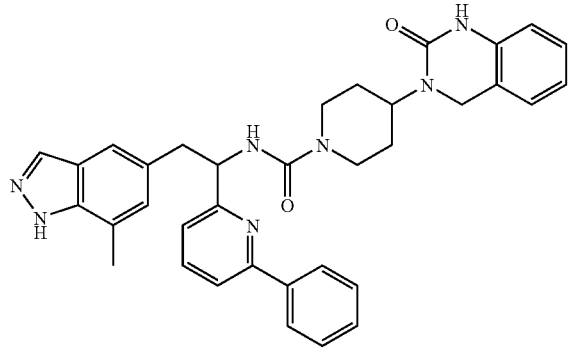

To a microwave tube charged with (±)-N-(1-(6-bromopyridin-2-yl)-2-(7-methyl-1H-indazol-5-yl)ethyl)-4-(2-oxo-1,2-dihydroquinazolin-3(4H)-yl)piperidine-1-carboxamide (24.6 mg, 0.0418 mmol, 1.0 equiv) was added phenyl boronic acid (7.1 mg, 0.0585 mmol, 1.4 equiv), Pd(PPh$_3$)$_4$ (4.8 mg, 0.1 equiv), toluene (1 mL), ethanol (0.2 mL), and potassium carbonate solution (2M, 0.085 mL). The vial was sealed and heated by microwave at 140° C. for 30 min. The mixture was extracted with ethyl acetate. The organic layer was washed with brine, dried and concentrated. Flash column chromatography (10% methanol/methylene chloride) afforded the desired product (20 mg, 81.6%) as an off-white solid: MS (ESI) [M+H]$^+$=586. $^1$H-NMR (400 MHz, CDCl$_3$) δ 8.00-7.86 (m, 3H), 7.65-6.82 (m, 12H), 6.74 (d, J=7.2 Hz, 1H), 6.66 (d, J=8.0 Hz, 1H), 6.32 (br., 1H), 5.35-5.20 (m, 1H), 4.62-4.48 (m, 1H), 4.30-4.08 (m, 4H), 3.40 (dd, J=13.2 and 4.2 Hz, 1H), 3.13 (dd, J=13.2 and 8.4 Hz, 1H), 3.02-2.83 (m, 2H), 2.42 (s, 3H), 1.80-1.55 (m, 4H). HPLC t$_R$=1.51 min.

EXAMPLE 38

(±)-N-(2-(7-Methyl-1H-indazol-5-yl)-1-(6-methylpyridin-2-yl)ethyl)-4-(2-oxo-1,2-dihydroquinazolin-3(4H)-yl)piperidine-1-carboxamide

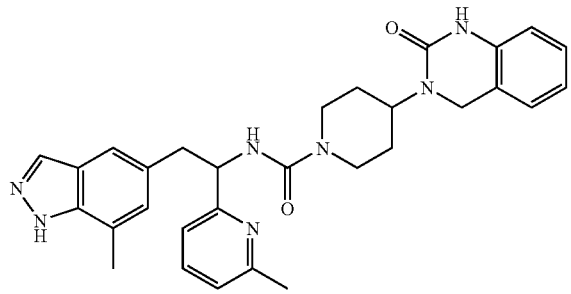

A microwave tube was charged with (±)-N-(1-(6-bromopyridin-2-yl)-2-(7-methyl-1H-indazol-5-yl)ethyl)-4-(2-oxo-1,2-dihydroquinazolin-3(4H)-yl)piperidine-1-carboxamide (11 mg, 0.0187 mmol, 1.0 equiv), Pd(PPh$_3$)$_4$ (2 mg, 0.1 equiv) and anhydrous tetrahydrofuran (0.5 mL) under nitrogen. ZnMeCl (2.0 M in tetrahydrofuran, 0.12 mL, 0.24 mmol) was added via syringe resulting in gas evolution. The vial was sealed and heated by microwave at 110° C. for 4 h. Tetrahydrofuran was removed in vacuo and the residue was partitioned between ethyl acetate and concentrated ammonium hydroxide solution. The organic layer was separated and washed with brine, dried and concentrated. Flash column chromatography (10% methanol/methylene chloride) afforded the desired product (9.2 mg, 94%) as a white powder. MS (ESI) [M+H]$^+$=524. $^1$H-NMR (400 MHz, CDCl$_3$) δ 7.91 (s, 1H), 7.33 (br., 1H), 7.22-6.80 (m, 7H), 6.65 (d, J=8.0 Hz, 1H), 6.59 (br., 1H), 6.20 (br., 1H), 5.20-5.08 (m, 1H), 4.62-4.48 (m, 1H), 4.22 (s, 2H), 4.20-4.03 (m, 2H), 3.40-3.28 (m, 1H), 3.10-2.97 (m, 1H), 2.97-2.78 (m, 2H), 2.54 (s, 3H), 2.45 (s, 3H), 1.95-1.50 (m, 5H). HPLC t$_R$=1.11 min.

EXAMPLE 39

(±)-1-(6-Bromopyridin-2-yl)-2-(7-methyl-1H-indazol-5-yl)ethyl 4-(8-fluoro-2-oxo-1,2-dihydroquinazolin-3(4H)-yl)piperidine-1-carboxylate

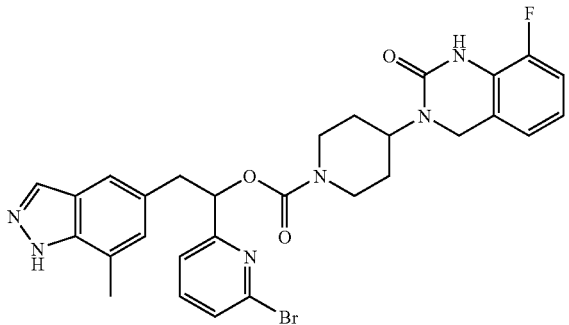

Yield: 74.2%. MS (ESI) [M+H]$^+$=607. $^1$H-NMR (400 MHz, CDCl$_3$) δ 7.98 (s, 1H), 7.60-6.60 (m, 8H), 5.92 (br., 1H), 4.65-3.80 (m, 5H), 3.55-3.07 (m, 2H), 3.02-2.60 (m, 2H), 2.49 (s, 3H), 1.90-1.00 (m, 6H). HPLC t$_R$=1.77 min.

EXAMPLE 40

(±)-1-(6-Bromopyridin-2-yl)-2-(7-methyl-1H-indazol-5-yl)ethyl 4-(2-oxo-1,2-dihydroquinazolin-3(4H)-yl)piperidine-1-carboxylate

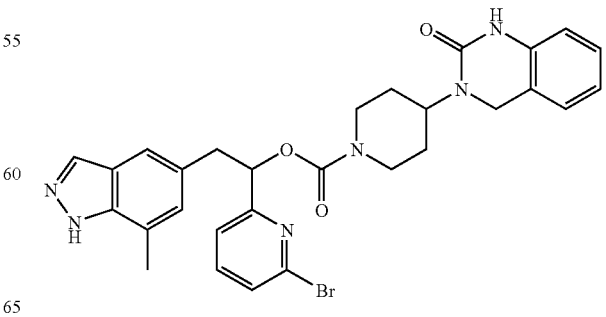

Yield: 26.7%. MS (ESI) [M+H]$^+$=589. HPLC t$_R$=1.76 min.

EXAMPLE 41

(±)-1-(6-tert-Butoxypyridin-2-yl)-2-(7-methyl-1H-indazol-5-yl)ethyl 4-(2-oxo-1,2-dihydroquinazolin-3(4H)-yl)piperidine-1-carboxylate

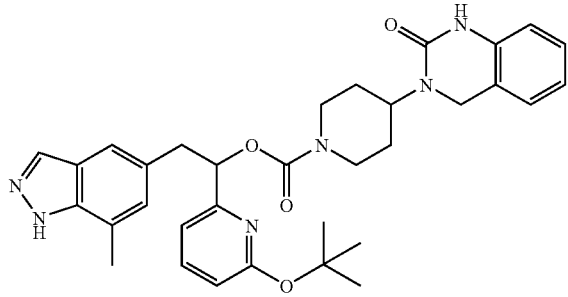

Yield: 43%. MS (ESI) [M+Na]$^+$=605. $^1$H-NMR (400 MHz, CDCl$_3$) δ 7.95 (s, 2H), 7.45-6.59 (m, 7H), 6.50 (d, J=8.4 Hz, 1H), 5.90-5.80 (m, 1H), 4.60-3.90 (m, 4H), 3.42-3.18 (m, 2H), 3.05-2.60 (m, 3H), 2.48 (s, 3H), 1.82-1.68 (m, 2H), 1.59 (s, 9H), 1.45-1.28 (m, 4H). HPLC t$_R$=2.42 min.

EXAMPLE 42

(±)-2-(7-Methyl-1H-indazol-5-yl)-1-(6-oxo-1,6-dihydropyridin-2-yl)ethyl 4-(2-oxo-1,2-dihydroquinazolin-3(4H)-yl)piperidine-1-carboxylate

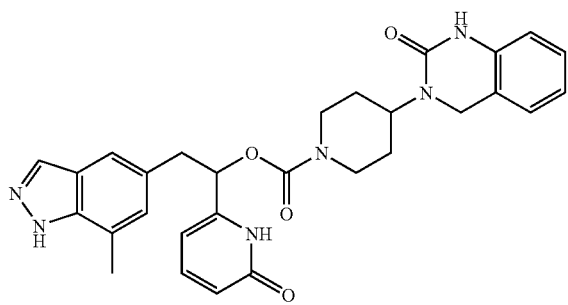

Solid (±)-1-(6-tert-butoxypyridin-2-yl)-2-(7-methyl-1H-indazol-5-yl)ethyl 4-(2-oxo-1,2-dihydroquinazolin-3(4H)-yl)piperidine-1-carboxylate (previous example) (20.6 mg) was treated with 1 mL formic acid (90%). After 2 h, the mixture was diluted with water and extracted three times with ethyl acetate. The combined organic layers were washed with water, saturated sodium bicarbonate solution, dried and concentrated. Further drying under high vacuum afforded the product (11.8 mg, 63.4%) as an off-white powder. MS (ESI) [M+H]$^+$=527. HPLC t$_R$=1.68 min.

EXAMPLE 43

(±)-1-(6-Isobutylpyridin-2-yl)-2-(7-methyl-1H-indazol-5-yl)ethyl 4-(8-fluoro-2-oxo-1,2-dihydroquinazolin-3(4H)-yl)piperidine-1-carboxylate

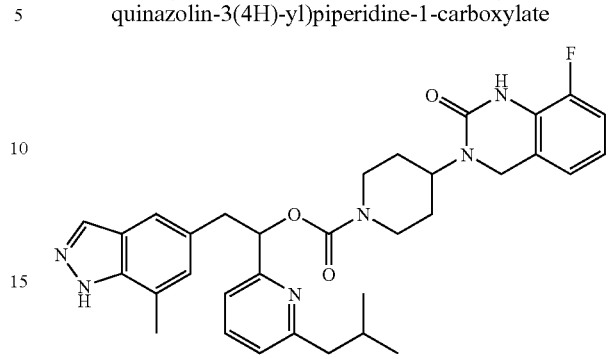

A microwave tube was charged with (±)-1-(6-bromopyridin-2-yl)-2-(7-methyl-1H-indazol-5-yl)ethyl 4-(8-fluoro-2-oxo-1,2-dihydroquinazolin-3(4H)-yl)piperidine-1-carboxylate (13.9 mg, 0.0229 mmol, 1.0 equiv) and Pd(PPh$_3$)$_4$ (ca. 2 mg). Isobutylzinc bromide (0.5 M in tetrahydrofuran, 0.46 mL, 0.23 mmol, 10 equiv) was then added via syringe under nitrogen. The vial was sealed and heated by microwave at 110° C. for 4 h. Tetrahydrofuran was removed in vacuo and the residue was partitioned between ethyl acetate and 0.5 N sodium hydroxide solution. The organic layer was separated and washed with brine, dried and concentrated. Flash column chromatography 10% methanol/methylene chloride) afforded the desired product (9.8 mg, 73.3%) as a glassy solid. MS (ESI) [M+H]$^+$=585. $^1$H-NMR (400 MHz, CDCl$_3$) δ 7.94 (s, 1H), 7.60-7.28 (m, 2H), 7.15-6.68 (m, 7H), 6.01 (br., 1H), 4.60-4.40 (m, 1H), 4.40-4.15 (m, 2H), 4.15-3.90 (m, 1H), 3.85-3.15 (m, 2H), 3.03-2.60 (m, 4H), 2.70 (s, 3H), 2.20-2.02 (m, 1H), 1.82-1.40 (m, 4H), 1.40-1.12 (m, 2H), 1.00-0.90 (m, 6H). HPLC t$_R$=1.44 min.

The following example was similarly prepared:

EXAMPLE 44

(±)-1-(6-(3,5-Difluorobenzyl)pyridin-2-yl)-2-(7-methyl-1H-indazol-5-yl)ethyl 4-(8-fluoro-2-oxo-1,2-dihydroquinazolin-3(4H)-yl)piperidine-1-carboxylate

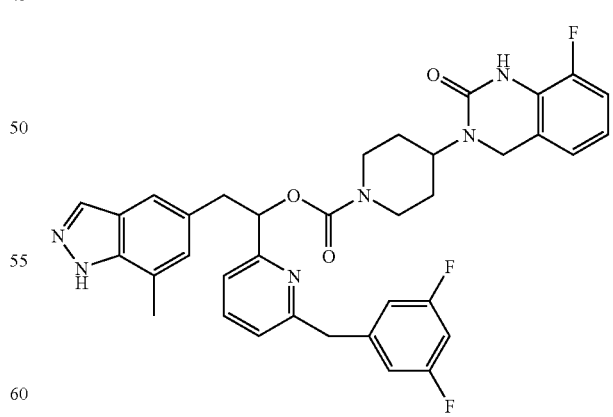

Yield: 43%. MS (ESI) [M+H]$^+$=655. $^1$H-NMR (400 MHz, CDCl$_3$) δ 8.05-7.85 (m, 1H), 7.60-7.40 (m, 1H), 7.15-6.52 (m, 9H), 5.98 (t, J=6.4 Hz, 1H), 4.65-3.88 (m, 8H), 3.52-3.18 (m, 2H), 3.05-2.60 (m, 4H), 2.46 (s, 3H), 1.82-1.38 (m, 4H). HPLC t$_R$=2.32 min.

EXAMPLE 45

(±)-1-(6-Cyanopyridin-2-yl)-2-(7-methyl-1H-indazol-5-yl)ethyl 4-(8-fluoro-2-oxo-1,2-dihydroquinazolin-3(4H)-yl)piperidine-1-carboxylate

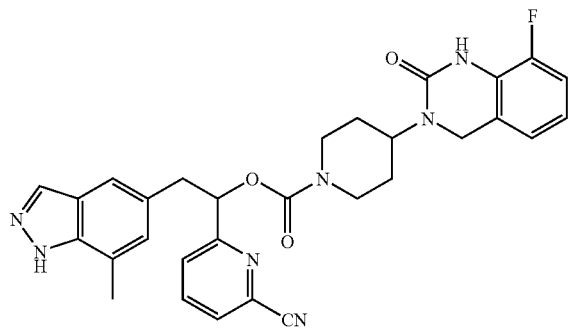

A microwave tube was charged with (±)-1-(6-bromopyridin-2-yl)-2-(7-methyl-1H-indazol-5-yl)ethyl 4-(8-fluoro-2-oxo-1,2-dihydroquinazolin-3(4H)-yl)piperidine-1-carboxylate (18 mg, 0.0296 mmol, 1.0 equiv) and Pd(PPh$_3$)$_4$ (ca. 4 mg) and Zn(CN)$_2$ (14 mg, 0.12 mmol, 4 equiv). DMF (0.5 mL) was added via syringe. The vial was sealed and heated by microwave at 200° C. for 20 min. Tetrahydrofuran was removed in vacuo and the residue was partitioned between ethyl acetate and ammonium hydroxide solution. The organic layer was separated and washed with water, brine, dried and concentrated. Flash column chromatography (10% methanol/methylene chloride) afforded the desired product (15.9 mg, 97%) as a white solid. MS (ESI) [M+H]$^+$=554. $^1$H-NMR (400 MHz, CDCl$_3$) δ 8.01 (s, 1H), 7.72 (br., 1H), 7.62-7.54 (m, 1H), 7.37 (br., 1H), 7.18-6.70 (m, 6H), 6.08-5.83 (m, 1H), 4.65-3.80 (m, 6H), 3.55-3.10 (m, 2H), 3.10-2.64 (m, 2H), 2.53 (s, 3H), 1.90-1.40 (m, 4H). HPLC t$_R$=1.90 min.

EXAMPLE 46

(±)-1-(4-(Hydroxymethyl)pyridin-2-yl)-2-(7-methyl-1H-indazol-5-yl)ethyl 4-(2-oxo-1,2-dihydroquinazolin-3(4H)-yl)piperidine-1-carboxylate

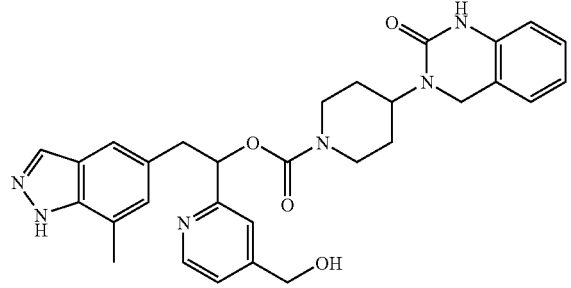

Yield: 64% (2 steps). MS (ESI) [M+H]$^+$=541. $^1$H-NMR (400 MHz, CD$_3$OD) δ 8.50 (d, 1H), 8.04-7.85 (m, 1H), 7.55-7.20 (m, 4H), 7.20-6.80 (m, 4H), 6.73 (d, J=8.0 Hz, 1H), 5.98-5.78 (m, 1H), 4.65 (s, 2H), 4.52-3.70 (m, 4H), 3.40-3.03 (m, 4H), 3.03-2.62 (m, 2H), 2.52 (s, 3H), 2.05-1.10 (m, 5H). HPLC t$_R$=1.43 min.

EXAMPLE 47

(±)-1-(4-Formylpyridin-2-yl)-2-(7-methyl-1H-indazol-5-yl)ethyl 4-(2-oxo-1,2-dihydroquinazolin-3(4H)-yl)piperidine-1-carboxylate

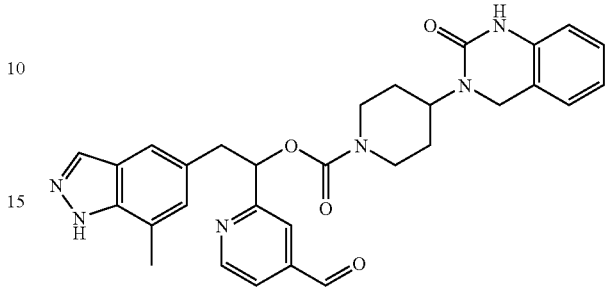

To solid (±)-1-(4-(hydroxymethyl)pyridin-2-yl)-2-(7-methyl-1H-indazol-5-yl)ethyl 4-(2-oxo-1,2-dihydroquinazolin-3(4H)-yl)piperidine-1-carboxylate (28 mg, 0.0518 mmol, 1.0 equiv) was added Dess-Martin reagent (44 mg, 0.104 mmol, 2.0 equiv) and anhydrous methylene chloride (4 mL). The cloudy solution was stirred at room temperature for 2 h. The reaction was quenched with 0.5 N sodium hydroxide. The layers were separated and the organic layer was washed with brine, dried and concentrated to give an off-white solid. Purification by flash column chromatography (10% methanol/methylene chloride) afforded the desired product (23 mg, 82.4%) as an off-white powder. MS (ESI) [M+Na]$^+$=559. $^1$H-NMR (400 MHz, CDCl$_3$) δ 10.02 (s, 1H), 8.88 (d, J=3.2 Hz, 1H), 7.97 (s, 1H), 7.70-7.40 (m, 3H), 7.26-6.75 (m, 5H), 6.67 (br., 1H), 6.13-5.90 (m, 1H), 4.65-3.75 (m, 4H), 3.50-3.10 (m, 3H), 3.10-2.68 (m, 2H), 2.50 (s, 3H), 1.95-1.38 (m, 5H). HPLC t$_R$=1.59 min.

EXAMPLE 48

(±)-2-(2-(7-Methyl-H-indazol-5-yl)-1-(4-(2-oxo-1,2-dihydroquinazolin-3(4H)-yl)piperidine-1-carbonyloxy)ethyl)isonicotinic acid

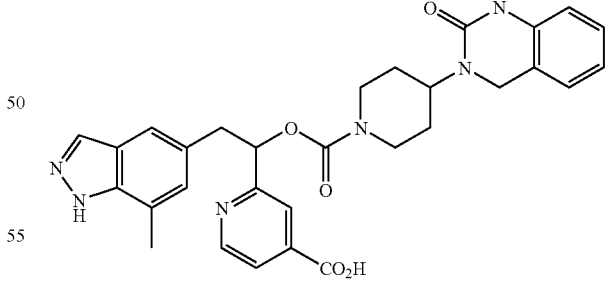

A solution of (±)-2-(2-(7-Methyl-2-((2-(trimethylsilyl)ethoxy)methyl)-2H-indazol-5-yl)-1-(4-(2-oxo-1,2-dihydroquinazolin-3(4H)-yl)piperidine-1-carbonyloxy)ethyl)isonicotinic acid (ca. 14.5 mg) in methylene chloride (0.8 mL) was treated with 0.4 mL trifluoroacetic acid overnight under nitrogen. After LCMS indicated complete conversion, the crude product was purified by prep-HPLC to afford the desired acid as a light yellow oil (4.5 mg, 38.5%). MS (ESI) [M+H]$^+$=555. HPLC t$_R$=1.75 min.

EXAMPLE 49

(±)-2-(7-Methyl-1H-indazol-5-yl)-1-(4-(piperidine-1-carbonyl)pyridin-2-yl)ethyl 4-(2-oxo-1,2-dihydroquinazolin-3(4H)-yl)piperidine-1-carboxylate

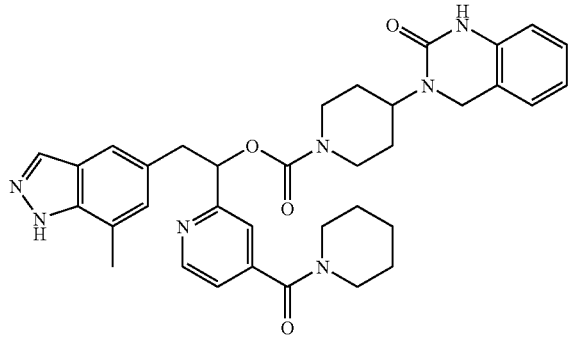

To a solution of (±)-2-(2-(7-methyl-2-((2-(trimethylsilyl)ethoxy)methyl)-2H-indazol-5-yl)-1-(4-(2-oxo-1,2-dihydroquinazolin-3(4H)-yl)piperidine-1-carbonyloxy)ethyl)isonicotinic acid (39.2 mg, 0.057 mmol, 1.0 equiv.) in methylene chloride (0.7 mL) was added a drop of dimethylformamide (catalytic) followed by dropwise addition of oxalyl chloride (2 M in methylene chloride, 0.15 mL, 0.3 mmol, 5 equiv) at room temperature under nitrogen. After 2 h, excess piperidine was added dropwise and the mixture was further stirred for 1 h. The mixture was concentrated to a gel and was suspended in methylene chloride (2 mL). Trifluoroacetic acid (1 mL) was added and the resulting clear tan solution was stirred at room temperature for 6 h. The solvents were removed in vacuo and the residue was partitioned between 1 N sodium hydroxide and ethyl acetate. The layers were separated. The organic layer was washed with brine, dried and concentrated. Purification by flash column chromatography (6% methanol/methylene chloride) afforded the desired product (30.4 mg, 85.4%) as an off-white powder. MS (ESI) [M+H]$^+$=622. $^1$H-NMR (400 MHz, CDCl$_3$) δ 8.69 (d, J=4.4 Hz, 1H), 7.95 (br., 1H), 7.70 (br., 1H), 7.50-6.80 (m, 6H), 6.68 (br., 1H), 6.05-5.94 (m, 1H), 4.65-3.80 (m, 4H), 3.64 (br., 2H), 3.50-3.18 (m, 2H), 3.18-2.60 (m, 4H), 2.48 (s, 3H), 1.85-1.44 (m, 9H), 1.44-1.10 (m, 4H). HPLC t$_R$=1.79 min.

1-(Furan-2-yl)-2-(7-methyl-2-((2-(trimethylsilyl)ethoxy)methyl)-2H-indazol-5-yl)ethyl 4-(2-oxo-1,2-dihydroquinazolin-3(4H)-yl)piperidine-1-carboxylate

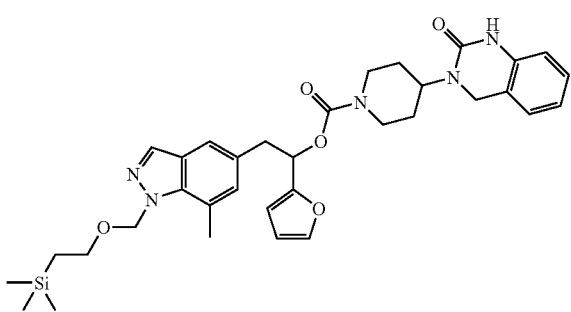

To a solution of 1-(furan-2-yl)-2-(7-methyl-2-((2-(trimethylsilyl)ethoxy)methyl)-2H-indazol-5-yl)ethanol (0.11 mmol) and 4-nitrophenyl 4-(2-oxo-1,2-dihydroquinazolin-3(4H)-yl)piperidine-1-carboxylate (0.13 mmol) in tetrahydrofuran (3 mL) was added sodium hydride (95%, 0.33 mmol) at room temperature under nitrogen. The reaction was stirred overnight. Methylene chloride (15 mL) was added and the mixture washed with water (4×5 mL). The organic layer was dried, filtered and concentrated to give the crude product, which was used without further purification.

The following intermediates were similarly prepared:

2-(7-Methyl-1-((2-(trimethylsilyl)ethoxy)methyl)-1H-indazol-5-yl)-1-(pyridin-4-yl)ethyl 4-(2-oxo-1,2-dihydroquinazolin-3(4H)-yl)piperidine-1-carboxylate

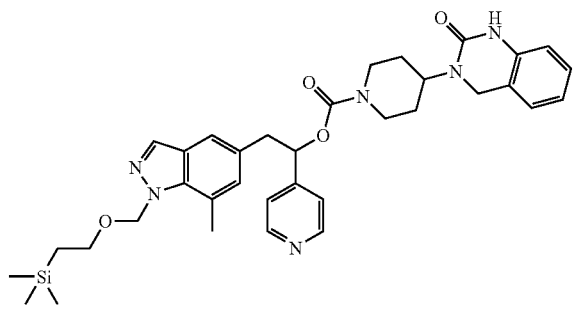

Not isolated.

2-(7-Methyl-1-((2-(trimethylsilyl)ethoxy)methyl)-1H-indazol-5-yl)-1-(pyridin-3-yl)ethyl 4-(2-oxo-1,2-dihydroquinazolin-3(4H)-yl)piperidine-1-carboxylate

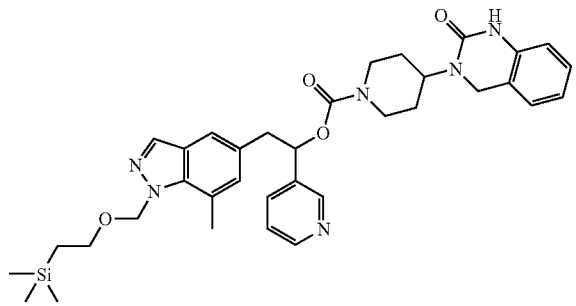

Not isolated.

2-(7-Methyl-1-((2-(trimethylsilyl)ethoxy)methyl)-1H-indazol-5-yl)-1-(pyridin-3-yl)ethyl 4-(8-fluoro-2-oxo-1,2-dihydroquinazolin-3(4H)-yl)piperidine-1-carboxylate

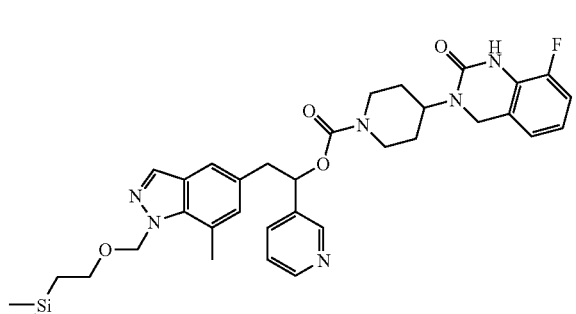

Not isolated.

1-(7-(Furan-2-yl)-1-((2-(trimethylsilyl)ethoxy)methyl)-1H-indazol-5-yl)propan-2-yl 4-(8-fluoro-2-oxo-1,2-dihydroquinazolin-3(4H)-yl)piperidine-1-carboxylate

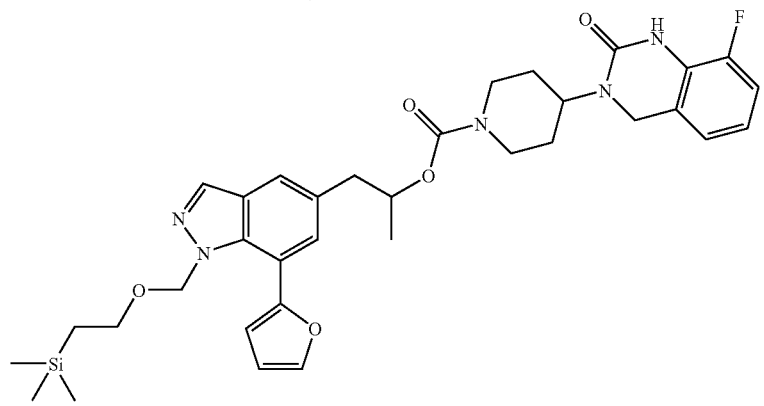

Not isolated.

2-(7-Methyl-1-((2-(trimethylsilyl)ethoxy)methyl)-1H-indazol-5-yl)-1-(quinolin-2-yl)ethyl 4-(2-oxo-1,2-dihydroquinazolin-3(4H)-yl)piperidine-1-carboxylate

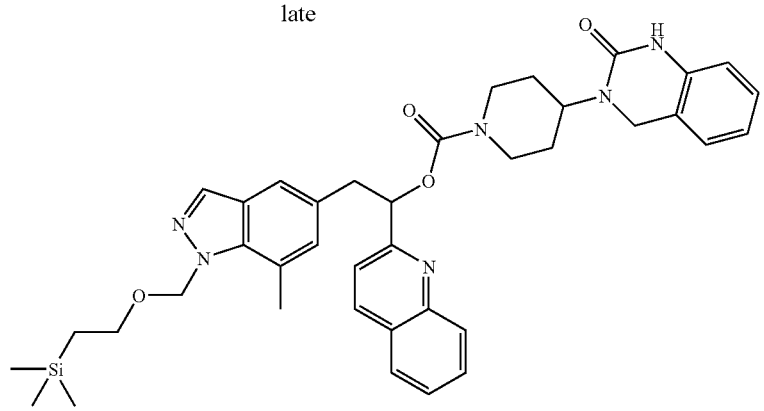

Not isolated.

1-(4,6-Dimethylpyrimidin-2-yl)-2-(7-methyl-1-((2-(trimethylsilyl)ethoxy)methyl)-1H-indazol-5-yl)ethyl 4-(8-fluoro-2-oxo-1,2-dihydroquinazolin-3(4H)-yl)piperidine-1-carboxylate

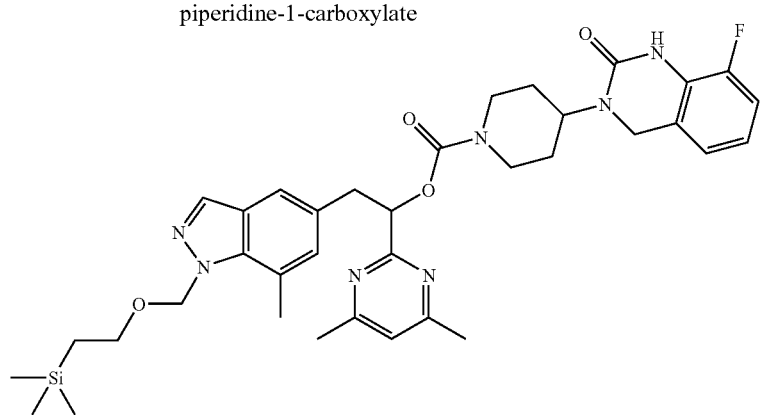

Not isolated.

1-(4,6-Dimethylpyrimidin-2-yl)-2-(7-methyl-1-((2-(trimethylsilyl)ethoxy)methyl)-1H-indazol-5-yl)ethyl 4-(2-oxo-1,2-dihydroquinolin-3-yl)piperidine-1-carboxylate

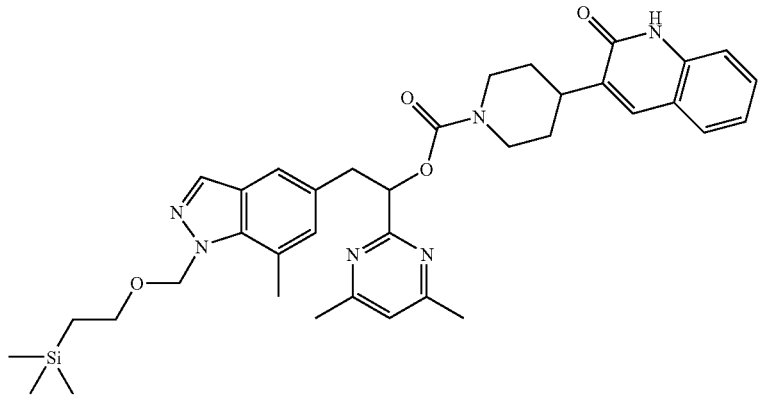

Not isolated.

1-(Benzofuran-2-yl)-2-(7-methyl-1-((2-(trimethylsilyl)ethoxy)methyl)-1H-indazol-5 yl)ethyl 4-(2-oxo-1,2-dihydroquinazolin-3(4H)-yl)piperidine-1-carboxylate Yield: 82%. ¹H-NMR (CDCl₃, 500 MHz) δ 8.65 (s, 1H), 7.96 (s, 1H), 7.67-7.60 (m, 1H), 7.25-7.19 (m, 2H), 6.98-6.96 (m, 2H), 6.94-6.91 (m, 2H), 6.66 (s, 1H), 6.04-5.95 (m, 1H), 5.71-5.57 (m, 2H), 4.54-4.45 (m, 1H), 4.35-4.16 (m, 3H), 3.97-3.90 (m, 0.6H), 3.65-3.52 (m, 2H), 3.40-3.25 (m, 2H), 2.94-2.74 (m, 2H), 2.58 (s, 3H), 1.63-1.55 (m, 3H), 1.40-1.35 (m, 0.4H), 0.94-0.91 (m, 3H), −0.04 (s, 9H). Mass spec.: 659 (MH)⁺.

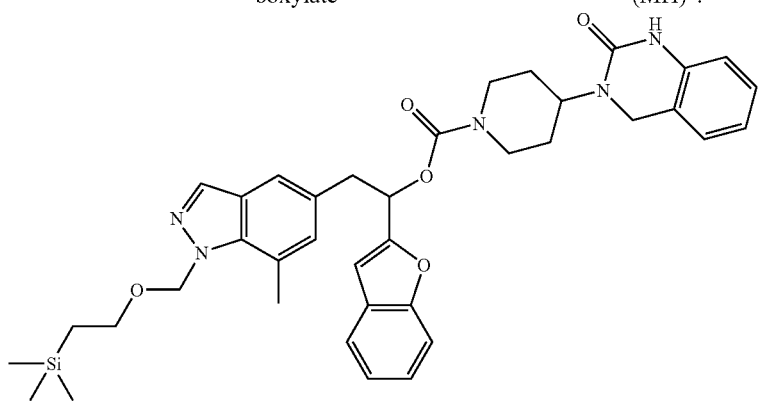

Not isolated.

2-(7-Methyl-2-((2-(trimethylsilyl)ethoxy)methyl)-2H-indazol-5-yl)-1-(pyridin-2-yl)ethyl 4-(8-fluoro-2-oxo-1,2-dihydroquinazolin-3(4H)-yl)piperidine-1-carboxylate

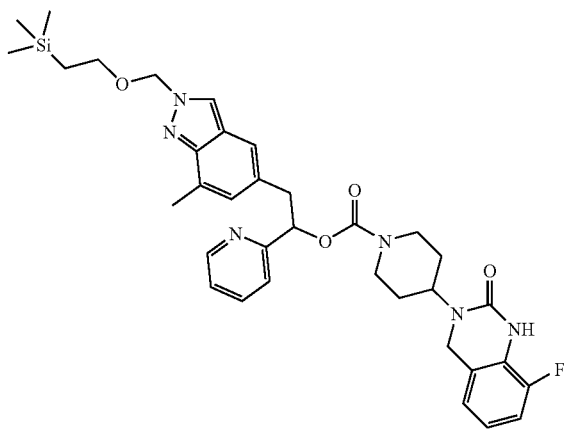

2-(7-Methyl-2-((2-(trimethylsilyl)ethoxy)methyl)-2H-indazol-5-yl)-1-(pyridin-2-yl)ethyl 4-(2-oxo-1,2-dihydroquinazolin-3(4H)-yl)piperidine-1-carboxylate

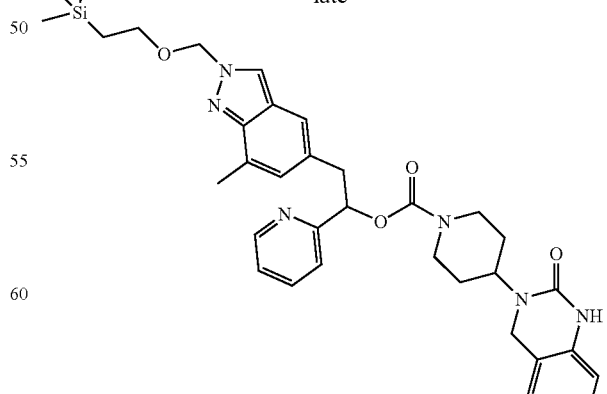

Yield: 54%. ¹H-NMR (CDCl₃, 300 MHz) δ 8.63 (s, 1H), 7.94 (s, 1H), 7.68-7.57 (m, 1H), 7.20-6.86 (m, 5H), 6.60 (d, J=8.1 Hz, 1H), 6.51 (s, 1H), 6.02-5.91 (m, 1H), 5.70-5.55 (m, 2H), 4.52-3.83 (m, 5H), 3.64-3.50 (m, 2H), 3.39-3.20 (m, 2H), 2.94-2.68 (m, 2H), 2.56 (s, 3H), 1.77-1.58 (m, 2H), 1.28-1.17 (m, 2H), 0.93-0.82 (m, 3H), −0.07 (s, 9H). Mass spec.: 641 (MH)⁺.

1-(Isoquinolin-3-yl)-2-(7-methyl-2-((2-(trimethylsilyl)ethoxy)methyl)-2H-indazol-5-yl)ethyl 4-(8-fluoro-2-oxo-1,2-dihydroquinazolin-3(4H)-yl)piperidine-1-carboxylate

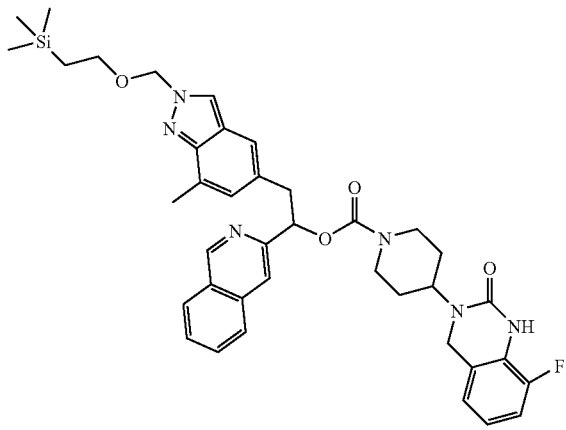

Yield: 74%. ¹H-NMR (CDCl₃, 500 MHz) δ 9.34 (bs, 1H), 8.05-7.99 (m, 1H), 7.95 (s, 1H), 7.82-7.64 (m, 4H), 7.06-6.86 (m, 4H), 6.64 (s, 1H), 6.21-6.14 (m, 1H), 5.70-5.59 (m, 2H), 4.50-4.04 (m, 5H), 3.63-3.54 (m, 2H), 3.48-3.39 (m, 2H), 2.94-2.74 (m, 2H), 2.58 (s, 3H), 1.72-1.56 (m, 4H), 0.93-0.87 (m, 2H), −0.05 (s, 9H). Mass spec.: 709 (MH)⁺.

1-(Isoquinolin-3-yl)-2-(7-methyl-2-((2-(trimethylsilyl)ethoxy)methyl)-2H-indazol-5-yl)ethyl 4-(2-oxo-1,2-dihydroquinazolin-3(4H)-yl)piperidine-1-carboxylate

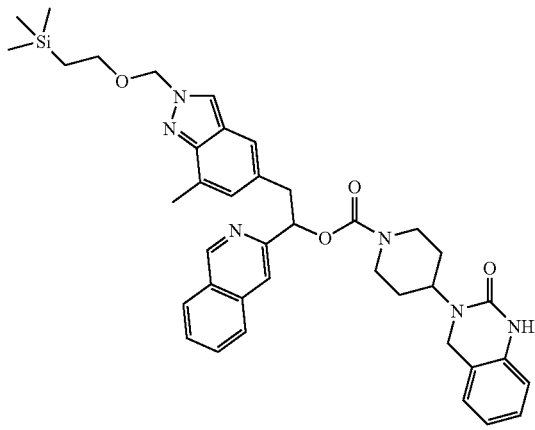

Yield: 48%. ¹H-NMR (CDCl₃, 300 MHz) δ 9.31 (s, 1H), 7.97 (d, J=8.0 Hz, 1H), 7.92 (s, 1H), 7.77-7.59 (m, 4H), 7.15-6.88 (m, 4H), 6.62-6.57 (m, 2H), 6.16-6.10 (m, 1H), 5.68-5.53 (m, 2H), 4.46-3.87 (m, 5H), 3.61-3.33 (m, 4H), 2.95-2.67 (m, 2H), 2.56 (s, 3H), 1.74-1.62 (m, 2H), 1.38-1.20 (m, 2H), 0.93-0.84 (m, 3H), −0.08 (s, 9H). Mass spec.: 691 (MH)⁺.

EXAMPLE 50

N-(1-(isoquinolin-3-yl)-2-(7-methyl-1H-indazol-5-yl)ethyl)-4-(2-oxo-1,2-dihydroquinazolin-3(4H)-yl)piperidine-1-carboxamide

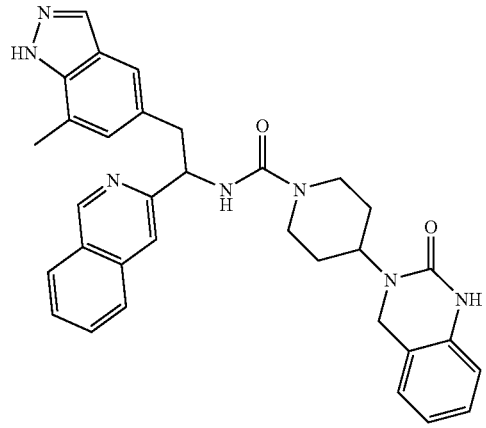

This was prepared as described above for Example 36 from N-(1-(isoquinolin-3-yl)-2-(7-methyl-2-((2-(trimethylsilyl)ethoxy)methyl)-2H-indazol-5-yl)ethyl)-4-(2-oxo-1,2-dihydroquinazolin-3(4H)-yl)piperidine-1-carboxamide in quantitative yield. ¹H-NMR (DMSO-d₆, 500 MHz) δ 13.00 (bs, 1H), 9.36 (s, 1H), 9.18 (s, 1H), 8.14 (d, J=8.2 Hz, 1H), 7.98 (s, 1H), 7.95 (d, J=8.2 Hz, 1H), 7.79-7.74 (m, 2H), 7.68-7.65 (m, 1H), 7.44 (s, 1H), 7.12 (t, J=7.6 Hz, 1H), 7.11 (s, 1H), 7.02 (t, J=7.6 Hz, 2H), 6.87 (t, J=7.6 Hz, 1H), 6.76 (d, J=7.9 Hz, 1H), 5.19-5.14 (m, 1H), 4.80-4.25 (m, 1H), 4.13-4.11 (m, 2H), 3.19-3.11 (m, 4H), 3.05-3.01 (m, 1H), 2.76-2.62 (m, 1H), 2.50 (s, 3H), 1.60-1.54 (m, 4H). Mass spec.: 560 (MH)⁺.

EXAMPLE 51

4-(8-fluoro-2-oxo-1,2-dihydroquinazolin-3(4H)-yl)-N-(1-(isoquinolin-3-yl)-2-(7-methyl-1H-indazol-5-yl)ethyl)piperidine-1-carboxamide

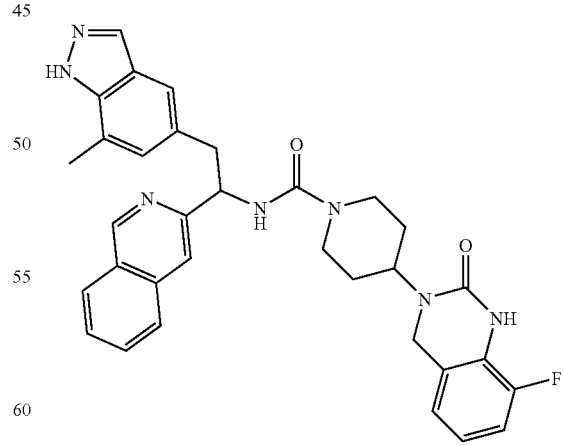

This was prepared as described above for Example 36 from 4-(8-fluoro-2-oxo-1,2-dihydroquinazolin-3(4H)-yl)-N-(1-(isoquinolin-3-yl)-2-(7-methyl-2-((2-(trimethylsilyl)ethoxy)methyl)-2H-indazol-5-yl)ethyl)piperidine-1-carboxamide in quantitative yield. ¹H-NMR (CDCl₃, 500 MHz) δ 10.34 (s, 1H), 9.24 (s, 1H), 7.95 (d, J=7.9 Hz, 1H), 7.87 (s, 0.8H), 7.80 (s, 0.2H), 7.85-7.63 (m, 2H), 7.57-7.54 (m, 1H), 7.26-7.24 (m, 1H), 7.13-7.11 (m, 1H), 6.96-6.93 (m, 2H), 6.88-6.77 (m, 3H), 5.98-5.94 (m, 1H), 5.35-5.31 (m, 1H), 4.56-4.51 (m, 1H), 4.22 (s, 2H), 4.14-4.11 (m, 2H), 3.42-3.36 (m, 1H), 3.22-3.17 (m, 1H), 2.92-2.82 (m, 3H), 2.63 (s, 0.6H), 2.42 (s, 2.4H), 1.64-1.60 (m, 3H). Mass spec.: 578 (MH)⁺.

EXAMPLE 52

1-(Isoquinolin-3-yl)-2-(7-methyl-1H-indazol-5-yl)ethyl 4-(8-fluoro-2-oxo-1,2-dihydroquinazolin-3(4H)-yl)piperidine-1-carboxylate

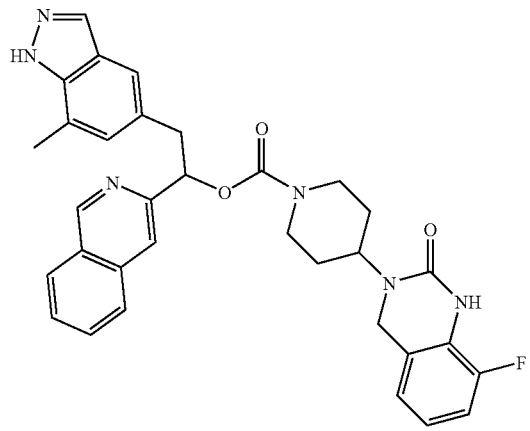

This was prepared as described above for Example 36 from 1-(isoquinolin-3-yl)-2-(7-methyl-2-((2-(trimethylsilyl)ethoxy)methyl)-2H-indazol-5-yl)ethyl 4-(8-fluoro-2-oxo-1,2-dihydroquinazolin-3(4H)-yl)piperidine-1-carboxylate in 59% yield. ¹H-NMR (CDCl₃, 500 MHz) δ 9.29 (s, 1H), 7.97 (d, J=8.2 Hz, 1H), 7.94-7.85 (m, 1H), 7.76 (d, J=8.2 Hz, 1H), 7.67-7.64 (m, 1H), 7.60-7.57 (m, 2H), 7.46-7.35 (m, 1H), 7.15-7.03 (m, 2H), 6.93-6.87 (m, 1H), 6.85-6.82 (m, 1H), 6.15-6.10 (m, 1H), 4.51-3.98 (m, 5H), 3.49-3.33 (m, 2H), 2.90-2.69 (m, 3H), 2.48 (s, 3H), 1.66-1.52 (m, 3H). Mass spec.: 579 (MH)⁺.

EXAMPLE 53

1-(Isoquinolin-3-yl)-2-(7-methyl-1H-indazol-5-yl)ethyl 4-(2-oxo-1,2-dihydroquinazolin-3(4H)-yl)piperidine-1-carboxylate

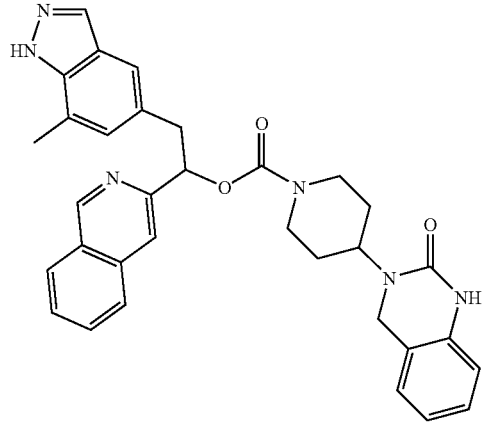

This was prepared as described above for Example 36 from 1-(isoquinolin-3-yl)-2-(7-methyl-2-((2-(trimethylsilyl)ethoxy)methyl)-2H-indazol-5-yl)ethyl 4-(2-oxo-1,2-dihydroquinazolin-3(4H)-yl)piperidine-1-carboxylate in 82% yield. ¹H-NMR (CDCl₃, 300 MHz) δ 9.31 (s, 1H), 7.99-7.87 (m, 2H), 7.77-7.57 (m, 4H), 7.40-7.35 (m, 0.5H), 7.15-6.88 (m, 5H), 6.62 (d, J=8.1 Hz, 1H), 6.12-6.08 (m, 1H), 6.90-6.85 (m, 0.5H), 4.46-3.93 (m, 5H), 3.49-3.33 (m, 2H), 3.02-2.72 (m, 3H), 2.67 (s, 0.5H), 2.46 (s, 2.5H), 1.80-1.64 (m, 2H), 1.26-1.17 (m, 1H). Mass spec.: 561 (MH)⁺.

EXAMPLE 54

2-(7-methyl-1H-indazol-5-yl)-1-(pyridin-2-yl)ethyl 4-(2-oxo-1,2-dihydroquinazolin-3(4H)-yl)piperidine-1-carboxylate

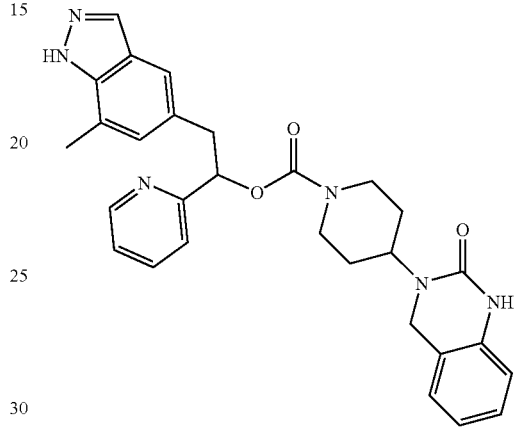

This was prepared as described above for Example 36 from 2-(7-methyl-2-((2-(trimethylsilyl)ethoxy)methyl)-2H-indazol-5-yl)-1-(pyridin-2-yl)ethyl 4-(2-oxo-1,2-dihydroquinazolin-3(4H)-yl)piperidine-1-carboxylate in 40% yield. ¹H-NMR (CDCl₃, 300 MHz) δ 8.66 (s, 1H), 7.95 (s, 0.7H), 7.88 (s, 0.3H), 7.68-7.63 (m, 1H), 7.40-6.90 (m, 6H), 6.71 (s, 0.3H), 6.67 (s, 0.7H), 6.62 (d, J=7.7 Hz, 1H), 5.99-5.84 (m, 2H), 4.52-3.87 (m, 5H), 3.44-3.12 (m, 2H), 3.03-2.71 (m, 2H), 2.68 (s, 1H), 2.47 (s, 2H), 1.78-1.66 (m, 2H), 1.25-1.20 (m, 1H). Mass spec.: 511 (MH)⁺.

EXAMPLE 55

2-(7-methyl-1H-indazol-5-yl)-1-(pyridin-2-yl)ethyl 4-(8-fluoro-2-oxo-1,2-dihydroquinazolin-3(4H)-yl)piperidine-1-carboxylate

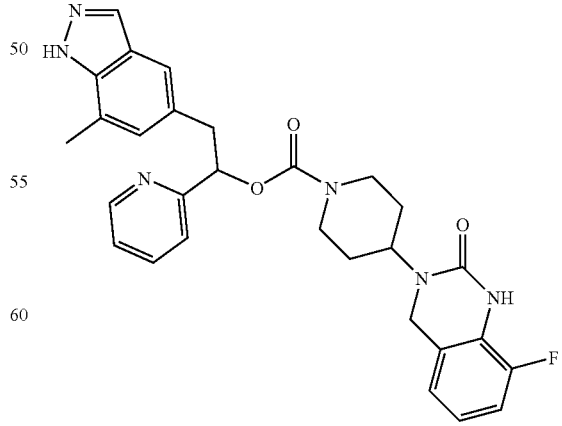

This was prepared as described above for Example 36 from 2-(7-methyl-2-((2-(trimethylsilyl)ethoxy)methyl)-2H-indazol-5-yl)-1-(pyridin-2-yl)ethyl 4-(8-fluoro-2-oxo-1,2-dihydroquinazolin-3(4H)-yl)piperidine-1-carboxylate in 64% yield. ¹H-NMR (CDCl₃, 500 MHz) δ 8.67 (s, 1H), 7.97 (s, 0.6H), 7.90 (s, 0.4H), 7.68-7.64 (m, 1H), 7.46-7.29 (m, 1H), 7.24-7.21 (m, 1H), 7.08-6.78 (m, 5H), 5.97-5.91 (m, 2H), 4.54-3.96 (m, 5H), 3.47-3.26 (m, 2H), 2.95-2.73 (m, 2H), 2.71 (s, 1H), 2.50 (s, 2H), 1.79-1.49 (m, 2H), 1.42-1.36 (m, 1H). Mass spec.: 529 (MH)⁺.

EXAMPLE 56

1-(Furan-2-yl)-2-(7-methyl-1H-indazol-5-yl)ethyl 4-(2-oxo-1,2-dihydroquinazolin-3(4H)-yl)piperidine-1-carboxylate

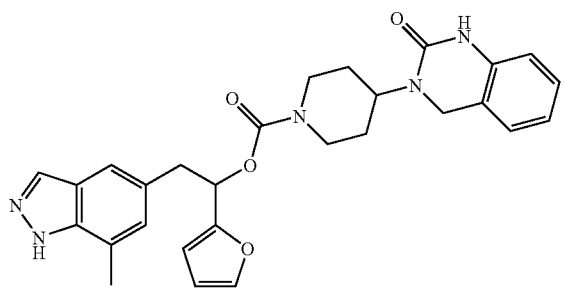

Prepared as described above for Example 30 in 77% yield. ¹H-NMR (400 MHz, CDCl₃) δ 7.99 (1H, s), 7.66 (1H, s), 7.41 (1H, s), 7.34 (1H, broad), 7.11 (1H, m), 7.09 (1H, m), 6.89 (1H, m), 6.69 (1H, s), 6.29 (1H, m), 6.25 (1H, m), 5.97 (1H, m), 4.47 (1H, broad), 4.24 (2H, m), 4.05 (1H, broad), 3.33 (2H, m), 2.98 (1H, m), 2.80 (2H, broad), 2.51 (3H, s), 1.78 (1H, m), 1.62 (2H, broad), 1.32 (2H, m). HPLC $t_R$=1.96 min, MS(ESI)[M+Na]⁺=522.07.

EXAMPLE 57

2-(7-Methyl-1H-indazol-5-yl)-1-(pyridin-4-yl)ethyl 4-(2-oxo-1,2-dihydroquinazolin-3(4H)-yl)piperidine-1-carboxylate

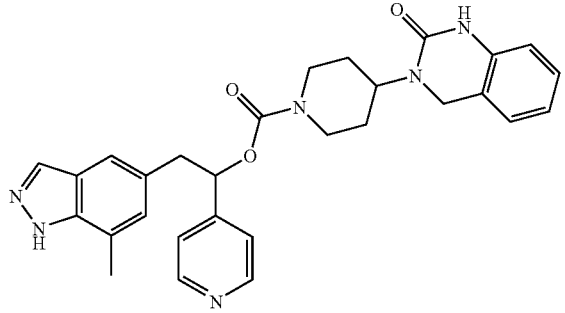

Prepared as described above for Example 30 in 6% yield (3 steps). HPLC $t_R$=1.48 min, MS(ESI)[M+H]⁺=511.21.

EXAMPLE 58

2-(7-Methyl-1H-indazol-5-yl)-1-(pyridin-3-yl)ethyl 4-(2-oxo-1,2-dihydroquinazolin-3(4H)-yl)piperidine-1-carboxylate

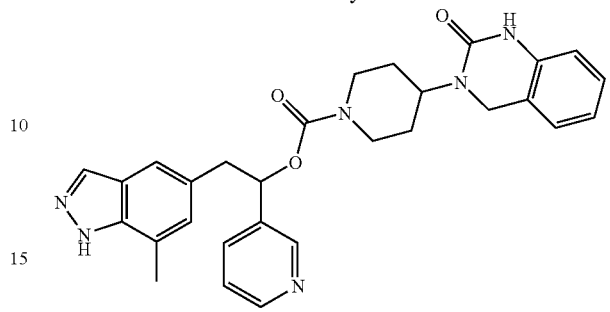

Prepared as described above for Example 30 in 29% yield. ¹H-NMR (400 MHz, CDCl₃) δ 8.53 (2H, m), 7.95 (1H, s), 7.56 (1H, s), 7.27 (2H, m), 7.16 (1H, m), 7.13-6.91 (4H, m), 6.66 (1H, d, J=8.0 Hz), 5.94 (1H, t, J=6.8 Hz), 4.50 (1H, br), 4.34-4.06 (4H, br), 3.31 (1H, br), 3.16 (1H, br), 2.90-2.68 (3H, br), 2.48 (3H, s), 1.80-0.49 (3H, br). HPLC $t_R$=1.48 min, MS(ESI)[M+H]⁺=511.26.

EXAMPLE 59

2-(7-Methyl-1H-indazol-5-yl)-1-(pyridin-3-yl)ethyl 4-(8-fluoro-2-oxo-1,2-dihydroquinazolin-3(4H)-yl)piperidine-1-carboxylate

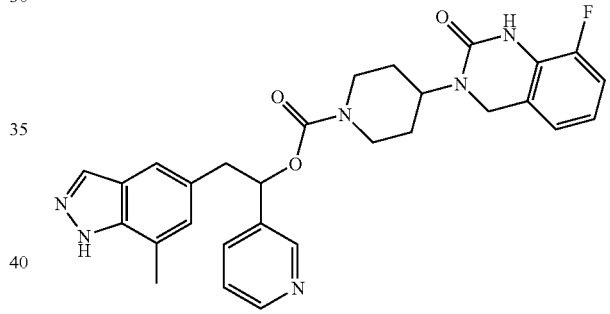

Prepared as described above for Example 30 in 64% yield. ¹H-NMR (400 MHz, CDCl₃) δ 8.52 (2H, m), 7.95 (1H, s), 7.56 (1H, s), 7.27 (2H, m), 6.90-6.71 (5H, m), 5.95 (1H, t, J=6.8 Hz), 4.50 (1H, br), 4.34-4.06 (4H, br), 3.31 (1H, br), 3.16 (1H, br), 2.90-2.68 (3H, br), 2.48 (3H, s), 1.80-1.49 (3H, br). HPLC $t_R$=1.50 min, MS(ESI)[M+H]⁺=529.24.

EXAMPLE 60

1-(Furan-2-yl)-2-(7-methyl-1H-indazol-5-yl)ethyl 4-(8-fluoro-2-oxo-1,2-dihydroquinazolin-3(4H)-yl)piperidine-1-carboxylate

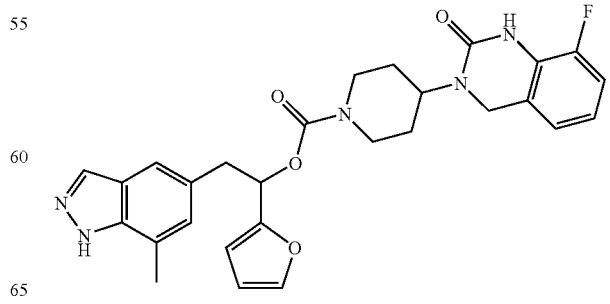

Prepared as described above for Example 30 in 22% yield. ¹H-NMR (400 MHz, CDCl₃) δ 8.02 (1H, s), 7.41 (1H, s), 7.36

(1H, s), 7.03-6.82 (6H, m), 6.29 (2H, m), 5.97 (1H, m), 4.48 (1H, broad), 4.30-4.04 (5H, m), 3.33 (2H, m), 2.51 (3H, s), 1.78 (1H, m), 1.62 (3H, broad). HPLC $t_R$=1.96 min, MS(ESI) [M+Na]$^+$=540.12.

EXAMPLE 61

2-(7-Methyl-1H-indazol-5-yl)-1-(quinolin-2-yl)ethyl 4-(2-oxo-1,2-dihydroquinazolin-3(4H)-yl)piperidine-1-carboxylate

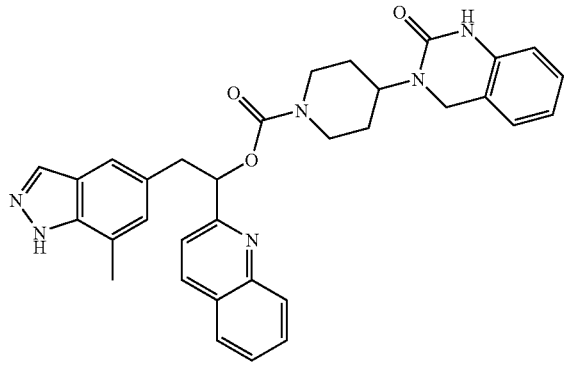

Prepared as described above for Example 30 in 8% yield. HPLC $t_R$=1.77 min, MS(ESI)[M+H]$^+$=561.14.

EXAMPLE 62

1-(4,6-Dimethylpyrimidin-2-yl)-2-(7-methyl-1H-indazol-5-yl)ethyl 4-(2-oxo-1,2-dihydroquinolin-3-yl)piperidine-1-carboxylate

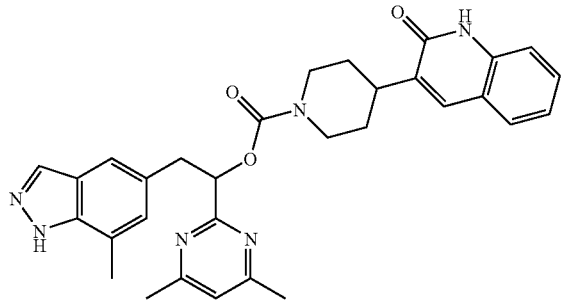

Prepared as described above for Example 30 in 45% yield. $^1$H-NMR (400 MHz, CDCl$_3$) δ 7.98 (1H, s), 7.49-7.10 (7H, m), 6.88 (1H,s), 5.84 (1H, m), 4.48-4.09 (2H, m), 3.45-2.70 (5H, m), 2.46 (9H, s), 2.00-1.35 (4H, m). HPLC $t_R$=1.90 min, MS(ESI)[M+H]$^+$=537.18.

EXAMPLE 63

1-(4,6-Dimethylpyrimidin-2-yl)-2-(7-methyl-1H-indazol-5-yl)ethyl 4-(8-fluoro-2-oxo-1,2-dihydroquinazolin-3(4H)-yl)piperidine-1-carboxylate

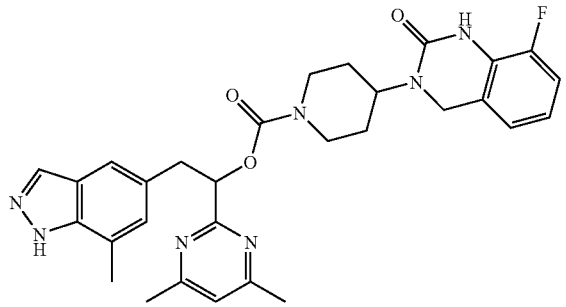

Prepared as described above for Example 30 in 2% yield. HPLC $t_R$=1.84 min, MS(ESI)[M+H]$^+$=558.

EXAMPLE 64

1-(Benzofuran-2-yl)-2-(7-methyl-1H-indazol-5-yl) ethyl 4-(2-oxo-1,2-dihydroquinazolin-3(4H)-yl)piperidine-1-carboxylate

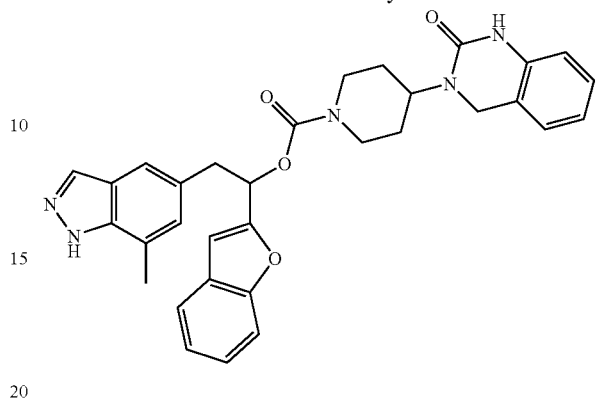

Prepared as described above for Example 30 in 41% yield. HPLC $t_R$=2.14 min, MS(ESI)[M+H]$^+$=550.09.

Methyl-2-(tert-butoxycarbonyl)-3-(7-methyl-2-[{2-[trimethylsilyl]ethoxy}methyl]-2H-indazol-5-yl) acrylate

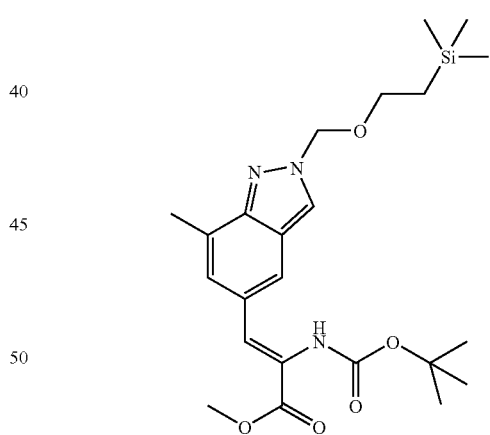

To a stirred solution of 7-methyl-2-((2-(trimethylsilyl) ethoxy)methyl)-2-H-indazole-5-carbaldehyde (8.5 g, 29.3 mmol) and methyl-2-(tert-butoxycarbonyl)-2-(dimethoxyphosphoryl)acetate (10 g, 32.2 mmol, 1.1 equiv) in tetrahydrofuran (30 mL) at 0° C. was added tetramethylguanidine (5.9 mL, 49.8 mmol, 1.7 equiv). After 10 min, the ice bath was removed and the reaction stirred at room temperature overnight. The solvent was evaporated and the residue purified by flash chromatography on silica gel to afford 11.2 g (83%). $^1$H-NMR (CD$_3$OD, 300 MHz) δ −0.05 (s, 9H), 0.84-0.96 (m, 2H), 1.14 (bs, 9H), 2.56 (s, 3H), 3.58-3.70 (m, 2H), 3.82 (s, 3H), 5.73 (s, 2H), 7.41 (s, 1H), 7.45 (s, 1H), 7.84 (s, 1H), 8.41 (s, 1H). Mass spec.: 462.5 (MH)$^+$.

(±)-Methyl-2-(tert-butoxycarbonyl)-3-(7-methyl-2-[{2-[trimethylsilyl]ethoxy}methyl]-2H-indazol-5-yl)propanoate

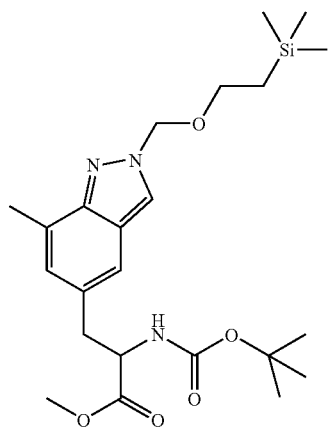

A solution of methyl-2-(tert-butoxycarbonyl)-3-(7-methyl-2-[{2-[trimethylsilyl]ethoxy}methyl]-2H-indazol-5-yl)acrylate (3.7 g, 8.0 mmol) in methanol (20 mL) was flushed with nitrogen (2×), and treated with palladium (10% on charcoal, 0.37 g). The flask was flushed with hydrogen and was shaken in a parr apparatus overnight at 60 psi. The reaction was flushed with nitrogen, filtered through celite, and concentrated. Column chromatography gave 2.3 g (63%). $^1$H-NMR (CDCl$_3$, 500 MHz) δ −0.03 (s, 9H), 0.92-0.97 (m, 2H), 1.41 (s, 9H), 2.59 (s, 3H), 3.00-3.17 (m, 2H), 3.59-3.67 (m, 2H), 3.71 (s, 1H), 4.54-4.64 (m, 1H), 4.92-5.01 (m, 1H), 5.71 (s, 2H), 6.82 (s, 1H), 7.12-7.19 (m, 2H), 8.01 (s, 1H). Mass spec.: 464.29 (MH)$^+$.

(±)-tert-Butyl-1-hydroxy-3-(7-methyl-2-[{2-[trimethylsilyl]ethoxy}methyl]-2H-indazol-5-yl)propan-2-ylcarbamate

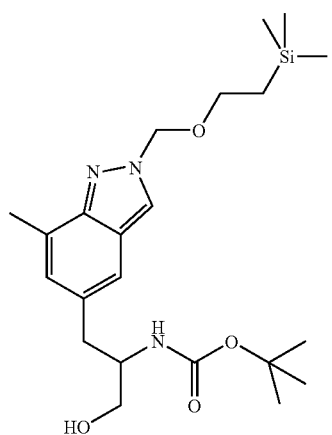

Methyl-2-(tert-butoxycarbonyl)-3-(7-methyl-2-[{2-[trimethylsilyl]ethoxy}methyl]-2H-indazol-5-yl)propanoate (2.35 g, 5.06 mmol) was dissolved in tetrahydrofuran (15 mL) and cooled to 0° C. To this solution was added lithium borohydride (0.45 g, 4.0 equiv). After 30 min, the ice bath was removed and the mixture stirred at room temperature for 3 h. The reaction mixture was diluted with ethyl acetate and carefully quenched with 10% citric acid. The organic layer was separated and washed with water (2×), brine (2×), dried over sodium sulfate, and concentrated to afford 2.12 g (quant.) of the title compound which was used for the next reaction without purification. $^1$H-NMR (CDCl$_3$, 500 MHz) δ −0.03 (s, 9H), 0.90-0.96 (m, 2H), 1.40 (s, 9H), 2.60 (s, 3H), 2.80-2.89 (m, 2H), 3.54-3.98 (m, 5H), 4.76 (d, J=7.6, 1H), 5.71 (s, 2H), 6.94 (s, 1H), 7.30 (s, 1H), 8.00 (s, 1H). Mass spec.: 436.4 (MH)$^+$.

(±)-tert-Butyl-3-(7-methyl-2-[{2-[trimethylsilyl]ethoxy}methyl]-2H-indazol-5-yl)-1-oxopropan-2-ylcarbamate

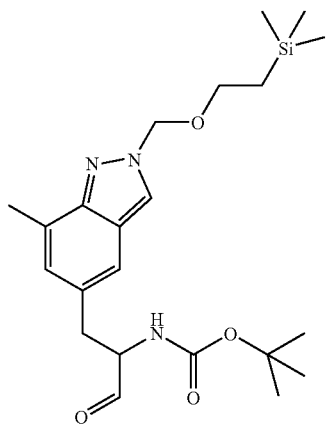

tert-Buty-1-hydroxy-3-(7-methyl-2-[{2-[trimethylsilyl]ethoxy}methyl]-2H-indazol-5-yl)propan-2-ylcarbamate (0.3 g, 0.69 mmol) was dissolved in anhydrous dimethyl sulfoxide (2.5 mL). Triethylamine (0.29 mL, 2.07 mmol) was then added and the reaction mixture cooled to ca. 5° C. using an ice bath. A solution of sulfur trioxide pyridine complex (0.33 g, 2.07 mmol) in dimethyl sulfoxide (2 mL) was added in one portion. After 1 min, the ice bath was removed and the reaction mixture stirred at room temperature for 20 min. The reaction mixture was poured into an ice slurry and extracted with ethyl acetate (3×). The combined organic extracts were washed with 10% citric acid (2×), water (2×), 5% sodium bicarbonate (2×), brine (2×), dried over sodium sulfate, and concentrated. Column chromatography afforded 0.2 g (74%). Mass spec. (in methanol): 466.25 (M+MeOH+H)$^+$.

(±)-tert-Butyl-1-(1H-imidazol-2-yl)-2-(7-methyl-2-[{2-[trimethylsilyl]ethoxy}methyl]-2H-indazol-5-yl)ethylcarbamate

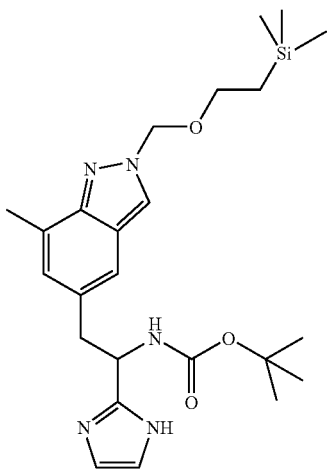

tert-Butyl-3-(7-methyl-2-[{2-[trimethylsilyl]ethoxy}methyl]-2H-indazol-5-yl)-1-oxopropan-2-ylcarbamate (0.57 g, 1.3 mmol) and glyoxal trimer (0.14 g, 2.0 mmol) were combined in a 1,4 dioxane/water mixture (6:1, 8 mL). To this mixture was added 28% ammonia in water (0.35 mL, 5.2 mmol) and the reaction mixture allowed to stir at 80° C. After 16 h, additional glyoxal (50 mg) and 28% ammonia in water (0.12 mL) was added and the reaction stirred at 80° C. for 5 h. After cooling to room temperature the solvents were removed and the crude mixture dissolved in methylene chloride which was washed with water (2×), brine (2×), dried over magnesium sulfate, and concentrated. Column chromatography afforded 0.33 g (54%). $^1$H-NMR (CDCl$_3$, 500 MHz) δ −0.04 (s, 9H), 0.88-0.96 (m, 2H), 1.33 (s, 9H), 2.51 (s, 3H), 3.18-3.31 (m, 2H), 3.58-3.65 (m, 2H), 5.02-5.10 (m, 1H), 5.68 (s, 1H), 6.78 (s, 1H), 6.88 (s, 2H), 7.17 (s, 1H), 7.25 (s, 1H), 7.94 (s, 1H). Mass spec.: 472.16 (MH)$^+$.

EXAMPLE 65

(±)-N-(1-(1H-Imidazol-2-yl)-2-(7-methyl-1H-indazol-5-yl)ethyl)-4-(2-oxo-1,2-dihydroquinazolin-3(4H)-yl)piperidine-1-carboxamide

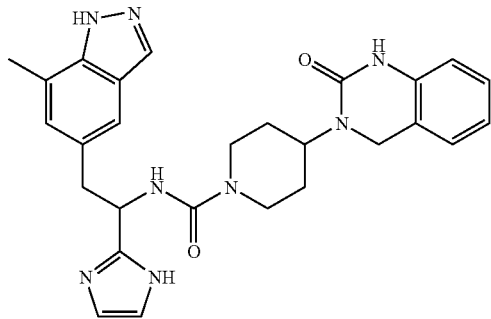

tert-Butyl-1-(1H-imidazol-2-yl)-2-(7-methyl-2-[{2-[trimethylsilyl]ethoxy}methyl]-2H-indazol-5-yl)ethylcarbamate (100 mg, 0.212 mmol) was dissolved in a trifluoroacetic acid/methylene chloride mixture (1:1, 2 mL) and stirred under nitrogen for 3 h. The solvent was removed in vacuo and the resulting crude mixture passed through a strong cationic exchange column. After washing the column with several volumes of methanol, the desired amine was obtained by washing the column with 2M ammonia in methanol. After concentration, the amine was dissolved in dimethylformamide (1.5 mL) at 0° C. and treated with carbonyl diimidazole (34.0 mg, 1.1 equiv). The reaction was stirred for 5 min at 0° C., warmed to room temperature, stirred for 10 min, and treated with 3-piperidin-4-yl-3,4-dihydro-1H-quinazolin-2-one (48.0 mg, 1.1 equiv). The mixture was stirred at room temperature overnight. The solvent was evaporated and the residue purified by column chromatography to afford 48 mg (50%). $^1$H-NMR (CD$_3$OD, 500 MHz) δ 1.50-1.70 (m, 4H), 2.55 (s, 3H), 2.70-2.95 (m, 3H), 3.40 (m, 1H), 4.00-4.50 (m, 6H), 5.23 (dd, J=6.4, 9.2, 1H), 6.79 (d, J=7.6, 1H), 6.93-7.05 (m, 5H), 7.04-7.20 (m, 2H), 7.40 (s, 1H), 7.40 (s, 1H). Mass spec.: 499.4 (MH)$^+$.

EXAMPLE 66

(±)-N-(1-(1-Methyl-1H-imidazol-2-yl)-2-(7-methyl-1H-indazol-5-yl)ethyl)-4-(2-oxo-1,2-dihydroquinazolin-3(4H)-yl)piperidine-1-carboxamide

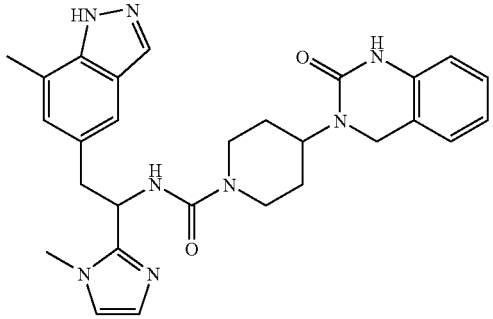

A solution of N-(1-(1H-Imidazol-2-yl)-2-(7-methyl-H-indazol-5-yl)ethyl)-4-(2-oxo-1,2-dihydroquinazolin-3(4H)-yl)piperidine-1-carboxamide (13 mg, 0.026 mmol) and iodomethane (4.0 µL, 2 equiv) in dimethyl sulfoxide (0.6 mL) was treated with potassium carbonate (11 mg, 3.0 equiv) and the reaction mixture was stirred under nitrogen for 16 h. The mixture was poured into ice water and extracted with ethyl acetate (2×). The organic layer was washed with brine (2×), dried over sodium sulfate, concentrated and purified by column chromatography to afford 2.0 mg (15%). $^1$H-NMR (CD$_3$OD, 500 MHz) δ 1.56-1.73 (m, 4H), 2.52 (s, 3H), 2.79-2.93 (m, 2H), 3.29 (s, 3H), 4.09-4.22 (m, 2H), 4.23 (s, 2H), 4.35-4.45 (m, 1H), 5.23 (dd, J=8.2, 7.4, 1H), 6.80 (d, J=7.9, 1H), 6.86 (s, 1H), 6.92 (s, 1H), 6.97 (s, 1H), 7.09-7.20 (m, 2H), 7.80 (s, 1H). Mass spec.: 513.1 (MH)$^+$.

EXAMPLE 67

(±)-N-(1-(1-Benzyl-1H-imidazol-2-yl)-2-(7-methyl-1H-indazol-5-yl)ethyl)-4-(2-oxo-1,2-dihydroquinazolin-3(4H)-yl)piperidine-1-carboxamide

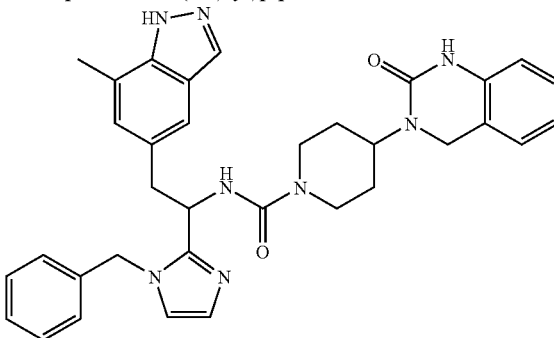

N-(1-(1H-Imidazol-2-yl)-2-(7-methyl-1H-indazol-5-yl)ethyl)-4-(2-oxo-1,2-dihydroquinazolin-3(4H)-yl)piperidine-1-carboxamide (100 mg, 0.2 mmol) and benzyl bromide (25.0 µL, 1.1 equiv) were combined in dimethyl sulfoxide (0.6 mL). After stirring at room temperature for 16 h, the reaction mixture was poured into ice water and extracted with ethyl acetate (2×). The organic layer was washed with brine (2×), dried over sodium sulfate, concentrated, and purified by column chromatography to afford 14.0 mg (12%). $^1$H-NMR (CD$_3$OD, 500 MHz) δ 1.58-1.70 (m, 4H), 2.48 (s, 3H), 2.75-2.84 (m, 2H), 3.36-3.43 (m, 2H), 4.02-4.14 (m, 3H), 4.23 (s, 2H), 4.86 (m, 1H), 5.23 (s, 2H), 5.29-5.38 (m, 1H), 6.85-7.01 (m, 3H), 7.10-7.84 (m, 10H), 7.96 (s, 1H). Mass spec.: 589.16 (MH)$^+$.

(±)-tert-Butyl 1-(1-(3-fluorobenzyl)-1H-imidazol-2-yl)-2-(7-methyl-2-((2-(trimethylsilyl)ethoxy)methyl)-2H-indazol-5-yl)ethylcarbamate

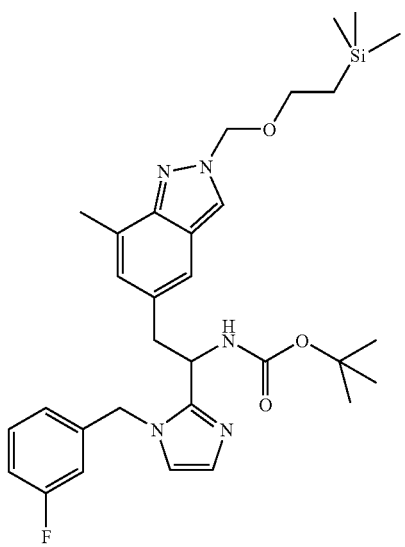

A mixture of tert-Butyl-1-(1H-imidazol-2-yl)-2-(7-methyl-2-[{2-[trimethylsilyl]ethoxy}methyl]-2H-indazol-5-yl)ethylcarbamate (20 mg, 0.042 mmol), 3-fluoro benzyl bromide (5.5 µL, 0.045 mmol, 1.1 equiv), and potassium carbonate (11.7 mg, 0.09 mmol) in dimethylformamide (0.6 mL) was stirred at room temperature for 16 h. The solvents were removed in vacuo and the residue purified by column chromatography to afford 15.2 mg (63%). Mass spec.: 580.04 (MH)+.

(±)-tert-Butyl 1-(1-(3,5-difluorobenzyl)-1H-imidazol-2-yl)-2-(7-methyl-2-((2-(trimethylsilyl)ethoxy)methyl)-2H-indazol-5-yl)ethylcarbamate

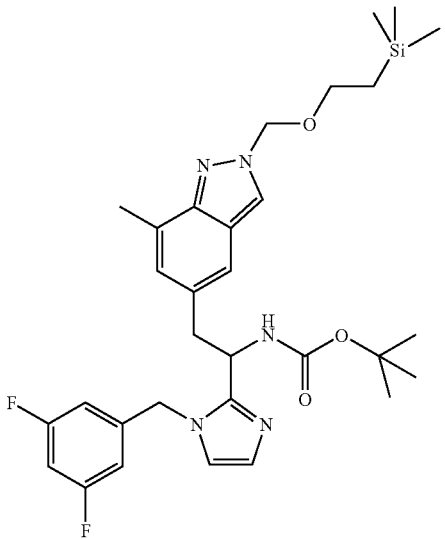

A mixture of tert-Butyl-1-(1H-imidazol-2-yl)-2-(7-methyl-2-[{2-[trimethylsilyl]ethoxy}methyl]-2H-indazol-5-yl)ethylcarbamate (40 mg, 0.085 mmol), 3,5-difluoro benzyl bromide (11.5 µL, 0.089 mmol, 1.05 equiv) and potassium carbonate (23.5 mg, 0.17 mmol) in dimethylformamide (1.0 mL) was stirred at room temperature for 16 h. The solvents were removed and the residue purified by column chromatography to afford 40.0 mg (79%). Mass spec.: 598.4 (MH)+.

(±)-tert-Butyl 1-(1-(4-tert-Butylbenzyl)-1H-imidazol-2-yl)-2-(7-methyl-2-((2-(trimethylsilyl)ethoxy)methyl)-2H-indazol-5-yl)ethylcarbamate

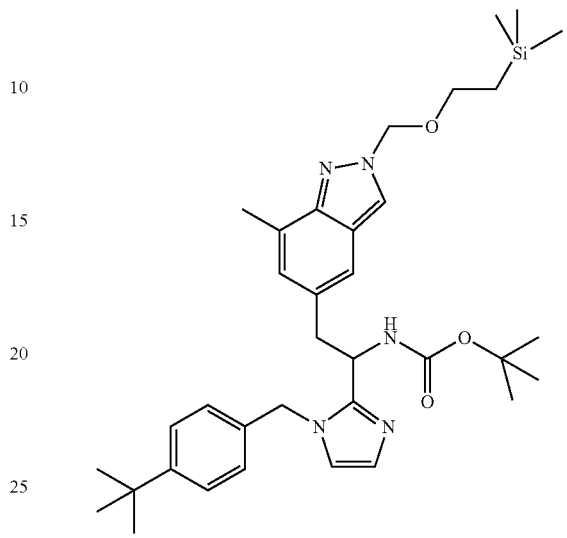

(tert-Butyl-1-(1H-imidazol-2-yl)-2-(7-methyl-2-[{2-[trimethylsilyl]ethoxy}methyl]-2H-indazol-5-yl)ethylcarbamate (40 mg, 0.085 mmol), 4-(tert-Butyl)-benzyl bromide (16.3 µL, 0.089 mmol, 1.05 equiv), and potassium carbonate (23.5 mg, 0.17 mmol) were combined in dimethylformamide (1.0 mL). After stirring at room temperature for 16 h, the solvents were removed and the residue purified by column chromatography to afford 36.0 mg (79%). Mass spec.: 618.6 (MH)+.

(±)-tert-Butyl 1-(1-(3-cyanobenzyl)-1H-imidazol-2-yl)-2-(7-methyl-2-((2-(trimethylsilyl)ethoxy)methyl)-2H-indazol-5-yl)ethylcarbamate

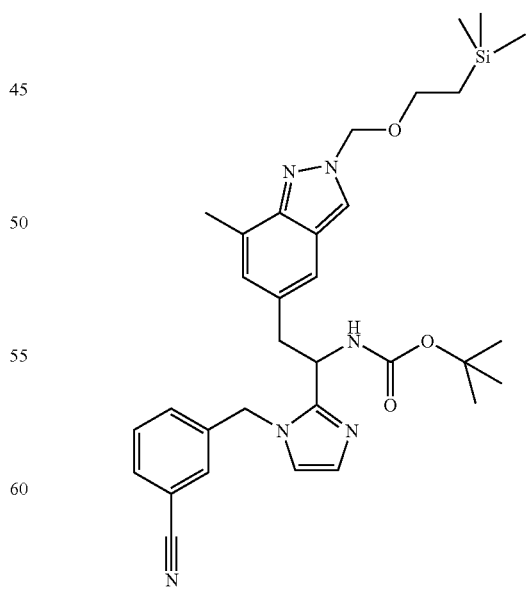

tert-Butyl-1-(1H-imidazol-2-yl)-2-(7-methyl-2-[{2-[trimethylsilyl]ethoxy}methyl]-2H-indazol-5-yl)ethylcarbamate (80 mg, 0.17 mmol), 3-cyano benzyl bromide (35.0 mg, 0.18 mmol, 1.05 equiv), and potassium carbonate (47.0 mg, 0.34 mmol) were combined in dimethylformamide (1.5 mL). After stirring at room temperature for 16 h, the solvents were removed and the residue purified by column chromatography to afford 85.0 mg (85%).

Mass spec.: 587.72 (MH)$^+$.

(±)-tert-Butyl 2-(7-methyl-2-((2-(trimethylsilyl)ethoxy)methyl)-2H-indazol-5-yl)-1-(1-phenethyl-1H-imidazol-2-yl)ethylcarbamate

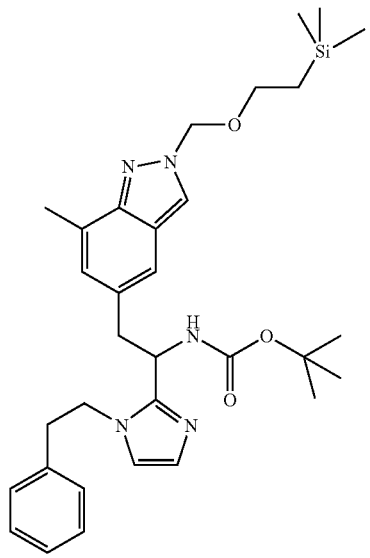

tert-Butyl-1-(1H-imidazol-2-yl)-2-(7-methyl-2-[{2-[trimethylsilyl]ethoxy}methyl]-2H-indazol-5-yl)ethylcarbamate (25 mg, 0.53 mmol), (2-bromoethyl)benzene (7.5 μL, 0.056 mmol, 1.05 equiv), and potassium carbonate (14.7 mg, 0.106 mmol) were combined in dimethylformamide (1.0 mL). After stirring at room temperature for 16 h, the solvents were removed and the residue purified by column chromatography to afford 9.0 mg (29%). Mass spec.: 576.5 (MH)$^+$.

(±)-tert-Butyl 2-(7-methyl-2-((2-(trimethylsilyl)ethoxy)methyl)-2H-indazol-5-yl)-1-(1-(pyridin-4-ylmethyl)-1H-imidazol-2-yl)ethylcarbamate

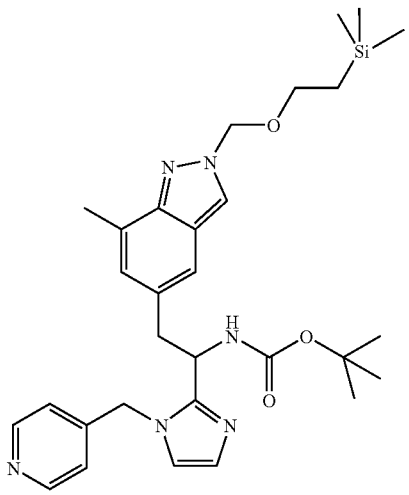

tert-Butyl-1-(1H-imidazol-2-yl)-2-(7-methyl-2-[{2-[trimethylsilyl]ethoxy}methyl]-2H-indazol-5-yl)ethylcarbamate (25 mg, 0.53 mmol), (4-bromomethyl) pyridine (14.1 mg 0.055 mmol, 1.05 equiv), and potassium carbonate (22.0 mg, 0.16 mmol) were combined in dimethylformamide (1.0 mL). After stirring at room temperature for 3 d, the solvents were removed and the residue purified by column chromatography to afford 23.0 mg (77%). Mass spec.: 563.3 (MH)$^+$.

(±)-tert-Butyl 1-(1-(2-fluorobenzyl)-1H-imidazol-2-yl)-2-(7-methyl-2-((2-(trimethylsilyl)ethoxy)methyl)-2H-indazol-5-yl)ethylcarbamate

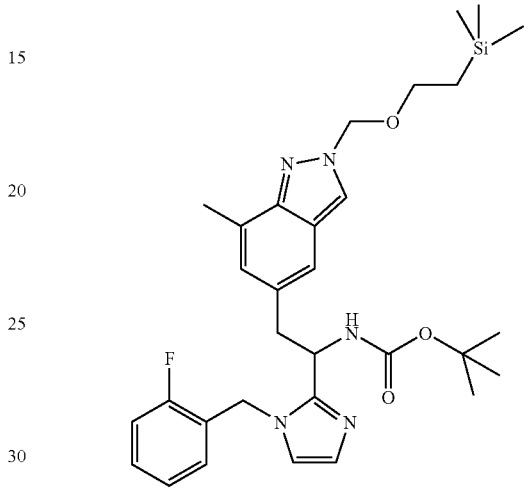

tert-Butyl-1-(1H-imidazol-2-yl)-2-(7-methyl-2-[{2-[trimethylsilyl]ethoxy}methyl]-2H-indazol-5-yl)ethylcarbamate (38.2 mg, 0.081 mmol), 2-fluorobenzyl bromide (11.3 μL, 0.09 mmol, 1.05 equiv), and potassium carbonate (28.0 mg, 0.2 mmol) were combined in dimethylformamide (1.0 mL). After stirring at room temperature for 16 h, the solvents were removed and the residue purified by column chromatography to afford 26.0 mg (56%). Mass spec.: 580.38 (MH)$^+$.

(±)-tert-Butyl 1-(1-(4-fluorobenzyl)-1H-imidazol-2-yl)-2-(7-methyl-2-((2-(trimethylsilyl)ethoxy)methyl)-2H-indazol-5-yl)ethylcarbamate

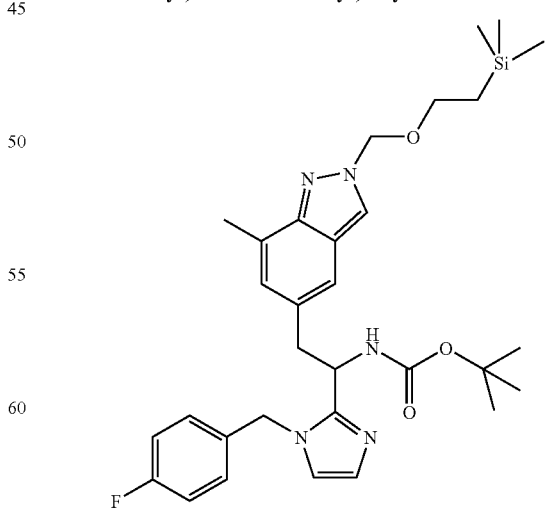

tert-Butyl-1-(1H-imidazol-2-yl)-2-(7-methyl-2-[{2-[trimethylsilyl]ethoxy}methyl]-2H-indazol-5-yl)ethylcarbamate (34.4 mg, 0.073 mmol), 4-fluorobenzyl bromide (10.5 μL, 0.084 mmol, 1.05 equiv), and potassium carbonate (25.0 mg, 0.18 mmol) were combined in dimethylformamide (1.0 mL). After stirring at room temperature for 16 h, the solvents were removed and the residue purified by column chromatography to afford 28.8 mg (68%). Mass spec.: 580.42 (MH)+.

EXAMPLE 68

(±)-N-(1-(1-(3-Fluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide

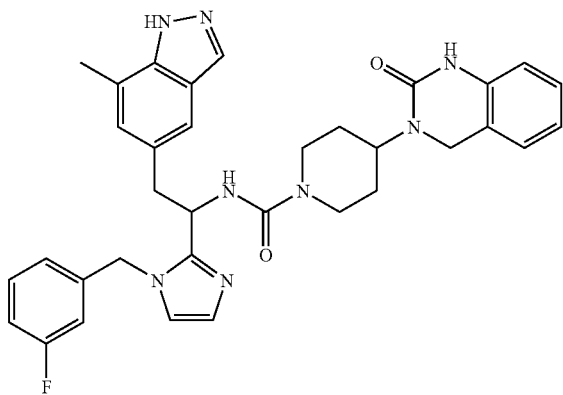

tert-Butyl 1-(1-(3-fluorobenzyl)-1H-imidazol-2-yl)-2-(7-methyl-2-((2-(trimethylsilyl)ethoxy)methyl)-2H-indazol-5-yl)ethylcarbamate (14.4 mg, 0.025 mmol) was dissolved in a minimum amount of ethyl acetate, followed by addition of hydrochloric acid (4 N in dioxane, 1.0 mL). The mixture was stirred under nitrogen for 3 days. After removing the solvents, the crude mixture was treated with diethyl ether to give a precipitate which was collected by filtration. The resulting solid was dissolved in dimethylformamide (1.0 mL). The mixture was cooled to 0° C. and treated with carbonyl diimidazole (4.7 mg, 1.1 equiv) and triethylamine (7.5 μL, 0.054 mmol). The reaction was stirred for 5 min at 0° C., warmed to room temperature, stirred for 10 min, and treated with 3-(piperidin-4-yl)-3,4-dihydroquinazolin-2(1H)-one (6.7 mg, 1.1 equiv). The mixture was stirred at room temperature overnight. The solvent was removed and the residue purified by column chromatography to afford 7.2 mg (47%, 2 steps). $^1$H-NMR (CD$_3$OD, 500 MHz) δ 1.49-1.68 (m, 4H), 2.44 (s, 3H), 2.71-2.84 (m, 2H), 3.20-3.27 (m, 4H), 4.01-4.15 (m, 2H), 4.19 (s, 2H), 4.35 (m, 1H), 5.12 (d, J=16.2, 1H), 5.21-5.30 (m, 2H), 6.57-6.69 (m, 2H), 6.80 (d, J=7.9, 1H), 6.82 (s, 1H), 6.88-7.20 (m, 8H), 7.91 (s, 1H). Mass spec.: 607.71 (MH)+.

The following examples were similarly prepared:

EXAMPLE 69

(±)-N-(1-(1-(3,5-Difluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide

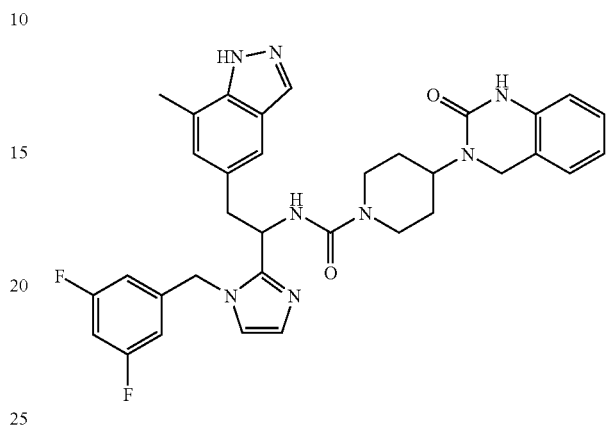

$^1$H-NMR (CD$_3$OD, 500 MHz) δ 1.50-1.67 (m, 4H), 2.46 (s, 3H), 2.71-2.82 (m, 2H), 3.06 (dd, J=7.0, 7.0, 1H), 3.21-3.31 (m, 2H), 3.37 (s, 2H), 4.06 (d, J=13.7, 1H), 4.13 (dd, J=13.1, 10.7, 1H), 4.20 (s, 2H), 4.32-4.40 (m, 1H), 5.08-5.32 (m, 3H), 5.50 (s, 1H), 6.44 (s, 1H), 6.45 (s, 1H), 6.68 (m, 1H), 6.80 (d, J=7.9, 1H), 6.83 (s, 1H), 6.94-6.99 (m, 1H), 7.06 (s, 1H), 7.11 (s, 2H), 7.14-7.19 (m, 1H), 7.25 (s, 1H), 7.89 (s, 1H). Mass spec.: 625.63 (MH)+.

EXAMPLE 70

(±)-N-(2-(7-Methyl-1H-indazol-5-yl)-1-(1-phenethyl-1H-imidazol-2-yl)ethyl)-4-(2-oxo-1,2-dihydroquinazolin-3(4H)-yl)piperidine-1-carboxamide

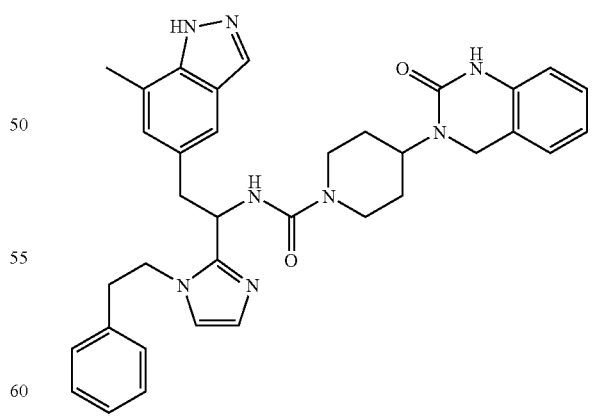

$^1$H-NMR (CD$_3$OD, 500 MHz) δ 1.40-1.67 (m, 4H), 1.50-1.70 (m, 3H), 2.52 (s, 3H), 2.60-2.70 (m, 1H), 2.76-2.91 (m, 2H), 3.08-3.16 (m, 1H), 3.24 (dd, J=7.6, 7.3, 2H), 4.00-4.20 (m, 3H), 4.35 (m, 1H), 5.20 (m, 3H), 6.69-6.88 (m, 1H), 6.92-7.54 (m, 10H), 7.60-7.83 (m, 1H), 7.98 (s, 1H). Mass spec.: 603.30 (MH)+.

EXAMPLE 71

(±)-N-(1-(1-(2-Fluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide

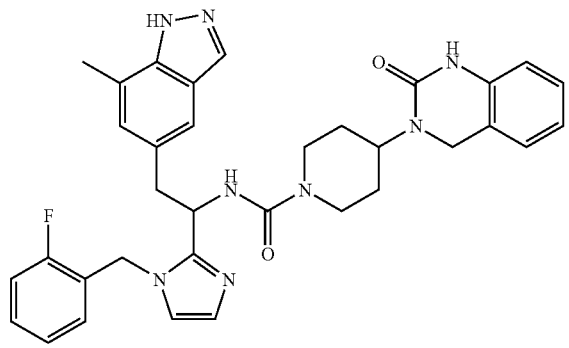

$^1$H-NMR (CD$_3$OD, 500 MHz) δ 1.62-1.70 (m, 4H), 2.50 (s, 3H), 2.76-2.88 (m, 2H), 3.37 (s, 1H), 4.00 (s, 1H), 4.04-4.13 (m, 2H), 4.40-4.80 (m, 1H), 4.27 (s, 2H), 5.36-5.44 (m, 3H), 6.79 (s, 1H), 6.81 (s, 1H), 6.91 (s, 1H), 6.95-7.00 (m, 2H), 7.08-7.20 (m, 4H), 7.33 (s, 1H), 7.58 (d, J=1.9, 1H), 7.87 (d, J=2.1, 1H), 7.98 (s, 1H). Mass spec.: 607.71 (MH)$^+$.

EXAMPLE 72

(±)-N-(1-(1-(4-Fluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide

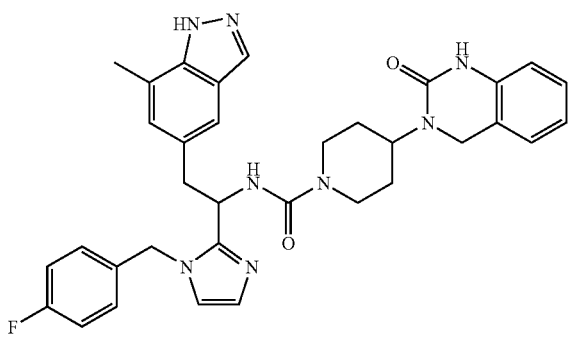

$^1$H-NMR (CD$_3$OD, 500 MHz) δ 1.60-1.72 (m, 4H), 2.50 (s, 3H), 2.78-2.90 (m, 2H), 3.51-3.58 (m, 1H), 4.00 (s, 1H), 4.06-4.16 (m, 2H), 4.28 (s, 2H), 4.32-4.41 (m, 1H), 5.28 (dd, J=15.6, 14.2, 2H), 5.41 (m, 1H), 6.80 (d, J=7.9, 1H), 6.91 (s, 1H), 6.90-7.00 (m, 6H), 7.14 (d, J=7.3, 1H), 7.15-7.20 (m, 1H), 7.31 (d, J=2.1, 1H), 7.32 (s, 1H), 7.58 (d, J=1.8, 1H), 7.99 (s, 1H). Mass spec.: 607.57 (MH)$^+$.

EXAMPLE 73

(±)-N-(2-(7-Methyl-1H-indazol-5-yl)-1-(1-(pyridin-4-ylmethyl)-1H-imidazol-2-yl)ethyl)-4-(2-oxo-1,2-dihydroquinazolin-3(4H)-yl)piperidine-1-carboxamide

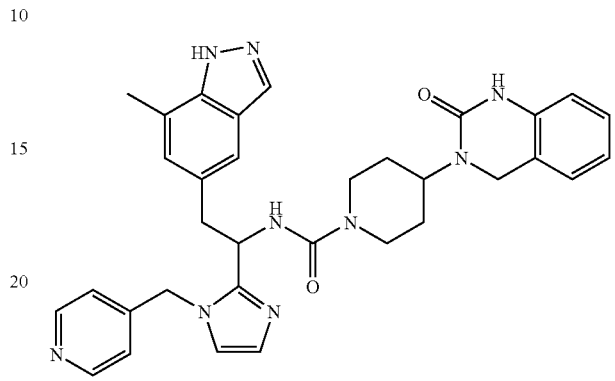

$^1$H-NMR (CD$_3$OD, 500 MHz) δ 1.57-1.70 (m, 4H), 2.49 (s, 3H), 2.70-2.82 (m, 2H), 3.37 (s, 2H), 3.53-3.60 (m, 1H), 4.05 (bs, 2H), 4.26 (s, 2H), 4.32-4.41 (m, 1H), 5.35-5.41 (m, 1H), 5.56-5.70 (m, 2H), 6.81 (d, J=7.9, 1H), 6.94 (s, 1H), 6.97 (dd, J=7.9, 7.9, 1H), 7.12-7.20 (m, 2H), 7.33 (s, 1H), 7.38 (m, 1H), 7.56 (d, J=2.1, 1H), 7.75 (d, J=1.8, 1H), 7.96 (s, 1H), 8.52 (s, 1H), 8.53 (s, 1H). Mass spec.: 590.06 (MH)$^+$.

EXAMPLE 74

(±)-N-(1-(1-(3-Cyanobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide

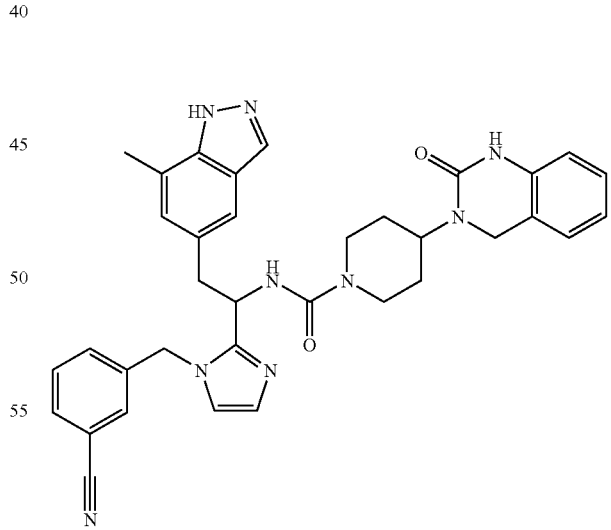

$^1$H-NMR (CD$_3$OD, 500 MHz) δ 1.51-1.66 (m, 4H), 2.46 (s, 3H), 2.69-2.80 (m, 2H), 3.20-3.30 (m, 2H), 4.00-4.15 (m, 1H), 5.14-5.35 (m, 3H), 5.51 (s, 2H), 6.80 (d, J=7.6, 1H), 6.83 (s, 1H), 6.97 (dd, J=7.9, 7.3, 1H), 7.06 (m, 1H), 7.08 (s, 1H), 7.13 (s, 2H), 7.16-7.20 (m, 3H), 7.24 (s, 1H), 7.30 (s, 1H), 7.49 (d, J=7.5, 1H), 7.91 (s, 1H). Mass spec.: 614.05 (MH)$^+$.

EXAMPLE 75

(±)-N-(1-(1-(4-tert-Butylbenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide

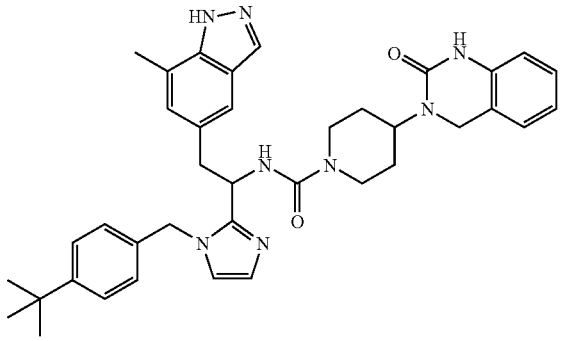

MS: $t_R$=2.46 min, 645.89 (MH)⁺.

EXAMPLE 76

(±)-3-((2-(2-(7-Methyl-1H-indazol-5-yl)-1-(4-(2-oxo-1,2-dihydroquinazolin-3(4H)-yl)piperidine-1-carboxamido)ethyl)-1H-imidazol-1-yl)methyl)benzoic acid

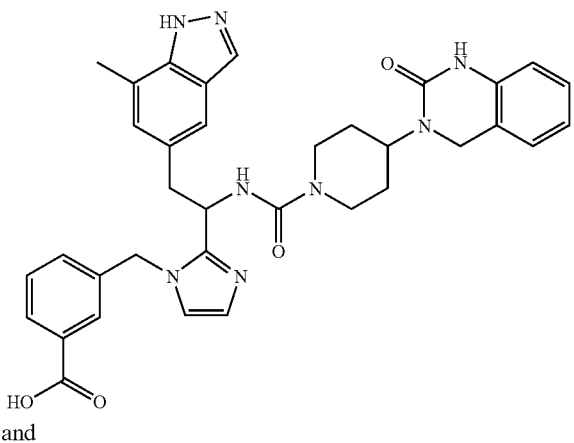

and

EXAMPLE 77

(±)-N-(1-(1-(3-Carbamoylbenzyl)-1H-imidazol-2-yl)-2-(7-methyl-1H-indazol-5-yl)ethyl)-(2-oxo-1,2-dihydroquinazolin-3(4H)-yl)piperidine-1-carboxamide

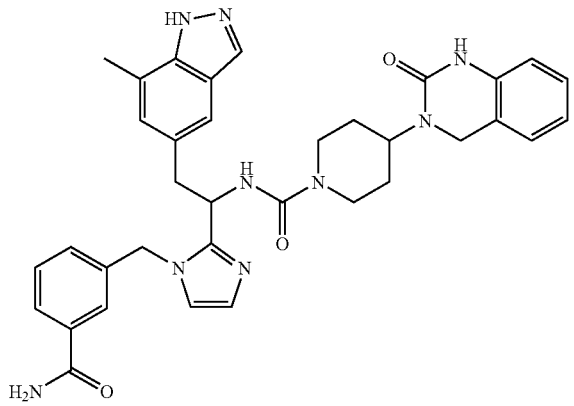

N-(1-(1-(3-Cyanobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide (33 mg, 0.053 mmol) was dissolved in methanol (0.8 mL). To this solution was added 1N sodium hydroxide (0.27 mL, 0.27 mmol) and the mixture stirred at room temperature overnight. The mixture was diluted with water and extracted with a mixture of chloroform/isopropanol (3×). The combined organic extracts were dried over sodium sulfate and concentrated. Purification by preparative HPLC afforded 6.1 mg (18%) of the acid and 2.5 mg (8%) of the carboxamide. 3-((2-(2-(7-Methyl-1H-indazol-5-yl)-1-(4-(2-oxo-1,2-dihydroquinazolin-3(4H)-yl)piperidine-1-carboxamido)ethyl)-1H-imidazol-1-yl)methyl)benzoic acid: ¹H-NMR (CD₃OD, 500 MHz) δ 1.49-1.73 (m, 3H), 2.50 (s, 3H), 2.67-2.89 (m, 2H), 3.37 (s, 1H), 3.46-3.59 (m, 1H), 3.98-4.13 (m, 2H), 4.23 (s, 2H), 5.31-5.53 (m, 4H), 6.80 (d, J=8.2, 1H), 6.88-7.01 (m, 1H), 7.09 (dd, J=7.3, 7.0, 1H) 7.12-7.22 (m, 2H), 7.29-7.36 (m, 3H), 7.39-7.64 (m, 3H), 7.97 (m, 2H). Mass spec.: 633.40 (MH)⁺. N-(1-(1-(3-Carbamoylbenzyl)-H-imidazol-2-yl)-2-(7-methyl-1H-indazol-5-yl)ethyl)-(2-oxo-1,2-dihydroquinazolin-3(4H)-yl)piperidine-1-carboxamide: ¹H-NMR (CD₃OD, 500 MHz) δ 1.30-1.60 (m, 4H), 2.46 (s, 3H), 2.68-2.80 (m, 2H), 3.15-3.27 (m, 3H), 3.97-4.12 (m, 2H), 4.17 (s, 2H), 5.13-5.31 (m, 3H), 6.97 (d, J=7.9, 1H), 6.83 (s, 1H), 6.93-6.99 (m, 2H), 7.01-7.24 (m, 7H), 7.26 (s, 1H), 7.70 (s, 1H), 7.76 (d, J=7.9, 1H), 7.93 (s, 1H). Mass spec.: 632.91 (MH)⁺.

2-(Methoxymethyl)-7-methyl-2H-indazole-5-carbaldehyde

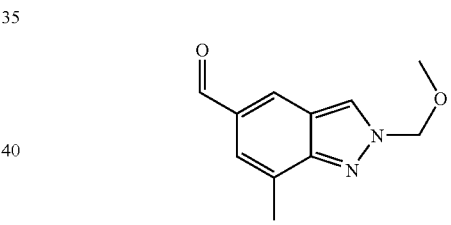

To a solution of 7-methylindazole-5-carboxaldehyde (8.80 g, 54.9 mmol) and N-methyl-dicyclohexylamine (23.6 mL, 110 mmol) in tetrahydrofuran (200 mL) at 0° C. was added chloromethyl methyl ether (7.50 mL, 1.8 equiv). The reaction was allowed to gradually warm to room temperature overnight. The reaction was concentrated, dissolved in diethyl ether, washed with water, then 1 M hydrochloric acid, then water, then brine, dried over magnesium sulfate, and concentrated to give an oil. The oil was dissolved in ethyl acetate and treated with hexanes until lasting turbidity. The suspension was heated until a clear solution was obtained and the flask placed in the freezer. The resulting crystalline solid was crushed with a spatula to break it up, reheated to dissolve some of the solids, and placed in the freezer. The solids were filtered, washed with very cold ether (−78° C.), and air-dried to give 5.43 g. The mother liquor was concentrated, redissolved in ca. 20 mL ether, cooled to −78° C., and treated with a seed crystal of the product. After 1 h, the resulting solids were filtered, washed with cold ether (−78° C.), and air-dried to give an additional 1.05 g (total yield=58%). ¹H-NMR (CDCl₃, 500 MHz) δ 2.66 (s, 3H), 3.44 (s, 3H), 5.73 (s, 2H), 7.59 (s, 1H), 8.09 (s, 1H), 8.32 (s, 1H), 9.97 (s, 1H). Mass spec.: 205.19 (MH)⁺.

Methyl 2-acetoxy-3-(2-(methoxymethyl)-7-methyl-2H-indazol-5-yl)acrylate

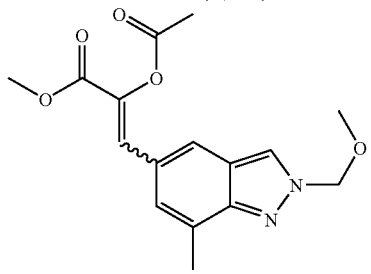

To a solution of methyl 2-acetoxy-2-(diethylphosphoryl)acetate (4.89 g, 18.2 mmol) in tetrahydrofuran (25 mL) was added lithium chloride (0.74 g, 17.5 mmol). The reaction was stirred until dissolution was complete. The reaction was cooled to −78° C., and treated with tetramethylguanidine (2.20 mL, 17.5 mmol) to give a white suspension which was stirred for 10 min. To this was added 2-(methoxymethyl)-7-methyl-2H-indazole-5-carbaldehyde (3.10 g, 15.2 mmol) in one portion. After 10 min, the ice bath was concentrated and the reaction stirred overnight. The reaction was poured onto water/diethyl ether, and the layers separated. The ethereal was washed with water, then brine, dried over magnesium sulfate, and concentrated. Column chromatography gave recovered 2-(methoxymethyl)-7-methyl-2H-indazole-5-carbaldehyde (0.57 g, 18%) and the title compound (2.86 g, 59%) as a colorless oil. NMR shows a 3:2 ratio of Z and E isomers which were not separated. Major (Z isomer): $^1$H-NMR (CDCl$_3$, 500 MHz) δ 2.25 (s, 3H), 2.62 (s, 3H), 3.40 (s, 3H), 3.71 (s, 3H), 5.69 (s, 2H), 6.88 (s, 1H), 7.09 (s, 1H), 7.72 (s, 1H), 8.10 (s, 1H). Mass spec.: 319.18 (MH)$^+$. Minor (E isomer): $^1$H-NMR (CDCl$_3$, 500 MHz) δ 2.35 (s, 3H), 2.62 (s, 3H), 3.40 (s, 3H), 3.85 (s, 3H), 5.69 (s, 2H), 7.32 (s, 1H), 7.38 (s, 1H), 7.78 (s, 1H), 8.14 (s, 1H). Mass spec.: 319.18 (MH)$^+$.

(R)-Methyl 2-acetoxy-3-(2-(methoxymethyl)-7-methyl-2H-indazol-5-yl)propanoate

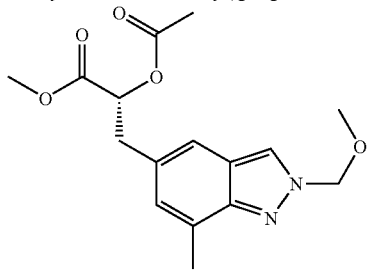

A solution of methyl 2-acetoxy-3-(2-(methoxymethyl)-7-methyl-2H-indazol-5-yl)acrylate (2.80 g, 8.8 mmol) in dichloromethane (20 mL) was degassed by passing a stream of nitrogen through the solution. To this solution was quickly added (−)-1,2-bis((2R,5R)-2,5-diethylphospholano)benzene (cyclooctadiene) rhodium (I) trifluoromethylsulfonate (100 mg, 0.016 equiv) as a solid. The reaction was placed under a hydrogen atmosphere (55 psi) and shaken overnight. The reaction was concentrated and purified by column chromatography (50% ethyl acetate/hexanes) to give 2.74 g (97%) as a colorless oil. $^1$H-NMR (CDCl$_3$, 500 MHz) δ 2.08 (s, 3H), 2.61 (s, 3H), 3.11 (dd, J=14.3, 8.9, 1H), 3.20 (dd, J=14.3, 4.6, 1H), 3.39 (s, 3H), 3.72 (s, 3H), 5.26 (dd, J=8.9, 4.6, 1H), 5.68 (s, 2H), 6.93 (s, 1H), 7.33 (s, 1H), 8.02 (s, 1H).

(R)-2-Hydroxy-3-(2-(methoxymethyl)-7-methyl-2H-indazol-5-yl)propanoic acid

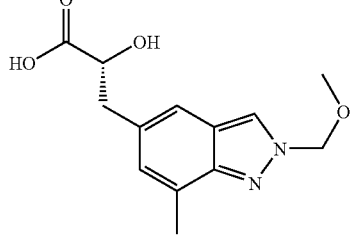

To a solution of (R)-methyl 2-acetoxy-3-(2-(methoxymethyl)-7-methyl-2H-indazol-5-yl)propanoate (2.70 g, 8.4 mmol) in tetrahydrofuran (20 mL) and methanol (20 mL) at 0° C. was added a solution of lithium hydroxide monohydrate (1.41 g, 4.0 equiv) in water (20 mL). The reaction was stirred at 0° C. for 1 h. The reaction was concentrated, dissolved in water (5 mL), cooled to 0° C., and treated with 1 M hydrochloric acid until mildly acidic. The solution was extracted extensively with ethyl acetate and then dichloromethane. The organics were combined, dried over magnesium sulfate, and concentrated to give 1.40 g (63%) as an oil which solidified to a crystalline solid upon standing. $^1$H-NMR (CDCl$_3$, 500 MHz) δ 2.40 (s, 3H), 2.78 (dd, J=14.0, 7.9, 1H), 3.00 (dd, J=14.0, 4.0, 1H), 3.18 (s, 3H), 4.24 (dd, J=7.9, 4.3, 1H), 5.47 (s, 2H), 6.85 (s, 1H), 7.22 (s, 1H), 7.90 (s, 1H). Mass spec.: 265.08 (MH)$^+$.

(R)-Methyl 2-hydroxy-3-(2-(methoxymethyl)-7-methyl-2H-indazol-5-yl)propanoate

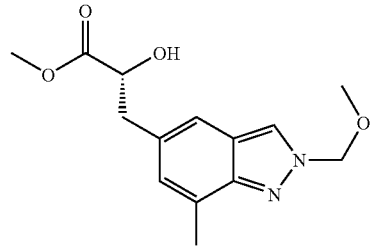

To a heterogeneous mixture of 5 M sodium hydroxide (20 mL) and diethyl ether (60 mL) at 0° C. was added N-methyl-N'-nitro-N-nitrosoguanidine (1.17 g, 7.95 mmol) in small portions with swirling (no stirbar). After addition was complete, the mixture was allowed to stand at 0° C. for 15 min with occasional swirling. The ethereal was transferred in portions to a suspension of (R)-2-hydroxy-3-(2-(methoxymethyl)-7-methyl-2H-indazol-5-yl)propanoic acid (1.40 g, 5.30 mmol) in dichloromethane (20 mL) until the solid had all dissolved and a yellow color persisted. The reaction was allowed to rest at room temperature for ca. 5 min. before bubbling nitrogen through the solution to remove unreacted diazomethane. The reaction was concentrated and purified by column chromatography (50%→75% ethyl acetate/hexanes) to give 1.47 g (100%) as a colorless oil. $^1$H-NMR (CDCl$_3$, 500 MHz) δ 1.60 (bs, 1H), 2.58 (s, 3H), 2.95 (dd, J=13.9, 7.0, 1H), 3.14 (dd, J=13.9, 4.0, 1H), 3.36 (s, 3H), 3.76 (s, 3H), 4.46 (bm, 1H), 5.65 (s, 2H), 6.90 (s, 1H), 7.31 (s, 1H), 7.99 (s, 1H). Mass spec.: 279.11 (MH)$^+$.

(R)-Methyl 3-(2-(methoxymethyl)-7-methyl-2H-indazol-5-yl)-2-((4-nitrophenoxy)carbonyloxy)propanoate

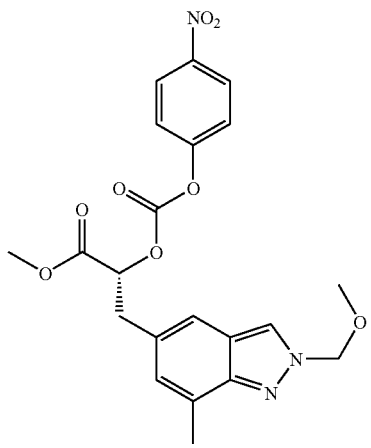

To a solution of (R)-methyl 2-hydroxy-3-(2-(methoxymethyl)-7-methyl-2H-indazol-5-yl)propanoate (1.45 g, 5.21 mmol) and diisopropylethylamine (2.73 mL, 3.0 equiv) in dichloromethane (27 mL) at 0° C. was added 4-nitrophenyl-chloroformate (1.58 g, 1.5 equiv) and N,N-dimethylaminopyridine (10 mg). The ice bath was removed and stirring continued for 7 h. The reaction was treated with an additional portion of diisopropylethylamine (1.5 mL, 1.65 equiv), 4-nitrophenyl-chloroformate (1.6 g, 1.5 equiv), and N,N-dimethylaminopyridine (10 mg) and stirred overnight. The reaction was concentrated, dissolved in ethyl acetate, washed with water, then 1 M potassium bisulfate, then saturated sodium bicarbonate (5×), then brine, dried over magnesium sulfate, and concentrated to give 6.00 g (quant.) as a light brown oil, which was used immediately without purification. Mass spec.: 444.10 (MH)+.

(R)-1-Methoxy-3-(2-(methoxymethyl)-7-methyl-2H-indazol-5-yl)-1-oxopropan-2-yl 4-(2-oxo-1,2-dihydroquinolin-3-yl)piperidine-1-carboxylate

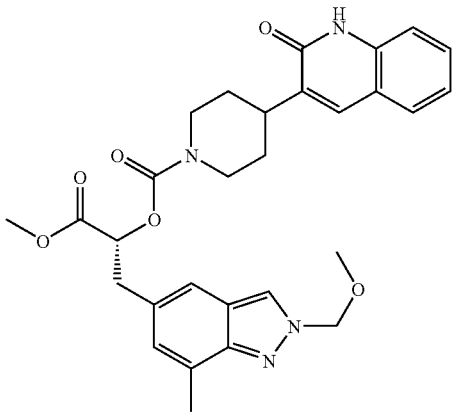

A flask was charged with crude (R)-methyl 3-(2-(methoxymethyl)-7-methyl-2H-indazol-5-yl)-2-((4-nitrophenoxy)carbonyloxy)propanoate (2.31 g, 5.20 mmol), 3-(piperidin-4-yl)quinolin-2(1H)-one (1.78 g, 1.5 equiv), diisopropylethylamine (1.82 mL, 2.0 equiv), and dimethylformamide (20 mL). The reaction was stirred at room temperature for 8 h and concentrated under vacuum. The resulting residue was dissolved in ethyl acetate and washed with water to give a suspension which was exhaustively extracted with ethyl acetate then dichloromethane. The organics were dried over magnesium sulfate and concentrated. Column chromatography (25% ethyl acetate/hexanes→10% methanol/ethyl acetate) gave 2.40 g (86%) as a light yellow foam solid. Mass spec.: 533.30 (MH)+.

(R)-1-Hydroxy-3-(2-(methoxymethyl)-7-methyl-2H-indazol-5-yl)propan-2-yl 4-(2-oxo-1,2-dihydroquinolin-3-yl)piperidine-1-carboxylate

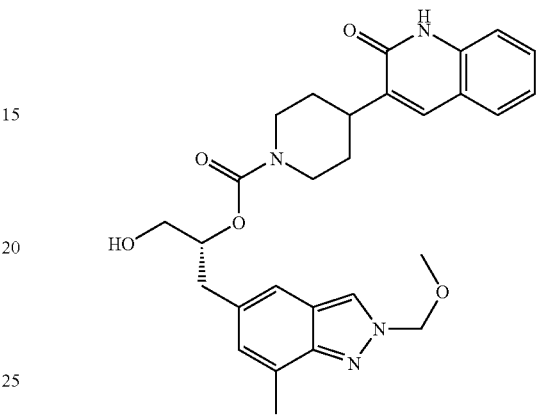

(R)-1-Methoxy-3-(2-(methoxymethyl)-7-methyl-2H-indazol-5-yl)-1-oxopropan-2-yl 4-(2-oxo-1,2-dihydroquinolin-3-yl)piperidine-1-carboxylate (0.70 g, 1.32 mmol) was dissolved in tetrahydrofuran (10 mL) and cooled to 0° C. To this solution was added lithium borohydride (0.12 g, 4.0 equiv). After 30 min, the ice bath was removed and the mixture stirred at room temperature for 3 h. The reaction mixture was diluted with ethyl acetate and carefully quenched with 10% citric acid. The organic layer was separated and washed with water (2×), brine (2×), dried over sodium sulfate, and concentrated to afford 0.68 g (99%) which was used without purification. Mass spec.: 505.3 (MH)+.

(R)-3-(2-(Methoxymethyl)-7-methyl-2H-indazol-5-yl)-1-oxopropan-2-yl 4-(2-oxo-1,2-dihydroquinolin-3-yl)piperidine-1-carboxylate

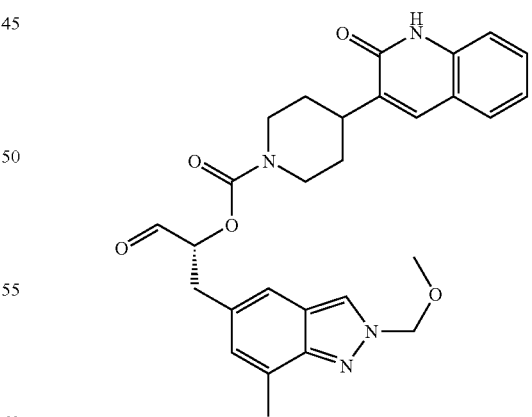

1-Hydroxy-3-(2-(methoxymethyl)-7-methyl-2H-indazol-5-yl)propan-2-yl 4-(2-oxo-1,2-dihydroquinolin-3-yl)piperidine-1-carboxylate (0.65 g, 1.29 mmol) was dissolved in anhydrous dimethyl sulfoxide (5.0 mL). Triethylamine (0.54 mL, 3.87 mmol) was added and the reaction mixture cooled to ca. 5° C. using an ice bath. A solution of sulfur trioxide pyridine complex (0.62 g, 3.87 mmol) in dimethyl sulfoxide (4.0 mL) was added in one portion. After 1 min, the ice bath was removed and the reaction mixture stirred at room temperature for 20 min. The reaction mixture was poured into an ice slurry and extracted with ethyl acetate (3×). The combined organic extracts were washed with 10% citric acid (2×), water (2×), 5% sodium bicarbonate (2×), brine (2×), dried over sodium sulfate, and concentrated. Column chromatography afforded 0.55 g (85%). $^1$H-NMR (DMSO. $d_6$, 500 MHz) δ 1.90 (s, 3H), 2.48 (s, 3H), 2.51 (m, 2H), 2.71-2.95 (m, 4H), 4.51 (m, 1H), 4.72-4.84 (m, 1H), 6.31-6.46 (m, 1H), 6.91 (d, J=4.0, 1H), 8.36 (s, 1H), 11.74 (s, 1H). Mass spec.: 503.3 (MH)$^+$.

(R)-1-(1H-Imidazol-2-yl)-2-(2-(methoxymethyl)-7-methyl-2H-indazol-5-yl)ethyl 4-(2-oxo-1,2-dihydro-quinolin-3-yl)piperidine-1-carboxylate

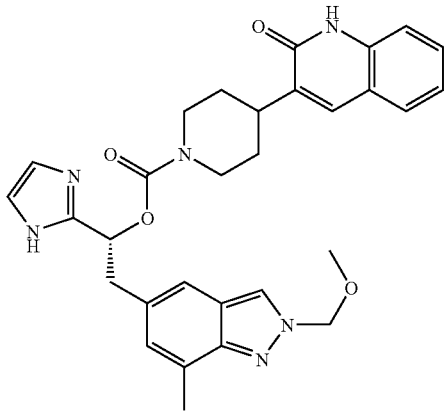

3-(2-(Methoxymethyl)-7-methyl-2H-indazol-5-yl)-1-oxopropan-2-yl 4-(2-oxo-1,2-dihydroquinolin-3-yl)piperidine-1-carboxylate (0.53 g, 1.06 mmol) and glyoxal trimer (0.22 g, 1.06 mmol) were combined in a 1,4 dioxane/water mixture (6:1, 7.0 mL). To this was added 28% ammonia in water (0.12 mL, 3.18 mmol) and the reaction stirred at 80° C. for 16 h. After cooling to room temperature, the solvents were removed and the crude mixture dissolved in methylene chloride which was washed with water (2×), brine (2×), dried over magnesium sulfate, and concentrated. Column chromatography afforded 0.22 g (40%). Mass spec.: 541.4 (MH)$^+$.

(R)-1-(1-(3,5-difluorobenzyl)-1H-imidazol-2-yl)-2-(2-(methoxymethyl)-7-methyl-2H-indazol-5-yl)ethyl 4-(2-oxo-1,2-dihydroquinolin-3-yl)piperidine-1-carboxylate

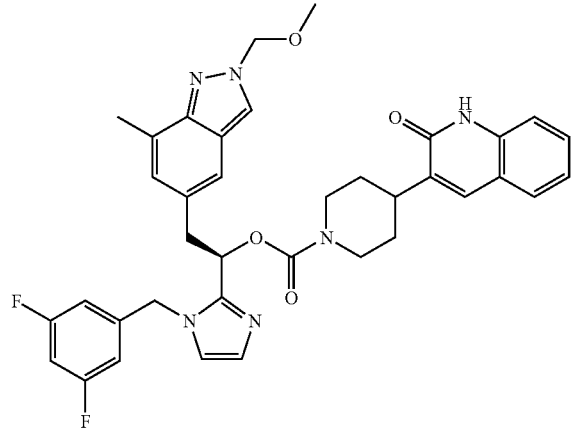

1-(1H-Imidazol-2-yl)-2-(2-(methoxymethyl)-7-methyl-2H-indazol-5-yl)ethyl 4-(2-oxo-1,2-dihydroquinolin-3-yl)

piperidine-1-carboxylate (102 mg, 0.19 mmol), 3,5-difluorobenzyl bromide (27.0 μL, 0.21 mmol, 1.1 equiv), and potassium carbonate (54 mg, 3.0 equiv) were combined in dimethylformamide (2.0 mL). After stirring at room temperature for 16 h, the reaction mixture was removed in vacuo and the residue purified by column chromatography to afford 72.0 mg (57%). Mass spec.: 667.4 (MH)$^+$.

EXAMPLE 78

(R)-1-(1-(3,5-difluorobenzyl)-1H-imidazol-2-yl)-2-(7-methyl-1H-indazol-5-yl)ethyl 4-(2-oxo-1,2-dihydroquinolin-3-yl)piperidine-1-carboxylate

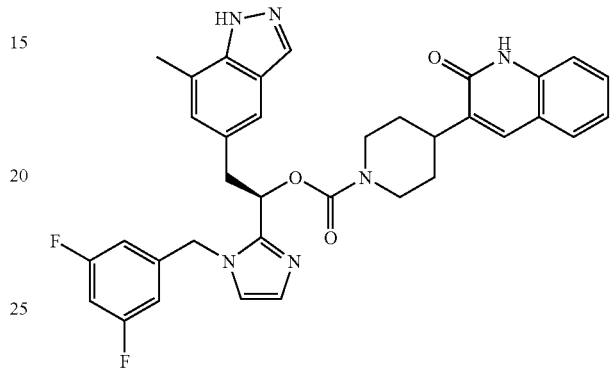

1-(1-(3,5-difluorobenzyl)-1H-imidazol-2-yl)-2-(2-(methoxymethyl)-7-methyl-2H-indazol-5-yl)ethyl 4-(2-oxo-1,2-dihydroquinolin-3-yl)piperidine-1-carboxylate (72.0 mg, 0.108 mmol) and acetyl chloride (0.18 mL) were combined in methanol (2.0 mL) and heated at reflux for 1 h. After cooling to room temperature, the solvents were removed in vacuo. Column chromatography afforded 47 mg (70%). $^1$H-NMR (CD$_3$OD, 500 MHz) δ 1.38-2.05 (m, 3H), 2.45 (s, 3H), 2.70-3.05 (m, 3H), 3.24 (dd, J=7.3, 7.3, 1H), 3.45-3.55 (m, 1H), 4.05-4.40 (m, 2H), 5.05-5.45 (m, 2H), 5.50 (s, 1H), 5.95 (bs, 1H), 6.34-6.90 (m, 4H), 7.17 (s, 1H), 7.25 (m, 2H), 7.34 (d, J=8.2, 1H), 7.45-7.75 (m, 3H), 7.90 (s, 1H). Mass spec.: 623.3 (MH)$^+$.

(±)-tert-Butyl 2-(7-methyl-2-((2-(trimethylsilyl)ethoxy)methyl)-2H-indazol-5-yl)-1-(1-(2-nitrophenyl)-1H-imidazol-2-yl)ethylcarbamate

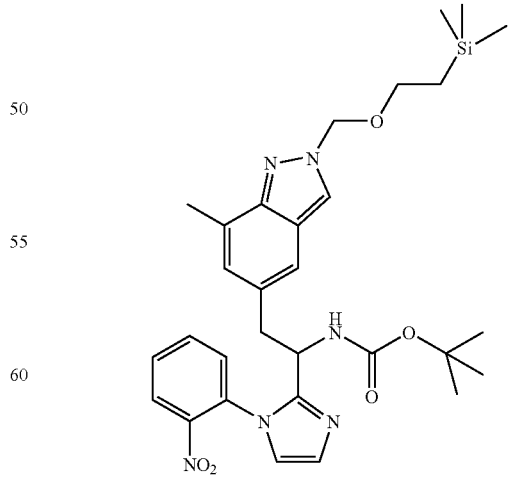

tert-Butyl-1-(1H-imidazol-2-yl)-2-(7-methyl-2-[{2-[trimethylsilyl]ethoxy}methyl]-2H-indazol-5-yl)ethylcarbamate (25 mg, 0.53 mmol), 1-fluoro-2-nitrobenzene (14 mg, 0.13 mmol), and potassium carbonate (18.2 mg, 0.13 mmol) were combined in acetonitrile (1.0 mL) and heated via microwave at 125° C. for 30 h. The reaction was concentrated, dissolved in methylene chloride, and washed with water (2×), brine (2×), dried over sodium sulfate, and concentrated. Purification by column chromatography afforded 20.4 mg (65%).

EXAMPLE 79

(±)-N-(2-(7-Methyl-1H-indazol-5-yl)-1-(1-(2-nitrophenyl)-1H-imidazol-2-yl)ethyl)-4-(2-oxo-1,2-dihydroquinazolin-3(4H)-yl)piperidine-1-carboxamide

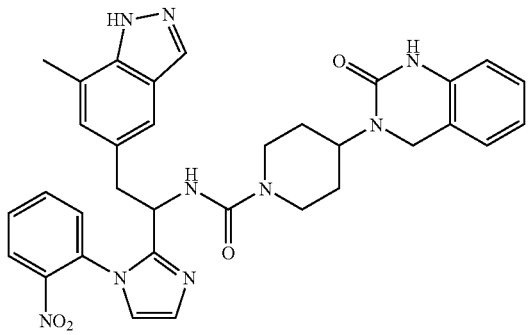

tert-Butyl 2-(7-methyl-2-((2-(trimethylsilyl)ethoxy)methyl)-2H-indazol-5-yl)-1-(1-(2-nitrophenyl)-1H-imidazol-2-yl)ethylcarbamate (20.4 mg, 0.034 mmol) was dissolved in a trifluoroacetic acid/methylene chloride mixture (1:1, 2 mL) and stirred under nitrogen for 3 h. The solvent was removed in vacuo and the resulting crude mixture passed through a strong cationic exchange column. After washing the column with several volumes of methanol, the desired amine was obtained by washing the column with 2 M ammonia in methanol which after concentration was immediately dissolved in dimethylformamide (1.0 mL). The mixture was cooled to 0° C. and treated with carbonyl diimidazole (6.0 mg, 0.036 mmol, 1.1 equiv). The reaction was stirred for 5 min at 0° C., warmed to room temperature, stirred for 10 min, treated with 3-(piperidin-4-yl)-3,4-dihydroquinazolin-2(1H)-one (8.3 mg, 0.036 mmol, 1.1 equiv), and stirred at room temperature overnight. The solvent was evaporated and the residue purified by column chromatography to afford 4.0 mg (13%, 2 steps). $^1$H-NMR (CD$_3$OD, 500 MHz) δ 1.50-1.78 (m, 5H), 2.50 (s, 3H), 2.70-2.95 (m, 2H), 3.90-4.35 (m, 4H), 4.40-4.60 (m, 1H), 5.50 (s, 1H), 6.71-7.88 (m, 11H), 7.70 (m, 1H), 7.95 (s, 1H), 8.26 (d, J=8.6, 1H). Mass spec.: 620.48 (MH)$^+$.

(±)-Methyl 2-(4-(8-fluoro-1,2-dihydro-2-oxoquinazolin-3(4H)-yl)piperidine-1-carboxamido)-3-(7-methyl-1H-indazol-5-yl)propanoate

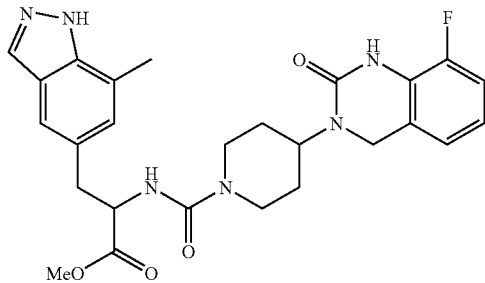

A stirred solution of 2-amino-3-(7-methyl-1H-indazol-5-yl)-propionic acid methyl ester (0.36 g, 1.54 mmol) in tetrahydrofuran (15 mL) at 0° C. was treated with carbonyl diimidazole (0.20, 1.1 equiv). The reaction was stirred for min at 0° C., warmed to room temperature, stirred 10 min, and treated with 8-fluoro-3,4-dihydro-3-(piperidin-4-yl)quinazolin-2(1H)-one (0.38 g, 1.1 equiv). The mixture was stirred at room temperature overnight. The solvent was evaporated and the residue purified by column chromatography to give 0.41 g (53%) as a white powder. $^1$H-NMR (CDCl$_3$, 500 MHz) δ 1.53-1.68 (m, 4H), 2.48 (s, 3H), 2.82 (m, 2H), 3.05 (m, 6H), 3.09 (dd, J$_{AB}$=13.7, 6.1, 1H), 3.14 (dd, J$_{AB}$=140.0, 6.1, 1H), 3.35 (bs, 1H), 3.68 (s, 3H), 3.88-4.02 (m, 2H), 4.22 (d, J$_{AB}$=15.6, 1H), 4.25 (d, J$_{AB}$=15.3, 1H), 4.44 (m, 1H), 4.71 (dd, J=6.1, 6.1, 1H), 6.78 (d, J=7.3, 1H), 6.84 (ddd, J=7.6, 7.6, 4.9, 1H), 6.88-6.95 (m, 2H), 7.28 (s, 1H), 7.91 (s, 1H). Mass spec.: 509.25 (MH)$^+$.

(±)-2-(4-(8-Fluoro-2-oxo-1,2-dihydroquinazolin-3 (4H)-yl)piperidine-1-carboxamido)-3-(7-methyl-1H-indazol-5-yl)propanoic acid

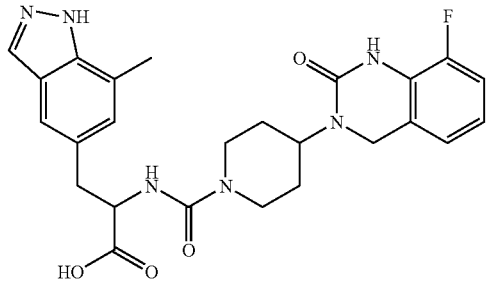

A suspension of (±)-methyl 2-(4-(8-fluoro-1,2-dihydro-2-oxoquinazolin-3(4H)-yl)piperidine-1-carboxamido)-3-(7-methyl-1H-indazol-5-yl)propanoate (0.4 g, 0.79 mmol) in 1:1 tetrahydrofuran/methanol (30 mL) at room temperature was treated with a solution of lithium hydroxide (83 mg, 2.5 equiv) in water (4 mL) and stirred at room temperature overnight. The solvents were evaporated and the pH was adjusted to ca. 1 with 1 N hydrochloric acid. The resulting white suspension was stored at 4° C. overnight and the product was collected by filtration, washed with a small amount of water, and dried in vacuo to afford 0.21 g (74%) as a white powder. Mass spec.: 495.06 (MH)$^+$.

Similarly prepared:

(±)-2-(4-(2-Oxo-1,2-dihydroquinazolin-3(4H)-yl) piperidine-1-carboxamido)-3-(7-methyl-1H-indazol-5-yl)propanoic acid

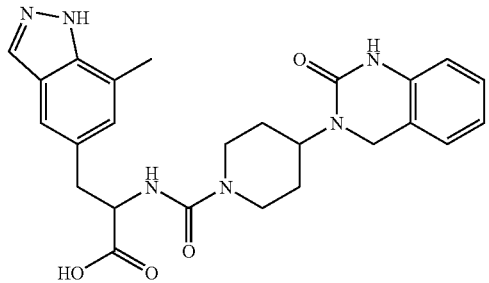

Mass spec.: 477.12 (MH)$^+$.

125

(±)-N-(1-Amino-3-{7-methyl-1H-indazol-5-yl}-1-oxopropan-2-yl)-3-(8-fluoro-2-oxo-1,2-dihydroquinazolin-3 [4H]-yl)piperidine-1-carboxamide

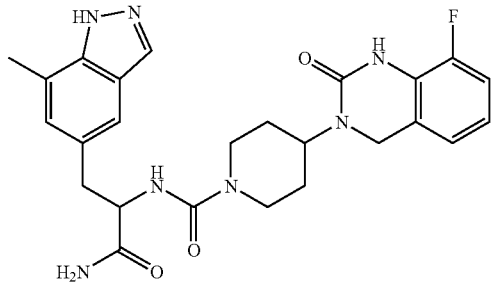

A stirred solution of 2-(4-{8-fluoro-2-oxo-1,2-dihydroquinazolin-3[4H]-yl}piperidine-1-carboxamido)-3-(7-methyl-1H-indazol-5-yl)propanoic acid (0.30 g, 0.61 mmol) in dimethylformamide (10 mL) was cooled to 0° C. and sequentially treated with methylene chloride (5 mL), 7 N ammonia in methanol (0.18 mL, 2 equiv), N,N-diisopropylethylamine (0.27 mL, 2.5 equiv), and PyBop™ (0.34 g, 0.73 mmol). The solution was stirred for 1.5 h and concentrated. The product was purified by column chromatography to give 0.25 g (82%). Mass spec.: 494.08 (MH)$^+$.

(±)-N-(1-Cyano-2-{7-methyl-1H-indazol-5-yl}ethyl)-4-(8-fluoro-2-oxo-1,2-dihydroquinazolin-3 [4H]-yl)piperidine-1-carboxamide

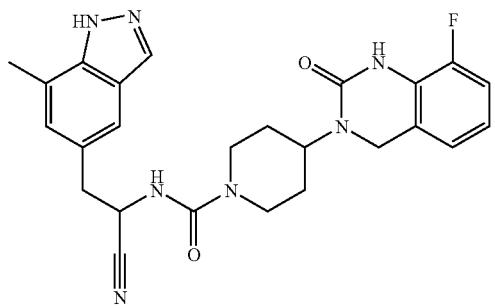

A stirred solution of N-(1-amino-3-{7-methyl-1H-indazol-5-yl}-1-oxopropan-2-yl)-3-(8-fluoro-2-oxo-1,2-dihydroquinazolin-3 [4H]-yl)piperidine-1-carboxamide (0.25 g, 0.5 mmol) in pyridine (8 mL) at 0° C. was treated with trifluoroacetic anhydride (0.35 mL, 5.0 equiv). The mixture was stirred for 30 min and quenched by the addition of excess methanol. The solvents were evaporated and the crude mixture dissolved in ethyl acetate which was washed with 5% citric acid (2×), water (2×), brine (2×), dried over sodium sulfate, and concentrated. The residue was purified by column chromatography to afford 0.25 g (100%). Mass spec.: 477.04 (MH)$^+$.

126

EXAMPLE 80

(±)-4-(8-Fluoro-2-oxo-1,2-dihydroquinazolin-3 [4H]-yl)-N-(2{7-methyl-1H-indazol-5-yl}-1-{1H-tetrazol-5-yl}ethyl)piperidin-1-carboxamide

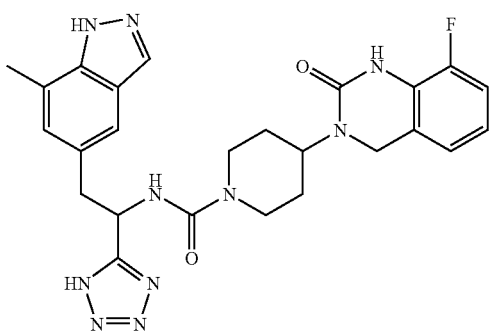

A stirred solution of 4-N-(1-cyano-2-{7-methyl-1H-indazol-5-yl}ethyl)-4-(8-fluoro-2-oxo-1,2-dihydroquinazolin-3 [4H]-yl)piperidine-1-carboxamide (0.25 g, 0.5 mmol) in tetrahydrofuran (6 mL) was treated with azidotrimethyltin (0.16 g, 0.77 mmol). The resulting suspension was heated at reflux overnight. The solvents were removed. The crude product was dissolved in ethyl acetate, washed with water (2×), brine (2×), dried over sodium sulfate, and concentrated. The residue was purified by column chromatography to afford 0.19 g (73%).

MS: $t_R$=1.44 min, 519.10 (MH)$^+$.

(±)-tert-Butyl-4-({5-(1-[4-(8-fluoro-2-oxo-1,2-dihydroquinazolin-3[4H]-yl)piperidine-1-carboxamido]-2-(7-methyl-1H-indazol-5-yl)ethyl)-1H-tetrazol-1-yl}methyl)piperidine-1-carboxylate

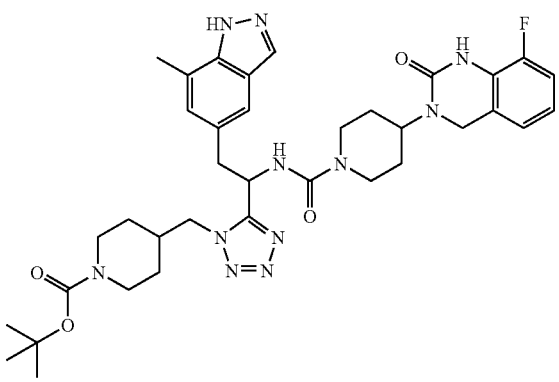

and (±)-tert-Butyl-4-({5-(1-[4-(8-fluoro-2-oxo-1,2-dihydroquinazolin-3[4H]-10 yl)piperidine-1-carboxamido]-2-(7-methyl-1H-indazol-5-yl)ethyl)-2H-tetrazol-1-yl}methyl)piperidine-1-carboxylate

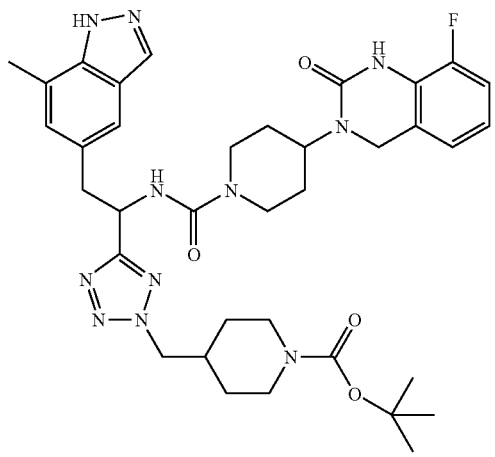

To a stirred solution of 4-(8-fluoro-2-oxo-1,2-dihydroquinazolin-3[4H]-yl)-N-(2{7-methyl-1H-indazol-5-yl}-1-{1H-tetrazol-5-yl}ethyl)piperidin-1-carboxamide (50 mg, 0.1 mmol) and tert-butyl 4-(hydroxymethyl)piperidine-1-carboxylate (22 mg, 0.11 mmol) in dry tetrahydrofuran (3.0 mL) at 0° C. was added in one portion triphenylphosphine (27.5 mg, 0.11 mmol) followed by a dropwise addition of diethylazodicarboxylate (10 μL, 0.105 mmol). The resulting mixture was stirred briefly at 0° C. and then allowed to warm to room temperature. After 16 h, the solvent was removed and the residue purified by column chromatography to afford tert-butyl-4-({5-(1-[4-(8-fluoro-2-oxo-1,2-dihydroquinazolin-3 [4H]-yl)piperidine-1-carboxamido]-2-(7-methyl-1H-indazol-5-yl)ethyl)-1H-tetrazol-1-yl}methyl)piperidine-1-carboxylate. MS: $t_R$=1.44 min, 716.17 $(MH)^+$ and tert-butyl-4-({5-(1-[4-(8-fluoro-2-oxo-1,2-dihydroquinazolin-3[4H]-yl)piperidine-1-carboxamido]-2-(7-methyl-1H-indazol-5-yl)ethyl)-2H-tetrazol-1-yl}methyl)piperidine-1-carboxylate. MS: $t_R$=1.45 min, 716.16 $(MH)^+$.

EXAMPLE 81

(±)-4-(8-Fluoro-2-oxo-1,2-dihydroquinazolin-3(4H)-yl)-N-(2-[7-methyl-1H-indazol-5-yl]-1-[1-(piperidin-4-ylmethyl)-1H-tetrazol-5-yl]ethyl)piperidin-1-carboxamide

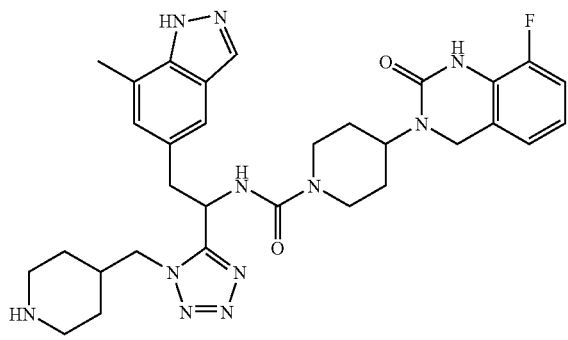

tert-Butyl-4-({5-(1-[4-(8-fluoro-2-oxo-1,2-dihydroquinazolin-3[4H]-yl)piperidine-1-carboxamido]-2-(7-methyl-1H-indazol-5-yl)ethyl)-1H-tetrazol-1-yl}methyl)piperidine-1-carboxylate (10 mg, 0.014 mmol) was dissolved in a 1:1 mixture of trifluoroacetic acid and methylene chloride (1.0 mL) and stirred at room temperature for 30 min. The solvent was removed under reduced pressure and the compound dried in vacuo for 2 h to afford 5.9 mg (68%). $^1$H-NMR (CD$_3$OD, 500 MHz) δ 1.20-1.48 (m, 4H), 1.50-1.79 (m, 5H) 2.24 (dd, J=12.5, 8.6, 1H), 2.50 (s, 3H), 2.57 (dd, J=11.6, 11.3, 1H), 3.18 (bs, 2H), 3.47 (s, 1H), 4.01-4.40 (m, 7H), 5.29 (dd, J=8.2, 7.9, 1H), 6.90-7.15 (m, 4H), 7.37 (s, 1H), 7.98 (s, 1H), 8.00 (s, 1H). Mass spec.: 616.20 $(MH)^+$.

EXAMPLE 82

(±)-4-(8-Fluoro-2-oxo-1,2-dihydroquinazolin-3(4H)-yl)-N-(2-[7-methyl-1H-indazol-5-yl]-1-[2-(piperidin-4-ylmethyl)-1H-tetrazol-5-yl]ethyl)piperidin-1-carboxamide

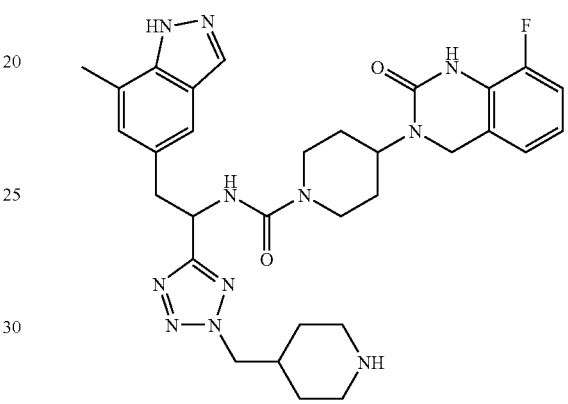

tert-Butyl-4-({5-(1-[4-(8-fluoro-2-oxo-1,2-dihydroquinazolin-3[4H]-yl)piperidine-1-carboxamido]-2-(7-methyl-1H-indazol-5-yl)ethyl)-2H-tetrazol-1-yl}methyl)piperidine-1-carboxylate (5.5 mg, 0.008 mmol) was dissolved in a trifluoroacetic acid/methylene chloride mixture (1:1, 1.0 mL) and stirred at room temperature for 30 min. The solvent was removed under reduced pressure and the compound dried in vacuo for 2 h to afford 2.6 mg (53%). $^1$H-NMR (CD$_3$OD, 500 MHz) δ 1.27-1.77 (m, 9H), 2.27 (bs, 1H), 2.54 (s, 3H), 2.65 (s, 1H), 2.74-2.95 (m, 4H), 4.06-4.25 (m, 4H), 4.87 (m, 1H), 4.52-4.62 (m, 2H), 5.42 (dd, J=8.5, 7.3, 1H), 6.90-7.03 (m, 3H), 7.12 (s, 1H), 7.36 (s, 1H), 7.96 (s, 1H). Mass spec.: 616.20$(MH)^+$.

(±)-2-(tert-Butoxycarbonyl)-3-(7methyl-1H-indazol-5-yl)propanoic acid

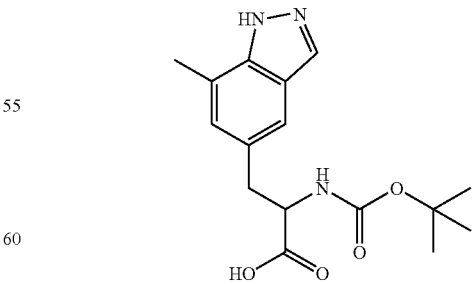

Methyl-2-amino-3-(7-methyl-1H-indazol-5-yl)propanoate (4.8 g, 20.6 mmol) and di-tert-butyl dicarbonate (11.2 g, 51.5 mmol) were combined in a 1,4-dioxane/water mixture (3:1, 108 mL). To this solution was added 10 N sodium hydroxide (35 mL) and the mixture stirred at room temperature overnight. After removing the solvents, the crude mixture was diluted with water and extracted with diethyl ether (2×). The aqueous phase was carefully acidified to ca. pH 2.0 by addition of concentrated hydrochloric acid and extracted with ethyl acetate (3×). The organics were pooled together, washed with brine (2×), dried over sodium sulfate, and concentrated to afford 15.6 g (76%). Mass spec.: 320.10 (MH)⁺.

(±)-tert-Butyl 1-{2-(pyridin-2-yl)hydrazinyl}-3-(7-methyl-1H-indazol-5-yl)-1-oxopropan-2-ylcarbamate

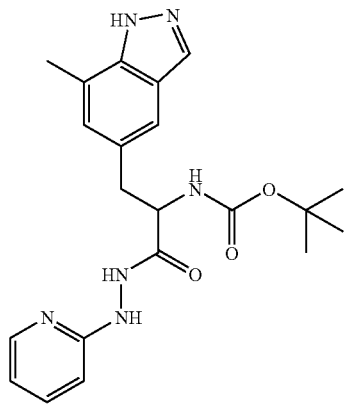

2-(tert-Butoxycarbonyl)-3-(7-methyl-1H-indazol-5-yl) propanoic acid (0.1 g, 0.31 mmol) and iso-butyl chloroformate (49 μL, 0.37 mmol) were combined in dry tetrahydrofuran (4.0 mL) at 0° C. Triethylamine (0.13 mL, 0.93 mmol) was added to the reaction mixture which was briefly stirred before addition of 2-hydrazinopyridine dihydrochloride salt (58 mg, 0.31 mmol). The reaction mixture was allowed to warm to room temperature overnight. The reaction was concentrated, redissolved in dichloromethane, washed with water (2×), brine (2×), dried over sodium sulfate, and concentrated. Column chromatography afforded 70.0 mg (55%). Mass spec.: 411.07 (MH)⁺.

(±)-tert-Butyl-1-([1,2,4]triazolo[4,3-a]pyridine-3-yl)-2-(7-methyl-1H-indazol-5-yl)ethylcarbamate

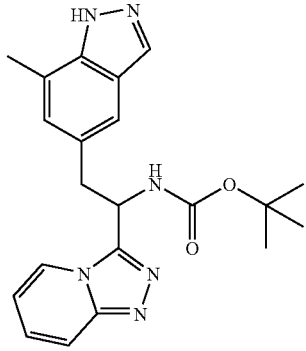

tert-Butyl 1-{2-(pyridin-2-yl)hydrazinyl}-3-(7-methyl-1H-indazol-5-yl)-1-oxopropan-2-ylcarbamate (70 mg, 0.17 mmol), triphenylphosphine (54 mg, 0.2 mmol), and trimethylsilyl azide (25 μL, 0.19 mmol) were combined in dry tetrahydrofuran (2.0 mL) at 0° C. Diethylazodicarbaoxylate (33 μL, 0.2 mmol) was added to the reaction mixture to afford a brown solution which was stirred at room temperature for 2 h. The solvents were removed in vacuo and the crude mixture purified by column chromatography to afford 45.2 mg (71%). Mass spec.: 393.04 (MH)⁺.

(±)-1-([1,2,4]Triazolo[4,3-a]pyridine-3-yl)-2-(7-methyl-1H-indazol-5-yl)ethanamine

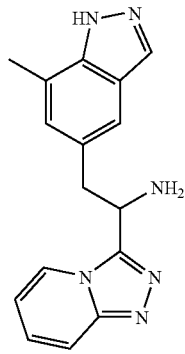

tert-Butyl-1-([1,2,4]triazolo[4,3-a]pyridine-3-yl)-2-(7-methyl-1H-indazol-5-yl)ethylcarbamate (43.2 mg, 0.11 mmol) was dissolved in a trifluoroacetic acid/methylene chloride mixture (1:1, 2 mL) and stirred under nitrogen for 1 h. The solvent was removed in vacuo and the resulting crude mixture passed through a strong cationic exchange column. After washing the column with several volumes of methanol, the desired amine was obtained by washing the column with 2M ammonia in methanol. Concentration afforded 33 mg (93%) of the crude product which was used without purification. ¹H-NMR (CD₃OD, 300 MHz) δ 2.41 (s, 3H), 3.50-3.66 (m, 2H), 5.50 (bs, 2H), 6.63 (dd, J=6.6, 6.2, 1H), 6.95 (s, 1H), 7.11-7.20 (s, 1H), 7.38 (s, 1H), 7.71 (d, J=9.2, 1H), 7.88 (d, J=7.0, 1H), 7.91 (s, 1H). Mass spec.: 293.02 (MH)⁺.

EXAMPLE 83

(±)-N-(1-([1,2,4]Triazolo [4,3-a]pyridin-3-yl)-2-(7-methyl-1H-indazol-5-yl)ethyl)-4-(8-fluoro-2-oxo-1,2-dihydroquinazolin-3(4H)-yl)piperidine-1-carboxamide

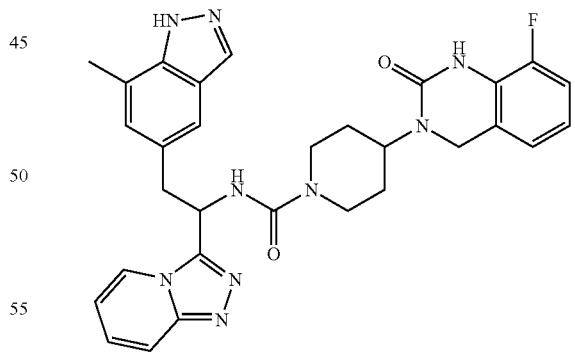

A stirred solution of 1-([1,2,4]triazolo[4,3-a]pyridine-3-yl)-2-(7-methyl-1H-indazol-5-yl)ethanamine (30 mg, 0.1 mmol) in dimethylformamide (1.0 mL) at 0° C. was treated with carbonyl diimidazole (17.5 mg, 1.1 equiv). The reaction was stirred for 5 min at 0° C., warmed to room temperature, stirred for 10 min, and treated with 8-fluoro-3-(piperidin-4-yl)-3,4-dihydroquinazolin-2(1H)-one (26.0 mg, 1.1 equiv). The mixture was then stirred at room temperature overnight. The solvent was evaporated and the residue purified by column chromatography to afford 30 mg (53%). $^1$H-NMR (CD$_3$OD, 300 MHz) δ 1.25-1.60 (m, 5H), 2.50 (s, 3H), 2.67-2.81 (m, 2H), 3.60 (s, 1H), 3.62 (s, 1H), 3.12-4.18 (m, 4H), 4.25-4.45 (m, 1H), 5.80 (dd, J=8.1, 8.1, 1H), 6.08-7.04 (m, 4H), 7.10 (s, 1H), 7.35-7.44 (s, 1H), 7.49 (s, 1H), 7.70 (m, 1H), 7.96 (s, 1H), 8.41 (d, J=7.0, 1H). Mass spec.: 568.10 (MH)$^+$.

(±)-Benzyl 3-(7-methyl-1H-indazol-5-yl)-1-(neopentylamino)-1-oxopropan-2-ylcarbamate

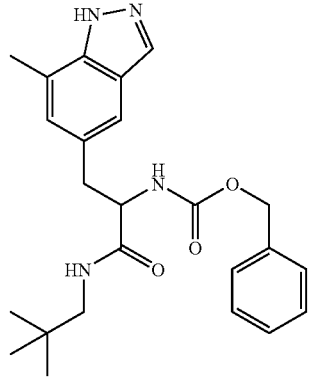

2-(Benzyloxycarbonyl)-3-(7-methyl-1H-indazol-5-yl) propanoic acid (0.2 g, 0.57 mmol), hydroxybenzotriazole (84 mg, 0.62 mmol), 1-(3-dimethyl aminopropyl)-3-ethyl carbodiimide hydrochloride (0.12 g, 0.62 mmol), and 2,2-dimethylpropan-1-amine (74 μL, 0.62 mmol) were combined in ethyl acetate (6.0 mL). To this solution was added triethylamine (0.24 mL, 1.7 mmol) and the reaction mixture stirred at 40° C. for 2 h. After cooling to room temperature, the mixture was diluted with ethyl acetate, washed with 5% citric acid (2×), brine (2×), dried over sodium sulfate, and concentrated to afford 0.21 g (88%). Mass spec.: 423.06 (MH)$^+$.

(±)-Benzyl 2-(7-methyl-1H-indazol-5-yl)-1-(1-neopentyl-1H-tetrazol-5-yl)ethylcarbamate

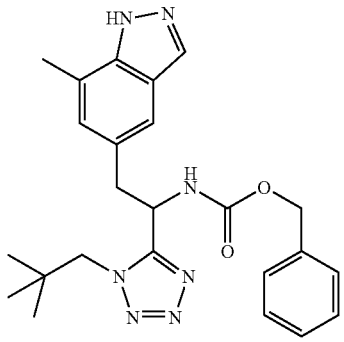

A solution of benzyl 3-(7-methyl-1H-indazol-5-yl)-1-(neopentylamino)-1-oxopropan-2-ylcarbamate (0.17 g, 0.402 mmol) in chloroform (0.5 mL) was added to a mixture of phosphorus pentachloride (0.17 g, 0.802 mmol) and quinoline (0.2 mL) in chloroform (1.0 mL). After stirring at room temperature for 2 h, the solvents were removed in vacuo. The crude mixture was dissolved in acetonitrile (2.0 mL) and treated with sodium azide (78 mg, 3.0 equiv). After stirring the mixture at 40° C. overnight, the solvents were removed and the crude mixture dissolved in methylene chloride which was washed with water (2×), brine (2×), dried over sodium sulfate, and concentrated. Column chromatography afforded 73 mg (40%, 2 steps). $^1$H-NMR (CD$_3$OD, 500 MHz) δ 0.82 (s, 9H), 2.46 (s, 3H), 2.30-3.46 (m, 2H), 3.69 (d, J=14.3, 1H), 3.93 (d, J=14.3, 1H), 4.98-5.13 (m, 2H), 5.30 (m, 1H), 6.02 (d, J=8.9, 1H), 6.86 (s, 1H), 7.25-7.35 (m, 5H), 7.94 (s, 1H). Mass spec.: 448.19 (MH)$^+$.

(±)-2-(7-Methyl-1H-indazol-5-yl)-1-(1-neopentyl-1H-tetrazol-5-yl)ethanamine

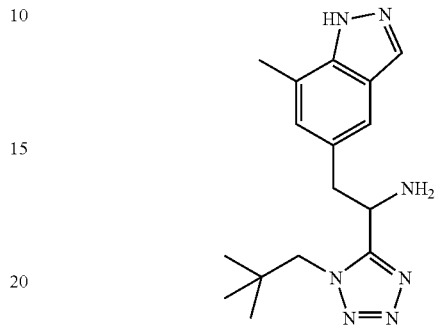

A solution of benzyl 2-(7-methyl-1H-indazol-5-yl)-1-(1-neopentyl-1H-tetrazol-5-yl)ethylcarbamate (70.0 mg, 0.156 mmol) in methanol (2.0 mL) was flushed with nitrogen, and treated with palladium (10% on charcoal, 7.0 mg). The flask was flushed with hydrogen and allowed to stir under a balloon of hydrogen overnight. The reaction was flushed with nitrogen, filtered through celite, and concentrated. Column chromatography gave 48.0 mg (quant.). Mass spec.: 314.17 (MH)$^+$.

EXAMPLE 84

(±)-N-(2-(7-Methyl-1H-indazol-5-yl)-1-(1-neopentyl-1H-tetrazol-5-yl)ethyl)-4-(2-oxo-1,2-dihydroquinazolin-3(4H)-yl)piperidine-1-carboxamide

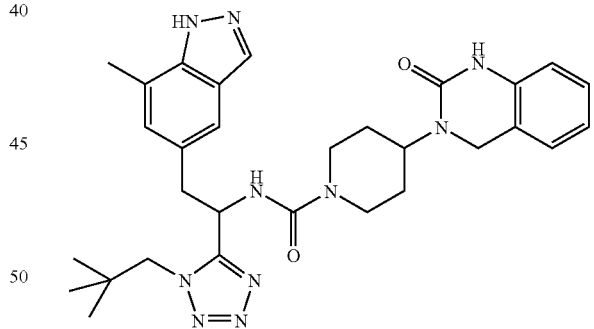

A stirred solution of 2-(7-methyl-1H-indazol-5-yl)-1-(1-neopentyl-1H-tetrazol-5-yl)ethanamine (20.0 mg, 0.06 mmol) in dimethylformamide (1.0 mL) at 0° C. was treated with carbonyl diimidazole (11.0 mg, 1.1 equiv). The reaction was stirred for 5 min at 0° C., warmed to room temperature, stirred for 10 min, and treated with 3-(piperidin-4-yl)-3,4-dihydroquinazolin-2(1H)-one (15.0 mg, 1.1 equiv). The mixture was stirred at room temperature overnight. The solvent was evaporated and the residue purified by column chromatography to afford 22.0 mg (64%). $^1$H-NMR (CD$_3$OD, 500 MHz) δ 0.90 (s, 9H), 1.35-1.60 (m, 4H), 2.53 (s, 3H), 2.71-2.85 (m, 2H), 3.41-3.52 (m, 2H), 3.98-4.14 (m, 5H), 4.24 (d, J=14.3, 1H), 4.34 (m, 1H), 6.77 (d, J=7.9, 1H), 6.94 (dd, J=7.6, 7.3, 1H), 7.06-7.17 (m, 3H), 7.45 (s, 1H), 7.88 (s, 1H), 7.98 (s, 1H). Mass spec.: 571.28 (MH)+.

Methyl 2-(benzyloxycarbonyl)acrylate

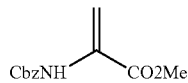

To a flame dried three neck round bottom flask, was added methyl 2-(benzyloxycarbonyl)-3-hydroxypropanoate (129 g, 509 mmol), anhydrous methylene chloride (2 L), and methanesulfonyl chloride (49.3 mL, 636 mmol). The mixture was cooled to −15° C.→20° C. for 20 min while stirring with a mechanical stirrer. Triethylamine (213 mL, 1527 mmol) was added dropwise ensuring the inner temperature of the reaction mixture did not exceed 0° C. (the addition of the first equivalent of triethylamine was exothermic). After the addition of triethylamine, the mixture was stirred at 0° C. for 30 min, then the cooling bath was removed and the mixture was stirred at room temperature for 1.5 h. Methanol (21 mL) was added to quench excess methanesulfonyl chloride. The mixture was washed portionwise with 0.5% aq. potassium hydrogen sulfate to pH 5, then sat. sodium bicarbonate/brine (1:2 by volume) and brine. The methylene chloride solution was dried over anhydrous sodium sulfate. After filtration, the solvents were removed and the residue was subjected to column chromatography on silica gel using 1:9 ethyl acetate/hexanes as eluent to afford the title compound as a colorless very viscous oil, which recrystalized upon standing at room temperature, 0° C. and −15° C. (111 g, 92% yield). $^1$H-NMR (DMSO-$d_6$) δ 8.96 (s, 1H), 7.39-7.35 (m, 5H), 5.76 (s, 1H), 5.60 (s, 1H), 5.10 (s, 2H), 3.71 (s, 3H); $^{13}$C-NMR (DMSO-$d_6$) δ 163.7, 153.5, 136.3, 133.3, 128.8, 128.3, 128.1, 127.8, 65.9, 52.3.

(Z)-Methyl 3-(4-amino-3,5-dimethylphenyl)-2-(benzyloxycarbonyl)acrylate

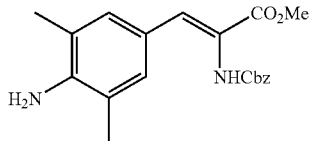

A 2 L round bottom flask, was charged with 4-iodo-2,6-dimethylbenzenamine hydrochloride salt (55 g, 194 mmol), methyl 2-(benzyloxycarbonyl)acrylate (59.2 g, 252 mmol), tetrabutylammonium chloride (59.2 g, 213 mmol), palladium acetate (4.34 g, 19.4 mmol), and tetrahydrofuran (1.2 L, degassed by a flow of nitrogen for 30 min). The mixture was stirred to form a suspension and degassed by a flow of nitrogen for 30 min. Triethylamine (110 mL, 789 mmol) was then added and the resulting mixture was heated at reflux for 3 h. After cooling to room temperature, the reaction mixture was filtered through a pad of celite and washed twice with tetrahydrofuran (2×100 mL). The solvents were removed and the residue was dissolved in methylene chloride which was extracted with water (3×), brine (2×), dried over sodium sulfate and concentrated. Column chromatography on silica gel using 1:9 ethyl acetate/methylene chloride as eluent afforded a tan solid, which was recrystalized from methanol (210 mL) and water (100 mL). After filtration, the solid was washed with ice cold 1:1 methanol/water mixture and then dried under high vacuum overnight at room temperature to afford the title compound (58.0 g, 65%) as a light tan solid. NMR shows a 2.7:1 ratio of Z and E isomers which were not separated. $^1$H-NMR (DMSO-$d_6$) δ 8.79 (s, 0.73 H), 8.51 (s, 0.27 H), 7.40-7.21 (m, 8H), 5.24 (s, 2H), 5.13 (s, 1.46 H), 5.00 (s, 0.54 H), 3.68 (s, 2.2 H), 3.61 (s, 0.8 H), 2.05 (s, 6H); $^{13}$C-NMR (DMSO-$d_6$) δ 166.0, 154.7, 146.9, 137.2, 135.8, 130.9, 128.3, 127.7, 127.3, 120.3, 120.0, 119.4, 65.3, 51.7, 17.8.

(R)-Methyl 3-(4-amino-3,5-dimethylphenyl)-2-(benzyloxycarbonyl)propanoate

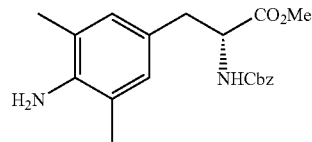

(Z)-Methyl 3-(4-amino-3,5-dimethylphenyl)-2-(benzyloxycarbonyl)acrylate (84.5 g, 239 mmol) was weighed into a flame-dried 2 L Parr shaker, followed by the addition of methylene chloride (300 mL) and methanol (300 mL). The bottle was swirled to form a light brown suspension, and this suspension was degassed by a flow of nitrogen for 30 min. Following addition of (−)-1,2-bis((2R,5R)-2,5-diethylphospholano)bezene(cyclooctadiene)rhodium(I)tetrafluoroborate ([(2R,5R)-Et-DuPhosRh]BF$_4$) (2.11 g, 3.20 mmol), the bottle was put onto a Parr Hydrogenator. After 5 cycles of purging with hydrogen (60 psi) and vacuum, the final hydrogen pressure was set at 65 psi and the suspension was agitated at room temperature for 16 h (after 3 h, the suspension became a clear solution), and the reaction was complete. Solvents were removed and the residue was subjected to flash chromatography on silica gel using ethyl acetate/methylene chloride (1:9) as the eluent to afford the title compound as a very light tan solid (82.9 g, 98% yield). $^1$H-NMR (DMSO-$d_6$) δ 7.70 (d, J=7.9 Hz, 1H), 7.37-7.28 (m, 5H), 6.68 (s, 2H), 5.00 (s, 2H), 4.41 (s, 2H), 4.15-4.10 (m, 1H), 3.62 (s, 3H), 2.82 (dd, J=13.7, 5.2 Hz, 1H), 2.65 (dd, J=13.4, 9.8 Hz, 1H), 2.04 (s, 6H); $^3$C-NMR (DMSO-$d_6$) δ 172.5, 155.9, 142.6, 136.9, 128.3, 128.2, 127.7, 127.5, 124.0, 120.4, 65.3, 56.1, 51.7, 35.9, 17.7.

(R)-Methyl 2-(benzyloxycarbonyl)-3-(7-methyl-1H-indazol-5-yl)propanoate

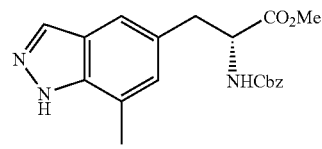

(R)-Methyl 3-(4-amino-3,5-dimethylphenyl)-2-(benzyloxycarbonyl) propanoate (50.0 g, 140 mmol) was weighed into a flame-dried 5 L three neck round bottom flask, followed by the addition of toluene (2.40 L) and glacial acetic acid (120 mL, 2.1 mol). The mixture was mechanically stirred at rt for 10 min to form a clear solution and potassium acetate (103 g, 1.05 mol) was added. To this white suspension, iso-amylnitrite (20.7 mL, 154 mmol) was added dropwise at room temperature and the resulting mixture was stirred at room temperature for 16 h. Saturated sodium bicarbonate (1 L) was added, followed by careful addition of solid sodium bicarbonate to neutralize acetic acid. The mixture was extracted with a mixture of methylene chloride (2 L) and brine (1.5 L). After separation, the aqueous layer was extracted with methylene chloride (500 mL). The combined organic layers were dried over sodium sulfate and filtered. Solvents were removed to afford a tan solid, which was washed with hexanes (2.0 L) and tolune (150 mL). The solid was recrystallized from acetone (260 mL) and hexanes (700 mL). The resulting slight cloudy mixture was cooled to room temperature slowly, then 0° C. for 1.5 h and −15° C. for 1.5 h. The solid was filtered and washed with ice-cold acetone/hexanes (1:1, 200 mL) to afford, after drying overnight under high vacuum, the title compound as creamy crystals (39.1 g, 76% yield) with >98% purity (checked by a 20 min analytical HPLC run). The ee was determined to be 99.8% (conditions: Chiralpak AD column, 4.6×250 mm, 10 μm; A=EtOH, B=0.05% DEA/heptane; 85% B @1.0 mL/min. for 55 min. The retention times for R was 44.6 min and for S was 28.8 min). $^1$H-NMR (DMSO-$d_6$) δ 13.1 (s, 1H), 7.99 (s, 1H), 7.83 (d, J=8.2 Hz, 1H), 7.41 (s, 1H), 7.29-7.27 (m, 3H), 7.24-7.22 (m, 2H), 7.03 (s, 1H), 4.97 (s, 2H), 4.32-4.27 (m, 1H), 3.63 (s, 3H), 3.10 (dd, J=13.7, 4.9 Hz, 1H), 2.93 (dd, J=13.4, 10.7 Hz, 1H), 2.48 (s, 3H); $^{13}$C-NMR (DMSO-$d_6$) δ 172.4, 155.9, 139.2, 136.8, 133.4, 129.3, 128.2, 127.6, 127.4, 127.2, 122.7, 119.6, 117.6, 65.3, 56.0, 51.8, 36.5, 16.7.

(R)-2-(Benzyloxycarbonyl)-3-(7-methyl-1H-indazol-5-yl)propanoic acid

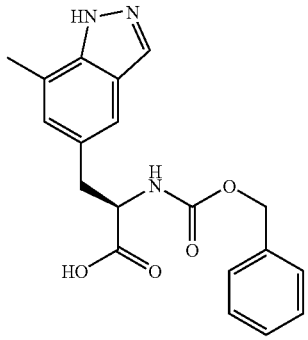

A suspension of (R)-methyl 2-(benzyloxycarbonyl)-3-(7-methyl-H-indazol-5-yl)propanoate (0.66 g, 1.71 mmol) in 1:1 tetrahydrofuran/methanol (60 mL) at room temperature was treated with a solution of lithium hydroxide monohydrate (189 mg, 2.5 equiv) in water (10 mL). The solution was stirred at room temperature for 1 h and the solvents evaporated. The resultant residue was diluted with water (10 mL) and was adjusted to ca. pH 1.0 with 1 N hydrochloric acid. The resultant white suspension was stored at 4° C. overnight. The product was collected by filtration, washed by a small amount of water, and dried in vacuo for several hours to give 0.58 g (96%). Mass spec.: 354.30 (MH)$^+$.

(R)-Benzyl 3-(7-methyl-1H-indazol-5-yl)-1-oxo-1-(pyridin-2-ylmethylamino)propan-2-ylcarbamate

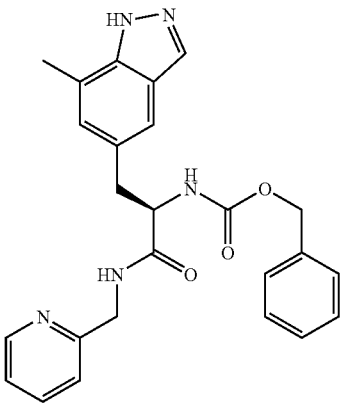

2-(Benzyloxycarbonyl)-3-(7-methyl-1H-indazol-5-yl) propanoic (0.47 g, 1.32 mmol), hydroxybenzotriazole (0.2 g, 1.46 mmol), 1-(3-dimethyl aminopropyl)-3-ethyl carbodiimide hydrochloride (0.28 g, 1.46 mmol), and 2-picolyl amine (0.56 mL, 1.46 mmol) were combined in ethyl acetate (10.0 mL). To this solution was added triethylamine (0.56 mL, 4.0 mmol) and the reaction mixture stirred at 40° C. for 2 h. After cooling to room temperature, the residue was diluted with ethyl acetate, washed with 5% citric acid (2×), brine (2×), dried over sodium sulfate, and concentrated to afford 0.42 g (72%). Mass spec.: 444.4 (MH)$^+$.

(R)-Benzyl 1-(H-imidazo[1,5-a]pyridin-3-yl)-2-(7-methyl-1H-indazol-5-yl)ethylcarbamate

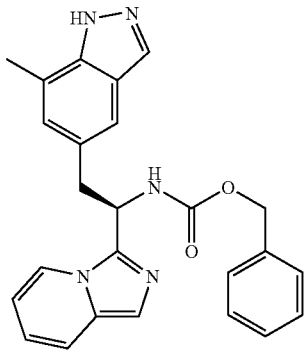

To a solution of benzyl 3-(7-methyl-1H-indazol-5-yl)-1-oxo-1-(pyridin-2-ylmethylamino)propan-2-ylcarbamate (75 mg, 0.17 mmol) in 1,2-dichloroethane (1.5 mL) was added phosphorus oxychloride (78 μL, 0.85 mmol) and pyridine (0.25 mL, 0.85 mmol). The reaction mixture was heated at reflux for 1 h, cooled to room temperature, and concentrated. The resulting residue was partitioned between ethyl acetate and saturated sodium bicarbonate. The organic layer was separated, washed with water (2×), brine (2×), dried over sodium sulfate, and concentrated to afford 22 mg (30%). $^1$H-NMR (CD$_3$OD, 300 MHz) δ 2.42 (s, 3H), 3.44 (s, 1H), 3.46 (s, 1H), 4.82-5.08 (m, 2H), 5.46 (m, 1H), 6.50 (m, 1H), 7.99 (d, J=6.2, 1H). Mass spec.: 426.20 (MH)$^+$.

(R)-1-(H-Imidazo[1,5-a]pyridin-3-yl)-2-(7-methyl-1H-indazol-5-yl)ethanamine

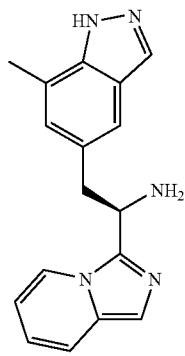

Benzyl 1-(H-imidazo[1,5-a]pyridin-3-yl)-2-(7-methyl-1H-indazol-5-yl)ethylcarbamate (50 mg, 0.11 mmol) was dissolved in methylene chloride (1.0 mL) and cooled to 0° C. Iodotrimethylsilane (67 μL, 4.0 equiv) was added and the reaction mixture allowed to warm to room temperature. After stirring for 1 h, triethylamine (57 μL, 3.0 equiv) was added to the reaction mixture and stirring continued for 30 min. The reaction was diluted with methylene chloride, washed with water (2×), brine (2×), dried over sodium sulfate, and concentrated to afford 26.0 mg (66%) which was used without purification. Mass spec.: 292.3 (MH)$^+$.

EXAMPLE 85

(R)-N-(1-(H-Imidazo[1,5-a]pyridin-3-yl)-2-(7-methyl-1H-indazol-5-yl)ethyl)-4-(2-oxo-1,2-dihydroquinazolin-3(4H)-yl)piperidine-1-carboxamide

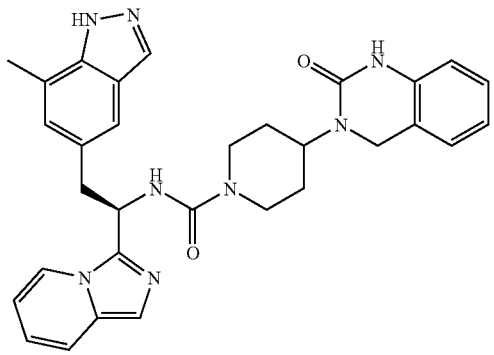

A stirred solution of 1-(H-imidazo[1,5-a]pyridin-3-yl)-2-(7-methyl-1H-indazol-5-yl)ethanamine (38.0 mg, 0.12 mmol) in dimethylformamide (1.0 mL) at 0° C. was treated with carbonyl diimidazole (21.0 mg, 1.1 equiv). The reaction was stirred for 5 min at 0° C., warmed to room temperature, stirred for 10 min, and treated with 3-(piperidin-4-yl)-3,4-dihydroquinazolin-2(1H)-one (29.8 mg, 1.1 equiv). The mixture was stirred at room temperature overnight. The solvent was evaporated and the residue purified by column chromatography to afford 29.4 mg (45%). $^1$H-NMR (CD$_3$OD, 500 MHz) δ 1.35-1.60 (m, 4H), 2.50 (s, 3H), 2.72-2.86 (m, 2H), 3.44-3.56 (m, 2H), 4.10 (s, 2H), 4.17 (dd, J=15.0, 13.1, 1H), 4.30-4.42 (m, 1H), 5.72 (dd, J=7.6, 7.3, 1H), 7.01 (s, 1H), 7.10-7.20 (m, 2H), 7.42 (s, 1H), 7.50 (d, J=9.5, 1H), 7.96 (s, 1H), 8.13 (d, J=7.3, 1H). Mass spec.: 549.68 (MH)$^+$.

(±)-tert-Butyl 1-(4-bromo-1H-imidazol-2-yl)-2-(7-methyl-2-((2(trimethylsilyl)ethoxy)methyl)-2H-indazol-5-yl)ethylcarbamate and (±)-tert-Butyl 1-(4,5-dibromo-1H-imidazol-2-yl)-2-(7-methyl-2-((2-(trimethylsilyl)ethoxy)methyl)-2H-indazol-5-yl)ethylcarbamate

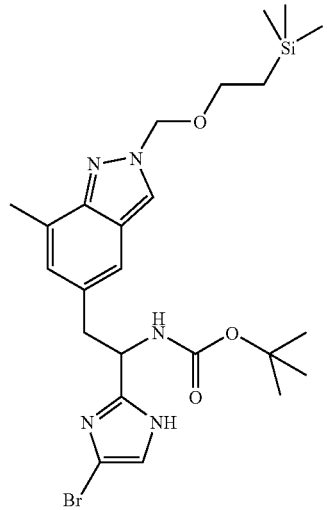

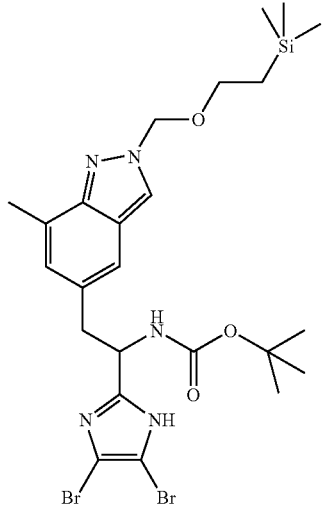

tert-Butyl-1-(1H-imidazol-2-yl)-2-(7-methyl-2-[{2-[trimethylsilyl]ethoxy}methyl]-2H-indazol-5-yl)ethylcarbamate (73 mg, 0.16 mmol) was dissolved in methylene chloride and cooled to −78° C. To this was added N-bromosuccinimide (24.8 mg, 0.14 mmol) and the mixture allowed to stir at −78° C. for 30 min. After warming to room temperature, the solvent was removed and the residue purified by column chromatography to afford 19 mg (22%) of the monobrominated product and 25 mg (26%) of the bis-brominated product. tert-butyl 1-(4-bromo-1H-imidazol-2-yl)-2-(7-methyl-2-((2(trimethylsilyl)ethoxy)methyl)-2H-indazol-5-yl)ethylcarbamate:
$^1$H-NMR (CDCl$_3$, 300 MHz) δ −0.10 (s, 9H), 0.86-0.95 (m, 2H), 1.33 (s, 9H), 2.51 (s, 3H), 3.26 (m, 2H), 4.79-4.93 (m, 1H), 5.67 (s, 2H), 6.80 (m, 2H), 7.18 (s, 1H), 7.94 (s, 1H). Mass spec.: 551.99 (MH)$^+$. tert-Butyl 1-(4,5-dibromo-1H-imidazol-2-yl)-2-(7-methyl-2-((2-(trimethylsilyl)ethoxy)methyl)-2H-indazol-5-yl)ethylcarbamate: $^1$H-NMR (CDCl$_3$, 300 MHz) δ 0.00 (s, 9H), 0.90 (m, 2H), 1.33 (s, 9H), 2.50 (s, 3H), 3.06-3.27 (m, 2H), 3.59 (m, 2H), 4.86 (m, 1H), 5.89 (m, 1H), 5.66 (s, 2H), 6.73 (s, 1H), 7.14 (s, 1H), 7.92 (s, 1H). Mass spec.: 630.59 (MH)$^+$.

EXAMPLE 86

(±)-N-(1-(4-Bromo-1H-imidazol-2-yl)-2-(7-methyl-1H-indazol-5-yl)ethyl)-4-(2-oxo-1,2-dihydroquinazolin-3(4H)-yl)piperidine-1-carboxamide

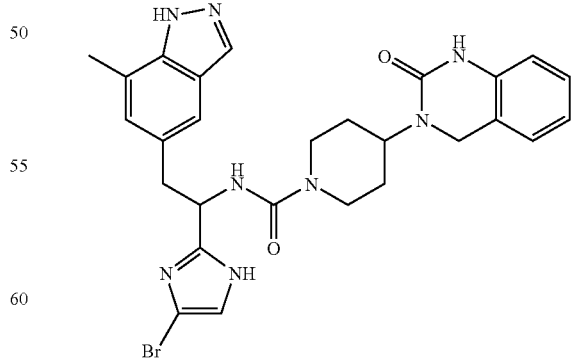

tert-Butyl 1-(4-bromo-1H-imidazol-2-yl)-2-(7-methyl-2-((2(trimethylsilyl)ethoxy)methyl)-2H-indazol-5-yl)ethylcarbamate (19.0 mg, 0.035 mmol) was dissolved in a minimum amount of ethyl acetate, and treated with hydrochloric acid (4 N in dioxane, 1.0 mL) (1.0 mL). The mixture was-stirred under nitrogen for 3 days. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (6.2 mg, 0.038 mmol, 1.1 equiv) and N'N-diisopropylethylamine (25.0 µL, 4.0 equiv). The reaction was stirred for 5 min at 0° C., warmed to room temperature, stirred for 10 min, and treated with 3-(piperidin-4-yl)-3,4-dihydroquinazolin-2(1H)-one (10.1 mg, 0.038, 1.1 equiv). The mixture was stirred at room temperature overnight. The solvent was evaporated and the residue purified by column chromatography to afford 7.3 mg, (36%, 2 steps). $^1$H-NMR (CD$_3$OD, 500 MHz) δ 1.50-1.71 (m, 4H), 2.55 (s, 3H), 2.74-2.93 (m, 2H), 3.16-3.25 (m, 2H), 4.03-4.20 (m, 4H), 4.78 (m, 1H), 5.12-5.19 (m, 1H), 6.63 (d, J=7.9, 1H), 6.94 (d, J=7.9, 1H), 6.94-7.00 (m, 2H), 7.04 (s, 1H), 7.12 (s, 1H), 7.12 (d, J=7.3, 1H), 7.16 (dd, J=7.6, 7.6, 1H), 7.40 (s, 1H), 7.99 (s, 1H). Mass spec.: 577.67 (MH)$^+$.

Similarly prepared:

EXAMPLE 87

(±)-N-(1-(4,5-Dibromo-1H-imidazol-2-yl)-2-(7-methyl-1H-indazol-5-yl)ethyl)-4-(2-oxo-1,2-dihydroquinazolin-3(4H)-yl)piperidine-1-carboxamide

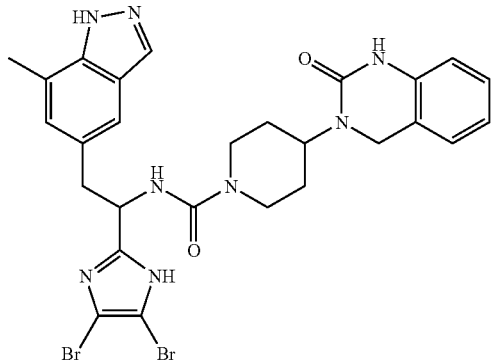

$^1$H-NMR (CD$_3$OD, 500 MHz) δ 1.29-1.70 (m, 4H), 2.55 (s, 3H), 2.73-2.93 (m, 3H), 4.02-4.21 (m, 4H), 4.88 (m, 1H), 5.10-5.19 (m, 1H), 6.79 (d, J=7.9, 1H), 6.97 (dd, J=7.6, 7.6, 1H), 7.01 (s, 1H), 7.12 (d, J=7.3, 1H), 7.16 (dd, J=7.9, 7.3, 1H), 7.42 (s, 1H), 8.00 (s, 1H). Mass spec.: 657.68 (MH)$^+$.

(±)-tert-Butyl 1-(1-(3,5-difluorobenzyl)-5-bromo-1H-imidazol-2-yl)-2-(7-methyl-2-((2-(trimethylsilyl)ethoxy)methyl)-2H-indazol-5-yl)ethylcarbamate

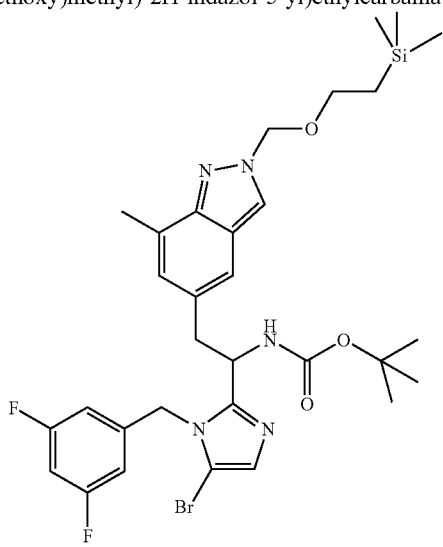

tert-Butyl 1-(1-(3,5-difluorobenzyl)-1H-imidazol-2-yl)-2-(7-methyl-2-((2-(trimethylsilyl)ethoxy)methyl)-2H-indazol-5-yl)ethylcarbamate (72.0 mg, 0.12 mmol) was dissolved in methylene chloride (3.0 mL) and cooled to −78° C. To this was added N-bromosuccinimide (18.3 mg, 0.11 mmol) and the mixture allowed to stir at −78° C. for 30 min. After warming to room temperature, the solvent was removed and the residue purified by column chromatography to afford 30 mg (40%). $^1$H-NMR (CD$_3$OD, 300 MHz) δ −0.06 (s, 9H), 0.89 (m, 2H), 1.33 (s, 9H), 2.44 (s, 3H), 3.15-3.25 (m, 1H), 3.57-3.66 (m, 2H), 4.80-5.09 (m, 2H), 6.26 (m, 2H), 6.47-6.66 (m, 2H), 7.12 (s, 1H), 7.20 (s, 1H), 7.91 (s, 1H). Mass spec.: 678.3 (MH)$^+$.

EXAMPLE 88

(±)-N-(1-(1-(3,5-Difluorobenzyl)-5-bromo-1H-imidazol-2-yl)-2-(7-methyl-2H-indazol-5-yl)ethyl)-4-(2-oxo-1,2-dihydroquinazolin-3(4H)-yl)piperidine-1-carboxamide

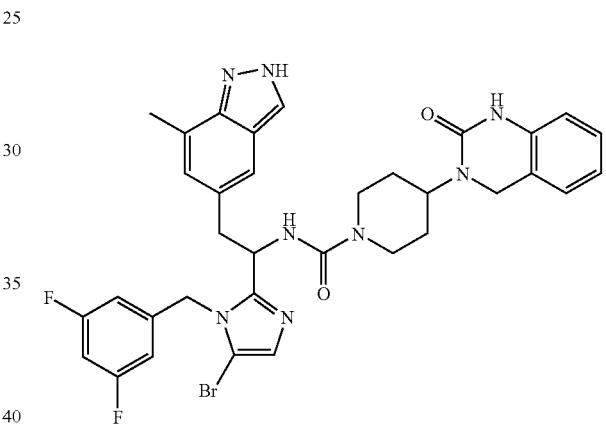

tert-Butyl 1-(1-(3,5-difluorobenzyl)-5-bromo-1H-imidazol-2-yl)-2-(7-methyl-2-((2-(trimethylsilyl)ethoxy)methyl)-2H-indazol-5-yl)ethylcarbamate (16.0 mg, 0.024 mmol) was dissolved in a minimum amount of ethyl acetate, and treated with hydrochloric acid (4 N in dioxane, 1.0 mL). The mixture was stirred under nitrogen for 3 days. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (4.0 mg, 0.025 mmol, 1.1 equiv) and N'N-diisopropylethylamine (16.7 µL, 3 equiv). The reaction was stirred for 5 min at 0° C., warmed to room temperature, stirred for 10 min, and treated with 3-(piperidin-4-yl)-3,4-dihydroquinazolin-2(1H)-one (5.8 mg, 0.025, 1.1 equiv). The mixture was stirred at room temperature overnight. The solvent was evaporated and the residue purified by column chromatography to afford 7.5 mg (52%, 2 steps). $^1$H-NMR (CD$_3$OD, 500 MHz) δ 1.40-1.58 (m, 4H), 2.42 (s, 3H), 2.61-2.72 (m, 2H), 3.14-3.24 (m, 2H), 3.92-4.06 (m, 2H), 4.15 (s, 2H), 4.25-4.38 (m, 1H), 4.10-5.24 (m, 2H), 5.42 (m, 1H), 6.32 (s, 1H), 6.33 (s, 1H), 6.61-6.78 (m, 3H), 6.82 (s, 1H), 6.90-6.99 (m, 1H), 7.08-7.13 (m, 2H), 7.86 (s, 1H). Mass spec.: 705.2 (MH)$^+$.

(±)-tert-Butyl 1-(4-methyl-1H-imidazol-2-yl)-2-(7-methyl-2-((2-(trimethylsilyl)ethoxy)methyl)-2H-indazol-5-yl)ethylcarbamate

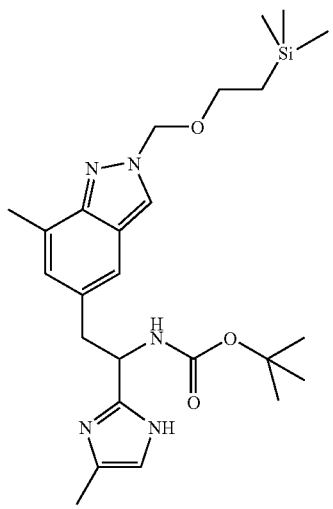

tert-Butyl-3-(7-methyl-2-[{2-[trimethylsilyl]ethoxy}methyl]-2H-indazol-5-yl)-1-oxopropan-2-ylcarbamate (0.14 g, 0.32 mmol) and pyruvic aldehyde (40.0 µL, 0.64 mmol, 2.0 equiv) were combined in a dioxane/water mixture (6:1, 4 mL). To this was added 28% ammonia in water (37.0 µL, 0.97 mmol) and the reaction was allowed to stir at 80° C. for 16 h. After cooling to room temperature, the solvents were removed and the crude mixture dissolved in methylene chloride which was washed with water (2×), brine (2×), dried over magnesium sulfate, and concentrated. Column chromatography afforded 65.0 mg (42%). Mass spec.: 486.30 (MH)⁺.

(±)-tert-Butyl 1-(1-(3-fluorobenzyl)-4-methyl-1H-imidazol-2-yl)-2-(7-methyl-2-((2-(trimethylsilyl)ethoxy)methyl)-2H-indazol-5-yl)ethylcarbamate

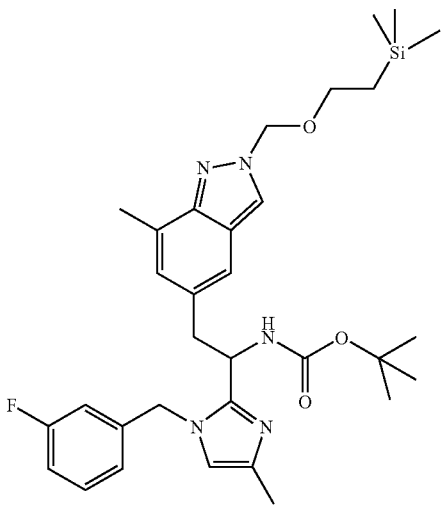

tert-Butyl 1-(4-methyl-1H-imidazol-2-yl)-2-(7-methyl-2-((2-(trimethylsilyl)ethoxy)methyl)-2H-indazol-5-yl)ethylcarbamate (38.4 mg, 0.079 mmol), 3-fluoro benzylbromide (10.8 µL, 0.083 mmol, 1.05 equiv), and potassium carbonate (22.0 mg, 0.16 mmol) were combined in dimethylformamide (1.0 mL). After stirring at room temperature for 16 h, the solvents were removed and the residue purified by column chromatography to afford 31.0 mg (64%). ¹H-NMR (CD₃OD, 300 MHz) δ −0.02 (s, 9H), 0.87-0.98 (m, 2H), 1.31 (s, 9H), 2.23 (s, 3H), 2.47 (s, 3H), 3.08-3.18 (m, 2H), 3.56-3.71 (m, 2H), 4.89-5.13 (m, 3H), 5.72 (s, 1H), 6.83-7.14 (m, 2H), 7.21 (s, 1H), 8.20 (s, 1H). Mass spec.: 594.47 (MH)⁺.

EXAMPLE 89

(±)-N-(1-(1-(3-Fluorobenzyl)-4-methyl-1H-imidazol-2-yl)-2-(7-methyl-1H-indazol-5-yl)ethyl)-4-(2-oxo-1,2-dihydroquinazolin-3(4H)-yl)piperidine-1-carboxamide

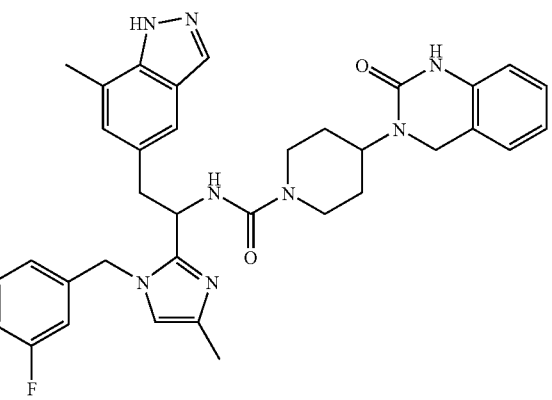

tert-Butyl 1-(1-(3-fluorobenzyl)-4-methyl-1H-imidazol-2-yl)-2-(7-methyl-2-((2-(trimethylsilyl)ethoxy)methyl)-2H-indazol-5-yl)ethylcarbamate (20.0 mg, 0.034 mmol) was dissolved in a minimum amount of ethyl acetate, and treated with hydrochloric acid (4 N in dioxane, 1.0 mL). The mixture was stirred under nitrogen for 3 days. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (6.0 mg, 0.037 mmol, 1.1 equiv) and N'N-diisopropylethylamine (24.3 µL, 3 equiv). The reaction was stirred for 5 min at 0° C., warmed to room temperature, stirred for 10 min, and treated with 3-(piperidin-4-yl)-3,4-dihydroquinazolin-2(1H)-one (8.5 mg, 0.037 mmol, 1.1 equiv). The mixture was stirred at room temperature overnight. The solvent was evaporated and the residue purified by column chromatography to afford 16.1 mg (74%, 2 steps). ¹H-NMR (CD₃OD, 500 MHz) δ 1.50-1.68 (m, 4H), 2.27 (s, 3H), 2.46 (s, 3H), 2.77 (m, 2H), 3.20 (m, 2H), 4.01-4.16 (m, 2H), 4.20 (s, 2H), 4.32-4.43 (m, 1H), 5.13-5.22 (m, 2H), 6.60-6.67 (m, 2H), 6.70 (s, 1H), 6.76-6.86 (m, 2H), 6.87-6.94 (m, 1H), 6.96 (dd, J=8.3, 6.7, 1H), 7.07-7.14 (m, 2H), 7.16 (dd, J=7.9, 7.6, 1H), 7.25 (s, 1H), 7.92 (s, 1H). Mass spec.: 621.4 (MH)⁺.

EXAMPLE 90

(±)-N-(1-(4-Methyl-1H-imidazol-2-yl)-2-(7-methyl-1H-indazol-5-yl)ethyl)-4-(2-oxo-1,2-dihydroquinazolin-3(4H)-yl)piperidine-1-carboxamide

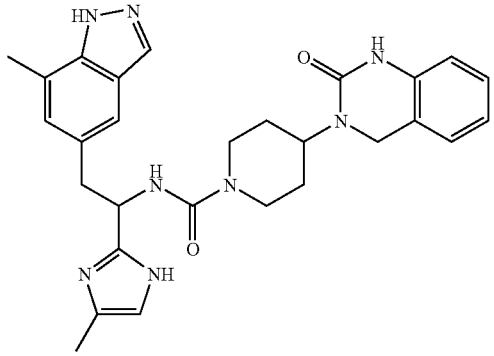

tert-Butyl 1-(4-methyl-1H-imidazol-2-yl)-2-(7-methyl-2-((2-(trimethylsilyl)ethoxy)methyl)-2H-indazol-5-yl)ethylcarbamate (25.2 mg, 0.052 mmol) was dissolved in a minimum amount of ethyl acetate, and treated with hydrochloric acid (4 N in dioxane, 1.5 mL). The mixture was stirred under nitrogen for 3 days. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (10.0 mg, 0.055 mmol, 1.1 equiv) and diisopropylethylamine (36.2 μL, 4.0 equiv). The reaction was stirred for 5 min at 0° C., warmed to room temperature, stirred for 10 min, and treated with 3-(piperidin-4-yl)-3,4-dihydroquinazolin-2(1H)-one (13.0 mg, 0.055, 1.1 equiv). The mixture was stirred at room temperature overnight. The solvent was evaporated and the residue purified by column chromatography to afford 10.1 mg (38%, 2 steps). $^1$H-NMR (CD$_3$OD, 500 MHz) δ 1.39-1.66 (m, 4H), 2.20 (s, 3H), 2.55 (s, 3H), 2.73-2.95 (m, 2H), 3.14-3.22 (m, 1H), 4.01-4.20 (m, 4H), 4.32-4.43 (m, 1H), 5.13-5.19 (m, 1H), 6.65 (s, 1H), 6.79 (d, J=7.6, 1H), 6.97 (dd, J=7.6, 7.3, 1H), 7.02 (s, 1H), 7.12 (d, J=7.3, 1H), 7.17 (dd, J=7.9, 7.3, 1H), 7.40 (s, 1H), 7.99 (s, 1H). Mass spec.: 513.3 (MH)$^+$.

2-Acetoxy-2-(diethoxyphosphoryl)acetic acid

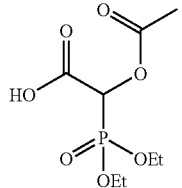

Glyoxylic acid monohydrate (4.00 g, 43.45 mmol) was suspended in diethyl phosphite (5.59 mL, 1.0 equiv) and warmed to 60° C. for 5 h. The reaction was cooled, diluted with dichloromethane (40 mL), and treated with pyridine (3.51 mL, 1.0 equiv) and acetyl chloride (3.09 mL, 1.0 equiv). A significant exotherm was noted. The reaction was stirred at room temperature for 2 h. The reaction was washed with 1 M hydrochloric acid (2×20 mL), then saturated sodium bicarbonate. The organics were dried over magnesium sulfate, and concentrated to give <2 g as an oil. The aqueous washes were combined and extracted with dichloromethane (4×). The organics were dried over magnesium sulfate and concentrated to give 5.85 g (53%) as an oil which solidified upon standing. $^1$H-NMR (CDCl$_3$, 500 MHz) δ 1.36 (t, J=7.0, 6H), 2.21 (s, 3H), 4.28 (m, 4H), 5.54 (d, J=17.7, 1H), 8.90 (bs, 1H). Mass spec.: 255.10 (MH)$^+$.

Methyl 2-acetoxy-2-(diethylphosphoryl)acetate

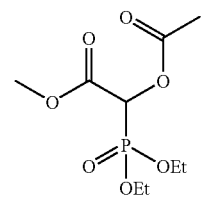

To a mixture of 5M sodium hydroxide (50 mL) and diethyl ether (100 mL) at 0° C. was added N-methyl-N'-nitro-N-nitrosoguanidine (6.37 g, 43.3 mmol) in small portions with swirling. After addition was complete, the mixture was allowed to stand at 0° C. for 15 min with occasional swirling. The ethereal layer was transferred in portions to a suspension of 2-acetoxy-2-(diethoxyphosphoryl)acetic acid (5.50 g, 21.6 mmol) in ether (ca. 50 mL) until the solid had completely dissolved and a yellow color persisted. The reaction was allowed to stand at 0° C. for 15 min before bubbling nitrogen through the solution to remove unreacted diazomethane. The reaction was concentrated to give 5.90 g (quant.) as a faint yellow oil. $^1$H-NMR (CDCl$_3$, 500 MHz) δ 1.36 (td, J=7.0, 2.4, 6H), 2.21 (s, 3H), 3.82 (s, 3H), 4.23 (m, 4H), 5.43 (d, J=16.8, 1H). Mass spec.: 269.17 (MH)$^+$.

(±)-tert-Butyl 2-(7-methyl-2-((2-(trimethylsilyl)ethoxy)methyl)-2H-indazol-5-yl)-1-(1-(pyridin-3-ylmethyl)-1H-imidazol-2-yl)ethylcarbamate

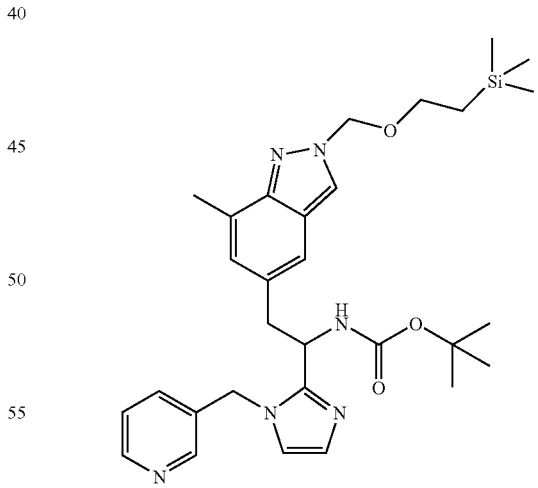

tert-Butyl-1-(1H-imidazol-2-yl)-2-(7-methyl-2-[{2-[trimethylsilyl]ethoxy}methyl]-2H-indazol-5-yl)ethylcarbamate (48 mg, 0.101 mmol), 3-(chloromethyl)pyridine (18.3 mg, 0.11 mmol, 1.05 equiv), and cesium carbonate (99.0 mg, 0.303 mmol) were combined in dimethylformamide (1.5 mL). After stirring at room temperature for 16 h, the solvents were removed and the residue purified by column chromatography to afford 51.0 mg (92%). Mass spec.: 563.3 (MH)$^+$.

EXAMPLE 91

(±)-N-(2-(7-Methyl-1H-indazol-5-yl)-1-(1-(pyridin-3-ylmethyl)-1H-imidazol-2-yl)ethyl)-4-(2-oxo-1,2-dihydroquinazolin-3(4H)-yl)piperidine-1-carboxamide

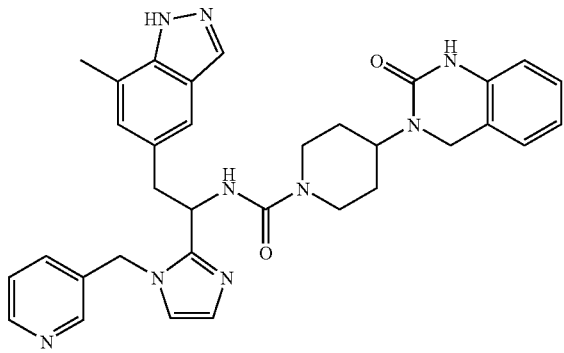

tert-Butyl 2-(7-methyl-2-((2-(trimethylsilyl)ethoxy)methyl)-2H-indazol-5-yl)-1-(1-(pyridin-3-ylmethyl)-1H-imidazol-2-yl)ethylcarbamate (51.0 mg, 0.091 mmol) was dissolved in a minimum amount of ethyl acetate, and treated with hydrochloric acid (4 N in dioxane, 1.5 mL). The mixture was stirred under nitrogen for 3 days. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (17.2 mg, 0.106 mmol, 1.05 equiv) and N'N-diisopropylethylamine (53.0 μL, 3 equiv). The reaction was stirred for 5 min at 0° C., warmed to room temperature, stirred for 10 min, and treated with 3-(piperidin-4-yl)-3,4-dihydroquinazolin-2(1H)-one (28.3 mg, 0.106 mmol, 1.05 equiv). The mixture was stirred at room temperature overnight. The solvent was evaporated and the residue purified by column chromatography to afford 23.2 mg (43%, 2 steps). $^1$H-NMR (CD$_3$OD, 500 MHz) δ 1.50-1.67 (m, 4H), 2.45 (s, 3H), 2.68-2.72 (m, 2H), 3.71-3.79 (m, 3H), 4.01-4.15 (m, 2H), 4.20 (s, 2H), 4.31-4.43 (m, 1H), 5.16-5.35 (m, 3H), 6.80 (d, J=7.9, 1H), 6.84 (s, 1H), 6.93-7.21 (m, 8H), 7.26 (s, 1H), 7.92 (s, 1H), 8.27 (s, 1H), 8.32 (s, 1H). Mass spec.: 590.3 (MH)$^+$.

(±)-tert-Butyl 2-(7-methyl-2-((2-(trimethylsilyl)ethoxy)methyl)-2H-indazol-5-yl)-1-(1-(pyridin-2-ylmethyl)-1H-imidazol-2-yl)ethylcarbamate

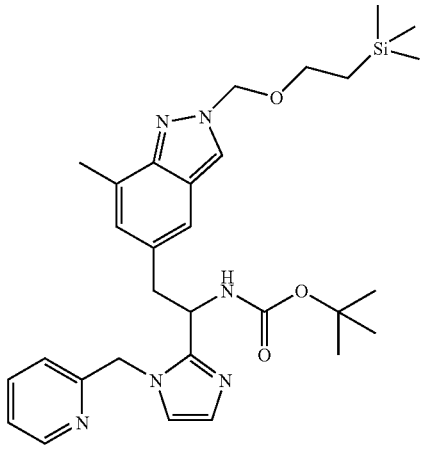

tert-Butyl-1-(1H-imidazol-2-yl)-2-(7-methyl-2-[{2-[trimethylsilyl]ethoxy}methyl]-2H-indazol-5-yl)ethylcarbamate (35.0 mg, 0.074 mmol), 2-(chloromethyl)pyridine (13.3 mg, 0.082 mmol, 1.05 equiv), and cesium carbonate (72.3 mg, 0.22 mmol) were combined in dimethylformamide (1.5 mL). After stirring at room temperature for 16 h, the solvents were removed and the residue purified by column chromatography to afford 35.2 mg (77%). Mass spec.: 563.3 (MH)$^+$.

EXAMPLE 92

(±)-N-(2-(7-Methyl-1H-indazol-5-yl)-1-(1-(pyridin-2-ylmethyl)-1H-imidazol-2-yl)ethyl)-4-(2-oxo-1,2-dihydroquinazolin-3(4H)-yl)piperidine-1-carboxamide

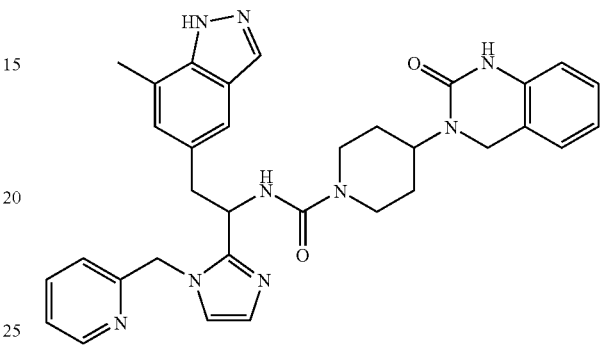

tert-Butyl 2-(7-methyl-2-((2-(trimethylsilyl)ethoxy)methyl)-2H-indazol-5-yl)-1-(1-(pyridin-2-ylmethyl)-1H-imidazol-2-yl)ethylcarbamate (35.2 mg, 0.063 mmol) was dissolved in a minimum amount of ethyl acetate, and treated with hydrochloric acid (4 N in dioxane, 1.0 mL). The mixture was stirred under nitrogen overnight. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (11.0 mg, 0.066 mmol, 1.05 equiv) and diisopropylethylamine (44.0 μL, 4.0 equiv). The reaction was stirred for 5 min at 0° C., warmed to room temperature, stirred for 10 min, and treated with 3-(piperidin-4-yl)-3,4-dihydroquinazolin-2(1H)-one (17.6 mg, 0.066 mmol, 1.05 equiv). The mixture was stirred at room temperature overnight. The solvent was evaporated and the residue purified by column chromatography to afford 4.6 mg (12%, 2 steps). $^1$H-NMR (CD$_3$OD, 500 MHz) δ 1.48-1.65 (m, 4H), 2.03 (s, 1H), 2.45 (s, 3H), 2.69-2.82 (m, 2H), 3.99-4.16 (m, 2H), 4.19 (s, 2H), 5.24 (d, J=16.5, 1H), 6.67 (d, J=7.6, 1H), 6.80 (d, J=7.9, 1H), 6.89 (s, 1H), 6.97 (dd, J=8.2, 7.6, 1H), 7.10-7.23 (m, 5H), 7.30 (s, 1H), 7.37-7.42 (m, 1H), 7.94 (s, 1H). Mass spec.: 590.3 (MH)$^+$.

(2-Chloro-6-methylpyridin-4-yl)methanol

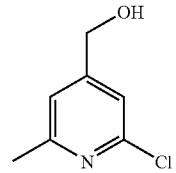

2-Chloro-6-methylpyridine-4-carboxylic acid (0.52 g, 3.04 mmol) and borane-tetrahydrofuran complex (6.08 mL, 6.08 mmol) were combined in tetrahydrofuran (10.0 mL) at 0° C. After 15 min, the ice bath was removed and mixture stirred at room temperature for 4 h. The mixture was cooled to 0° C., and treated with methanol until no bubbles were observed. The solvents were removed and the crude mixture dissolved in ethyl acetate which was washed with water (2×), brine (2×), dried over sodium sulfate, and concentrated to afford 0.25 g (53%) which was used without purification. $^1$H-NMR (CDCl$_3$, 500 MHz) δ 2.53 (s, 3H), 4.7 (s, 2H), 7.06 (s, 1H), 7.15 (s, 1H). Mass spec.: 158.0 (MH)$^+$.

2-Chloro-4-(chloromethyl)-6-methylpyridine

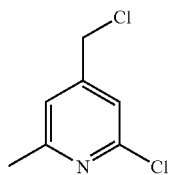

(2-Chloro-6-methylpyridin-4-yl)methanol (0.212 g, 1.35 mmol) and thionyl chloride (0.12 mL, 1.62 mmol) were combined in methylene chloride (4 mL) and stirred at room temperature for 4 h. The solvents were removed and the product dried under vacuum for several hours to afford 0.24 g (quant.) as a clear oil which was used without purification. Mass spec.: 176.0 (MH)$^+$.

(±)-tert-Butyl 1-(1-((2-chloro-6-methylpyridin-4-yl) methyl)-1H-imidazol-2-yl)-2-(7-methyl-2-((2-(trimethylsilyl)ethoxy)methyl)-2H-indazol-5-yl)ethylcarbamate

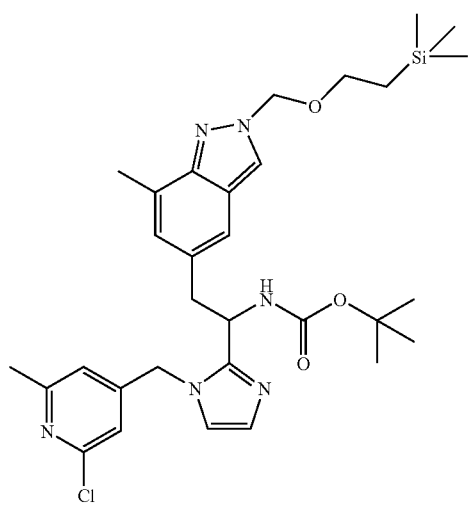

tert-Butyl-1-(1H-imidazol-2-yl)-2-(7-methyl-2-[{2-[trimethylsilyl]ethoxy}methyl]-2H-indazol-5-yl)ethylcarbamate (0.1 g, 0.212 mmol), 2-chloro-4-(chloromethyl)-6-methylpyridine (39.0 mg, 0.222 mmol, 1.05 equiv), and cesium carbonate (0.21 g, 0.64 mmol) were combined in dimethylformamide (2.0 mL). After stirring at room temperature for 16 h, the solvents were removed and the residue purified by column chromatography to afford 0.1 g (77%). Mass spec.: 611.21 (MH)$^+$.

EXAMPLE 93

(±)-N-(1-(1-((2-Chloro-6-methylpyridin-4-yl)methyl)-1H-imidazol-2-yl)-2-(7-methyl-1H-indazol-5-yl)ethyl)-4-(2-oxo-1,2-dihydroquinazolin-3(4H)-yl) piperidine-1-carboxamide

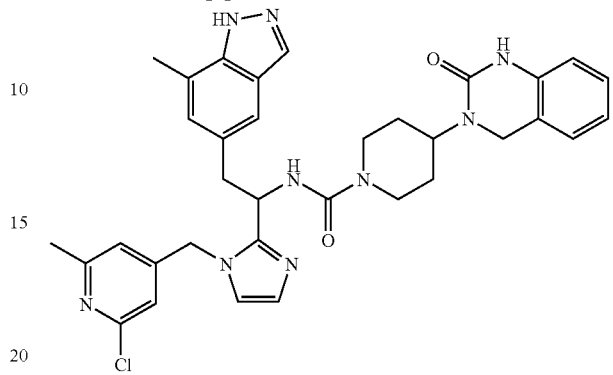

tert-Butyl 1-(1-((2-chloro-6-methylpyridin-4-yl)methyl)-1H-imidazol-2-yl)-2-(7-methyl-2-((2-(trimethylsilyl) ethoxy)methyl)-2H-indazol-5-yl)ethylcarbamate (100 mg, 0.16 mmol) was dissolved in a minimum amount of ethyl acetate, and treated with hydrochloric acid (4 N in dioxane, 2.0 mL). The mixture was stirred under nitrogen overnight. After removal of the solvents, the crude mixture was treated with diethyl ether to give a precipitate which was filtered. The resulting solid was dissolved in dimethylformamide (1.0 mL), cooled to 0° C., and treated with carbonyl diimidazole (27.0 mg, 0.165 mmol, 1.05 equiv) and N'N-diisopropylethylamine (66.0 μL, 3.0 equiv). The reaction was stirred for 5 min at 0° C., warmed to room temperature, stirred for 10 min, and treated with 3-(piperidin-4-yl)-3,4-dihydroquinazolin-2 (1H)-one (44.0 mg, 0.165 mmol, 1.05 equiv). The mixture was stirred at room temperature overnight. The solvent was evaporated and the residue purified by column chromatography to afford 67.1 mg (65%, 2 steps). $^1$H-NMR (CD$_3$OD, 500 MHz) δ 1.43-1.62 (m, 4H), 2.27 (s, 3H), 2.46 (s, 3H), 2.65-2.77 (m, 3H), 3.22-3.30 (m, 1H), 3.95-4.07 (m, 2H), 4.19 (s, 2H), 4.30-4.38 (m, 1H), 5.14-5.37 (m, 3H), 6.61 (s, 1H), 6.70 (s, 1H), 6.80 (d, J=7.9, 1H), 6.88 (s, 1H), 6.96 (dd, J=7.6, 7.3, 1H), 7.10 (s, 1H), 7.13 (s, 1H), 7.14-7.20 (m, 2H), 7.28 (s, 1H). Mass spec.: 638.1 (MH)$^+$.

EXAMPLE 94

(±)-N-(2-(7-Methyl-1H-indazol-5-yl)-1-(1-((2-methylpyridin-4-yl)methyl)-1H-imidazol-2-yl)ethyl)-4-(2-oxo-1,2-dihydroquinazolin-3(4H)-yl)piperidine-1-carboxamide

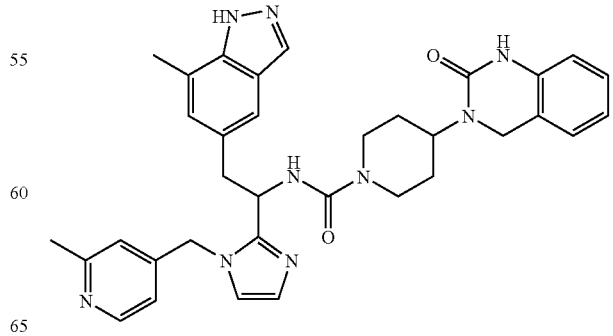

N-(1-(1-((2-Chloro-6-methylpyridin-4-yl)methyl)-1H-imidazol-2-yl)-2-(7-methyl-1H-indazol-5-yl)ethyl)-4-(2- oxo-1,2-dihydroquinazolin-3(4H)-yl)piperidine-1-carboxamide (15.0 mg, 0.024 mmol) in methanol (1.0 mL) was flushed with nitrogen, and treated with palladium (10% on charcoal, 1.5 mg). The flask was flushed with hydrogen and allowed to stir under an atmosphere of hydrogen overnight. After 24 h, the reaction was charged with additional palladium (10% on charcoal, 1.5 mg). The flask was flushed with hydrogen and allowed to stir under an atmosphere of hydrogen overnight. The reaction was flushed with nitrogen, filtered through celite, and concentrated in vacuo. Column chromatography gave 2.4 mg (17%). $^1$H-NMR (CD$_3$OD, 500 MHz) δ 1.49-1.63 (m, 4H), 2.32 (s, 3H), 2.43 (s, 3H), 2.69-2.78 (m, 2H), 3.98-4.12 (m, 2H), 5.11-5.24 (m, 3H), 5.39 (d, J=17.1, 1H), 6.55 (d, J=0.9, 1H), 6.72 (s, 1H), 6.80 (d, J=7.9, 1H), 6.85 (s, 1H), 6.97 (dd, J=7.6, 7.3, 1H), 7.06 (s, 1H), 7.10-7.76 (m, 6H), 8.03 (d, J=5.2, 1H). Mass spec.: 604.96 (MH)$^+$.

4-tert-Butyl 1-methyl 2-((7-methyl-1H-indazol-5-yl)methyl)succinate

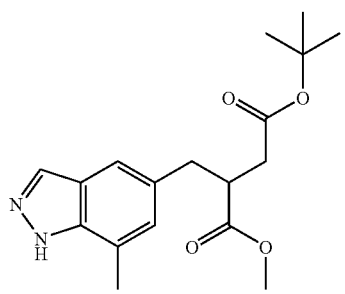

To a solution of 4-methoxy-3-((7-methyl-1H-indazol-5-yl)methyl)-4-oxobutanoic acid (0.9764 g, 3.54 mmol) and t-butyl-2,2,2-trichloroacetoimidate (3.78 mL, 21.22 mmol) in tetrahydrofuran (25 mL) was added 1M boron trifluoride etherate (0.2 mL) at room temperature. Heat generation was observed and the reaction was stirred for 3.5 h before passing it through a pad of silica gel. Evaporation of the filtrate gave a white solid. Methylene chloride (20 mL) was added and the resulting white solid was removed by filtration. The filtrate was concentrated and the final product was obtained via silica gel chromatography eluting with 0% to 50% ethyl acetate/hexane. (0.605 g, 52%) HPLC t$_R$=1.51 min, MS(ESI)[M+H]$^+$= 332.77.

4-tert-Butyl 1-methyl 2-((7-methyl-2-((2-(trimethylsilyl)ethoxy)methyl)-2H-indazol-5-yl)methyl)succinate

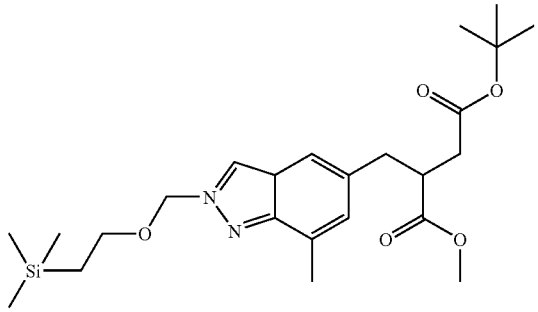

To a solution of 4-tert-butyl 1-methyl 2-((7-methyl-1H-indazol-5-yl)methyl)succinate (0.6053 g, 1.82 mmol) and N-cyclohexyl-N-methylcyclohexanamine (0.4686 mL, 2.19 mmol) in tetrahydrofuran (10 mL) was added trimethylsilylethoxymethyl chloride (0.3859 mL, 2.19 mmol) at room temperature under nitrogen. The reaction was stirred overnight and the solvent was removed in vacuo. The crude product was taken up in ethyl acetate (10 mL) and washed with water (3×5 mL). The ethyl acetate layer was dried, filtered and concentrated. The final product was obtained by flash chromatography, eluting with 0% to 20% ethyl acetate/hexane. (0.5873 g, 70%) HPLC t$_R$=1.89 min, MS(ESI)[M+H]$^+$= 462.94.

tert-Butyl 3-(hydroxymethyl)-4-(7-methyl-2-((2-(trimethylsilyl)ethoxy)methyl)-2H-indazol-5-yl)butanoate

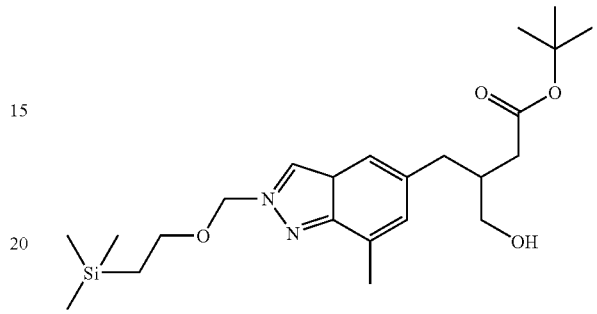

4-tert-butyl 1-methyl 2-((7-methyl-2-((2-(trimethylsilyl)ethoxy)methyl)-2H-indazol-5-yl)methyl)succinate (0.5873 g, 1.27 mmol) was dissolved in tetrahydrofuran (4 mL) and water (1 mL). Lithium hydroxide (0.1750 g, 5.08 mmol) was added and the reaction was stirred at room temperature overnight. The tetrahydrofuran was evaporated and 1 N HCl (2 mL) was added. The acid was extracted with ethyl acetate (3×10 mL) and the ethyl acetate layer was dried, filtered and concentrated to give the corresponding acid (0.5214 g, 92%).

To a solution of the above acid (0.5214 g, 1.16 mmol) in tetrahydrofuran (10 mL) and triethylamine (0.1942 mL, 1.40 mmol) at 0° C. under nitrogen was added isobutylchloroformate (0.1810 mL, 1.40 mmol). After 1 h, the reaction was allowed to warm to room temperature and stirred for 4 h. A solution of sodium borohydride (14 mmol in 5 mL water) was added slowly to the reaction mixture at room temperature and stirring was continued for a further 2 h. After concentration in vacuo, the residue was taken up in ethyl acetate (35 mL) and washed by water (3×10 mL). The ethyl acetate layer was dried, filtered and concentrated. The final product was obtained by flash chromatography eluting with 0% to 50% ethyl acetate/hexane (95%). HPLC t$_R$=1.89 min, MS(ESI) [M+H]$^+$=434.93. $^1$H-NMR (400 MHz, CDCl$_3$) δ 7.94 (1H, s), 7.23 (1H, s), 6.89 (1H, s), 5.66 (2H, s), 3.59 (2H, t, J=8.0 Hz), 3.52 (1H, m), 2.69 (1H, m), 2.58 (1H, m), 2.57 (1H, m), 2.56 (3H, s), 2.33-2.23 (3H, m), 1.39 (9H, s), 0.90 (2H, t, J=8.0 Hz), 0.07 (9H, s).

tert-Butyl 3-formyl-4-(7-methyl-2-((2-(trimethylsilyl)ethoxy)methyl)-2H-indazol-5-yl)butanoate

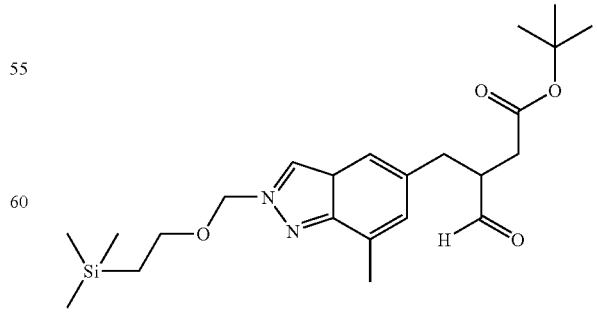

To a solution of tert-butyl 3-(hydroxymethyl)-4-(7-methyl-2-((2-(trimethylsilyl)ethoxy)methyl)-2H-indazol-5-yl)butanoate (0.5500 g, 1.27 mmol) in methylene chloride (25 mL) was added Dess-Martin reagent (0.6449 g, 1.52 mmol) at room temperature. The reaction was stirred overnight before washing with 1 N sodium hydroxide (10 mL) and water (2×10 mL). The organic layer was dried, filtered and concentrated. The final product was obtained by flash chromatography using 0% to 50% ethyl acetate/hexane (0.2773 g, 51%) HPLC $t_R$=2.02 min, $^1$H-NMR (400 MHz, CDCl$_3$) δ 9.42 (1H, s), 7.94 (1H, s), 7.19 (1H, s), 6.82 (1H, s), 5.64 (2H, s), 3.57 (2H, t, J=8.40 Hz), 3.02 (2H, m), 2.58 (1H, m), 2.54 (3H, s), 2.49 (1H, m), 2.30 (1H, m), 1.33 (9H, s), 0.87 (2H, t, J=8.40 Hz), −0.01 (9H, s).

tert-butyl 3-(1H-Imidazol-2-yl)-4-(7-methyl-2-((2-(trimethylsilyl)ethoxy)methyl)-2H-indazol-5-yl)butanoate

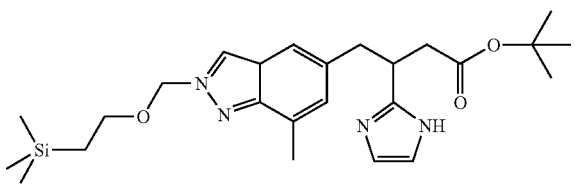

A solution of tert-butyl 3-formyl-4-(7-methyl-2-((2-(trimethylsilyl)ethoxy)methyl)-2H-indazol-5-yl)butanoate (0.64 mmol), glyoxal (1.3 mmol) and ammonium hydroxide (1.3 mmol) in dioxane (10 mL) was heated at 70° C. for 4 h. The crude product was extracted with ethyl acetate (3×20 mL). The ethyl acetate portions were combined, dried and filtered. Flash chromatography using 0% to 100% ethyl acetate/hexane gave the desired product (65%). $^1$H-NMR (400 MHz, CDCl$_3$) δ 7.93 (1H, s), 7.15 (1H, s), 6.89 (2H, s), 6.79 (1H, s), 5.66 (2H, s), 3.60 (2H, t, J=8.40 Hz), 3.55 (1H, m), 3.16 (1H, dd), 2.97 (1H, dd), 2.70 (1H, dd), 2.60 (1H, dd), 2.52 (3H, s), 1.34 (9H, s), 0.91 (2H, t, J=8.40 Hz), 0.05 (9H, s). MS(ESI) [M+H]$^+$=471.

tert-Butyl 3-(1-(4-tert-butylbenzyl)-1H-imidazol-2-yl)-4-(7-methyl-2-((2-(trimethylsilyl)ethoxy)methyl)-2H-indazol-5-yl)butanoate

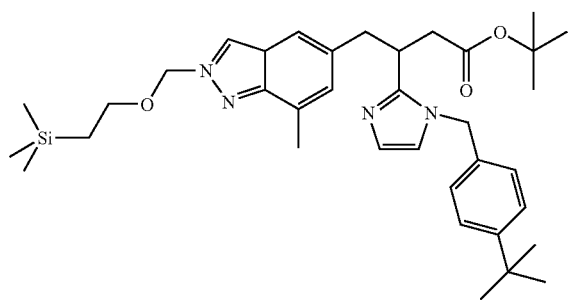

A mixture of tert-butyl 3-(1H-imidazol-2-yl)-4-(7-methyl-2-((2-(trimethylsilyl)ethoxy)methyl)-2H-indazol-5-yl)butanoate (0.16 mmol), 4-tert-butylbenzyl bromide (1.0 equiv), and potassium carbonate (1.0 equiv) in dimethylformamide (2 mL) was stirred at room temperature overnight. The mixture was diluted with ethyl acetate (20 mL) and washed with water (3×5 mL). The ethyl acetate layer was dried, filtered and concentrated in vacuo. The product was obtained by flash chromatography using 0% to 50% ethyl acetate/hexane (65%). $^1$H-NMR (400 MHz, CDCl$_3$) δ 7.93 (1H, s), 7.23 (2H, m), 7.03 (2H, m), 6.82 (2H, m), 6.63 (1H, s), 6.49 (1H,s), 5.68 (2H, s), 4.82 (2H, d, J=4.0 Hz), 3.60 (2H, t, 8.0 Hz), 3.41 (1H, m), 2.86 (2H, d, J=8.0 Hz), 2.79 (1H, dd, J1=8.0 Hz, J2=16 Hz), 2.61 (1H, dd, J1=8.0 Hz, J2=16 Hz), 2.49 (3H, s), 1.31 (9H, s), 1.25 (9H, s), 0.91 (2H, t, J=8.0 Hz), −0.06 (9H,s). MS(ESI)[M+H]+=617.

EXAMPLE 95

3-(1-(3-(1-(4-tert-Butylbenzyl)-1H-imidazol-2-yl)-4-(7-methyl-3a,7a-dihydro-1H-indazol-5-yl)butanoyl) piperidin-4-yl)-3,4-dihydroquinazolin-2(1H)-one

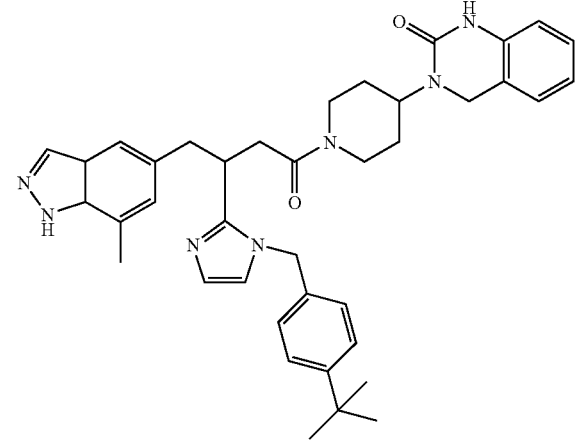

A solution of tert-butyl 3-(1-(4-tert-butylbenzyl)-1H-imidazol-2-yl)-4-(7-methyl-2-((2-(trimethylsilyl)ethoxy)methyl)-2H-indazol-5-yl)butanoate (0.10 mmol) in methylene chloride (1 mL) and trifluoroacetic acid (1 mL) was stirred at room temperature overnight. The solvents were removed in vacuo. The crude carboxylic acid was immediately coupled to 3-(piperidin-4-yl)-3,4-dihydroquinazolin-2(1H)-one as described above for Example 89 (51%). $^1$H-NMR (400 MHz, CDCl$_3$) δ 7.93 (1H, d, J=2.8 Hz), 7.31-6.61 (13H, m), 4.90 (2H, m), 4.64 (1H, m); 4.50 (1H, m); 4.22-3.89 (3H, m), 3.65 (1H, m), 3.26 (1H, m), 2.98 (3H, m), 2.70-2.30 (6H, m), 1.74-1.32 (3H, m), 1.23 (9H, s). MS (ESI)[M+H]$^+$=644.36.

Similarly prepared:

EXAMPLE 96

3-(1-(3-(1-(4-tert-Butylbenzyl)-1H-imidazol-2-yl)-4-(7-methyl-3a,7a-dihydro-1H-indazol-5-yl)butanoyl) piperidin-4-yl)-8-fluoro-3,4-dihydroquinazolin-2(1H)-one

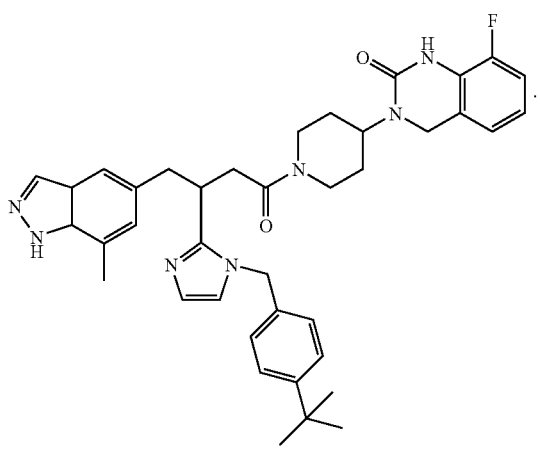

Yield: 71% $^1$H-NMR (400 MHz, CDCl$_3$) δ 7.93 (1H, d, J=2.8 Hz), 7.31-6.61 (12H, m), 4.90 (2H, m), 4.64 (1H, m);

4.50 (1H, m); 4.22-3.89 (3H, m), 3.65 (1H, m), 3.26 (1H, m), 2.98 (3H, m), 2.70-2.30 (6H, m), 1.74-1.32 (3H, m), 1.23 (9H, s). MS(ESI)[M+H]$^+$=662.34.

EXAMPLE 97

3-(1-(4-(7-Methyl-3a,7a-dihydro-1H-indazol-5-yl)-3-(1-(pyridin-4-ylmethyl)-1H-imidazol-2-yl)butanoyl)piperidin-4-yl)-3,4-dihydroquinazolin-2(1H)-one

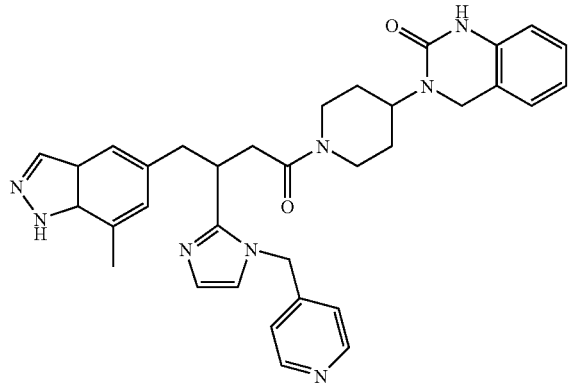

Yield: 81%. $^1$H-NMR (400 MHz, CDCl$_3$) δ 8.09 (1H, m), 7.93 (1H, s), 7.38-6.90 (6H, m), 6.67-6490 (5H, m), 5.27 (1H, m), 4.82 (1H, m), 4.66-4.52 (2H, m), 4.27-3.99 (3H, m); 3.61-2.51 (7H, m), 2.26 (3H, s), 1.78-1.23(4H, m). MS (ESI)[M+H]$^+$=589.16.

N-(2-Aminophenyl)-2-((7-methyl-3a,7a-dihydro-1H-indazol-5-yl)methyl)-4-oxo-4-(4-(2-oxo-1,2-dihydroquinazolin-3(4H)-yl)piperidin-1-yl)butanamide

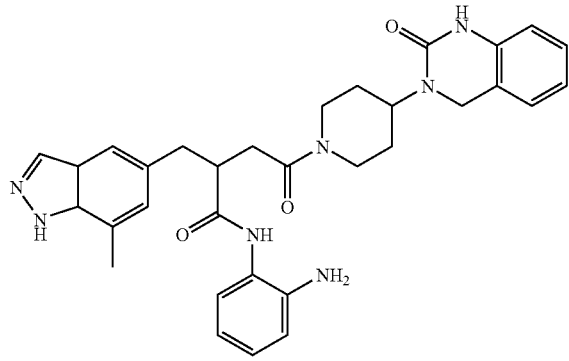

A solution of (±)-2-(4-(2-oxo-1,2-dihydroquinazolin-3(4H)-yl)piperidine-1-carboxamido)-3-(7-methyl-1H-indazol-5-yl)propanoic acid (98.9 mg, 0.21 mmol), benzene-1,2-diamine (46.7 mg, 0.43 mmol) and triethylamine (0.1 mL, 0.72 mmol) in 1:1 methylene chloride/dimethylformamide (4 mL) was stirred at room temperature for 4 h. The solvents were removed in vacuo and the residue was purified using a 20 g SCX cartridge. The cartridge was washed with methanol and methylene chloride and the product was eluted using 2M ammonia in methanol (68%).

EXAMPLE 98

3-(1-(3-(1H-Benzo[d]imidazol-2-yl)-4-(7-methyl-3a,7a-dihydro-1H-indazol-5-yl)butanoyl)piperidin-4-yl)-3,4-dihydroquinazolin-2(1H)-one

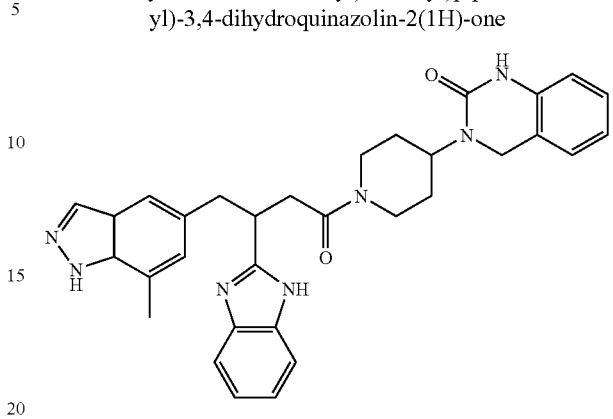

A solution of N-(2-aminophenyl)-2-((7-methyl-3a,7a-dihydro-1H-indazol-5-yl)methyl)-4-oxo-4-(4-(2-oxo-1,2-dihydroquinazolin-3(4H)-yl)piperidin-1-yl)butanamide in 1,2-dichloroethane (8 mL) and acetic acid (1 mL) was heated under nitrogen at 65° C. for 5 h. The solvent was evaporated and the residue taken up in ethyl acetate (20 mL). The ethyl acetate layer was washed with 1M sodium hydroxide (5 mL) and water (2×5 mL), dried, filtered and concentrated. The final product was obtained by flash chromatography using 0% to 10% 2 M ammonia in methanol/methylene chloride. MS(ESI)[M+H]$^+$=550.

N-(2-(Ethylamino)phenyl)-2-((7-methyl-3a,7a-dihydro-1H-indazol-5-yl)methyl)-4-oxo-4-(4-(2-oxo-1,2-dihydroquinazolin-3(4H)-yl)piperidin-1-yl)butanamide

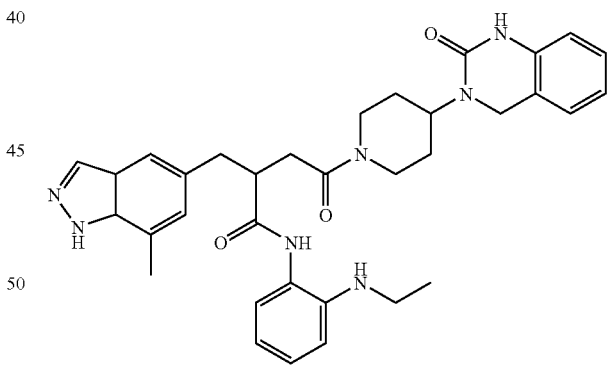

A solution of N-(2-aminophenyl)-2-((7-methyl-3a,7a-dihydro-1H-indazol-5-yl)methyl)-4-oxo-4-(4-(2-oxo-1,2-dihydroquinazolin-3(4H)-yl)piperidin-1-yl)butanamide (0.24 mmol) in methanol (5 mL) was treated with acetaldehyde (1 mL) at room temperature. The mixture was stirred for 2 h at room temperature before the solvent was removed in vacuo. The residue was taken up in methanol (5 mL) and then sodium borohydride (0.48 mmol) was added. After 30 min, the methanol was removed in vacuo and the residue was taken up in methylene chloride (15 mL). The final product was obtained by filtration through a pad of celite and concentration of the filtrate. (95%) MS(ESI)[M+H]$^+$=594.

EXAMPLE 99

3-(1-(3-(1-Ethyl-1H-benzo [d]imidazol-2-yl)-4-(7-methyl-3a,7a-dihydro-1H-indazol-5-yl)butanoyl)piperidin-4-yl)-3,4-dihydroquinazolin-2(1H)-one

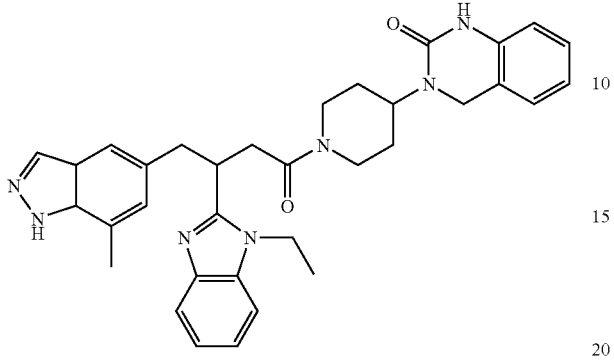

Prepared as described above for Example 93. HPLC $t_R$=1.18 min, MS(ESI)[M+H]$^+$=576.16.

tert-Butyl (Z)-1-(methoxycarbonyl)-2-(2-((2-(trimethylsilyl)ethoxy)methyl)-7-methyl-2H-indazol-5-yl)vinylcarbamate

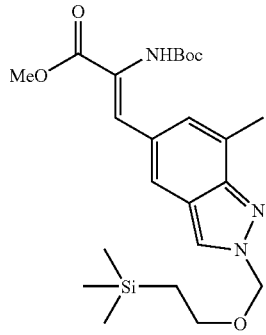

To a solution of 2-((2-(trimethylsilyl)ethoxy)methyl)-7-methyl-2H-indazole-5-carbaldehyde (4.46 g, 15.4 mmol) and N-(tert-butoxycarbonyl)-methyl-2-(dimethylphosphono)glycinate (4.80 g, 1.0 equiv) in tetrahydrofuran (40 mL) at room temperature was added N,N,N'N'-tetramethylguanidine (3.29 mL, 1.7 equiv). The reaction was allowed to stir at room temperature for 3 days. The reaction was diluted with ethyl acetate and water, and then poured into diethyl ether. The organic phase was washed with water (2×), then brine, dried over magnesium sulfate and concentrated. Column chromatography (30% ethyl acetate/hexanes->40% ethyl acetate/hexanes) gave 5.90 g (83%) as a foam.

Mass spec.: 462.40 (MH)$^+$.

Methyl 3-(2-((2-(trimethylsilyl)ethoxy)methyl)-7-methyl-2H-indazol-5-yl)-2-hydroxypropanoate

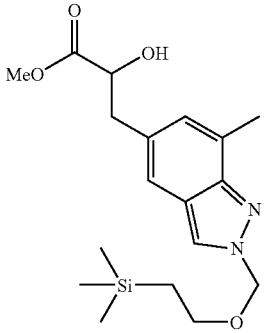

To a solution of tert-butyl (Z)-1-(methoxycarbonyl)-2-(2-((2-(trimethylsilyl)ethoxy)methyl)-7-methyl-2H-indazol-5-yl)vinylcarbamate (200 mg, 0.43 mmol) in dichloromethane (2 mL) at 0° C. was added trifluoroacetic acid (1 mL). The ice bath was removed. After 30 min, the reaction was poured into a separatory funnel containing ethyl acetate and water, neutralized with solid sodium bicarbonate, and the layers were separated. The organic phase was washed with saturated sodium bicarbonate, then brine, dried over magnesium sulfate, and concentrated. The yellow residue was treated with sodium cyanoborohydride (200 mg, 7.4 equiv) and tetrahydrofuran (2 mL). The reaction was stirred at room temperature overnight, diluted with ethyl acetate, washed with water (2×), then brine, dried over magnesium sulfate, and concentrated. Column chromatography on silica gel (25% ethyl acetate/hexanes) gave 20.4 mg (13%) as a light yellow oil. Mass spec.: 365.40 (MH)$^+$.

1-(Methoxycarbonyl)-2-(2-((2-(trimethylsilyl)ethoxy)methyl)-7-methyl-2H-indazol-5-yl)ethyl 4-nitrophenyl Carbonate

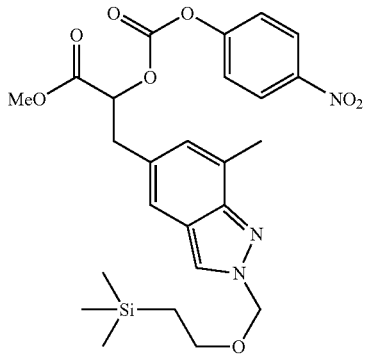

To a solution of methyl 3-(2-((2-(trimethylsilyl)ethoxy)methyl)-7-methyl-2H-indazol-5-yl)-2-hydroxypropanoate (20 mg, 55 μmoles) in pyridine (1 mL) was added 4-nitrophenylchloroformate (55 mg, 5 equiv). The reaction was stirred at room temperature overnight. The reaction was treated with an additional portion of 4-nitrophenylchloroformate (30 mg, 2.7 equiv) and stirred at room temperature for 8 h. The reaction was poured into diethyl ether, washed with 1M potassium bisulfate, saturated bicarbonate, and 1M sodium hydroxide until most of the p-nitrophenyl had been removed. The solution was then washed with brine, dried over sodium sulfate, and concentrated to give 50 mg (quant.) of a pale yellow solid which was used immediately in the next reaction. Mass spec.: 530.30 (MH)$^+$.

1-(Methoxycarbonyl)-2-(2-((2-(trimethylsilyl)ethoxy)methyl)-7-methyl-2H-indazol-5-yl)ethyl 4-(1,2-dihydro-2-oxoquinazolin-3(4H)-yl)piperidine-1-carboxylate

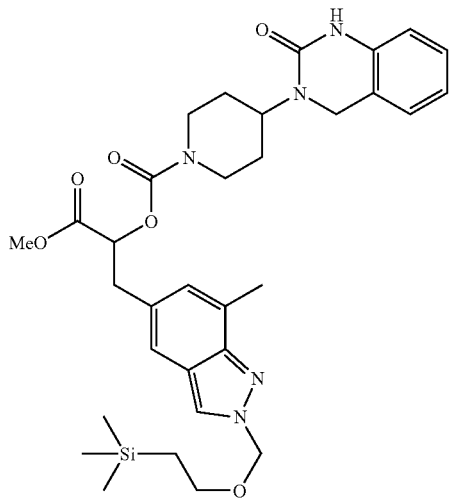

A flask was charged with 1-(methoxycarbonyl)-2-(2-((2-(trimethylsilyl)ethoxy)methyl)-7-methyl-2H-indazol-5-yl) ethyl 4-nitrophenyl carbonate (27 mg, 51 mmoles) and 3,4-dihydro-3-(piperidin-4-yl)quinazolin-2(1H)-one (34 mg, 2.8 equiv). The solids were dissolved in dimethylformamide (1 mL) and treated with diisopropylethylamine (0.1 mL, 11 equiv). The reaction was stirred at room temperature for 2 d. The reaction was concentrated, dissolved in ethyl acetate, washed with 20% potassium hydroxide (3×), then brine, dried over magnesium sulfate, and concentrated. Column chromatography (100% ethyl acetate) removed baseline material to give 50 mg (quant.). Mass spec.: 622.50 (MH)$^+$.

(R)-1-Methoxy-3-(7-methyl-2-((2-(trimethylsilyl)ethoxy)methyl)-2H-indazol-5-yl)-1-oxopropan-2-yl 4-(2-oxo-1,2-dihydroquinolin-3-yl)piperidine-1-carboxylate

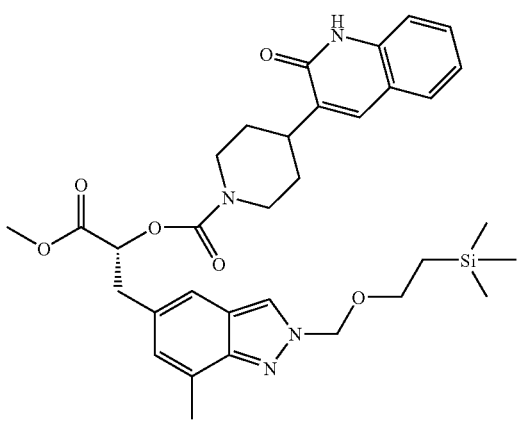

To a solution of 1-(methoxycarbonyl)-2-(2-((2-(trimethylsilyl)ethoxy)methyl)-7-methyl-2H-indazol-5-yl)ethyl 4-nitrophenyl carbonate (0.859 mmol) was added 3-(piperidin-4-yl)quinolin-2(1H)-one-hydrochloride (682 mg, 2.58 mmol), in one portion, followed by dropwise addition of diisopropylethylamine (0.37 mL, 2.15 mmol) at room temperature. The resulting yellow suspension was stirred at room temperature overnight. The mixture was extracted with ethyl acetate (2×2 mL) and the organic phase was washed with brine and dried over sodium sulfate. The crude product was purified using preparative HPLC to afford (R)-1-methoxy-3-(7-methyl-2-((2-(trimethylsilyl)ethoxy)methyl)-2H-indazol-5-yl)-1-oxopropan-2-yl 4-(2-oxo-1,2-dihydroquinolin-3-yl)piperidine-1-carboxylate (157 mg, 30%). Mass spec. 619.24 (MH$^+$).
$^1$H-NMR (CDCl$_3$, 400 MHz) δ 8.0 (s, 1H), 7.53 (br s, 2H), 7.47-7.43 (m, 1H), 7.34-7.31 (m, 1H), 7.21-7.18 (m, 1H), 6.96 (s, 1H), 5.7 (s, 2H), 5.23 (dd, J=8.6, 4.6 Hz, 1H), 4.28 (br s, 2H), 3.74 (s, 3H), 3.61 (m, 2H), 3.13 (m, 3H), 2.93 (m, 2H), 2.59 (s, 3H), 1.94 (m, 2H), 0.92 (m, 2H), −0.064 (s, 9H).

(R)-3-(7-Methyl-2-((2-(trimethylsilyl)ethoxy)methyl)-2H-indazol-5-yl)-2-(4-(2-oxo-1,2-dihydroquinolin-3-yl)piperidine-1-carbonyloxy)propanoic acid

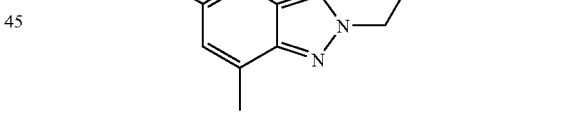

Aqueous lithium hydroxide (1M, 130 mL, 0.13 mmol) was added dropwise to a stirred solution of (R)-1-methoxy-3-(7-methyl-2-((2-(trimethylsilyl)ethoxy)methyl)-2H-indazol-5-yl)-1-oxopropan-2-yl 4-(2-oxo-1,2-dihydroquinolin-3-yl)piperidine-1-carboxylate (40 mg, 0.0646 mmol) in dioxane (2 mL) at 0° C., and the mixture was stirred for 2 h. The reaction was quenched with 1N hydrochloric acid, poured into ethyl acetate (30 mL), washed with brine (10 mL), dried over magnesium sulfate and concentrated in vacuo to afford a tan foamy solid (32 mg, 82%), which was used without further purification. $^1$H-NMR (CDCl$_3$, 400 MHz) δ 8.02 (s,1H), 7.60 (s,1H), 7.52-7.32 (m, 3H), 7.29-7.13 (m, 2H), 7.05 (s,1H), 5.71 (s,2H), 5.29 (dd, J=9.0, 3.8 Hz, 1H), 4.28 (br, 2H), 3.34 (br, 2H), 3.34 (dd, J=14.1, 3.9 Hz, 2H), 3.21 (dd, J=14.4, 9.2 Hz, 2H) 3.13-2.75 (m, 4H), 2.60 (s, 3H), 1.95-1.72 (m, 4H), 0.95-1.85 (m, 2H), 0.051 (s, 9H).

Mass spec. 605.34 (MH$^+$).

(R)-1-(3-(Ethoxycarbonyl)-1,2,4-oxadiazol-5-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate

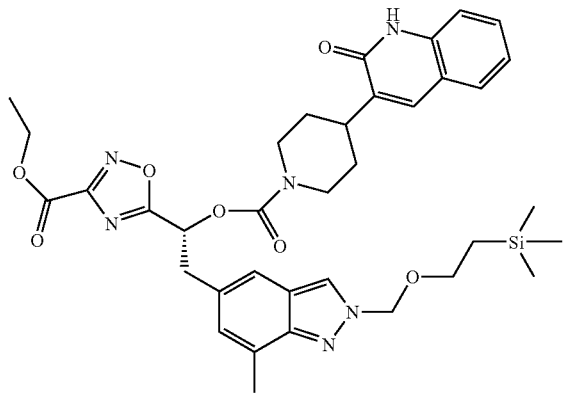

A stirred solution of (R)-3-(7-methyl-2-((2-(trimethylsilyl)ethoxy)methyl)-2H-indazol-5-yl)-2-(4-(2-oxo-1,2-dihydroquinolin-3-yl)piperidine-1-carbonyloxy)propanoic acid (28.5 mg, 0.0471 mmol) in anhydrous diglyme (2.5 mL) was treated with ethyl 2-amino-2-(hydroxyimino)acetate (6.54 mg, 0.0495 mmol) and 1-[3-(dimethylamino)propyl]3-ethylcarbodiimide hydrochloride (0.49 mg, 0.0495 mmol) at room temperature. The mixture was stirred overnight at room temperature and then overnight at 110° C. After cooling to room temperature and removal of the solvent in vacuo, the crude compound was purified using preparative HPLC to afford a tan gum (11.2 mg, 34%). $^1$H-NMR (CDCl$_3$, 400 MHz) δ 8.0 (s,1H), 7.58 (s, 1H), 7.57 (s, 1H), 7.46 (m, 1H), 7.30 (s,1H), 7.24-7.20 (m, 2H), 6.93 (s,1H), 6.17-6.15 (m, 1H), 5.71 (s, 2H), 4.50-4.48 (m, 2H), 4.29-4.20 (m, 2H), 3.65-3.55 (m, 2H), 3.40-3.38 (m, 2H), 3.20-2.81 (m, 4H), 2.59 (s, 3 h), 2.03-1.72 (m, 4H), 1.44-1.38 (m, 3H), 0.95-0.86 (m, 2H), −0.045 (s, 9H).

Mass spec. 701.22 (MH$^+$).

(R)-1-(3-(Hydroxymethyl)-2,3-dihydro-1,2,4-oxadiazol-5-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate

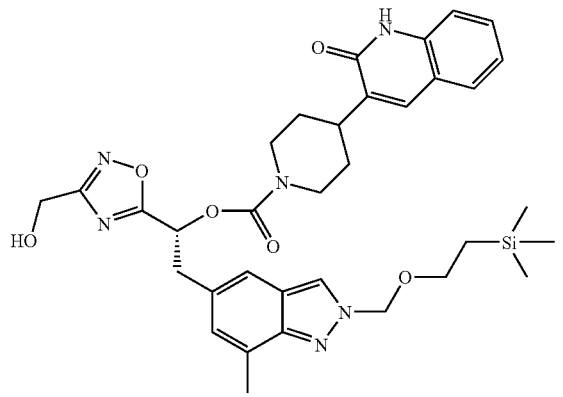

Solid lithium borohydride (1.5 mg, 0.0689 mmol) was added to a stirred solution of (R)-1-(3-(ethoxycarbonyl)-1,2,4-oxadiazol-5-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate (2.3 mg, 0.00328 mmol) in ethanol (2 mL) at room temperature. The mixture was stirred for 3 h, and then quenched with saturated ammonium chloride and extracted with methylene chloride (15 mL). The organic layer was washed with brine (5 mL), dried over magnesium sulfate, and concentrated in vacuo to afford the expected product (2.02 mg, 94%).

Mass spec. 661.45(MH$^+$).

(R)-1-(3-(4-Fluorophenyl)-1,2,4-oxadiazol-5-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate

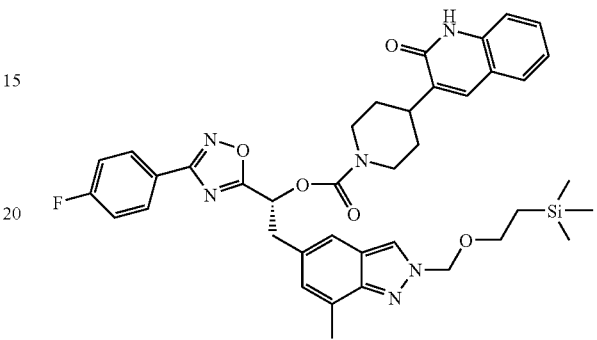

A stirred solution of (R)-3-(7-methyl-2-((2-(trimethylsilyl)ethoxy)methyl)-2H-indazol-5-yl)-2-(4-(2-oxo-1,2-dihydroquinolin-3-yl)piperidine-1-carbonyloxy)propanoic acid (22.4 mg, 0.0370 mmol) in anhydrous diglyme (2 mL) was treated with 4-fluorobenzamidoxime (5.3 mg, 0.0389 mmol) and 1-[3-(dimethylamino)propyl]3-ethylcarbodiimide hydrochloride (7.5 mg, 0.0389 mmol) to at room temperature. The mixture was stirred overnight. The stirred mixture was then heated to 110° C. overnight. After cooling to room temperature, the solvent was removed in vacuo and the crude product was purified using preparative HPLC to afford a tan gum (16.2 mg, 61%). $^1$H-NMR (CDCl$_3$, 400 MHz) δ 8.8.06 (bs, 2H), 7.88 (s, 1H), 7.69-7.46 (m, 2H), 7.40 (s, 1H), 7.35-7.20 (m,2H), 7.18-7.07 (m, 2H), 7.07 (s, 1H), 6.19-6.15 (m, 1H), 5.79 (s, 2H), 4.40-4.20 (m, 2H), 3.55-3.40 (m, 4H), 3.20-2.83 (m, 4H), 2.70 (s, 3H), 2.72-2.35 (m, 2H), 2.08-1.9 (m, 2H), 0.90-0.77 (m, 2H), −0.11 (s, 9H). Mass spec. 723.3 (MH$^+$).

The following intermediates were similarly prepared:

(R)-2-(7-Methyl-2-((2-(trimethylsilyl)ethoxy)methyl)-2H-indazol-5-yl)-1-(3-(pyridin-4-yl)-1,2,4-oxadiazol-5-yl)ethyl 4-(2-oxo-1,2dihydroquinazolin-3(4H)-yl)piperidine-1-carboxylate

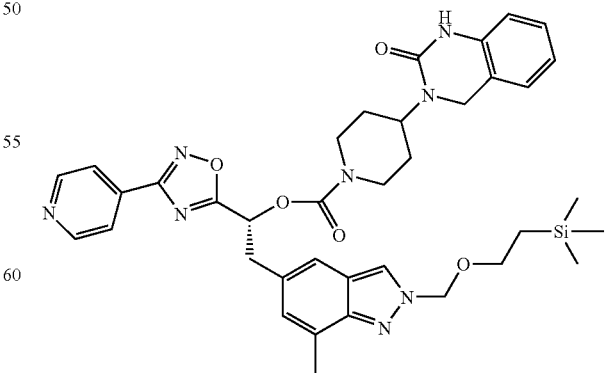

Yield: 58%. $^1$H-NMR (CDCl$_3$, 400 MHz) δ 8.95 (d, J=3.2 Hz, 2H), 8.48 (s, 1H), 8.38 (d, J=5.6 Hz, 2H), 7.92 (s,1H), 7.39 (d, J=6.8 Hz, 1H), 7.22-7.18 (m,1H), 7.10-6.96 (m, 2H), 6.76 (d, J=7.6 Hz, 1H), 6.16 (overlaping dd, J=6.8, 6.8 Hz, 1H), 5.79 (s, 2H), 4.50-4.20 (m, 5H), 3.65-3.55 (m, 2H), 3.40-3.38 (m, 2H), 3.20-2.81 (m, 4H), 2.59 (s, 3H), 2.03-1.72 (m, 4H), 0.90-0.82 (m, 2H), −0.112 (s, 9H).

Mass spec. 709.34 (MH+).

(R)-2-(7-Methyl-2-((2-(trimethylsilyl)ethoxy)methyl)-2H-indazol-5-yl)-1-(3-(pyridin-3-yl)-1,2,4-oxadiazol-5-yl)ethyl 4-(2-oxo-1,2-dihydroquinolin-3-yl)piperidine-1-carboxylate

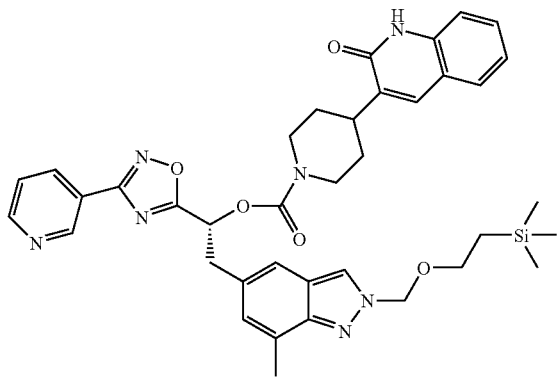

Yield: 43%. ¹H-NMR (CDCl₃, 400 MHz) δ 9.65 (s,1H), 9.42 (s, 1H), 9.02 (s, 1H), 8.85-8.70 (m, 2H), 7.93 (s, 1H), 7.88-7.70 (m, 2H), 7.65-7.50 (m, 2H), 7.40 (s, 1H), 7.09 (s,1H), 6.22-6.15 (m, 1H), 5.81 (s, 2H), 4.40-4.22 (m, 2H), 3.56-3.42 (m, 4H), 3.17-2.85 (m, 4H), 2.72 (s, 3H), 2.05-1.75 (m, 4H), 0.88-0.76 (m, 2H), −0.12 (s, 9H). Mass spec. 706.33 (MH+).

EXAMPLE 100

(R)-1-(3-(4-Fluorophenyl)-1,2,4-oxadiazol-5-yl)-2-(7-methyl-1H-indazol-5-yl)ethyl 4-(2-oxo-1,2-dihydroquinolin-3-yl)piperidine-1-carboxylate

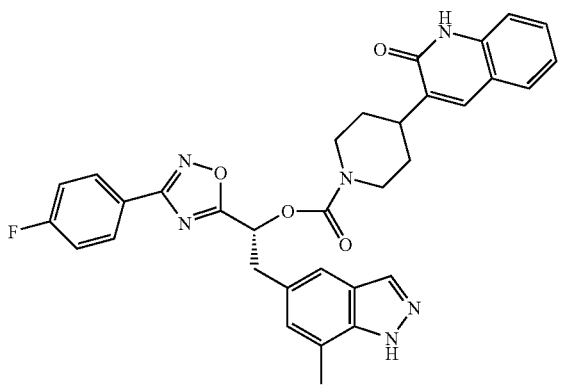

A stirred solution of (R)-1-(3-(4-fluorophenyl)-1,2,4-oxadiazol-5-yl)-2-(7-methyl-2-((2-(trimethylsilyl)ethoxy)methyl)-2H-indazol-5-yl)ethyl 4-(2-oxo-1,2-dihydroquinolin-3-yl)piperidine-1-carboxylate (16.2 mg, 0.0224 mmol) in 1:1 trifluoroacetic acid/methylene chloride 91 mL) was stirred at room temperature for 2 h. Removal of the solvents in vacuo followed by purification using preparative HPLC afforded a tan gum (8.6 mg, 65%). ¹H-NMR (CDCl₃, 400 MHz) δ 8.22 (s, 1H), 8.12-8.01 (m,2H), 7.80 (s, 1H), 7.76-7.45 (m, 5H), 7.35-7.45 (m, 2H), 7.30 (s,1H), 7.20-7.07 (m,2H), 6.28-6.15 (m,1H), 4.42-4.25 (m,2H), 3.57-3.45 (m,2H) 3.31-2.85 (m, 4H), 2.60 (s,3H), 2.09-1.88 (m,2H), 1.70-1.53 (m,2H). Mass spec. 593.28 (MH+).

The following Examples were similarly prepared:

EXAMPLE 101

(R)-2-(7-Methyl-1H-indazol-5-yl)-1-(3-(pyridin-4-yl)-1,2,4-oxadiazol-5-yl)ethyl 4-(2-oxo-1,2-dihydroquinazolin-3(4H)-yl)piperidine-1-carboxylate

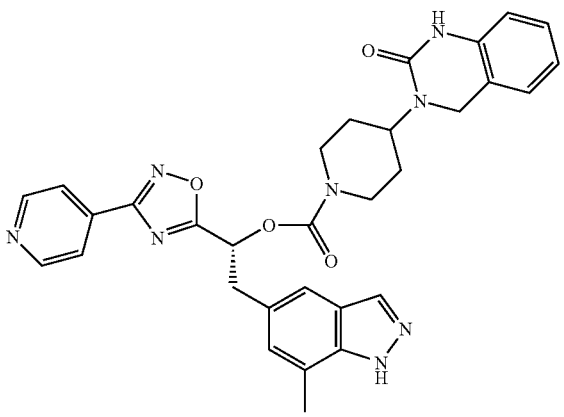

Yield: 56%. ¹H-NMR (CDCl₃, 400 MHz) δ 8.97 (bs, 2H), 8.61 (bs,2H), 7.49-7.42 (m, 1H), 7.35-7.15 (m, 2H), 7.20 (s,1H), 7.06-6.97 (m,2H), 6.80-6.73 (m,1H), 6.32-6.12 (m,1H), 4.42-4.17 (m, 5H), 3.57-3.40 (m,2H), 3.15-2.85 (m, 2H), 2.60 (s,3H), 1.95-1.68 (m,2H). Mass spec. 579.13 (MH+).

EXAMPLE 102

(R)-2-(7-Methyl-1H-indazol-5-yl)-1-(3-(pyridin-3-yl)-1,2,4-oxadiazol-5-yl)ethyl 4-(2-oxo-1,2-dihydroquinolin-3-yl)piperidine-1-carboxylate

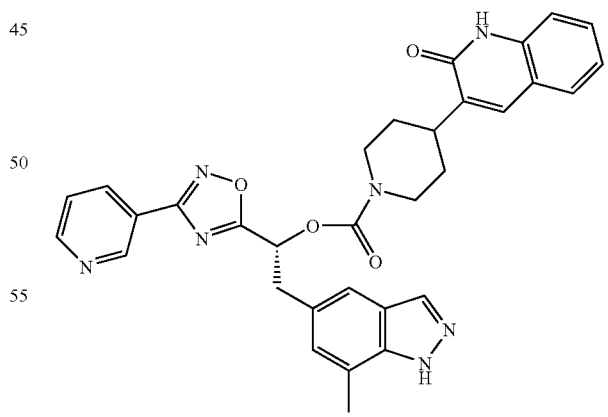

Yield: 56%. ¹H-NMR (CDCl₃, 400 MHz) δ 9.45 (s,1H), 9.27 (s,1H), 8.96 (d, J=9.6 Hz, 1H), 8.81 (d, J=7.6 Hz, 1H), 8.17 (s, 1H), 7.87 (dd, J=7.6, 5.6 Hz, 1H), 7.72-7.42 (m, 5H), 7.37 (d, J=7.6 Hz, 1H), 6.20 (m, 1H), 4.42-4.18 (m, 2H), 3.53-3.42 (m, 2H), 3.15-2.82 (m, 3H), 2.58 (s, 3H), 2.08-1.90 (m, 2H), 1.85-1.35 (m, 2H). Mass spec. 576.29 (MH+).

EXAMPLE 103

(R)-1-(3-(Ethoxycarbonyl)-1,2,4-oxadiazol-5-yl)-2-(7-methyl-1H-indazol-5-yl)ethyl 4-(2-oxo-1,2-dihydroquinolin-3-yl)piperidine-1-carboxylate

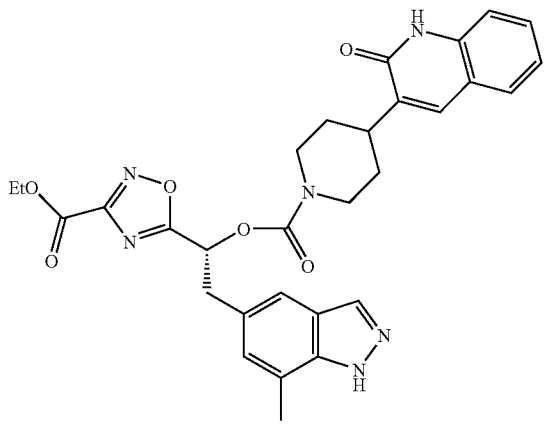

Yield: 100%. $^1$H-NMR (CDCl$_3$, 400 MHz) δ 8.22 (s, 1H), 7.91 (s, 1H), 7.72-7.59 (m, 2H), 7.54-7.38 (m, 4H), 6.27-6.13 (m, 1H), 4.56-4.45 (m, 2H), 4.26 (q, J=12.4 Hz, 2H), 3.56-3.42 9 m, 2H), 3.20-2.83 (m, 3H), 2.74 (s, 1H), 2.68-2.54 (m, 3H), 2.03-1.88 (m, 2H), 1.75-1.52 (m, 2H), 1.44 (t, J=11.6 Hz). Mass spec. 571.19 (MH$^+$).

CGRP Binding Assay

Tissue Culture. SK-N-MC cells were grown at 37° C. in 5% CO$_2$ as a monolayer in medium consisting of MEM with Earle's salts and L-glutamine (Gibco) supplemented with 10% fetal bovine serum (Gibco).

Cell Pellets. The cells were rinsed twice with phosphate-buffered saline (155 mM NaCl, 3.3 mM Na$_2$HPO$_4$, 1.1 mM KH$_2$PO$_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was then aliquoted and stored at −80° C. until needed.

Radioligand Binding Assay. The compounds of invention were solubilized and carried through serial dilutions using 100% DMSO. Aliquots from the compound serial dilutions were further diluted 25 fold into assay buffer (50 mM Tris-Cl pH 7.5, 5 mM MgCl$_2$, 0.005% Triton X-100) and transferred (volume 50 µl) into 96 well assay plates. [$^{125}$I]-CGRP (Amersham Biosciences) was diluted to 60 pM in assay buffer and a volume of 50 µl was added to each well. SK-N-MC pellets were thawed, diluted in assay buffer with fresh 0.1% mammalian protease inhibitor cocktail (Sigma), and homogenized again. SK-N-MC homogenate (5 µg/well) was added in a volume of 100 µl. The assay plates were then incubated at room temperature for 2 h. Assays were stopped by addition of excess cold wash buffer (20 mM Tris-Cl pH 7.5, 0.1% BSA) immediately followed by filtration over glass fiber filters (Whatman GF/B) previously soaked in 0.5% PEI. Non-specific binding was defined with 1 µM beta-CGRP. Protein bound radioactivity was determined using a gamma or scintillation counter. The IC$_{50}$ was defined as the concentration of a compound of invention required to displace 50% of radioligand binding.

TABLE 1

| A < 10 nm, B 10 nM < 100 nm, C 100 nM < 1,000 nM | |
|---|---|
| Example Number | Human CGRP1 Receptor IC$_{50}$, nM |
| 1 | A |
| 2 | A |
| 3 | B |
| 4 | B |
| 5 | B |
| 6 | B |
| 7 | B |
| 8 | B |
| 9 | C |
| 10 | A |
| 11 | B |
| 12 | B |
| 13 | C |
| 14 | C |
| 15 | A |
| 16 | B |
| 17 | B |
| 18 | A |
| 19 | A |
| 20 | B |
| 21 | B |
| 22 | B |
| 23 | B |
| 24 | B |
| 25 | A |
| 26 | B |
| 27 | A |
| 28 | A |
| 29 | A |
| 30 | A |
| 31 | A |
| 32 | A |
| 33 | A |
| 34 | A |
| 35 | A |
| 36 | A |
| 37 | B |
| 38 | A |
| 39 | A |
| 40 | A |
| 41 | C |
| 42 | C |
| 43 | B |
| 44 | A |
| 45 | A |
| 46 | A |
| 47 | A |
| 48 | B |
| 49 | A |
| 50 | A |
| 51 | A |
| 52 | A |
| 53 | A |
| 54 | A |
| 55 | A |
| 56 | B |
| 57 | C |
| 58 | C |
| 59 | C |
| 60 | B |
| 61 | A |
| 62 | C |
| 63 | C |
| 64 | B |
| 65 | B |
| 66 | A |
| 67 | A |
| 68 | A |
| 69 | A |
| 70 | A |

TABLE 1-continued

A < 10 nm, B 10 nM < 100 nm, C 100 nM < 1,000 nM

| Example Number | Human CGRP1 Receptor IC$_{50}$, nM |
|---|---|
| 71 | A |
| 72 | A |
| 73 | A |
| 74 | A |
| 75 | A |
| 76 | A |
| 77 | A |
| 78 | A |
| 79 | A |
| 80 | C |
| 81 | A |
| 82 | B |
| 83 | A |
| 84 | A |
| 85 | A |
| 86 | A |
| 87 | A |
| 88 | A |
| 89 | A |
| 90 | C |
| 91 | A |
| 92 | A |
| 93 | A |
| 94 | A |
| 95 | A |
| 96 | A |
| 97 | A |
| 98 | A |
| 99 | A |
| 100 | C |
| 101 | B |
| 102 | B |
| 103 | B |

What is claimed is:
1. A compound of Formula (I)

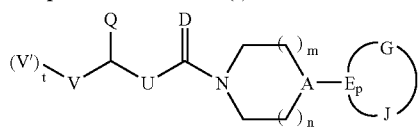

(I)

or a pharmaceutically acceptable salt or solvate thereof
wherein
V is
a 5-membered ring selected from the group consisting of imidazolyl, pyrazolyl, thiazolyl, isothiazolyl, oxazolyl, furanyl, isoxazolyl, oxadiazolyl, triazolyl, thiadiazolyl and tetrazolyl; or
a 6-membered ring selected from the group consisting of pyridyl, pyrimidinyl, triazinyl, pyrazinyl, pyridazinyl and tetrazinyl; or
a fused bicyclic ring system selected from the group consisting of indolyl, isoindolyl, indazolyl, benzimidazolyl, benzythiazolyl, triazolopyridinyl, imidazopyridinyl, quinolinyl, isoquinolinyl, cinnolinyl, phthalazinyl, quinazolinyl, quinoxalinyl and benzfuranyl;
wherein V is optionally substituted with one to three of the same or different substituents selected from the group consisting of $C_{1-4}$alkyl, $C_{1-4}$alkoxy, $C_{1-4}$hydroxyalkyl, $C(O)OC_{2-3}$alkyl, $C_{1-4}$alkylcarbonyl, carboxy, $C_{1-4}$alkylcarboxy, trifluoromethyl, halo, cyano, amino, amido, nitro, carbamoyl, ureido, $C_{1-4}$alkylamino, $C_{1-4}$dialkylamino, $C_{1-4}$dialkylamino$C_{1-2}$alkyl, sulphonamide and sulphonyl;

provided that if t is 1, then V is optionally substituted with one of the substituents selected from the group consisting of halo, $C_{1-4}$alkyl, $C_{1-4}$alkylidine, $_4$alkylidine, $C_{1-4}$alkoxy, $C_{1-4}$hydroxyalkyl, $C_{1-4}$alkylcarbonyl, trifluoromethyl, halo and cyano;
(V')$_t$ wherein t is 0 or 1; and
V' is selected from the group consisting of $C_{3-7}$cycloalkyl, phenyl, adamantyl, quinuclidyl, azabicyclo [2.2.1]heptyl, azetidinyl, tetrahydrofuranyl, furanyl, dioxolanyl, thienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, pyrazinyl, pyridazinyl, triazinyl, piperidinyl, piperazinyl, morpholino, thiomorpholino and dioxolanyl; and wherein
V' is optionally substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_{1-4}$alkylamino, $C_{1-4}$dialkylamino, $(C_{1-3}$alkyl$)_{0-2}$ ureido, $C(O)OC_{2-3}$alkyl, carboxy, amido, nitro, phenyl and benzyl; and
V and V' are optionally interrupted by $C_{1-3}$alkylene, O, —(CH$_2$)$_{0-2}$C(O)—(CH$_2$)$_{0-2}$—; or —N—$C_{1-4}$alkyl, said $C_{1-3}$alkylene being optionally interrupted by or having attached thereto O, N or S;
U is CH$_2$, O, or NH;
Q is (S$^y$)$_s$R$^3$;
wherein S$^y$ is $C_{1-3}$alkylene or $C_{1-3}$alkylidene and s is 0 or 1;
R$^3$ is R$^{3a}$
wherein
R$^{3a}$ is indazolyl
wherein R$^{3a}$ is optionally substituted with 1 to 3 of the same or different substituents selected from the group consisting of benzyl, phenyl, —O-phenyl, —O—$C_{1-3}$alkylenephenyl, —$C_{1-3}$alkylene-OC(O)-phenyl, cyano, amino, nitro, halo, $C_{1-6}$alkyl, $C_{1-3}$mono-bi-tri-haloalkyl, $C_{1-3}$mono-bi-tri-haloalkyloxy, $(C_{1-3}$alkyl$)_{1-2}$amine, —OR$^{3'}$, —C(O)R$^{3'}$, —C(O)O—R$^{3'}$, —O—C(O)R$^{3'}$, —N(R$^{3'}$)$_2$, —C(O)N(R$^{3'}$)$_2$, —N(R$^{3'}$)C(O)(R$^{3'}$)$_2$, —N(R$^{3'}$)C(O)N(R$^{3'}$)$_2$, —N(R$^{3'}$)C(O)OR$^{3'}$, —O—C(O)N(R$^{3'}$)$_2$, —N(R$^{3'}$)SO$_2$R$^{3'}$, —SO$_2$N(R$^{3'}$)$_2$ and —SO$_2$R$^{3'}$;
R$^{3'}$ is H or —$C_{1-6}$alkyl;
D is O, NCN or NSO$_2$C$_{1-3}$alkyl;
A is C, or CH;
m and n are independently 0, 1 or 2;
provided that
if m is 2, then n is not 2; or
if n is 2, then m is not 2;
E is N, CH or C;
p is 1; and
G, J and E together form a 2-oxodihydroquinazoline ring which is optionally substituted with $C_{1-4}$alkyl, $C_{1-4}$alkoxy, $C_{1-4}$haloalkyl, cyano, $C_{3-7}$cycloalkyl, phenyl, halophenyl, halo, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl or morpholino.
2. A compound according to claim 1 wherein m is 1 and n is 1.
3. A compound according to claim 1 wherein E is N.

4. A compound according to claim 1 wherein E is C.

5. A compound according to claim 1 wherein E is CH.

6. A compound according to claim 1 wherein G, J and E form b 3,4-dihydro-1H-quinazolin-2-onyl.

7. A compound according to claim 1 wherein G, J and E form 3,4-dihydro-1H-quinazolin-2-onyl optionally halogenated.

8. A compound according to claim 1 wherein G, J and E form 8-fluoro-2-oxo-1,2-dihydroquinazolin-3(4H)-yl.

9. A compound according to claim 1 wherein s is 1 and $S^y$ is methylene.

10. A compound according to claim 1 wherein is s is 1, $S^y$ is methylene and $R^3$ is $R^{3a}$.

11. A compound according to claim 1 wherein is s is 1, $S^y$ is methylene and $R^3$ is $R^{3a}$ wherein $R^{3a}$ is 7-methyl-1H-indazol-5-yl.

12. A compound according to claim 1 wherein is s is 1, $S^y$ is methylene and $R^3$ is $R^{3a}$ wherein $R^{3a}$ is 7-ethyl-3-methyl-1H-indazol-5-yl.

13. A compound according to claim 1 wherein D is O and U is O.

14. A compound according to claim 1 wherein t is 0.

15. A compound according to claim 1 wherein t is 1.

16. A compound according to claim 1 wherein t is 1 and V' is selected from the group consisting of $C_{3-7}$cycloalkyl, phenyl, tetrahydrofuranyl, furanyl, thienyl, pyrrolyl, pyrrolinyl, pyrrolidinyl, imidazolyl, imidazolinyl, imidazolidinyl, pyrazolyl, pyrazolinyl, pyrazolidinyl, oxazolyl, isoxazolyl, thiazolyl, isothiazolyl, oxadiazolyl, thiadiazolyl, triazolyl, pyranyl, pyridyl, pyrimidinyl, triazinyl, piperidinyl, piperazinyl, morpholino and thiomorpholino and dioxolanyl.

17. A compound according to claim 1 wherein t is 1 and V' is selected from the group consisting of phenyl, pyridyl and piperidinyl.

18. A compound according to claim 1 wherein t is 1 and V' is selected from the group consisting of phenyl, pyridyl and piperidinyl and V' is substituted with 1 or 2 of the same or different substituents selected from the group consisting of halo, cyano, $C_{1-4}$alkyl, $C_{1-4}$haloalkyl, $C_{1-4}$alkoxy, hydroxy, amino, $C_{3-7}$cycloalkyl, $C_4$alkylamino, $C_{1-4}$dialkylamino, $(C_{1-3}$alkyl$)_{0-2}$ureido, $C(O)OC_{2-3}$alkyl, carboxy, amido, nitro, phenyl and benzyl.

19. A compound according to claim 1 wherein t is 1 and V' is selected from the group consisting of phenyl, pyridyl and piperidinyl and V' is substituted with 1 or 2 of the same or different substituents selected from the group consisting of $C_{1-4}$dialkylamino, $C(O)OC_{2-3}$alkyl, carboxy, amido, nitro and phenyl.

20. A compound according to claim 1 wherein V is said 5-membered ring.

21. A compound according to claim 1 wherein V is said 6-membered ring.

22. A compound according to claim 1 wherein V is said fused bicyclic ring system.

23. A compound according to claim 1 wherein V is furanyl, imidazolyl, oxadiazolyl, tetrazolyl, pyridyl, pyrimidine, quinolinyl, indazolyl, triazolopyridinyl or imidazopyridinyl.

24. A compound according to claim 1 wherein V is furanyl, imidazolyl, oxadiazolyl, tetrazolyl, pyridyl, pyrimidine, quinolinyl, indazolyl or [1,2,4]Triazolo[4,3-a]pyridin-3-yl or H-Imidazo[1,5-a]pyridin-3-yl).

25. A compound according to claim 1 wherein V and V' are interrupted by methylene, ethylene and —$(CH_2)_{0-2}C(O)$—$(CH_2)_{0-2}$—.

26. A compound according to claim 1 wherein V and V' are interrupted by methylene, ethylene and —$(CH_2)_{0-2}C(O)$—$(CH_2)_{0-2}$— wherein said interrupting substituents are unsubstituted.

27. A compound according to claim 1 wherein
s is 1, $S^y$ is methylene and $R^3$ is $R^{3a}$ wherein $R^{3a}$ is an optionally $C_{1-3}$alkyl-substituted indazolyl;
U is $CH_2$, O, or NH;
D is O;
A is CH;
m and n are each 1;
E is N;
p is 1; and
G, J and E together form halogenated dihydroquinazolinone.

28. A compound according to claim 1 wherein
V is furanyl, imidazolyl, oxadiazolyl, tetrazolyl, pyridyl, pyrimidine, quinolinyl, indazolyl, triazolopyridinyl or imidazopyridinyl;
t is 0 or 1;
V' is selected from the group consisting of phenyl, pyridyl and piperidinyl and V' is substituted with 1 or 2 of the same or different substituents selected from the group consisting of $C_{1-4}$dialkylamino, $C(O)OC_{2-3}$alkyl, carboxy, amido, nitro and phenyl;
wherein V and V' are interrupted by methylene, ethylene and —$(CH_2)_{0-2}C(O)$—$(CH_2)_{0-2}$— wherein said interrupting substituents are unsubstituted;
s is 1, $S^y$ is methylene and $R^3$ is $R^{3a}$ wherein $R^{3a}$ is an optionally $C_{1-3}$alkyl-substituted indazolyl;
U is $CH_2$, O, or NH;
D is O;
A is CH;
m and n are each 1;
E is N;
p is 1; and
G, J and E together form an optionally halogenated dihydroquinazolinone.

29. (±)-3-{1-[4-(7-Methyl-1H-indazol-5-yl)-3-pyridin-2-yl-butyryl]-piperidin-4-yl}-3,4-dihydro-1H-quinazolin-2-one;

(±)-3-{1-[3-(3-Benzyl-[1,2,4]oxadiazol-5-yl)-4-(7-methyl-1H-indazol-5-yl)-butyryl]-piperidin-4-yl}-3,4-dihydro-1H-quinazolin-2-one;

(±)-3-{1-[4-(7-Methyl-1H-indazol-5-yl)-3-(3-piperidin-1-ylmethyl-[1,2,4]oxadiazol-5-yl)-butyryl]-piperidin-4-yl}-3,4-dihydro-1H-quinazolin-2-one;

(±)-3-{1-[4-(7-Methyl-1H-indazol-5-yl)-3-(3-phenyl-[1,2,4]oxadiazol-5-yl)-butyryl]-piperidin-4-yl}-3,4-dihydro-1H-quinazolin-2-one;

(±)-3-{1-[4-(7-Methyl-1H-indazol-5-yl)-3-(3-methyl-[1,2,4]oxadiazol-5-yl)-butyryl]-piperidin-4-yl}-3,4-dihydro-1H-quinazolin-2-one;

(±)-3-{1-[4-(7-Methyl-1H-indazol-5-yl)-3-(3-pyridin-4-ylmethyl-[1,2,4]oxadiazol-5-yl)-butyryl]-piperidin-4-yl}-3,4-dihydro-1H-quinazolin-2-one;

(±)-3-{1-[3-(3-Dimethylaminomethyl-[1,2,4]oxadiazol-5-yl)-4-(7-methyl-1H-indazol-5-yl)-butyryl]-piperidin-4-yl}-3,4-dihydro-1H-quinazolin-2-one;

(±)-4-(2-Oxo-1,4-dihydro-2H-quinazolin-3-yl)-piperidine-1-carboxylic acid [1-(3-benzyl-[1,2,4]oxadiazol-5-yl)-2-(7-methyl-1H-indazol-5-yl)-ethyl]-amide;

(±)-4-(2-Oxo-1,4-dihydro-2H-quinazolin-3-yl)-piperidine-1-carboxylic acid [2-(7-methyl-1H-indazol-5-yl)-1-(3-methyl-[1,2,4]oxadiazol-5-yl)-ethyl]-amide;

(±)-4-(2-Oxo-1,4-dihydro-2H-quinazolin-3-yl)-piperidine-1-carboxylic acid [2-(7-methyl-1H-indazol-5-yl)-1-(3-pyridin-4-ylmethyl-[1,2,4]oxadiazol-5-yl)-ethyl]-amide;

(±)-4-(2-Oxo-1,4-dihydro-2H-quinazolin-3-yl)-piperidine-1-carboxylic acid [1-(3-dimethylaminomethyl-[1,2,4]oxadiazol-5-yl)-2-(7-methyl-1H-indazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-(1H-tetrazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-(phenethyl-1H-tetrazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-(2-phenethyl-2H-tetrazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-(1-methyl-1H-tetrazol-5-yl)-ethyl]-amide;

(±)-4-(2-Oxo-1,4-dihydro-2H-quinazolin-3-yl)-piperidine-1-carboxylic acid [1-(1-benzyl-1H-tetrazol-5-yl)-2-(7-ethyl-3-methyl-1H-indazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-pyridin-4-yl methyl-1H-tetrazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-(2-oxo-2Phenethyl-2H-tetrazol-5-yl)-ethyl]-amide;

(±)-4-(2-Oxo-1,4-dihydro-2H-quinazolin-3-yl)-piperidine-1-carboxylic acid [2-(7-ethyl-3-methyl-1H-indazol-5-yl)-1-[1-(2-oxo-2-phenyl-ethyl)-1H-tetrazol-5-yl)-ethyl]-amide;

(±)-3-(1-(3-(4-Ethylpyridin-2-yl)-4-(7-methyl-1H-indazol-5-yl)butanoyl)piperidin-4-yl)-3,4-dihydroquinazolin-2(1H)-one;

(±)-8-Fluoro-3-(1-(4-(7-methyl-1H-indazol-5-yl)-3-(pyridin-2-yl)butanoyl)piperidin-4-yl)-3,4-dihydroquinazolin-2(1H)-one;

(±)-3-(1-(4-(7-Methyl-1H-indazol-5-yl)-3-(3-methylpyridin-2-yl)butanoyl)piperidin-4-yl)-3,4-dihydroquinazolin-2(1H)-one;

(±)-3-(1-(4-(7-Methyl-1H-indazol-5-yl)-3-(5-methylpyridin-2-yl)butanoyl)piperidin-4-yl)-3,4-dihydroquinazolin-2(1H)-one;

(±)-3-(1-(3-(5-(Hydroxymethyl)pyridin-2-yl)-4-(7-methyl-1H-indazol-5-yl)butanoyl)piperidin-4-yl)-3,4-dihydroquinazolin-2(1H)-one;

(±)-6-(1-(7-Methyl-1H-indazol-5-yl)-4-oxo-4-(4-(2-oxo-1,2-dihydroquinazolin-3(4H)-yl)piperidin-1-yl)butan-2-yl)nicotinaldehyde;

(±)-3-(1-(4-(7-Methyl-1H-indazol-5-yl)-3-(5-(piperidin-1-ylmethyl)pyridin-2-yl)butanoyl)piperidin-4-yl)-3,4-dihydroquinazolin-2(1H)-one;

(±)-N-(1-(6-Bromopyridin-2-yl)-2-(7-methyl-1H-indazol-5-yl)ethyl)-4-(2-oxo-1,2-dihydroquinazolin-3(4H)-yl)piperidine-1-carboxamide;

(±)-N-(2-(7-Methyl-1H-indazol-5-yl)-1-(pyridin-2-yl)ethyl)-4-(2-oxo-1,2-dihydroquinazolin-3(4H)-yl)piperidine-1-carboxamide;

(±)-N-(2-(7-Methyl-1H-indazol-5-yl)-1-(4-nitropyridin-2-yl)ethyl)-4-(2-oxo-1,2-dihydroquinazolin-3(4H)-yl)piperidine-1-carboxamide;

(±)-N-(1-(4-Fluoropyridin-2-yl)-2-(7-methyl-1H-indazol-5-yl)ethyl)-4-(2-oxo-1,2-dihydroquinazolin-3(4H)-yl)piperidine-1-carboxamide;

(±)-N-(2-(7-Methyl-1H-indazol-5-yl)-1-(quinolin-2-yl)ethyl)-4-(2-oxo-1,2-dihydroquinazolin-3(4H)-yl)piperidine-1-carboxamide;

(±)-4-(8-Fluoro-2-oxo-1,2-dihydroquinazolin-3(4H)-yl)-N-(2-(7-methyl-1H-indazol-5-yl)-1-(quinolin-2-yl)ethyl)piperidine-1-carboxamide;

(±)-N-(2-(7-Methyl-1H-indazol-5-yl)-1-(6-phenylpyridin-2-yl)ethyl)-4-(2-oxo-1,2-dihydroquinazolin-3(4H)-yl)piperidine-1-carboxamide;

(±)-N-(2-(7-Methyl-1H-indazol-5-yl)-1-(6-methylpyridin-2-yl)ethyl)-4-(2-oxo-1,2-dihydroquinazolin-3(4H)-yl)piperidine-1-carboxamide;

(±)-1-(6-Bromopyridin-2-yl)-2-(7-methyl-1H-indazol-5-yl)ethyl-4-(8-fluoro-2-oxo-1,2-dihydroquinazolin-3(4H)-yl)piperidine-1-carboxylate;

(±)-1-(6-Bromopyridin-2-yl)-2-(7-methyl-1H-indazol-5-yl)ethyl-4-(2-oxo-1,2-dihydroquinazolin-3(4H)-yl)piperidine-1-carboxylate;

(±)-1-(6-tert-Butoxypyridin-2-yl)-2-(7-methyl-1H-indazol-5-yl)ethyl-4-(2-oxo-1,2-dihydroquinazolin-3(4H)-yl)piperidine-1-carboxylate;

(±)-2-(7-Methyl-1H-indazol-5-yl)-1-(6-oxo-1,6-dihydropyridin-2-yl)ethyl 4-(2-oxo-1,2-dihydroquinazolin-3(4H)-yl)piperidine-1-carboxylate;

(±)-1-(6-Isobutylpyridin-2-yl)-2-(7-methyl-1H-indazol-5-yl)ethyl 4-(8-fluoro-2-oxo-1,2-dihydroquinazolin-3(4H)-yl)piperidine-1-carboxylate;

(±)-1-(6-(3,5-Difluorobenzyl)pyridin-2-yl)-2-(7-methyl-1H-indazol-5-yl)ethyl 4-(8-fluoro-2-oxo-1,2-dihydroquinazolin-3(4H)-yl)piperidine-1-carboxylate;

(±)-1-(6-Cyanopyridin-2-yl)-2-(7-methyl-1H-indazol-5-yl)ethyl 4-(8-fluoro-2-oxo-1,2-dihydroquinazolin-3(4H)-yl)piperidine-1-carboxylate;

(±)-1-(4-(Hydroxymethyl)pyridin-2-yl)-2-(7-methyl-1H-indazol-5-yl)ethyl 4-(2-oxo-1,2-dihydroquinazolin-3(4H)-yl)piperidine-1-carboxylate;

(±)-1-(4-Formylpyridin-2-yl)-2-(7-methyl-1H-indazol-5-yl)ethyl 4-(2-oxo-1,2-dihydroquinazolin-3(4H)-yl)piperidine-1-carboxylate;

(±)-2-(2-(7-Methyl-1H-indazol-5-yl)-1-(4-(2-oxo-1,2-dihydroquinazolin-3(4H)-yl)piperidine-1-carbonyloxy)ethyl)isonicotinic acid;

(±)-2-(7-Methyl-1H-indazol-5-yl)-1-(4-(piperidine-1-carbonyl)pyridin-2-yl)ethyl 4-(2-oxo-1,2-dihydroquinazolin-3(4H)-yl)piperidine-1-carboxylate;

N-(1-(isoquinolin-3-yl)-2-(7-methyl-1H-indazol-5-yl)ethyl)-4-(2-oxo-1,2-dihydroquinazolin-3(4H)-yl)piperidine-1-carboxamide;

4-(8-fluoro-2-oxo-1,2-dihydroquinazolin-3(4H)-yl)-N-(1-(isoquinolin-3-yl)-2-(7-methyl-1H-indazol-5-yl)ethyl)piperidine-1-carboxamide;

1-(Isoquinolin-3-yl)-2-(7-methyl-1H-indazol-5-yl)ethyl 4-(8-fluoro-2-oxo-1,2-dihydroquinazolin-3(4H)-yl)piperidine-1-carboxylate;

1-(Isoquinolin-3-yl)-2-(7-methyl-1H-indazol-5-yl)ethyl 4-(2-oxo-1,2-dihydroquinazolin-3(4H)-yl)piperidine-1-carboxylate;

2-(7-methyl-1H-indazol-5-yl)-1-(pyridin-2-yl)ethyl 4-(2-oxo-1,2-dihydroquinazolin-3(4H)-yl)piperidine-1-carboxylate;

2-(7-methyl-1H-indazol-5-yl)-1-(pyridin-2-yl)ethyl 4-(8-fluoro-2-oxo-1,2-dihydroquinazolin-3(4H)-yl)piperidine-1-carboxylate;

1-(Furan-2-yl)-2-(7-methyl-1H-indazol-5-yl)ethyl 4-(2-oxo-1,2-dihydroquinazolin-3(4H)-yl)piperidine-1-carboxylate;
2-(7-Methyl-1H-indazol-5-yl)-1-(pyridin-4-yl)ethyl 4-(2-oxo-1,2-dihydroquinazolin-3(4H)-yl)piperidine-1-carboxylate;
2-(7-Methyl-1H-indazol-5-yl)-1-(pyridin-3-yl)ethyl 4-(2-oxo-1,2-dihydroquinazolin-3(4H)-yl)piperidine-1-carboxylate;
2-(7-Methyl-1H-indazol-5-yl)-1-(pyridin-3-yl)ethyl 4-(8-fluoro-2-oxo-1,2-dihydroquinazolin-3(4H)-yl)piperidine-1-carboxylate;
1-(Furan-2-yl)-2-(7-methyl-1H-indazol-5-yl)ethyl 4-(8-fluoro-2-oxo-1,2-dihydroquinazolin-3(4H)-yl)piperidine-1-carboxylate;
2-(7-Methyl-1H-indazol-5-yl)-1-(quinolin-2-yl)ethyl 4-(2-oxo-1,2-dihydroquinazolin-3(4H)-yl)piperidine-1-carboxylate;
1-(4,6-Dimethylpyrimidin-2-yl)-2-(7-methyl-1H-indazol-5-yl)ethyl 4-(8-fluoro-2-oxo-1,2-dihydroquinazolin-3(4H)-yl)piperidine-1-carboxylate;
1-(Benzofuran-2-yl)-2-(7-methyl-1H-indazol-5-yl)ethyl 4-(2-oxo-1,2-dihydroquinazolin-3(4H)-yl)piperidine-1-carboxylate;
(±)-N-(1-(1H-Imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-Methyl-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-Benzyl-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-(3-Fluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-(3,5-Difluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(2-(7-Methyl-1H-indazol-5-yl)-1-(1-phenethyl-1H-imidazol-2-yl)ethyl)-4-(2-oxo-1,2-dihydroquinazolin-3(4H)-yl)piperidine-1-carboxamide;
(±)-N-(1-(1-(2-Fluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-(4-Fluorobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(2-(7-Methyl-1H-indazol-5-yl)-1-(1-(pyridin-4-ylmethyl)-1H-imidazol-2-yl)ethyl)-4-(2-oxo-1,2-dihydroquinazolin-3(4H)-yl)piperidine-1-carboxamide;
(±)-N-(1-(1-(3-Cyanobenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-(4-tert-Butylbenzyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-3-((2-(2-(7-Methyl-1H-indazol-5-yl)-1-(4-(2-oxo-1,2-dihydroquinazolin-3(4H)-yl)piperidine-1-carboxamido)ethyl)-1H-imidazol-1-yl)methyl)benzoic acid;
(±)-N-(1-(1-(3-Carbamoylbenzyl)-1H-imidazol-2-yl)-2-(7-methyl-1H-indazol-5-yl)ethyl)-(2-oxo-1,2-dihydroquinazolin-3(4H)-yl)piperidine-1-carboxamide;
(±)-N-(2-(7-Methyl-1H-indazol-5-yl)-1-(1-(2-nitrophenyl)-1H-imidazol-2-yl)ethyl)-4-(2-oxo-1,2-dihydroquinazolin-3(4H)-yl)piperidine-1-carboxamide;
(±)-N-(2-(7-Methyl-1H-indazol-5-yl)-1-(1-(2-nitrophenyl)-1H-imidazol-2-yl)ethyl)-4-(2-oxo-1,2-dihydroquinazolin-3(4H)-yl)piperidine-1-carboxamide;
(±)-4-(8-Fluoro-2-oxo-1,2-dihydroquinazolin-3[4H]-yl)-N-(2{7-methyl-1H-indazol-5-yl}-1-{1H-tetrazol-5-yl}ethyl)piperidin-1-carboxamide;
(±)-4-(8-Fluoro-2-oxo-1,2-dihydroquinazolin-3(4H)-yl)-N-(2-[7-methyl-1H-indazol-5-yl]-1-[1-(piperidin-4-ylmethyl)-1H-tetrazol-5-yl]ethyl)piperidin-1-carboxamide;
(±)-4-(8-Fluoro-2-oxo-1,2-dihydroquinazolin-3(4H)-yl)-N-(2-[7-methyl-1H-indazol-5-yl]-1-[2-(piperidin-4-ylmethyl)-1H-tetrazol-5-yl]ethyl)piperidin-1-carboxamide;
(±)-N-(1-([1,2,4]Triazolo[4,3-a]pyridin-3-yl)-2-(7-methyl-1H-indazol-5-yl)ethyl)-4-(8-fluoro-2-oxo-1,2-dihydroquinazolin-3(4H)-yl)piperidine-1-carboxamide;
(±)-N-(2-(7-Methyl-1H-indazol-5-yl)-1-(1-neopentyl-1H-tetrazol-5-yl)ethyl)-4-(2-oxo-1,2-dihydroquinazolin-3(4H)-yl)piperidine-1-carboxamide;
(R)-N-(1-(H-Imidazo[1,5-a]pyridin-3-yl)-2-(7-methyl-1H-indazol-5-yl)ethyl)-4-(2-oxo-1,2-dihydroquinazolin-3(4H)-yl)piperidine-1-carboxamide;
(±)-N-(1-(4-Bromo-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(4,5-Dibromo-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(1-(3,5-Difluorobenzyl)-5-bromo-1H-imidazol-2-yl)-2-(7-methyl-2H-indazol-5-yl)ethyl)-4-(2-oxo-1,2-dihydroquinazolin-3(4H)-yl)piperidine-1-carboxamide;
(±)-N-(1-(1-(3-Fluorobenzyl)-4-methyl-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(1-(4-Methyl-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(2-(7-Methyl-1H-indazol-5-yl)-1-(1-(pyridin-3-ylmethyl)-1H-imidazol-2-yl)ethyl)-4-(2-oxo-1,2-dihydroquinazolin-3(4H)-yl)piperidine-1-carboxamide;
(±)-N-(2-(7-Methyl-1H-indazol-5-yl)-1-(1-(pyridin-2-ylmethyl)-1H-imidazol-2-yl)ethyl)-4-(2-oxo-1,2-dihydroquinazolin-3(4H)-yl)piperidine-1-carboxamide;
(±)-N-(1-(1-((2-Chloro-6-methylpyridin-4-yl)methyl)-1H-imidazol-2-yl)-2-(7-methyl-1H-indazol-5-yl)ethyl)-4-(2-oxo-1,2-dihydroquinazolin-3(4H)-yl)piperidine-1-carboxamide;
(±)-N-(2-(7-Methyl-1H-indazol-5-yl)-1-(1-((2-methylpyridin-4-yl)methyl)-1H-imidazol-2-yl)ethyl)-4-(2-oxo-1,2-dihydroquinazolin-3(4H)-yl)piperidine-1-carboxamide;
3-(1-(3-(1-(4-tert-Butylbenzyl)-1H-imidazol-2-yl)-4-(7-methyl-3a,7a-dihydro-1H-indazol-5-yl)butanoyl)piperidin-4-yl)-3,4-dihydroquinazolin-2(1H)-one;
3-(1-(3-(1-(4-tert-Butylbenzyl)-1H-imidazol-2-yl)-4-(7-methyl-3a,7a-dihydro-1H-indazol-5-yl)butanoyl)piperidin-4-yl)-8-fluoro-3,4-dihydroquinazolin-2(1H)-one;
3-(1-(4-(7-Methyl-3a,7a-dihydro-1H-indazol-5-yl)-3-(1-(pyridin-4-ylmethyl)-1H-imidazol-2-yl)butanoyl)piperidin-4-yl)-3,4-dihydroquinazolin-2(1H)-one;
3-(1-(3-(1H-Benzo[d]imidazol-2-yl)-4-(7-methyl-3a,7a-dihydro-1H-indazol-5-yl)butanoyl)piperidin-4-yl)-3,4-dihydroquinazolin-2(1H)-one;

3-(1-(3-(1-Ethyl-1H-benzo[d]imidazol-2-yl)-4-(7-methyl-3a,7a-dihydro-1H-indazol-5-yl)butanoyl)piperidin-4-yl)-3,4-dihydroquinazolin-2(1H)-one; or (R)-2-(7-Methyl-1H-indazol-5-yl)-1-(3-(pyridin-4-yl)-1,2,4-oxadiazol-5-yl)ethyl 4-(2-oxo-1,2-dihydroquinazolin-3(4H)-yl)piperidine-1-carboxylate;

or a pharmaceutically acceptable salt or solvate thereof.

30. A pharmaceutical composition comprising a compound according to claim 1.

31. A method of treating migraine in a patient in need thereof comprising the administration of an anti-migraine effective amount of a pharmaceutical composition comprising a compound according to claim 1.

\* \* \* \* \*

UNITED STATES PATENT AND TRADEMARK OFFICE
CERTIFICATE OF CORRECTION

| | |
|---|---|
| PATENT NO. | : 7,569,578 B2 |
| APPLICATION NO. | : 11/004706 |
| DATED | : August 4, 2009 |
| INVENTOR(S) | : Guanglin Luo et al. |

It is certified that error appears in the above-identified patent and that said Letters Patent is hereby corrected as shown below:

On the Title Page:

Item (73), Assignee, change "Bristol-Meyers" to -- Bristol-Myers --.

In the Claims:

Claim 1:

Column 165, line 56, change "benzythiazolyl," to -- benzothiazolyl, --.

Column 166, line 3, after "$C_{1-4}$ alkylidine,", delete "$_4$alkylidine,".

Column 166, line 50, after "C", delete ",".

Claim 6:

Column 167, line 4, after "form", delete "b".

Claim 10:

Column 167, line 13, after "wherein", delete "is".

Claim 11:

Column 167, line 15, after "wherein", delete "is".

Claim 12:

Column 167, line 18, after "wherein", delete "is".

Claim 18:

Column 167, line 42, change "$C_4$alkylamino," to -- $C_{1-4}$alkylamino, --.

Claim 24:

Column 167, line 64, after "pyridin-3-yl", delete ")".

Claim 27:

Column 168, line 14, after "form", insert -- an optionally --.

Signed and Sealed this

Eighteenth Day of October, 2011

David J. Kappos
*Director of the United States Patent and Trademark Office*

CERTIFICATE OF CORRECTION (continued)
U.S. Pat. No. 7,569,578 B2

In the Claims:

Claim 29:

Column 169, line 31, change "2Phenethyl" to -- 2-phenethyl --.